(12) United States Patent
Regev et al.

(10) Patent No.: US 11,180,730 B2
(45) Date of Patent: Nov. 23, 2021

(54) COMPOSITIONS AND METHODS FOR EVALUATING AND MODULATING IMMUNE RESPONSES BY DETECTING AND TARGETING GATA3

(71) Applicants: The Broad Institute, Inc., Cambridge, MA (US); Massachusetts Institute of Technology, Cambridge, MA (US); The Brigham and Women's Hospital, Inc., Boston, MA (US)

(72) Inventors: Aviv Regev, Cambridge, MA (US); Ana Carrizosa Anderson, Brookline, MA (US); Le Cong, Cambridge, MA (US); Vijay K. Kuchroo, Chestnut Hill, MA (US); Meromit Singer, Somerville, MA (US); Chao Wang, Cambridge, MA (US)

(73) Assignees: The Broad Institute, Inc., Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 128 days.

(21) Appl. No.: 15/966,290

(22) Filed: Apr. 30, 2018

(65) Prior Publication Data

US 2019/0106679 A1   Apr. 11, 2019

Related U.S. Application Data

(63) Continuation-in-part of application No. PCT/US2016/059487, filed on Oct. 28, 2016.

(60) Provisional application No. 62/247,446, filed on Oct. 28, 2015, provisional application No. 62/384,577, filed on Sep. 7, 2016.

(51) Int. Cl.
| | |
|---|---|
| *C12N 5/0783* | (2010.01) |
| *A61K 35/17* | (2015.01) |
| *A61K 39/00* | (2006.01) |
| *G01N 33/50* | (2006.01) |
| *A61K 45/06* | (2006.01) |
| *C12N 15/10* | (2006.01) |
| *C12Q 1/6883* | (2018.01) |

(52) U.S. Cl.
CPC .......... *C12N 5/0638* (2013.01); *A61K 35/17* (2013.01); *A61K 39/0011* (2013.01); *A61K 45/06* (2013.01); *C12N 15/1079* (2013.01); *C12Q 1/6883* (2013.01); *G01N 33/505* (2013.01); *G01N 33/5023* (2013.01); *G01N 33/5047* (2013.01); *C12Q 2600/106* (2013.01); *C12Q 2600/136* (2013.01); *C12Q 2600/158* (2013.01); *G01N 2333/4703* (2013.01); *G01N 2800/52* (2013.01)

(58) Field of Classification Search
CPC ..................................................... C12N 5/0636
See application file for complete search history.

(56) References Cited

U.S. PATENT DOCUMENTS

| | | |
|---|---|---|
| 4,690,915 A | 9/1987 | Rosenberg |
| 4,844,893 A | 7/1989 | Honsik et al. |
| 5,177,196 A | 1/1993 | Meyer, Jr. et al. |
| 5,543,158 A | 8/1996 | Gref et al. |
| 5,580,859 A | 12/1996 | Felgner et al. |
| 5,589,466 A | 12/1996 | Felgner et al. |
| 5,593,972 A | 1/1997 | Weiner et al. |
| 5,686,281 A | 11/1997 | Roberts |
| 5,843,728 A | 12/1998 | Seed et al. |
| 5,846,946 A | 12/1998 | Huebner et al. |
| 5,851,828 A | 12/1998 | Seed et al. |
| 5,855,913 A | 1/1999 | Hanes et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,985,309 A | 11/1999 | Edwards et al. |
| 6,004,811 A | 12/1999 | Seed et al. |
| 6,007,845 A | 12/1999 | Domb et al. |
| 6,040,177 A | 3/2000 | Riddell et al. |

(Continued)

FOREIGN PATENT DOCUMENTS

| | | |
|---|---|---|
| EP | 0 097 994 A2 | 1/1984 |
| EP | 1 519 714 A1 | 4/2005 |

(Continued)

OTHER PUBLICATIONS

Tzong-Shyuan et al., (2013, J. Immunology, vol. 190, pp. 428-437). (Year: 2013).*

(Continued)

*Primary Examiner* — Thaian N. Ton
*Assistant Examiner* — David A Montanari
(74) *Attorney, Agent, or Firm* — Johnson, Marcou, Isaacs & Nix, LLC; F. Brent Nix, Esq.; Michael B. Scher, Esq.

(57) ABSTRACT

The present invention provides markers, marker signatures and molecular targets that correlate with dysfunction of immune cells and are advantageously independent of the immune cell activation status. The present markers, marker signatures and molecular targets provide for new ways to evaluate and modulate immune responses. Specifically, GATA3 and/or FOXO1 modulation are provided for use as markers, marker signatures and molecular targets. Therapeutic methods are also provided to treat a patient in need thereof who would benefit from an increased immune response.

20 Claims, 55 Drawing Sheets
Specification includes a Sequence Listing.

(56) References Cited

U.S. PATENT DOCUMENTS

| | | |
|---|---|---|
| 6,261,569 B1 | 7/2001 | Comis et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,489,458 B2 | 12/2002 | Hackett et al. |
| 6,534,055 B1 | 3/2003 | June et al. |
| 6,753,162 B1 | 6/2004 | Seed et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,232,566 B2 | 6/2007 | June et al. |
| 7,259,015 B2 | 8/2007 | Kingsman et al. |
| 7,303,910 B2 | 12/2007 | Bebbington et al. |
| 7,351,585 B2 | 4/2008 | Mitrophanous et al. |
| 7,427,605 B2 | 9/2008 | Davis et al. |
| 7,446,190 B2 | 11/2008 | Sadelain et al. |
| 7,572,631 B2 | 8/2009 | Berenson et al. |
| 7,741,465 B1 | 6/2010 | Eshhar et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,838,658 B2 | 11/2010 | MacLachlan et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 7,985,739 B2 | 7/2011 | Kay et al. |
| 8,034,334 B2 | 10/2011 | Dudley et al. |
| 8,044,019 B2 | 10/2011 | Uno et al. |
| 8,058,069 B2 | 11/2011 | Yaworski et al. |
| 8,088,379 B2 | 1/2012 | Robbins et al. |
| 8,101,741 B2 | 1/2012 | MacLachlan et al. |
| 8,188,263 B2 | 5/2012 | MacLachlan et al. |
| 8,211,422 B2 | 7/2012 | Eshhar et al. |
| 8,227,432 B2 | 7/2012 | Hackett et al. |
| 8,236,943 B2 | 8/2012 | Lee et al. |
| 8,283,333 B2 | 10/2012 | Yaworski et al. |
| 8,372,951 B2 | 2/2013 | Chang et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,575,305 B2 | 11/2013 | Gait et al. |
| 8,614,194 B1 | 12/2013 | Chen et al. |
| 8,637,307 B2 | 1/2014 | June et al. |
| 8,697,359 B1 | 4/2014 | Zhang |
| 8,697,854 B2 | 4/2014 | Schendel et al. |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0013648 A1 | 1/2004 | Kingsman et al. |
| 2004/0171156 A1 | 9/2004 | Hartley et al. |
| 2004/0224402 A1 | 11/2004 | Bonyhadi et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0152654 A1 | 6/2008 | Reich |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0111106 A1 | 4/2009 | Mitrophanous et al. |
| 2010/0104509 A1 | 4/2010 | King et al. |
| 2010/0317109 A1 | 12/2010 | Maden et al. |
| 2011/0117189 A1 | 5/2011 | Mazzone et al. |
| 2011/0195123 A1 | 8/2011 | Shemi |
| 2011/0265198 A1 | 10/2011 | Gregory et al. |
| 2011/0293571 A1 | 12/2011 | Widdowson et al. |
| 2011/0293703 A1 | 12/2011 | Mahon et al. |
| 2012/0017290 A1 | 1/2012 | Cui et al. |
| 2012/0244133 A1 | 9/2012 | Rosenberg et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0071414 A1 | 3/2013 | Dotti et al. |
| 2013/0236946 A1 | 9/2013 | Gouble |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0251648 A1 | 9/2016 | Wang et al. |
| 2017/0306335 A1 | 10/2017 | Zhang et al. |
| 2019/0100801 A1 | 4/2019 | Regev et al. |
| 2019/0106678 A1 | 4/2019 | Regev et al. |
| 2019/0106710 A1 | 4/2019 | Zhang et al. |
| 2019/0262399 A1 | 8/2019 | Wang et al. |

FOREIGN PATENT DOCUMENTS

| | | |
|---|---|---|
| EP | 1 664 316 A1 | 6/2006 |
| EP | 1 766 035 A1 | 3/2007 |
| EP | 1 781 593 A2 | 5/2007 |
| EP | 2 771 468 A1 | 9/2014 |
| EP | 2 784 162 A1 | 10/2014 |
| EP | 2 764 103 B1 | 8/2015 |
| EP | 3 368 689 A2 | 9/2018 |
| WO | 92/15322 A1 | 9/1992 |
| WO | 94/02595 A1 | 2/1994 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |

(56) References Cited

FOREIGN PATENT DOCUMENTS

| | | |
|---|---|---|
| WO | 2006/000830 A2 | 1/2006 |
| WO | 2006/007712 A1 | 1/2006 |
| WO | 2006125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/079000 A1 | 6/2012 |
| WO | 2012/135025 A2 | 10/2012 |
| WO | 2013/039889 A1 | 3/2013 |
| WO | 2013/040371 A2 | 3/2013 |
| WO | 2013044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/134351 A2 | 9/2014 |
| WO | 2014/145631 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/065964 A1 | 5/2015 |
| WO | 2015/089351 A1 | 6/2015 |
| WO | 2015/089419 A2 | 6/2015 |
| WO | 2015/120096 A2 | 8/2015 |
| WO | 2015/130968 A2 | 9/2015 |
| WO | 2015/142675 A2 | 9/2015 |
| WO | 2015/187528 A1 | 12/2015 |
| WO | 2016/000304 A1 | 1/2016 |
| WO | 2016/011210 A2 | 1/2016 |
| WO | 2016/040476 A1 | 3/2016 |
| WO | 2016/049251 A1 | 3/2016 |
| WO | 2016/061456 A2 | 4/2016 |
| WO | 2016/070061 A1 | 5/2016 |
| WO | 2016/191756 A1 | 12/2016 |
| WO | 2016/196388 A1 | 12/2016 |
| WO | 2017/004153 A1 | 1/2017 |
| WO | 2017/004916 A1 | 1/2017 |
| WO | 2017/011804 A1 | 1/2017 |
| WO | 2017/070395 A1 | 4/2017 |
| WO | 2017/075294 A1 | 5/2017 |
| WO | 2017/075451 A1 | 5/2017 |
| WO | 2017/075465 A1 | 5/2017 |
| WO | 2017/075478 A2 | 5/2017 |
| WO | 2018/049025 A1 | 3/2018 |
| WO | 2018/049025 A3 | 5/2018 |

OTHER PUBLICATIONS

Ho et al., 2009, Nat. Rev. Immunol. vol. 9(2), pp. 125-135 (Year: 2009).*
Xie et al., 2014, Genome Res., vol. 24, pp. 1526-1533 (Year: 2014).*
Medsger et al., (2011, Arthritis & Rheumatism, vol. 63(6), pp. 1738-1747) (Year: 2011).*
Anderson, et al., "Lag-3, Tim-3, and TIGIT: Co-inhibitory Receptors with Specialized Functions in Immune Regulation", Immunity, vol. 44, No. 5, May 17, 2016, 989-1004.
Apetoh, et al., "Consensus 1-60 Nomenclature for CD8 + T Cell Phenotypes in Cancer", Oncoimmunology, vol. 4, No. 4, Feb. 1, 2015, 10 pages.
The Broad Institute, Inc., "International Search Report and Written Opinion issued in International Application No. PCT/US2016/059487", dated Feb. 17, 2017, 12 pages.
Baitsch, et al., "Exhaustion of Tumor-Specific CD8+ T cells in Metastases from Melanoma Patients", Journal of Clinical Investigation, vol. 121, No. 6, May 2011, 2350-2360.
Baitsch, et al., "The Three Main Stumbling Blocks for Anticancer T Cells", Trends in Immunology, vol. 33, No. 7, Jul. 2012, 364-372.
Barber, et al., "Restoring Function in Exhausted CD8 T Cells During Chronic Viral Infection", Nature, vol. 439, No. 7077, Feb. 9, 2006, 682-687.
Bikard, et al., "Programmable Repression and Activation of Bacterial Gene Expression using an Engineered CRISPR-Cas System", Nucleic Acids Research, vol. 41, No. 12, Jun. 2013, 7429-7437.
Blackburn, et al., "Coregulation of CD8+ T Cell Exhaustion by Multiple Inhibitory Receptors During Chronic Viral Infection", Nature Immunology, vol. 10, No. 1, Jan. 2009, 29-37.
Buggert, et al., "T-bet and Eomes Are Differentially Linked to the Exhausted Phenotype of CD8+ T Cells in HIV Infection", PLoS Pathogens, e1004251, vol. 10, No. 7, Jul. 17, 2014, 15 pages.
Chihara, et al., "Induction and Transcriptional Regulation of the Co-Inhibitory Gene Module in T Cells", Nature, vol. 558, No. 7710, Jun. 2018, 454-459.
Doering, et al., "Network Analysis Reveals Centrally Connected Genes and Pathways Involved in CD8+ T cell Exhaustion versus Memory", Immunity, vol. 37, No. 6, Dec. 2012, 1130-1144.
Eden, et al., "Discovering Motifs in Ranked Lists of DNA Sequences", PLoS Computational Biology, vol. 3, Issue 3, Mar. 2007, 0508-0522.
Fourcade, et al., "Upregulation of Tim-3 and PD-1 Expression is Associated with Tumor Antigen-Specific CD8+ T Cell Dysfunction in Melanoma Patients", Journal of Experimental Medicine, vol. 207, No. 10, Sep. 27, 2010, 2175-2186.
Fuschiotti, "CD8 T Cells in Systemic Sclerosis", Immunologic Research, vol. 50, No. 2-3, Jun. 2011, 188-194.
Giordano, et al., "Molecular Profiling of CD8 T Cells In Autochthonous Melanoma Identifies Maf As Driver of Exhaustion", European Molecular Biology Organization Journal, vol. 34, No. 15, Jul. 2, 2015, 2042-2058.
Kim, et al., "Features of Responding T Cells in Cancer and Chronic Infection", Current Opinion in Immunology, vol. 22, No. 2, Apr. 2010, 223-230.
Kim, et al., "Stable Inhibitory Activity of Regulatory T Cells Requires the Transcription Factor Helios", Science, vol. 350, No. 6258, Oct. 16, 2015, 334-339.
Klein, et al., "Droplet Barcoding for Single-Cell Transcriptomics Applied to Embryonic Stem Cells", Cell, vol. 161, No. 5, May 21, 2015, 1187-1201.
Mali, et al., "CAS9 Transcriptional Activators for Target Specificity Screening and Paired Nickases for Cooperative Genome Engineering", Nature Biotechnology, vol. 31, No. 9, Sep. 2013, 833-838.
Marraco, et al., "Inhibitory Receptors Beyond T Cell Exhaustion", Frontiers in Immunology, vol. 6, Article 310, Jun. 26, 2015, 14 pages.

(56) References Cited

OTHER PUBLICATIONS

Matsuzaki, et al., "Tumor-infiltrating NY-ESO-1-specific CD8+ T Cells are Negatively Regulated by LAG-3 and PD-1 in Human Ovarian Cancer", Proceedings of the National Academy of Sciences of the United States of America, vol. 107, No. 17, Apr. 27, 2010, 7875-7880.
McKinney, et al., "T-cell Exhaustion, co-Stimulation and Clinical Outcome in Autoimmunity and Infection", Nature, vol. 523, No. 7562, 2015, 612-616.
Moskophidis, et al., "Virus Persistence in Acutely Infected Immunocompetent Mice by Exhaustion of Antiviral Cytotoxic Effector T Cells", Nature, vol. 362, No. 6422, Apr. 22, 1993, 758-761.
The Broad Institute, Inc., "International Preliminary Report on Patentability issued in International Application No. PCT/US2016/059487", dated May 11, 2018, 8 pages.
Paley, et al., "Progenitor and Terminal Subsets of CD8+ T Cells Cooperate to Contain Chronic Viral Infection", Science, vol. 338, No. 6111, Nov. 30, 2012, 1220-1225.
Restifo, et al., "Acquired Resistance to Immunotherapy and Future Challenges", Nature Reviews Cancer, vol. 16, No. 2, Jan. 29, 2016, 121-126.
Sakuishi, et al., "Targeting Tim-3 and PD-1 Pathways to Reverse T cell Exhaustion and Restore Anti-Tumor Immunity", Journal of Experimental Medicine, vol. 207, No. 10, Sep. 2010, 2187-2194.
Sarkar, et al., "Functional and Genomic Profiling of Effector CD8 T Cell Subsets with Distinct Memory Fates", Journal of Experimental Medicine, vol. 205, No. 3, Mar. 17, 2008, 625-640.
Singer, et al., "A Distinct Gene Module for Dysfunction Uncoupled from Activation in Tumor-Infiltrating T Cells", Cell, vol. 166, No. 6, Sep. 8, 2016, 1500-1511.
Spranger, et al., "Mechanism of Tumor Rejection with Doublets of CTLA-4, PD-1/PD-L1, or IDO Blockade Involves Restored IL-2 Production and Proliferation of CD8+ T Cells Directly within the Tumor Microenvironment", Journal for ImmunoTherapy of Cancer, vol. 2 No. 3, Feb. 18, 2014, 14 pages.
Staron, et al., "The Transcription Factor FoxO1 Sustains Expression of the Inhibitory Receptor PD-1 and Survival of Antiviral CD8+ T Cells during Chronic Infection", Immunity, vol. 41, Issue 5, Nov. 2014, 802-814.
Tai, et al., "GATA-3 Regulates the Homeostasis and Activation of CD8+ T Cells", Journal of Immunology, vol. 190, No. 1, Jan. 1, 2013, 428-437.
Tindemans, et al., "GATA-3 Function in Innate and Adaptive Immunity", Immunity, vol. 41, No. 2, Aug. 21, 2014, 191-206.
Tirosh, et al., "Dissecting The Multicellular Ecosystem of Metastatic Melanoma By Single-Cell RNA-Seq", Science, vol. 352, No. 6282, Apr. 8, 2016, 189-196.
Wagner, "GO-PCA: An Unsupervised Method to Explore Gene Expression Data Using Prior Knowledge", Plos One, vol. 10, No. 11, 2015, 26 pages.
Wherry, et al., "Molecular and Cellular Insights into T Cell Exhaustion", Nature Reviews Immunology, vol. 15, No. 8, Aug. 2015, 486-499.
Wherry, et al., "Molecular Signature of CD8+ T Cell Exhaustion During Chronic Viral Infection", Immunity, vol. 27, No. 4, Oct. 1, 2007, 670-684.
Wherry, et al., "Viral Persistence Alters CD8 T-Cell Immunodominance and Tissue Distribution and Results in Distinct Stages of Functional Impairment", Journal of Virology, vol. 77, No. 8, Apr. 2003, 4911-4927.
Yu, et al., "Dynamic Expression of Transcription Factors T-bet and GATA-3 by Regulatory T Cells Maintains Immune Tolerance", Nature Immunology, vol. 16, No. 2, Dec. 15, 2014, 197-206.
Zhou, et al., "Coexpression of Tim-3 and PD-1 Identifies A CD8+ T-Cell Exhaustion Phenotype in Mice with Disseminated Acute Myelogenous Leukemia", Blood, vol. 117, No. 17, Apr. 28, 2011, 4501-4510.
Zuniga, et al., "Innate and Adaptive Immune Regulation During Chronic Viral Infections", Annual Review of Virology, vol. 2 No. 1, Nov. 2015, 573-597.
The Broad Institute, Inc., et al., "Communication pursuant to Article 94(3) EPC for EP 16795490.8", Jul. 12, 2019, 5 pages.
The Broad Institute, Inc., et al., "Communication Pursuant to Article 94(3) EPC for EP 16795490.8", Feb. 27, 2019, 4 pages.

* cited by examiner

Wherry2012 day [D15C vs. D15A] UNION [D30C vs. D30A]

Wherry2012 day [D15C vs. D15A] INTERSECT [D30C vs. D30A]

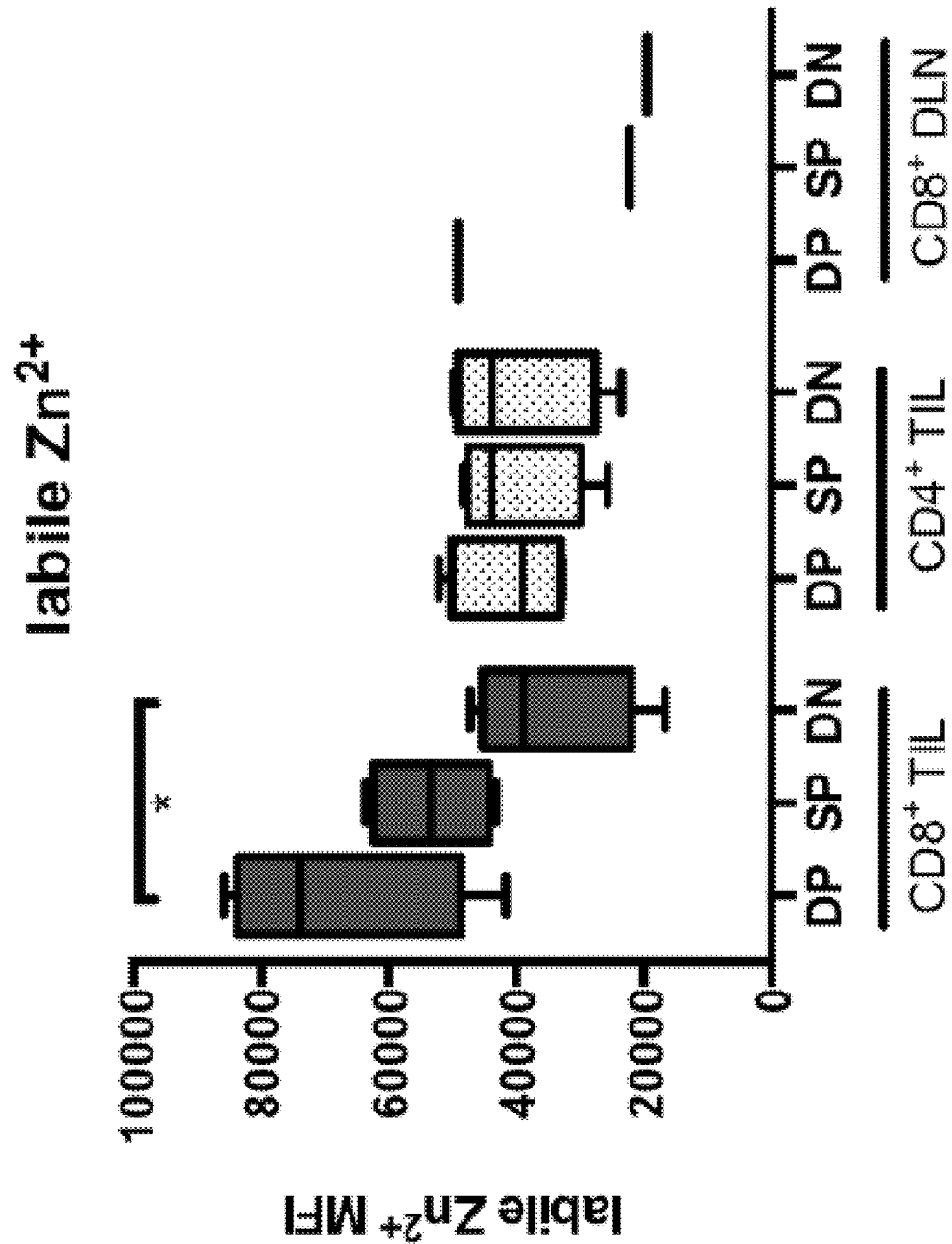

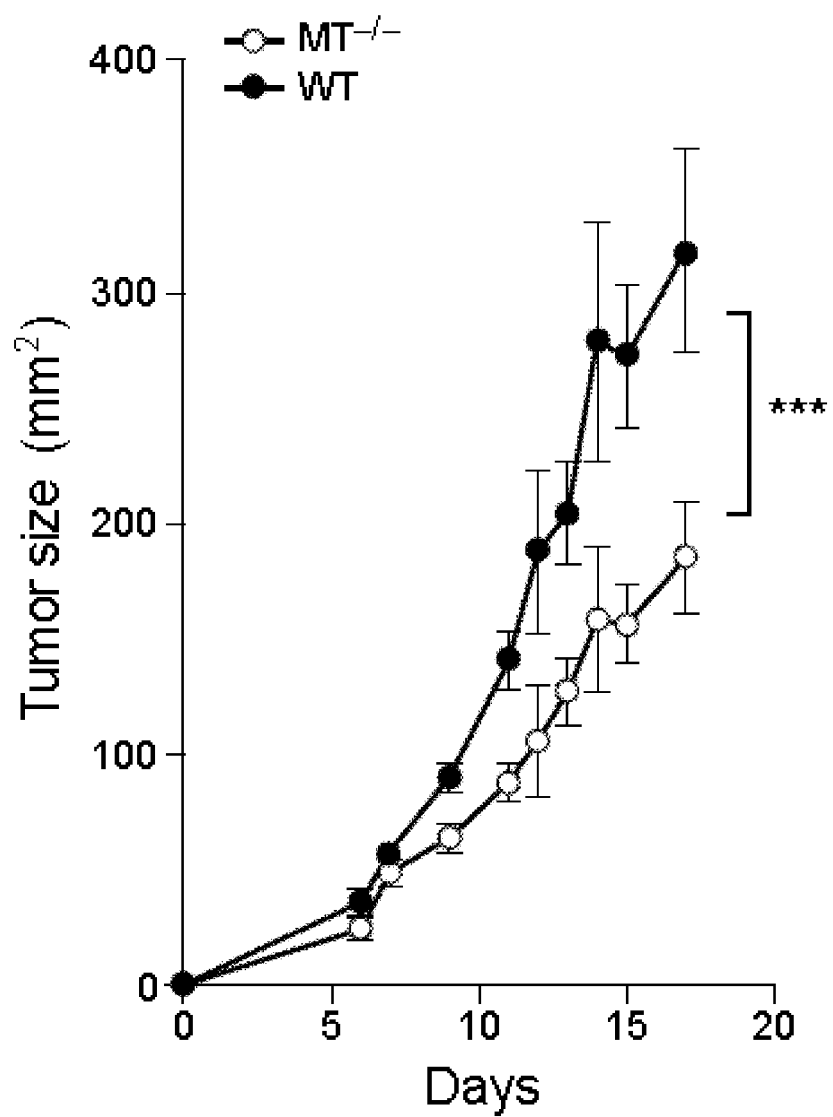

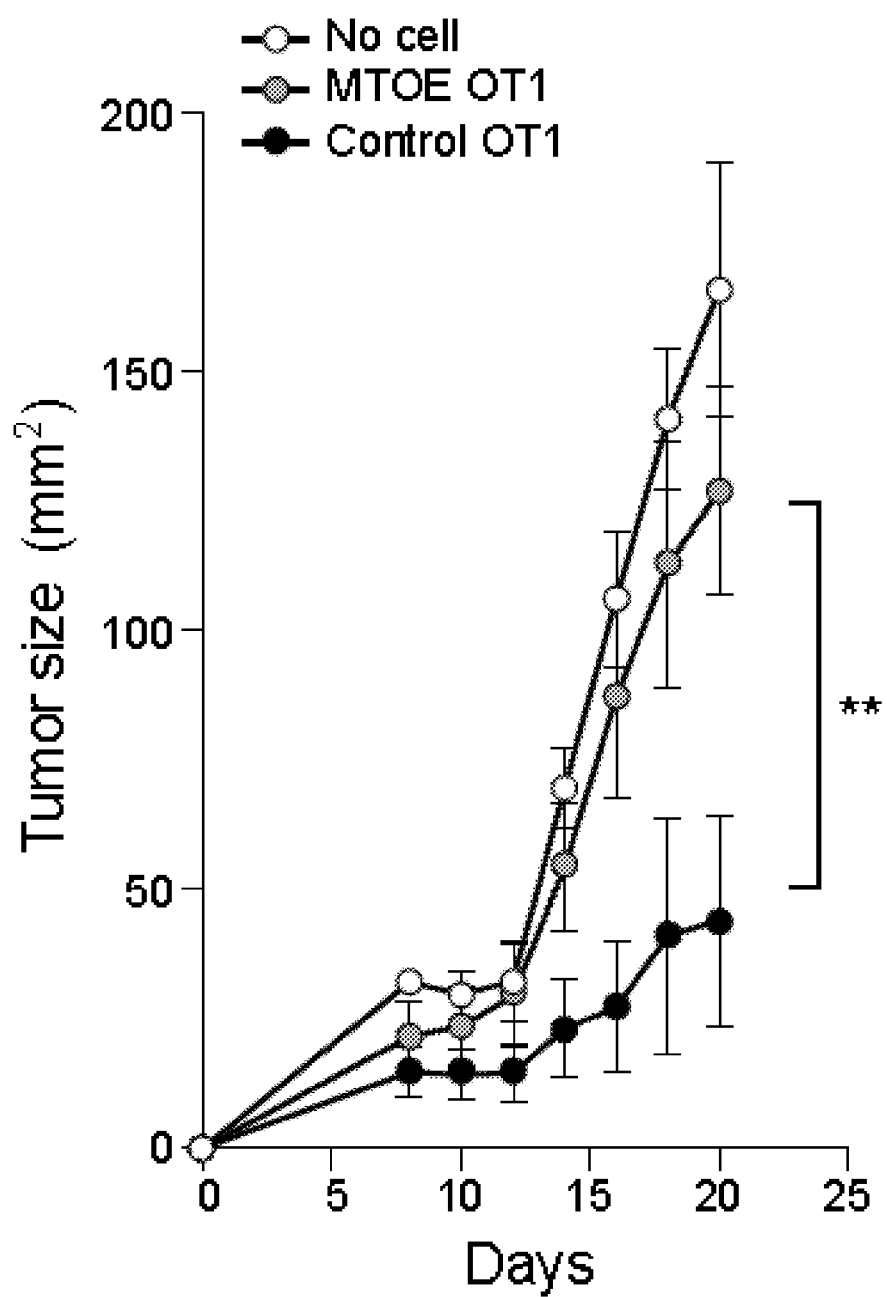

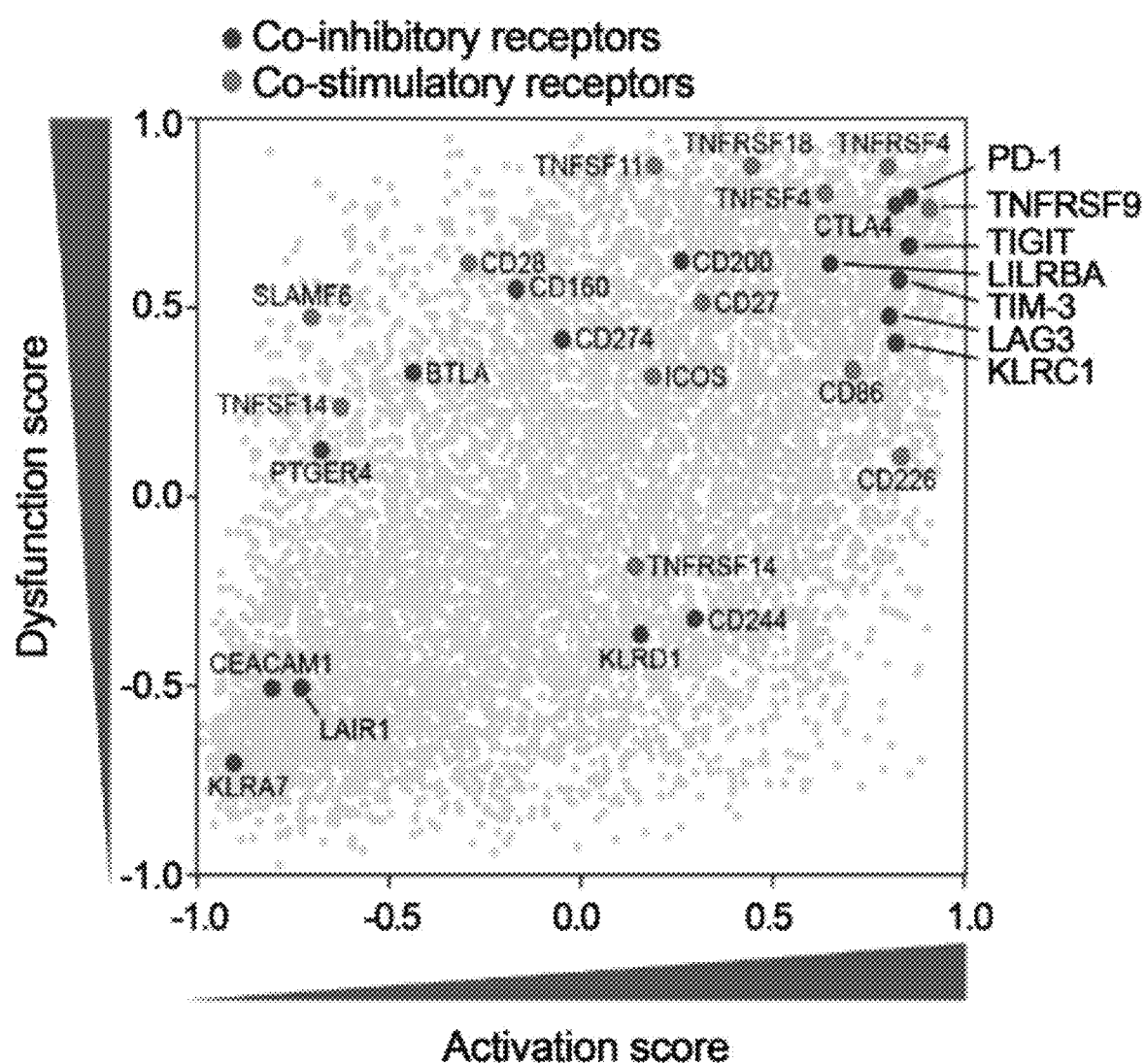

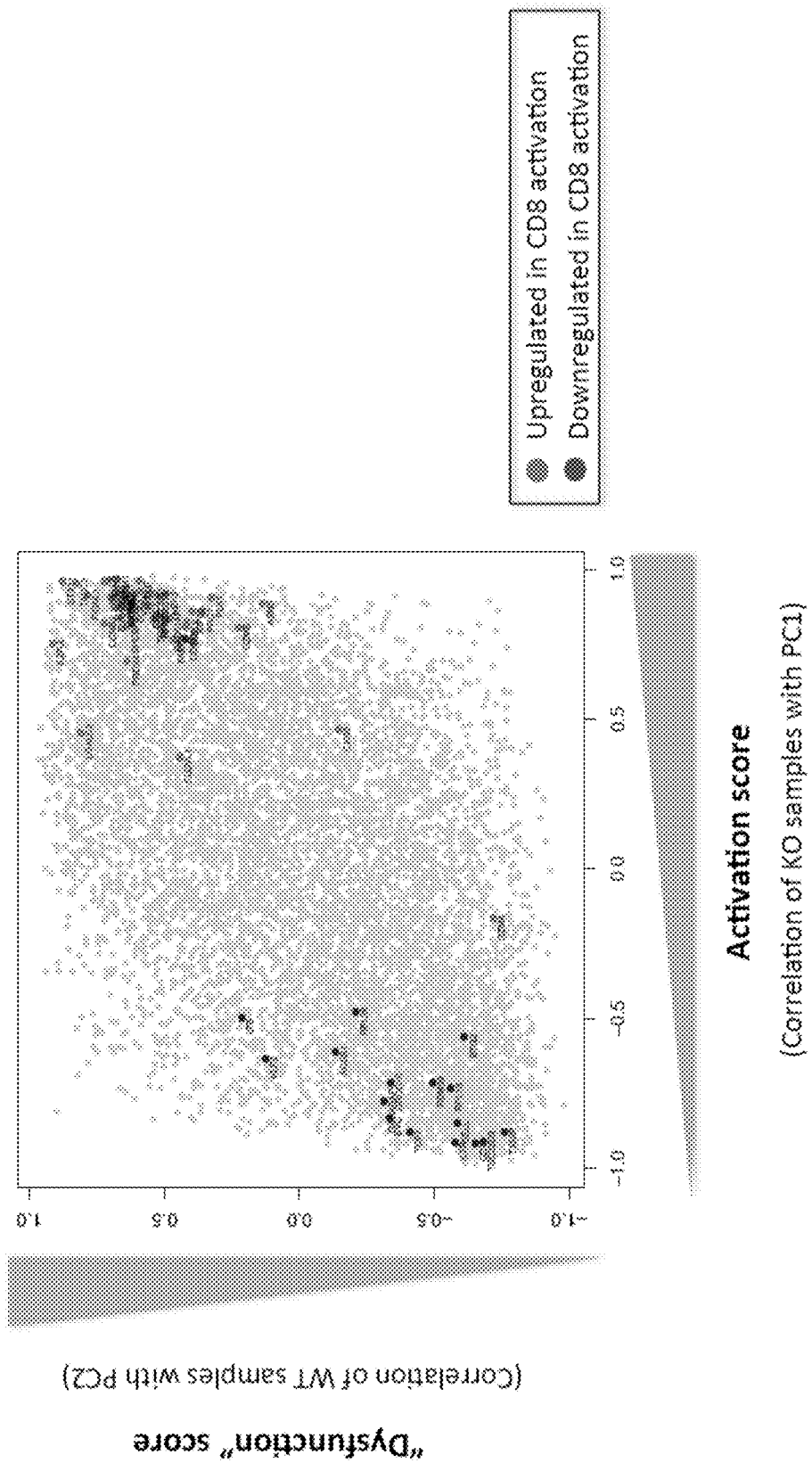

|  | wilcox.test | KS.test |
| --- | --- | --- |
| DYS-specific vs. ACT-specific | 0.036 | 0.027 |

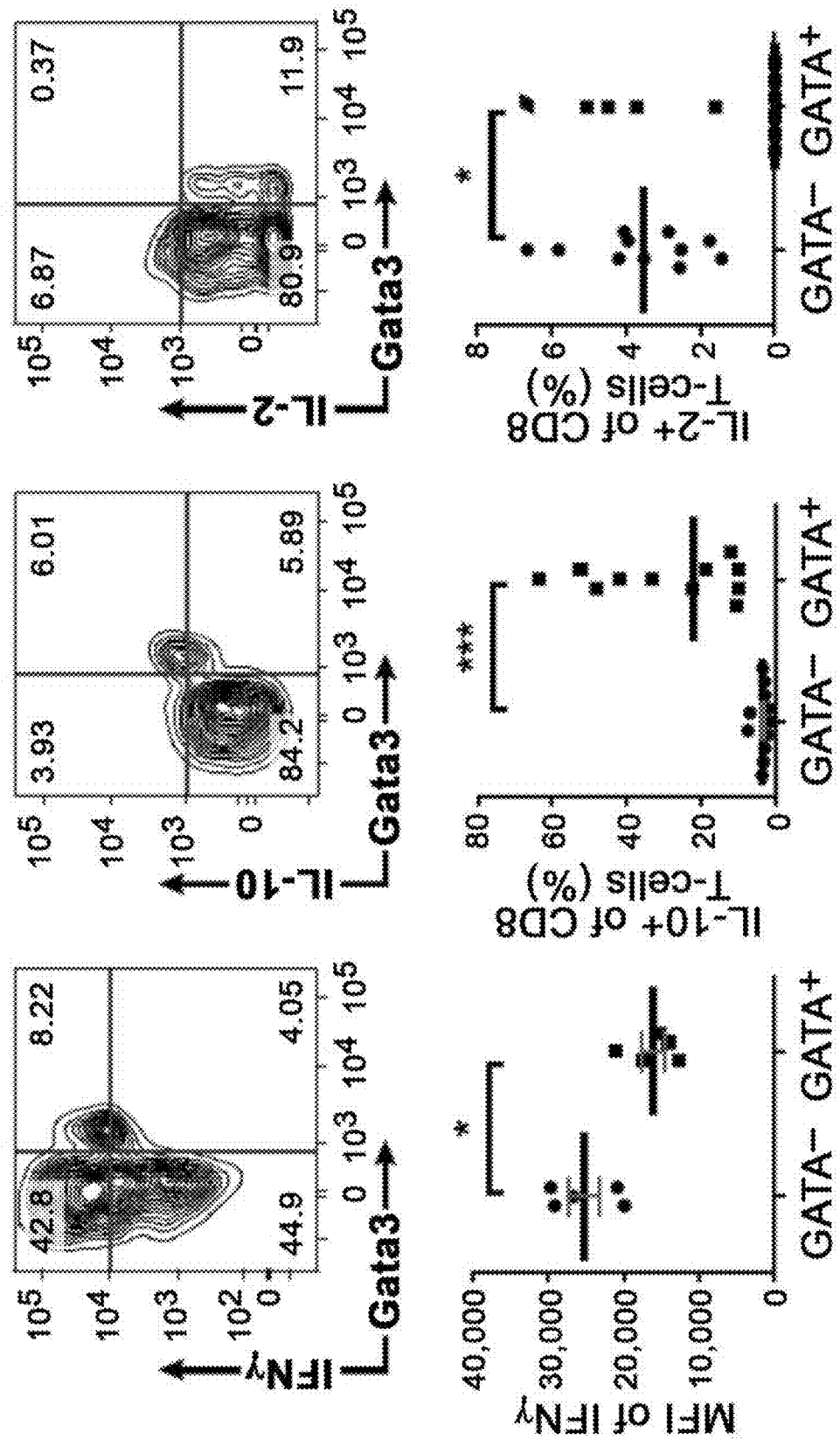

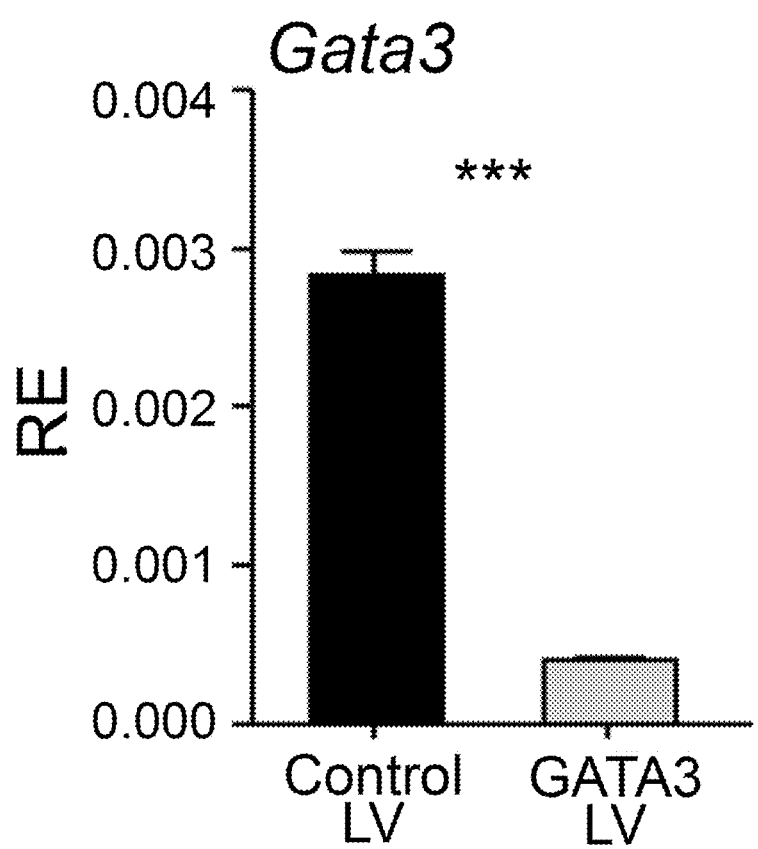

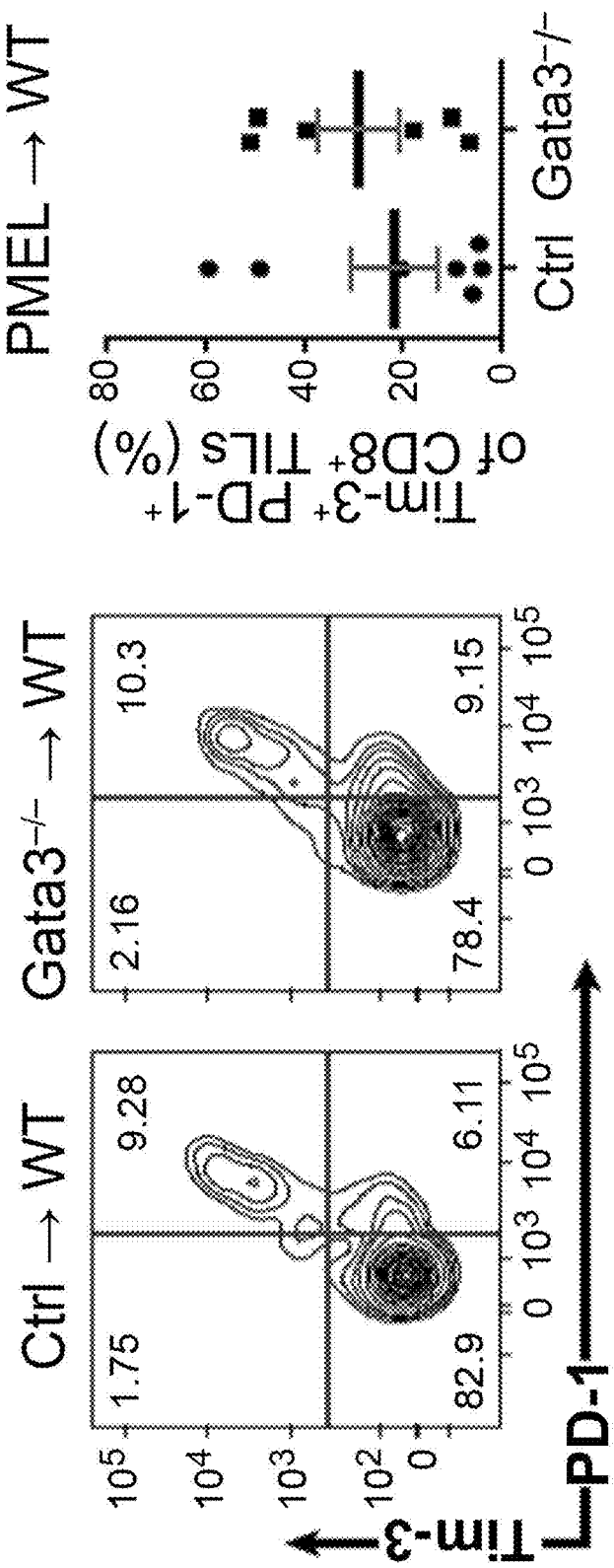

Exp 1: total Pou2af1 KO (Mixed SNP profile of B6 and 129S6/SvEvTac): 73.47% B6; the WT used in this experiment is 100% B6

SEQUENCE LISTING

```
<160> NUMBER OF SEQ ID NOS: 19

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
```

```
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Homo sapiens

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 6
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40
```

```
<210> SEQ ID NO 7
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 7

Pro Pro Lys Lys Ala Arg Glu Asp
1               5

<210> SEQ ID NO 8
<211> LENGTH: 8
<212> TYPE: PRT
<213> ORGANISM: Homo sapiens

<400> SEQUENCE: 8

Pro Gln Pro Lys Lys Lys Pro Leu
1               5

<210> SEQ ID NO 9
<211> LENGTH: 12
<212> TYPE: PRT
<213> ORGANISM: Mus musculus

<400> SEQUENCE: 9

Ser Ala Leu Ile Lys Lys Lys Lys Lys Met Ala Pro
1               5                   10

<210> SEQ ID NO 10
<211> LENGTH: 5
<212> TYPE: PRT
<213> ORGANISM: Influenza virus

<400> SEQUENCE: 10

Asp Arg Leu Arg Arg
1               5

<210> SEQ ID NO 11
<211> LENGTH: 7
<212> TYPE: PRT
<213> ORGANISM: Influenza virus

<400> SEQUENCE: 11

Pro Lys Gln Lys Lys Arg Lys
1               5

<210> SEQ ID NO 12
<211> LENGTH: 10
<212> TYPE: PRT
<213> ORGANISM: Hepatitis delta virus

<400> SEQUENCE: 12

Arg Lys Leu Lys Lys Lys Ile Lys Lys Leu
1               5                   10

<210> SEQ ID NO 13
<211> LENGTH: 10
<212> TYPE: PRT
<213> ORGANISM: Mus musculus

<400> SEQUENCE: 13
```

Arg Glu Lys Lys Lys Phe Leu Lys Arg Arg
1               5                   10

<210> SEQ ID NO 14
<211> LENGTH: 20
<212> TYPE: PRT
<213> ORGANISM: Homo sapiens

<400> SEQUENCE: 14

Lys Arg Lys Gly Asp Glu Val Asp Gly Val Asp Glu Val Ala Lys Lys
1               5                   10                  15

Lys Ser Lys Lys
            20

<210> SEQ ID NO 15
<211> LENGTH: 17
<212> TYPE: PRT
<213> ORGANISM: Homo sapiens

<400> SEQUENCE: 15

Arg Lys Cys Leu Gln Ala Gly Met Asn Leu Glu Ala Arg Lys Thr Lys
1               5                   10                  15

Lys

<210> SEQ ID NO 16
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 16

Val Ser Arg Lys Arg Pro Arg Pro
1               5

<210> SEQ ID NO 17
<211> LENGTH: 288
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
                20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Ala Pro Ser Pro Ala Phe
        50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala

```
                115                 120                 125
Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

<210> SEQ ID NO 18
<211> LENGTH: 183
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

```
<210> SEQ ID NO 19
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Aminohexanoyl
<220> FEATURE:
<221> NAME/KEY: MOD_RES
<222> LOCATION: (5)..(5)
<223> OTHER INFORMATION: Aminohexanoyl
<220> FEATURE:
<221> NAME/KEY: MOD_RES
<222> LOCATION: (8)..(8)
<223> OTHER INFORMATION: Aminohexanoyl
<220> FEATURE:
<221> NAME/KEY: MOD_RES
<222> LOCATION: (11)..(11)
<223> OTHER INFORMATION: Aminohexanoyl

<400> SEQUENCE: 19

Arg Xaa Arg Arg Xaa Arg Arg Xaa Arg Arg Xaa Arg
1               5                   10
```

COMPOSITIONS AND METHODS FOR EVALUATING AND MODULATING IMMUNE RESPONSES BY DETECTING AND TARGETING GATA3

RELATED APPLICATIONS AND INCORPORATION BY REFERENCE

This application is a continuation-in-part application of international patent application Serial No. PCT/US2016/059487 filed on Oct. 28, 2016, which published as PCT Publication No. WO2017/075465 on May 4, 2017 and which claims priority and benefit of U.S. provisional application Ser. No. 62/247,446 filed Oct. 28, 2015 and 62/384,577 filed Sep. 7, 2016.

Reference is made to PCT Publication No. WO/2014/134351 published on Feb. 27, 2014, PCT Publication No. WO/2014/145631 published on Sep. 18, 2014, PCT Publication No. WO/2014/172606 published on Oct. 23, 2014 and PCT Publication No. WO/2015/130968 published on Feb. 26, 2015. Reference is also made to International application serial number PCT/US2016/040015 filed on Jun. 29, 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under MH105960, NS045937, AI073748 and CA187975 awarded by the National Institutes of Health. The government has certain rights in the invention.

SEQUENCE LISTING

The instant application contains a sequence listing which has been submitted electronically in ascii format and is hereby incorporated by reference in its entirety. Said ASCII copy, created on Jan. 11, 2017, is named 48009_99_2013_SL.txt and is 9 bytes in size.

FIELD OF THE INVENTION

The invention relates to substances, compositions and methods useful in evaluating and modulating immune responses.

BACKGROUND OF THE INVENTION

T cell fitness is closely linked to health and disease. Activated $CD8^+$ T lymphocytes have been reported to exist in various functional states characterized by different cytokine secretion potentials, proliferation capabilities and the ability and potential to become long-term memory cells. The types of $CD8^+$ subpopulations and their functional states can vary kinetically in response to different pathogens and are dependent on the status of pathogen clearance. Characterizing the different $CD8^+$ T cell subpopulations and their underlying driving mechanisms is an active field of research contributing to our understanding of protective immunity in successful pathogen clearance, and of T cell regulation during uncontrolled tumor growth and chronic infections. Recent advances on this front have enabled the development of improved vaccines and novel immune-based therapies for various cancers. It is believed that the breadth of the functional potential of $CD8^+$ T cells is far from understood, and that gaining a deeper understanding will lead to further advancements.

During persistent immune activation, such as uncontrolled tumor growth or chronic viral infections, the ability of $CD8^+$ lymphocytes to secrete pro-inflammatory cytokines and elaborate cytotoxic function becomes compromised to different extents (Anderson et al., 2016, Immunity 44, 989-1004; Baitsch et al., 2012, Trends Immunol 33, 364-372; Kim and Ahmed, 2010, Curr Opin Immunol 22, 223-230; Wherry and Kurachi, 2015, Nature reviews Immunology 15, 486-499; Zuniga et al., 2015, Annu Rev Virol 2, 573-597). These $CD8^+$ populations are frequently referred to as "dysfunctional" or "exhausted", and are believed to constitute a barrier to successful anti-tumor and anti-viral immunity. Such dysfunctional or exhausted $CD8^+$ lymphocytes are typically compromised for their ex vivo cytokine secretion capabilities and are present in an environment in which there is persistent antigen. Gaining a clear molecular understanding of the dysfunctional T cell state can thus help develop successful therapeutic interventions.

Dysfunctional $CD8^+$ T cells can be both protective and detrimental against disease control. Attempts to manipulate pathways associated with T cell dysfunction have resulted in different biological consequences to the host. On one hand, blocking co-inhibitory pathways such as PD-1 and Tim3 that frequently coincide with T cell dysfunction has promoted T cell function and is particularly effective in promoting tumor regression in several types of cancer. On the other hand, the targeted deletion of PD-1 at disease onset causes immune pathology and death of the host in a chronic viral infection model, suggesting that T cell dysfunction may have evolved to prevent immunopathology (Barber et al., 2006, Nature, vol. 439, 682-687). Also, current therapies targeting co-inhibitory or immune checkpoint receptors such as CTLA-4 and PD-1 that are highly expressed on dysfunctional T cells are showing promise in the clinic. However, not all patients respond and some cancers remain largely refractory to these therapies. Furthermore, depletion of exhausted T cells by targeting known regulators such as Tbet and Eomes resulted in high viral load suggesting that dysfunctional T cells provide partially effective immune control (Paley et al., 2012, Science, vol. 338, 1220-1225). These findings highlight the complex roles of dysfunctional $CD8^+$ T cells during unsuccessful antigen clearance. The ability to delineate the diverse roles of dysfunctional $CD8^+$ T cells at the molecular level can help with more specific targeting of truly exhausted T cells while sparing those dysfunctional T cells that may be still protective.

$CD8^+$ T cell function is associated with their cytokine profiles. It has been reported that effector $CD8^+$ T cells with the ability to simultaneously produce multiple cytokines (polyfunctional $CD8^+$ T cells) are associated with protective immunity in patients with controlled chronic viral infections as well as cancer patients responsive to immune therapy (Spranger et al., 2014, J. Immunother. Cancer, vol. 2, 3). In the presence of persistent antigen $CD8^+$ T cells were found to have lost cytolytic activity completely over time (Moskophidis et al., 1993, Nature, vol. 362, 758-761). It was subsequently found that dysfunctional T cells can differentially produce IL-2, TNFa and IFNg in a hierarchical order (Wherry et al., 2003, J. Virol., vol. 77, 4911-4927). Recent studies also suggest that Tbet and Eomes regulate early and terminally exhausted T cells with distinct cytokine profiles (Paley et al., 2012, supra) and that these subpopulations coexist in both murine models and in humans with chronic infections over a long period of time (Buggert et al., 2014, PLoS Pathog., vol. 10, e1004251).

These findings show that even dysfunctional T cells can exist in various functional states. It is therefore likely that a plethora of different $CD8^+$ T cell dysfunctional states, regulated by multiple molecular pathways, is present across different diseases and during different stages of disease progression, distinctively contributing to immune control. Deciphering molecular pathways associated with the various cytokine profiles of dysfunctional $CD8^+$ T cells is crucial to gain a better understanding of the heterogeneity and function of the $CD8^+$ response during unsuccessful antigen clearance, and can greatly contribute to the design of targeted therapies.

Dysfunctional $CD8^+$ T cells from LCMV infected mice (Blackburn et al., 2009, Nature immunology 10, 29-37; Wherry et al., 2007, Immunity 27, 670-684) and cancer (Baitsch et al., 2011, J Clin Invest 121, 2350-2360; Fourcade et al., 2010, The Journal of experimental medicine 207, 2175-2186; Matsuzaki et al., 2010, Proceedings of the National Academy of Sciences of the United States of America 107, 7875-7880; Sakuishi et al., 2010, The Journal of experimental medicine 207, 2187-2194) differ profoundly from memory $CD8^+$ T cells, and co-express multiple co-inhibitory receptors such as PD-1, Lag-3, and Tim-3. Indeed, therapeutic targeting of co-inhibitory receptors with blocking antibodies has achieved great success in cancer patients. However, many patients still fail to respond and some cancers are refractory to these therapies (Restifo et al., 2016, Nat Rev Cancer 16, 121-126). Thus, to identify novel therapeutic targets and stratify patients, it is important to better understand the dysfunctional T cell state.

A major challenge to developing therapies that specifically target the dysfunctional $CD8^+$ T cell state is that current markers and transcriptional signatures of dysfunction are closely intertwined with the activated $CD8^+$ T cell state (Doering et al., 2012, Immunity 37, 1130-1144; Fuertes Marraco et al., 2015, Frontiers in immunology 6, 310; Tirosh et al., 2016, Science 352, 189-196). This is not surprising given that T cell dysfunction arises in the face of chronic T cell activation. Thus, both dysfunctional $CD8^+$ T cells and activated $CD8^+$ T cells up-regulate genes involved in activation of the cell cycle, T cell homing and migration, as well as effector molecules, such as granzymes and co-stimulatory and co-inhibitory receptors that mark T cells for subsequent regulation (Giordano et al., 2015, EMBO J 34, 2042-2058; Wherry et al., 2007, supra). Moreover, both cell types down-regulate memory cell gene signatures (Doering et al., 2012, supra; Wherry et al., 2007, supra). Indeed, T cell dysfunction likely evolved as a physiological process to balance T cell activation with self-regulation in the face of chronic antigen persistence, thereby limiting immunopathology. As a result, it has been challenging to identify markers and approaches that would specifically target the dysfunctional T cell state, while preserving the activated T cell state, as well as to identify bona fide dysfunctional T cells in vivo.

Consequently, there exists a continuous need to provide additional and preferably improved markers, products and methods allowing to determine the functional state of immune cells. Likewise, there exists a continuous need to provide additional and preferably improved molecular targets involved in immune responses, as well as therapeutically useful substances and compositions impinging on such molecular targets to modulate immune responses.

Citation or identification of any document in this application is not an admission that such document is available as prior art to the present invention.

SUMMARY OF THE INVENTION

The various aspects of the invention as disclosed in this specification are based, at least in part, on the novel discovery of useful markers, marker signatures and molecular targets associated with immune cell dysfunction and/or activation. More particularly, certain of the present markers, marker signatures and molecular targets correlate with the loss of effector function of the immune cells and are advantageously distinct, separate or uncoupled from, or independent of the immune cell activation status. Certain other of the present markers, marker signatures and molecular targets correlate with immune cell activation and are advantageously distinct, separate or uncoupled from, or independent of the immune cell dysfunction status.

Previously, obtaining molecular signatures for T cell dysfunction has been complicated by the fact that T cell dysfunction arises from chronic T cell activation, whereby molecular signatures of T cell dysfunction and activation are closely intertwined. Hence, co-inhibitory receptors that mark dysfunctional T cells are also up-regulated during T cell activation, where they function to contract the effector T cell population and restore immune homeostasis. Furthermore, dysfunctional $CD8^+$ T cells and activated $CD8^+$ T cells both up-regulate genes that regulate activation of the cell cycle, T cell homing and migration and effector molecules such as granzymes, and both down-regulate memory cell gene signatures (Wherry et al. 2007, supra; Doering et al. 2012, supra). Indeed, T cell "dysfunction" may have likely evolved as a physiological process to carefully balance T cell activation and self-regulation in the face of chronic antigen persistence, thereby limiting immunopathology and minimizing collateral damage to the host.

The present inventors devised an integrated experimental and computational approach to systematically dissect the molecular pathways associated with activation and "dysfunction" within $CD8^+$ tumor-infiltrating lymphocytes (TILs), allowing to uncouple molecular signatures for T cell dysfunction and activation. The present analysis identifies gene modules that are uniquely associated with the dysfunctional T cell state and activated T cell state, and key molecular nodes that control them. The present markers, marker signatures and molecular targets thus provide for new ways to evaluate and modulate immune responses, such as to specifically evaluate and target the dysfunctional T cell state while leaving T cell activation programs intact.

Accordingly, an aspect of the invention provides an isolated immune cell modified to comprise an altered expression or activity of GATA3 or FOXO1. Further aspects provide an isolated immune cell modified to comprise an altered expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory like module". A further aspect provides a cell population of said modified immune cells.

Another aspect relates to a method for generating said modified immune cell, the method comprising (i) providing an isolated immune cell, and (ii) modifying said isolated immune cell such as to comprise an altered expression or activity of GATA3 or FOXO1. Further aspects provide a method for generating said modified immune cell, the method comprising (i) providing an isolated immune cell, and (ii) modifying said isolated immune cell such as to comprise an altered expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

A further aspect of the invention provides an isolated immune cell modified to comprise an agent capable of inducibly altering expression or activity of GATA3 or FOXO1. Further aspects provide an isolated immune cell modified to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module". A further aspect provides a cell population of said modified immune cells.

Another aspect relates to a method for generating said modified immune cell, the method comprising (i) providing an isolated immune cell, and (ii) modifying said isolated immune cell such as to comprise an agent capable of inducibly altering expression or activity of GATA3 or FOXO1. Further aspects provide a method for generating said modified immune cell, the method comprising (i) providing an isolated immune cell, and (ii) modifying said isolated immune cell such as to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

Another aspect of the invention provides a pharmaceutical composition comprising the isolated immune cell or the cell population as defined above.

A further aspect of the invention relates to the isolated immune cell or the cell population as defined above for use in therapy.

Another aspect of the invention provides the isolated immune cell or the cell population as defined above for use in immunotherapy or adoptive immunotherapy.

A further aspect of the invention relates to a method of treating a subject in need thereof, comprising administering to said subject the isolated immune cell or the cell population as defined above.

Another aspect of the invention provides a method of treating a subject in need thereof, comprising: (a) providing an isolated immune cell from the subject, or isolating an immune cell from a subject; (b) modifying said isolated immune cell such as to comprise an altered expression or activity of GATA3 and/or FOXO1, or modifying said isolated immune cell such as to comprise an agent capable of inducibly altering expression or activity of GATA3 and/or FOXO1; and (c) reintroducing the modified isolated immune cell to the subject. Further aspects provide a method of treating a subject in need thereof, comprising: (a) providing an isolated immune cell from the subject, or isolating an immune cell from a subject; (b) modifying said isolated immune cell such as to comprise an altered expression or activity of, or modifying said isolated immune cell such as to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module"; and (c) reintroducing the modified isolated immune cell to the subject.

The method of treatment may be for a condition, disease or disorder where an enhanced immune respone is required, such as but not limited to a cancer, or a condition, disease or disorder where a decreased immune response is required, such as but not limited to an autoimmune disease. The immune cell may be modified, such that expression of a gene signature is altered. The immune cell may be modified by treatment with an agent specific for downregulating expression or activity of at least one gene of one gene signature. The immune cell may be modified by treatment with an agent specific for upregulating expression or activity in at least one gene of an opposing gene signature. A gene in the dysfunctional gene signature and a gene in the activation signature may be such modified. Not being bound by a theory, cancer may be treated by obtaining a dysfunctional T cell and treating with an agent that activates the cell. Not being bound by a theory, introducing dysfunctional cells to a subject with an autoimmune disease may be performed. Dysfunctional cells secrete suppressive cytokines that may suppress immune cells causing the autoimmunity. A gene, gene signature or immune cell may be modified ex vivo. A gene, gene signature or immune cell may be modified ex vivo. A gene, gene signature or immune cell may be modified in vivo. Not being bound by a theory, modifying immune cells in vivo, such that dysfunctional immune cells are decreased can provide a therapeutic effect by enhancing an immune response in a subject. A gene, gene signature or immune cell may be modified by a small molecule, a DNA targeting agent, or a therapeutic antibody or antibody fragment thereof. As described herein, a DNA targeting agent may be a CRISPR system.

In another aspect, a method of treatment may comprise treating a subject with an agent specific for, e.g., capable of suppressing or activating, a cell type as defined by any one gene signature as taught herein, e.g., any one of the gene signatures, or portions thereof, as set forth in Table 3, Table 5A or Table 5B. In certain embodiments, the agent is capable of suppressing an immune cell defined by any one of the gene signatures set forth in Table 3, Table 5A or Table 5B. In certain other embodiments, the agent is capable of activating an immune cell defined by any one of the gene signatures set forth in Table 3, Table 5A or Table 5B. In a preferred embodiment a dysfunctional T cell is targeted with an agent specific for a gene present only in the dysfunctional gene signature. In another embodiment an activated T cell is targeted with an agent specific for a gene present only in the activation gene signature. The gene may encode a surface protein. The agent may be a drug conjugated antibody. Not being bound by a theory, suppressing, such as by ablating dysfunctional T cells can increase cellular mediated toxicity of remaining T cells.

A further aspect of the invention relates to BTLA, NRP1, CD160, CD274, PTGER4, MT1 et al.) a method of detecting dysfunctional immune cells comprising detection of a gene expression signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14.

A related aspect relates to a method of detecting dysfunctional immune cells comprising detection of a gene expression signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14. A further aspect of the invention relates to a method of detecting dysfunctional immune cells comprising detection of a gene expression signature comprising one or more markers of dysfunction selected from the group consisting of NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, and BTLA. A related aspect provides a method of detecting dysfunctional immune cells comprising detection of a gene expression signature comprising one or more markers of dysfunction selected from the group consisting of the markers listed in Table 3, part "Dysfunction_module", Table 5A or Table 5B.

A further aspect of the invention relates to a method of detecting activated immune cells comprising detection of a gene expression signature comprising one or more markers of activation selected from the group consisting of TMCO1, PRMT5, EXOC4, TYR, HDHD2, RCN1, LMNB2, TCTEX1D2, VMA21, HCFC2, MRPS27, DUSP19, CD200R4, SRSF10, NAP1L4, ZADH2, ERGIC1, STARD3NL, RCC1, CD38, ZFP142, METTL10, MOGS, S100PBP, AREG, 1700052N19RIK, NDUFA13, RFT1, TAF12, ELP2, TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BCO26590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127 and KPNB1.

A further aspect of the invention relates to a method of detecting dysfunctional and/or activated immune cells comprising detection of a gene expression signature comprising one or more markers selected from the group consisting of SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, and TOPBP1.

A further aspect of the invention relates to a method of detecting naïve-memory-like immune cells comprising detection of a gene expression signature comprising one or more markers selected from the group consisting of GPR183, THA1, TREML2, ZNRF3, CDK2AP2, CREB3, RPS16, BLOC1S2A, ATP1B3, BLNK, RPS29, SHARPIN, TSC22D1, KLRA1, HSD11B1, RPS15, AKAP8L, PHC1, RPL31, S1PR1, GM5547, SRSF5, ACSS2, ADK, AMICA1, ATP1B1, CNP, SNHG8, FCRLA, H2-T23, RAB33B, TLR12, RPF1, SP140, SH3GL1, CTSL, RPGRIP1, 5430417L22RIK, CXXC5, RABGGTA, KCNJ8, DYM, FRAT1, SPIB, ADRB2, COX6A2, TMEM219, GPR18, CCPG1, PLCB2, CALM2, KYNU, CRLF3, IDNK, TNFRSF26, DNAJB9, TXNIP, UPB1, GM11346, PHF1, RPL18A, DNTT, HAAO, PIM2, RABAC1, APOPT1, BIN2, OXR1, GPR171, RASGRP2, SLC9A9, 5830411N06RIK, PIAS1, PYDC3, ZCCHC18, TCSTV3, KLRA7, NPC2, CD180, SMIM14, P2RY14, PDLIM1, MYLIP, PDE2A, PPIF, KLRA17, FBXO32, DIRC2, ELOVL6, PJA1, SP110, KLRA6, USP7, HCST, KLRA23, GAB3, TOM1, ACP5, PBLD1, SMPD5, EVI2A, KLF13, MFSD11, IFNGR1, POU6F1, USE1, HDAC4, SMIM5, MAF1, 1810034E14RIK, TSC22D3, GAS5, RPL21, RELL1, SERTAD2, BC147527, KMO, SKAP1, TCF4, SP100, RNF167, TMEM59, IRGM1, CD69, DNAJC7, PIK3IP1, TAZ, HAVCR1, LY6D, RPL23, DAPP1, FLT3, ITM2B, NUCB2, RPS14, GIMAP9, HBP1, MAN2A2, RNF122, SOCS3, CD7, PNCK, 2610019F03RIK, SLC27A1, BPTF, H2-Q9, KLHL6, RPL17, SEMA4B, LDLRAD4, TCEA2, GM14207, CIRBP, FAM189B, ZFP707, ATP10D, RNASET2A, ATP2A1, BST2, EYA2, IRF7, ITPR2, STK17B, CYBASC3, TRIM11, KLK1B27, ZMYND8, LEF1, RNASE6, EIF4A2, HS3ST1, NIPBL, STX4A, UGCG, CAMK1D, PPFIA4, UVRAG, CDKN2D, ZBTB21, LEFTY1, APBB1IP, GIMAP3, H13, RGS10, RNF138, RPL12, SLC7A6OS, FADS2, SELPLG, CXCR4, GPR146, ZFP386, BCL11A, TRIM34A, RPS7, TLR9, PACSIN1, PAIP1, PGAM2 and JAKMIP1.

A yet further aspect of the invention relates to a kit of parts comprising means for detection of the above signature of dysfunction. Also provided is a kit of parts comprising means for detection of the signature of dysfunction, activation, activation and/or dysfunction, or memory as taught herein.

Another aspect of the invention provides a method for determining whether or not an immune cell has a dysfunctional immune phenotype and/or whether or not an immune cell would benefit from upregulation of an immune response, said method comprising: (a) determining in said immune cell the expression of GATA3 and/or FOXO1, whereby expression of GATA3 and/or FOXO1 indicates that the immune cell has a dysfunctional immune phenotype and/or would benefit from upregulation of an immune response; or (b) determining in said immune cell the expression of the signature of dysfunction as defined herein, whereby expression of the signature indicates that the immune cell has a dysfunctional immune phenotype and/or would benefit from upregulation of an immune response.

Also provided is a method for determining whether or not an immune cell has an activation, activation and/or dysfunction or memory immune phenotype and/or whether or not an immune cell would benefit from modulation (e.g., down-regulation or upregulation) of an immune response, said method comprising: determining in said immune cell the expression of the signature of activation, activation and/or dysfunction, or memory, as defined herein, whereby expression of the signature indicates that the immune cell has respectively an activation, activation and/or dysfunction or memory immune phenotype and/or would benefit from modulation of an immune response.

A further aspect of the invention provides a method for determining whether or not a patient would benefit from a therapy aimed at reducing dysfunction of immune cells or a therapy aimed at upregulating of an immune response, the method comprising: (a) determining, in immune cells from said patient the expression of GATA3 and/or FOXO1, whereby expression of GATA3 and/or FOXO1 indicates that the patient will benefit from the therapy; or (b) determining, in immune cells from said patient the expression of the signature of dysfunction as defined above, whereby expression of the signature indicates the patient will benefit from the therapy.

Also provided is a method for determining whether or not a patient would benefit from a therapy aimed at modulating (e.g., reducing or increasing) activation, activation and/or dysfunction or memory phenotype of immune cells, or a therapy aimed at modulating (e.g., reducing or increasing) of an immune response, said method comprising determining, in immune cells from said patient the expression of the signature of activation, activation and/or dysfunction, or memory, as defined herein, whereby expression of the signature indicates that the patient will benefit from the therapy aimed at modulating respectively the activation, activation and/or dysfunction or memory phenotype of immune cells, or will benefit from the therapy aimed at modulating the immune response.

Another aspect of the invention relates to a method for determining the efficacy of a treatment of a patient with a therapy, said method comprising: (a) determining in immune cells from said patient the expression of GATA3 and/or FOXO1 before and after said treatment and determining the efficacy of said therapy based thereon, whereby unchanged or increased expression of GATA3 and/or FOXO1 indicates that the treatment should be adjusted; or (b) determining in immune cells from said patient the expression of the signature of dysfunction as defined above before and after said treatment and determining the efficacy of said therapy based thereon, whereby unchanged or increased expression of the signature indicates that the treatment should be adjusted.

Also provided is a method for determining the efficacy of a treatment of a patient with a therapy, said method comprising determining in immune cells from said patient the expression of the signature of activation, activation and/or dysfunction, or memory, as defined herein, before and after said treatment and determining the efficacy of said therapy based thereon, whereby unchanged or increased expression of the signature indicates that the treatment should be adjusted.

Another aspect of the invention provides a method for determining the suitability of a compound as a checkpoint inhibitor, said method comprising: (a) contacting an immune cell expressing GATA3 and/or FOXO1 with said compound and determining whether or not said compound can affect the expression of GATA3 and/or FOXO1 by said cell, whereby decreased expression indicates that the compound is suitable as a checkpoint inhibitor; or (b) contacting an immune cell expressing the signature of dysfunction as defined above with said compound and determining whether or not said compound can affect the expression of the signature by said cell, whereby decreased expression indicates that the compound is suitable as a checkpoint inhibitor.

Also provided is a method for determining the suitability of a compound as a checkpoint inhibitor, said method comprising contacting an immune cell expressing the signature of activation, activation and/or dysfunction, or memory, as defined herein, with said compound and determining whether or not said compound can affect the expression of the signature by said cell, whereby altered expression indicates that the compound is suitable as a checkpoint inhibitor (e.g., whereby increased expression of the signature of activation indicates that the compound is suitable as a checkpoint inhibitor).

A further aspect of the invention provides a method for determining the suitability of a compound for reducing an dysfunctional immune phenotype and/or upregulating of an immune response, said method comprising: (a) contacting an immune cell expressing GATA3 and/or FOXO1 with said compound and determining whether or not said compound can affect the expression of GATA3 and/or FOXO1 by said cell, whereby decreased expression indicates that the compound is suitable for reducing dysfunctional immune phenotype and/or upregulating of an immune response; or (b) contacting an immune cell expressing the signature of dysfunction as defined above with said compound and determining whether or not said compound can affect the expression of the signature by said cell, whereby decreased expression indicates that the compound is suitable for reducing dysfunctional immune phenotype and/or upregulating of an immune response.

Also provided is a method for determining the suitability of a compound for modulating (e.g., reducing or increasing) activation, activation and/or dysfunction or memory phenotype of immune cells, and/or modulating (e.g., reducing or increasing) of an immune response, said method comprising contacting an immune cell expressing the signature of activation, activation and/or dysfunction, or memory, as defined herein, with said compound and determining whether or not said compound can affect the expression of the signature by said cell, whereby altered expression indicates that the compound is suitable for modulating respectively the activation, activation and/or dysfunction or memory phenotype of immune cells, and/or modulating of the immune response.

A yet another aspect of the invention provides a method for stratification of immune cells into one or more cell populations comprising at least a first cell population having a comparatively more dysfunctional immune phenotype and a second population having a comparatively less dysfunctional immune phenotype, comprising: (a) determining in said immune cells the expression of GATA3 and/or FOXO1, and allotting cells having no or comparatively lower expression of GATA3 and/or FOXO1 into said second population, and cells having comparatively higher expression of GATA3 and/or FOXO1 into said first population; or (b) determining in said immune cells the expression of the signature of dysfunction as defined above, and allotting cells having no or comparatively lower expression of said signature into said second population, and cells having comparatively higher expression of said signature into said first population.

Also provided is a method for stratification of immune cells into one or more cell populations comprising at least a first cell population having a comparatively more activation, activation and/or dysfunction or memory phenotype and a second population having a comparatively less activation, activation and/or dysfunction or memory phenotype, said method comprising determining in said immune cells the expression of the signature of activation, activation and/or dysfunction, or memory, as defined herein, and allotting cells having no or comparatively lower expression of said signature into said second population, and cells having comparatively higher expression of said signature into said first population.

Also provided is a method for stratification of immune cells into one or more cell populations comprising at least a first cell population having a comparatively more activation, activation and/or dysfunction or memory phenotype and a second population having a comparatively less activation, activation and/or dysfunction or memory phenotype, said method comprising determining in said immune cells the expression of the signature of activation, activation and/or dysfunction, or memory, as defined herein, and allotting cells having no or comparatively lower expression of said signature into said second population, and cells having comparatively higher expression of said signature into said first population.

A yet another aspect provides a method of isolating an immune cell as taught herein comprising binding of an affinity ligand to a signature gene expressed on the surface of the immune cell.

A further aspect provides a method of treating a subject in need thereof, comprising administering to said subject an agent capable of modulating the immune cell as taught herein.

A further aspect provides a method of treatment comprising administering one or more checkpoint inhibitors to a patient in need thereof, wherein immune cells obtained from the patient have a gene signature as taught herein, such as the gene signature of dysfunction as taught herein.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1A outlines the experimental setup for obtaining Tim3$^+$ PD-1$^+$ (DP), Tim3$^-$ PD-1$^+$ (SP), and Tim3$^-$PD-1$^-$ (DN) TIL cell populations. FIG. 1B illustrates that differentially expressed genes across the Tim-3/PD-1 defined subpopulations define a dysfunctional signature in CD8$^+$ TILs, and presents a heatmap of the 3031 genes determined as differentially expressed across the TILs subpopulations (Näive: CD8$^+$ CD62L$^{hi}$CD44$^{low}$ cells from spleens of non-tumor-bearing Balb/c mice, EffMem: Effector memory CD8$^+$ CD62L$^{low}$CD44$^{hi}$ cells extracted from non-tumor bearing Balb/c mice, DN: CD8$^+$Tim3$^-$PD-1$^-$, SP: CD8$^+$Tim3$^-$PD-1$^+$, DP: CD8$^+$Tim3$^+$PD-1$^+$ TILs). FIG. 1C illustrates clustering of the genes differentially expressed across the TILs subpopulations, and in conjunction with Table 1 demonstrates that dysfunctional CD8$^+$ TILs are enriched for CD8 effector-like and cell cycle features. FIG. 1D provides an enlarged representation of cluster C2 of FIG. 1C, which in the present experiments appeared to best represent a CD8$^+$ dysfunctional signature. FIG. 1E illustrates that TILs' cluster C2 is associated with both activation and exhaustion signatures, y-axis is −log 10(p-value enrichment) for genes upregulated in signature (values plotted in red) and +log 10(p-value enrichment) for genes downregulated in signature (values plotted in blue). Cluster C2 is significant for enrichment with genes upregulated in both CD8$^+$ activation and viral exhaustion, and cluster C3 is enriched for genes downregulated during CD8$^+$ activation. Upper panel: enrichments for CD8$^+$ activation (data from Doering et al., 2012, Immunity, vol. 37(6), 1130-44 2012; day 15 acute vs. naïve); lower panel: enrichments for CD8$^+$ LCMV exhaustion (data from Doering et al., 2012, supra; day 15 chronic vs. day 15 acute). FIG. 1F illustrates that Cluster 2 is significantly enriched with genes up-regulated in a CD8$^+$ viral exhaustion signature (Doering et al., 2012, supra) as well as an in vivo CD8$^+$ activation signature (Sarkar et al., 2008, supra). p-values determined by hypergeometric test. Dashed line marks p=0.05 significance threshold. FIG. 1G compares with previous activation signatures. FIG. 1H compares with previous exhaustion signatures. FIG. 1I illustrates heatmap of the top ranking genes from cluster C2. FIG. 1J illustrates expression of co-inhibitory and co-stimulatory receptors in CD8$^+$ TILs populations. Shown are genes from pre-determined co-inhibitory and co-stimulatory lists, that were upregulated in the DP subpopulation.

FIG. 2A-2D illustrates experimental results related to metallothionein and zinc metabolism. FIG. 2A illustrates the expression of MT1 and MT2 as determined by qPCR in sorted CD8 TILs isolated from mice bearing CT26 colon carcinoma and B16 melanoma tumors. FIG. 2B illustrates that 158 zinc related genes were in the present DE (differentially expressed) set, and a significant proportion of the downregulated genes were zinc associated. FIG. 2C illustrates that dysregulation of Zinc metabolism was reflected also at the level of increasing of free Zn in $Tim3^+PD-1^+$ of $CD8^+$ but not $CD4^+$ TIL or DLN. FIG. 2D shows availability of intracellular zinc in $CD8^+$ TILs populations. WT and MT-/- TILs were stained with Zinpyr-1 for measuring free Zn followed by cell surface staining and analyzed by flow cytometry.

FIG. 3A-3I illustrate that metallothionein deficiency improves tumor control and reverses $CD8^+$ T cell dysfunction. FIG. 3A, mice deficient in both MT1 and MT2 (i.e., $MT^{-/-}$ mice) and wild type (WT) littermate controls were implanted subcutaneously with B16F10 melanoma, plot shows mean tumor growth. FIG. 3B, tumor draining lymph node (dLN, upper panel) and tumor-infiltrating lymphocytes (TIL, lower panel) were isolated from WT and $MT^{-/-}$ mice 15 days post tumor inoculation and stimulated with tumor antigen gp100 or irrelevant peptide in vitro. On day 3, tumor antigen-specific proliferation was measured by $^3H$ incorporation. FIG. 3C, recipients of $MT^{-/-}$ pmel $CD8^+$ T cells show slower tumor growth compared to those transferred with wild type pmel $CD8^+$ T cells. FIG. 3D, naïve OT-1 cells were sorted, activated, and infected with empty retrovirus (ctl OT1) or MT1 retrovirus (MTOE OT1) prior to transfer into WT mice that were subsequently implanted with MC38-OVA tumor. Mean tumor growth is shown. FIGS. 3E-G and 3I, TIL were isolated and stimulated with PMA/ionomyicin in the presence of brefeldin A for 4 hours prior to extracellular and intracellular staining and analysis by flow cytometry. FIG. 3H, reduced zinc level in DP TILs in $MT^{-/-}$ as compared to WT. FIG. 3I, Granzyme expression in WT and $MT^{-/-}$ $CD8^+$ TILs.

FIG. 4A outlines the experimental setup for transcriptional profiling of $MT^{-/-}$ $CD8^+$ TILs. FIG. 4B illustrates unbiased PCA analysis of WT and $MT^{-/-}$ DN, SP, and DP TILs populations. FIG. 4C illustrates bar plots showing the mean of values of each of DN, SP, and DP subpopulation from WT and $MT^{-/-}$ for PC1 (first panel) and PC2 (second panel) separately. Error bars are the standard error of the mean estimator. P-values for significance are computed using standard t-test. (*) p-value <0.05 (**) p-value <0.01. FIG. 4D illustrates that genes differentially expressed between the WT DN and DP populations and between the WT DP and MT-/- DP populations were split into four groups based on their expression trend. Groups I and II show a trend of further increased or decreased expression, respectively. Groups III and IV show reversal of expression. FIG. 4E illustrates overlay of naïve and in vitro activated $CD8^+$ T cell transcriptomes on PC1 and PC2, which supports association of PC1, but not PC2, with $CD8^+$ activation. FIG. 4F illustrates that correlations of PC1 and PC2 values with various signatures show a strong association of PC1 with activation signatures, previously annotated signatures of exhaustion, and our cluster 2 gene signature and of PC2 with genes showing a reversal of expression in WT and $MT^{-/-}$ TILs (Groups III and IV from D).

FIG. 5A-5I illustrate identification of gene modules associated with T cell activation and dysfunction, leading up to a novel signature which decouples dysfunction from activation of CD8 TILs. FIG. 5A illustrates the distribution of genes by their dysfunction and activation scores, which reveals genes associated to different extents with the dysfunction and/or activation transcriptional programs, i.e., each gene's placement in the "Activation-Dysfunction space". Each gene is projected onto both diagonal axes to determine a score of its association with the two modules each axis represents (lower panel). FIG. 5B illustrates placement of known co-inhibitory and co-stimulatory receptors in the "Activation-Dysfunction space". The majority of co-inhibitory receptors (blue) and co-stimulatory receptors (red) are associated with both activation and dysfunction, as previously reported in the literature. FIG. 5C illustrates placement of CD8 activation signature genes in the "Activation-Dysfunction space". FIG. 5D illustrates the placement of genes reported as constituting the viral LCMV exhaustion signature (Doering et al. 2012, supra) in the "Activation-Dysfunction space". FIG. 5E illustrates enrichments of different signatures for the different modules of the dysfunction/activation plot (Sarkar 2008: Sarkar et al. 2008, J Exp Med, vol. 205(3), 625-40). Dashed line marks p=0.05 significance threshold. FIG. 5F illustrates genes from an exhaustion and activation signature defined in a human melanoma study (Tirosh et al., 2016, Science 352, 189-196) separate on the Dysfunction<—>Activation axis Applicants have defined (as shown in A). Shown is the distribution of genes on the Dysfunction/Activation plot (top) and the Kolmogorov-Smirnov plot of the values of the human signatures on the Dysfunction<—>Activation axis (Axis 1-2 in (A)) (Kolmogorov-Smirnoff test p-value=0.027). ( ) FIG. 5G illustrates the distribution of genes by their dysfunction and activation scores, highlighting the position of Gata3, a zinc-binding TF, and Top 5 transcription factors (TFs) for each module from the set of differentially expressed TFs in the original dysfunctional signature (upper panel); a heatmap of the ranking for the marked TFs in each of the four modules (lower panel). FIG. 5H illustrates that NRP1 receptor was highly expressed in PD-$1^+$Tim$3^+$ CD8 TILs.

FIG. 6A-6I illustrate further experimental corroboration of the involvement of Gata3 in regulating CD8 T cell dysfunction in cancer. FIG. 6A-C, WT mice were implanted subcutaneously with B16F10 melanoma cells. TILs were isolated on day 15 post tumor cell injection and analyzed for Gata3 expression and T cell function. A, representative flow cytometry data showing Gata3 expression gated on $CD8^+$ TIL, B, Foxp3 expression by Gata3$^+$ $CD8^+$ T cells, C, cytokine expression of Gata3$^+$ and Gata3$^-$ $CD8^+$ TIL. FIG. 6D, schematics of experimental setup. FIG. 6E, F, I, TIL were isolated on day 21 after tumor cell injection and analyzed for surface molecule expression and function by flow cytometry. FIG. 6G, $1 \times 10^6$ CRISPR/Cas9-targeted cells (Gata3$^{-/-}$) were transferred to WT mice (n=5/group) bearing B16F10 melanoma tumors (day 5 post tumor grafting). Mean tumor growth is shown. Data are representative of 3 independent experiments. Statistical analysis was performed using linear regression. **p-value <0.01. FIG. 6H, targeted deletion of Gata3 using crispr/cas9 genome editing. Naïve $CD8^+$ T cells were sorted from PMEL transgenic mice, infected with control or Gata3 LV and activated with plate-bound anti-CD3 and anti-CD28 antibodies in the presence of IL-2 (Experimental procedures). Representative qPCR results showing Gata3 mRNA level in control versus Gata3 LV targeted CD8 T cells.

FIG. 11A, Expression of the dysfunction module at the single-cell level is negatively correlated with expression of the activation module (left, r=−0.42) and of an in vivo CD8+ activation signature (Sarkar et al., 2008, supra) (right, r=−0.47). FIG. 11B, Expression of an in vivo CD8+ activation signature at the single-cell level is positively correlated with expression of the activation module (r=0.57), the activation/dysfunction module (r=0.79), a viral LCMV exhaustion signature (r=0.85) and the cluster 2 genes (FIG. 1B) (r=0.68). FIG. 11C,D,E, A tSNE visualization (van der Maaten and Hinton, 2008) of the 1061 single-cells analyzed, colored by (C) the partitioning into 7 clusters (infomap), (G) gene signatures of the four gene modules defined (by quantile), and (E) mouse type (WT or MT−/−) FIG. 11F, Association of different gene signatures with the single-cell clusters (XL-mHG test, threshold at top 30% of list). Dashed line marks p=0.05 significance threshold. FIG. 11G, Counts of cells from WT/MT−/− in the different clusters. Clusters significantly enriched for presence of WT (blue) or MT−/− cells (red) are marked. *p-value <0.05, p-value <0.01, * p-value <0.001 (hypergeometric test).

DETAILED DESCRIPTION OF THE INVENTION

Figure 1A:
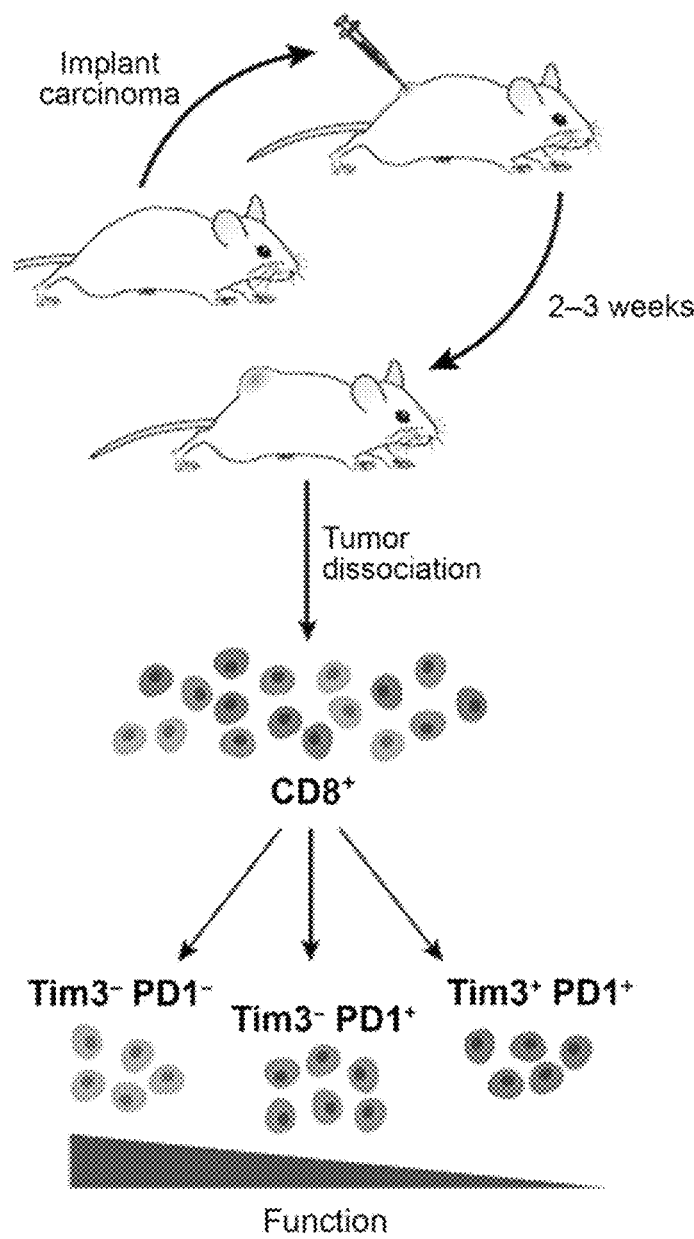
FIG. 1A-1J illustrate experimental results related to determination of a signature of CD8$^+$ T cell exhaustion in cancer.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

As used herein, the singular forms "a", "an", and "the" include both singular and plural referents unless the context clearly dictates otherwise.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The term "optional" or "optionally" means that the subsequent described event, circumstance or substituent may or may not occur, and that the description includes instances where the event or circumstance occurs and instances where it does not.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The present invention relates generally to novel markers, marker signatures and molecular targets useful for evaluating and modulating immune responses.

The term "gene expression signature" refers to a panel of genes whose expression correlates with a specific phenotype. According to certain aspects of the present invention, "high" expression of GATA3 and/or FOXO1 correlates with an immune cell that has a dysfunctional phenotype. Additionally, high expression of GATA3 and/or FOXO1 and any of POU2AF1, BTLA, NRP1, PD1, CTLA4, TIGIT, TIM3, LAG3, or KLRC1 correlates with an immune cell that has a dysfunctional phenotype. The gene expression signature may also be used to determine cells with a phenotype that does not correlate with an immune cell that has a dysfunctional phenotype.

A gene expression signature may be determined by any method known in the art. Gene expression can be determined by sequencing, preferably RNA-seq, quantitative reverse transcription PCR, western blot, ELISA, immunofluorescence, FACS, or microarray.

The term "low" as used herein generally means lower by a statically significant amount; for the avoidance of doubt, "low" means a statistically significant value at least 10% lower than a reference level, for example a value at least 20% lower than a reference level, at least 30% lower than a reference level, at least 40% lower than a reference level, at least 50% lower than a reference level, at least 60% lower than a reference level, at least 70% lower than a reference level, at least 80% lower than a reference level, at least 90% lower than a reference level, up to and including 100% lower than a reference level (i.e. absent level as compared to a reference sample).

The term "high" as used herein generally means a higher by a statically significant amount relative to a reference; for the avoidance of doubt, "high" means a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, at least 2-fold higher, at least 3-fold higher, at least 4-fold higher, at least 5-fold higher, at least 10-fold higher or more, as compared to a reference level.

The term "statistically significant" or "significantly" refers to statistical significance and generally means a two standard deviation below normal, or lower, concentration of the marker. The term refers to statistical evidence that there is a difference. It is defined as the probability of making a decision to reject the null hypothesis when the null hypothesis is actually true. The decision is often made using the p-value.

As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub)populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (being it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of immune cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10 or more. In certain embodiments, the signature may comprise or consist of two or more genes and/or proteins, such as for instance 2, 3, 4, 5, 6, 7, 8, 9, 10 or more. In certain embodiments, the signature may comprise or consist of three or more genes and/or proteins, such as for instance 3, 4, 5, 6, 7, 8, 9, 10 or more. In certain embodiments, the signature may comprise or consist of four or more genes and/or proteins, such as for instance 4, 5, 6, 7, 8, 9, 10 or more. In certain embodiments, the signature may comprise or consist of five or more genes and/or proteins, such as for instance 5, 6, 7, 8, 9, 10 or more. In certain embodiments, the signature may comprise or consist of six or more genes and/or proteins, such as for instance 6, 7, 8, 9, 10 or more. In certain embodiments, the signature may comprise or consist of seven or more genes and/or proteins, such as for instance 7, 8, 9, 10 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10 or more. In certain embodiments, the signature may comprise or consist of ten or more genes and/or proteins, such as for instance 10, 11, 12, 13, 14, 15, or more. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level, or may be differentially expressed on a cell population level.

Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least two, at least three, at least four, at least five, at least six, or all genes/proteins of the signature.

Signatures may be functionally validated as being uniquely associated with a particular immune phenotype. Induction or suppression of a particular signature may consequentially be associated with or causally drive a particular immune phenotype.

Various aspects and embodiments of the invention may involve analyzing gene signatures, protein signature, and/or other genetic signature based on single cell analyses (e.g. single cell RNA sequencing) or alternatively based on cell population analyses, as is defined herein elsewhere.

In further aspects, the invention relates to gene signatures, protein signature, and/or other genetic signature of particular immune cell subpopulations, as defined herein. The invention hereto also further relates to particular immune cell subpopulations, which may be identified based on the methods according to the invention as discussed herein; as well as methods to obtain such cell (sub)populations and screening methods to identify agents capable of inducing or suppressing particular immune cell (sub)populations.

The invention further relates to various uses of the gene signatures, protein signature, and/or other genetic signature as defined herein, as well as various uses of the immune cells or immune cell (sub)populations as defined herein. Particular advantageous uses include methods for identifying agents capable of inducing or suppressing particular immune cell (sub)populations based on the gene signatures, protein signature, and/or other genetic as defined herein. The invention further relates to agents capable of inducing or suppressing particular immune cell (sub)populations based on the gene signatures, protein signature, and/or other genetic signature as defined herein, as well as their use for modulating, such as inducing or repressing, a particular gene signature, protein signature, and/or other genetic signature. In related aspects, modulating, such as inducing or repressing, a particular gene signature, protein signature, and/or other genetic signature may modify overall immune cells composition, such as activated or dysfunctional immune cell composition, or distribution, or functionality.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. Not being bound by a theory, the signature genes can be used to deconvolute the cells present in a tumor based on comparing them to data from bulk analysis of a tumor sample. The signature gene may indicate the presence of one particular cell type. In one embodiment, the signature genes may indicate that dysfunctional or activated tumor infiltrating T-cells are present. The presence of cell types within a tumor may indicate that the tumor will be resistant to a treatment. In one embodiment the signature genes of the present invention are applied to bulk sequencing data from a tumor sample to transform the data into information relating to disease outcome and personalized treatments. In one embodiment, the novel signature genes are used to detect multiple cell states that occur in a subpopulation of tumor cells that are linked to resistance to targeted therapies and progressive tumor growth. In preferred embodiments, immune cell states of tumor infiltrating lymphocytes are detected.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS), in an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as $CD28^+$, $CD4^+$, CDC, $CD45RA^+$, and $CD45RO^+$ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of $CD8^+$ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

Further, monocyte populations (i.e., $CD14^+$ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific 'I' cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation And Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-WIC tetramers (Altman, et al., *Science*. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-WIC tetramers can be generated using techniques known in the art and can be made with any WIC molecule of interest and any antigen of interest as described herein. Specific epitopes to be used in this context can be identified using numerous assays known in the art. For example, the ability of a polypeptide to bind to WIC class I may be evaluated indirectly by monitoring the ability to promote incorporation of $^{125}$I labeled β2-microglobulin ((32m) into WIC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one I cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.) FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, 1 cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In one embodiment, the signature genes are detected by immunofluorescence, mass cytometry (CyTOF), FACS, drop-seq, RNA-seq, single cell qPCR, MERFISH (multiplex (in situ) RNA FISH), microarray and/or by in situ hybridization. Other methods including absorbance assays and colorimetric assays are known in the art and may be used herein. In some aspects, measuring expression of signature genes comprises measuring protein expression levels. Protein expression levels may be measured, for example, by performing a Western blot, an ELISA or binding to an antibody array. In another aspect, measuring expression of said genes comprises measuring RNA expression levels. RNA expression levels may be measured by performing RT-PCR, Northern blot, an array hybridization, or RNA sequencing methods.

An enzyme-linked immunosorbent assay, or ELISA, may be used to measure the differential expression of a plurality of signature genes. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

Detection of signature genes may be by FACS. The term "fluorescent activated cell sorting" or "FACS", as used herein, refers to a technique for counting, examining, and sorting microscopic particles suspended in a stream of fluid. It allows simultaneous multiparametric analysis of the physical and/or chemical characteristics of single cells flowing through an optical and/or electronic detection apparatus. Generally, a beam of light (usually laser light) of a single wavelength is directed onto a hydro-dynamically focused stream of fluid. A number of detectors are aimed at the point where the stream passes through the light beam; one in line with the light beam (Forward Scatter, correlates to cell volume) and several perpendicular to the beam, (Side Scatter, correlates to the inner complexity of the particle and/or surface roughness) and one or more fluorescent detectors. Each suspended particle passing through the beam scatters the light in some way, and fluorescent chemicals found in the particle or attached to the particle may be excited into emitting light at a lower frequency than the light source. By analyzing the combinations of scattered and fluorescent light picked up by the detectors it is then possible to derive information about the physical and chemical structure of each individual particle.

Detection of signature genes may involve a cell sorting step to enrich for cells of interest and thus facilitate or enhance their sensitive and specific detection. Cell sorting techniques are commonly based on tagging the cell with antibody against the cell membrane antigen specific to the target subpopulation of cells. The antibody is conjugated to a magnetic bead and/or fluorophore or other label to enable cell sorting and detection. Such methods may include affinity chromatography, particle magnetic separation, centrifugation, or filtration, and flow cytometry (including fluorescence activated cell sorting; FACS). Approaches based on antibody-coated microbeads can use magnetic fields (Racila et at, 1998), column chromatography, centrifugation, filtration or FACS to achieve separation.

Cells may be sequenced by any method known in the art for determining a gene signature. Methods of preparing cDNA is known in the art. Single cells may be sequenced for detection of a gene signature. Single cells of the present invention may be divided into single droplets using a microfluidic device. The single cells in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; Zheng, et al., 2016, "Haplotyping germline and cancer genomes with high-throughput linked-read sequencing" Nature Biotechnology 34, 303-311; and International patent publication number WO 2014210353 A2, all the contents and disclosure of each of which are herein incorporated by reference in their entirety.

In accordance with the present invention, model cellular systems using cell lines, primary cells, or tissue samples may be maintained in growth medium and may be treated with compounds that may be at a single concentration or at a range of concentrations. At specific times after treatment, cellular RNAs may be isolated from the treated cells, primary cells or tumors, which RNAs are indicative of expression of selected genes from a signature described herein. The cellular RNA is analyzed for the presence and/or quantity of specific RNA transcripts. Transcripts may be amplified for detection purposes using standard methodologies, such as, for example, reverse transcriptase polymerase chain reaction (RT-PCR), etc. The presence or absence, or levels, of specific RNA transcripts are determined from these measurements and a metric derived for the type and degree of response of the sample to the treated compound compared to control samples. Also in accordance with the present invention, there are disclosed herein characteristic, or signature, sets of genes and gene sequences whose expression is, or can be, as a result of the methods of the present invention, linked to, or used to characterize, the dysfunction, activation or immune state of the immune cells of the present invention. Thus, the methods of the present invention identify novel immunotherapeutic agents based on their alteration of expression of small sets of characteristic, or indicator, or signature genes in specific model systems. The methods of the invention may therefore be used with a variety of cell lines or with primary samples from tumors maintained in vitro under suitable culture conditions for varying periods of time, or in situ in suitable animal models. In preferred embodiments, tumor infiltrating lymphocytes (TILs) are screened.

More particularly, certain genes have been identified that are differentially expressed in dysfunctional or activated T cells. In one instance, the identified genes are expressed at higher levels in dysfunctional T cells than in activated T cells, and vice versa.

Aspects of the invention relate to an isolated immune cell modified to comprise an altered expression or activity of GATA3 or FOXO1, and to a population of such immune cells. Further aspects relate to an isolated immune cell modified to comprise an agent capable of inducibly altering expression or activity of GATA3 or FOXO1, and to a population of such immune cells.

The Applicants have demonstrated that altering the expression or activity of GATA3 or FOXO1, or both GATA3 and FOXO1, in an immune cell allows modulation of at least one function of the immune cell. Without limitation, altering the expression or activity of GATA3 or FOXO1, or both GATA3 and FOXO1, may allow modulation of the immune cell's proliferation (e.g., in response to a cytokine, such as IFN-gamma) or cell division, entrance into the cell cycle, differentiation, cytokine production, cytotoxicity, migration and trafficking, phagocytotic activity, or any combination thereof.

Further aspects relate to an isolated immune cell modified to comprise an altered expression of, or modified to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module", and to a population of such immune cells.

As used herein, the term "modulation of at least one function of the immune cell" includes the modulation of any of a variety of T cell-related functions and/or activities, including by way of non-limiting example, controlling or otherwise influencing the networks that regulate T cell differentiation; controlling or otherwise influencing the networks that regulate T cell maintenance, for example, over the lifespan of a T cell; controlling or otherwise influencing the networks that regulate T cell function; controlling or otherwise influencing the networks that regulate helper T cell (Th cell) differentiation; controlling or otherwise influencing the networks that regulate Th cell maintenance, for example, over the lifespan of a Th cell; controlling or otherwise influencing the networks that regulate Th cell function; controlling or otherwise influencing the networks that regulate Th17 cell differentiation; controlling or otherwise influencing the networks that regulate Th17 cell maintenance, for example, over the lifespan of a Th17 cell; controlling or otherwise influencing the networks that regulate Th17 cell function; controlling or otherwise influencing the networks that regulate regulatory T cell (Treg) differentiation; controlling or otherwise influencing the networks that regulate Treg cell maintenance, for example, over the lifespan of a Treg cell; controlling or otherwise influencing the networks that regulate Treg cell function; controlling or otherwise influencing the networks that regulate other $CD4^+$ T cell differentiation; controlling or otherwise influencing the networks that regulate other $CD4^+$ T cell maintenance; controlling or otherwise influencing the networks that regulate other $CD4^+$ T cell function; controlling or otherwise influencing the networks that regulate other $CD8^+$ T cell differentiation; controlling or otherwise influencing the networks that regulate other $CD8^+$ T cell maintenance; or controlling or otherwise influencing the networks that regulate other $CD8^+$ T cell function.

The term "isolated" with reference to a particular component generally denotes that such component exists in separation from—for example, has been separated from or prepared and/or maintained in separation from—one or more other components of its natural environment. More particularly, the term "isolated" as used herein in relation to a cell or cell population denotes that such cell or cell population does not form part of an animal or human body.

The term "immune cell" as used herein generally encompasses any cell derived from a hematopoietic stem cell that plays a role in the immune response. Immune cells include, without limitation, lymphocytes, such as T cells and B cells, antigen-presenting cells (APC), dendritic cells, monocytes, macrophages, natural killer (NK) cells, mast cells, basophils, eosinophils, or neutrophils, as well as any progenitors of such cells. In certain preferred embodiments, the immune cell may be a T cell. As used herein, the term "T cell" (i.e., T lymphocyte) is intended to include all cells within the T cell lineage, including thymocytes, immature T cells, mature T cells and the like. The term "T cell" may include $CD4^+$ and/or $CD8^+$ T cells, T helper ($T_h$) cells, e.g., $T_h1$, $T_h2$ and $T_h17$ cells, and T regulatory ($T_{reg}$) cells.

In certain more preferred embodiments, the immune cell is a $CD8^+$ T cell, also known as cytotoxic T cell or $T_C$. A $CD8^+$ T cell is a T cell expressing the CD8 cell surface marker, and recognizes antigens in the context of MHC class I presentation. $CD8^+$ T cells have cytotoxic activity and proliferate in response to IFN-gamma and other cytokines. Engagement of $CD8^+$ T-cell to the TCR receptor of a $CD8^+$ T-cell antigen presented by Class I MHC molecules and co-stimulating molecules lead to cytotoxic activity, proliferation and/or cytokine production.

The term "modified" as used herein broadly denotes that an immune cell has been subjected to or manipulated by a man-made process, such as a man-made molecular- or cell biology process, resulting in the modification of at least one characteristic of the immune cell. Such man-made process may for example be performed in vitro or ex vivo.

The term "altered expression" denotes that the modification of the immune cell alters, i.e., changes or modulates, the expression of the recited gene(s) or polypeptides(s). The term "altered expression" encompasses any direction and any extent of said alteration. Hence, "altered expression" may reflect qualitative and/or quantitative change(s) of expression, and specifically encompasses both increase (e.g., activation or stimulation) or decrease (e.g., inhibition) of expression.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least t 50%, or least 60%, or least 70%, or least 80%, at least 90% or more, up to and including a 100% decrease (i.e., absent level as compared to a reference sample), or any decrease between 10-100% as compared to a reference level, as that term is defined herein. The term "abolish" or "abolished" may in particular refer to a decrease by 100%, i.e., absent level as compared to a reference sample.

The modification may produce an immune cell comprising altered expression or activity of GATA3 or FOXO1 or of the one or more genes or gene products as taught herein; or the modification may produce an immune cell which does not comprise altered expression or activity of GATA3 or FOXO1 or of the one or more genes or gene products as taught herein, but which has acquired the ability to exhibit altered expression or activity of GATA3 or FOXO1 or of the one or more genes or gene products as taught herein in response to an external signal. The latter cell has thus been modified to comprise an agent capable of inducibly (i.e., in response to a signal, more particularly to an external signal, such as to an external chemical, biological and/or physical signal) altering expression or activity of GATA3 or FOXO1 or of the one or more genes or gene products as taught herein.

Hence, in certain embodiments, the modification may comprise exposing the immune cell to an agent or contacting the immune cell with an agent or introducing into the immune cell an agent capable of altering the expression or activity of GATA3 or FOXO1 or of the one or more genes or gene products as taught herein, whereby the expression or activity of GATA3 or FOXO1 or of the one or more genes or gene products as taught herein in the immune cell is altered. In certain embodiments, the agent or one or more elements thereof may be under inducible control. For example, the expression of the agent or one or more elements thereof by the immune cell and/or the activity of the agent or one or more elements thereof in the cell may be under inducible control. The immune cell thereby acquires the ability to exhibit altered expression or activity of GATA3 or FOXO1 or of the one or more genes or gene products as taught herein in response to an external signal configured to modulate the agent or one or more elements thereof, such as the expression and/or the activity of the agent or one or more elements thereof.

Any one or more of the several successive molecular mechanisms involved in the expression of a given gene or polypeptide may be targeted by the immune cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localisation of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalised polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell.

Hence, "altered expression" may particularly denote altered production of the recited gene products by the modified immune cell. As used herein, the term "gene product(s)" includes RNA transcribed from a gene (e.g., mRNA), or a polypeptide encoded by a gene or translated from RNA.

Also, "altered expression" as intended herein may encompass modulating the activity of GATA3 and/or FOXO1 and/or of the one or more genes or gene products as taught herein. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, e.g., GATA3 and/or FOXO1 and/or the one or more genes or gene products as taught herein, or alternatively increasing the activity of the target or antigen, e.g., GATA3 and/or FOXO1 and/or the one or more genes or gene products as taught herein, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, e.g., GATA3 and/or FOXO1 and/or the one or more genes or gene products as taught herein, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve effecting a change (which can either be an increase or a decrease) in affinity, avidity, specificity and/or selectivity of a target or antigen, e.g., GATA3 and/or FOXO1 and/or the one or more genes or gene products as taught herein, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

The term "agent" as used herein generally refers to any substance or composition, such as a chemical entity or biological product, or combination of chemical entities or biological products, capable of achieving a desired effect in a system, more particularly in a biological system, e.g., in a cell, tissue, organ, or an organism. In the present context, an agent may be exposed to, contacted with or introduced into an immune cell to modify at least one characteristic of the immune cell, such as to (inducibly) alter the expression or activity of GATA3 or FOXO1 or of the one or more genes or gene products as taught herein by the immune cell. Further in the present context, an agent may be administered to a subject to treat or prevent or control a disease or condition, for example by (inducibly) altering the expression or activity of GATA3 or FOXO1 or of the one or more genes or gene products as taught herein by immune cells of the subject.

The chemical entity or biological product is preferably, but not necessarily a low molecular weight compound, but may also be a larger compound, or any organic or inorganic molecule effective in the given situation, including modified and unmodified nucleic acids such as antisense nucleic acids, RNAi, such as siRNA or shRNA, CRISPR-Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments the agent is a small molecule having a chemical moiety. Agents can be known to have a desired activity and/or property, or can be selected from a library of diverse compounds.

As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments RNAi agents which serve to inhibit or gene silence are useful in the methods, kits and compositions disclosed herein to alter the expression of, such as in particular inhibit the expression of a GATA3 and/or FOXO1 gene and/or of the one or more genes as taught herein.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g., an adenine, "A", a guanine, "G", a thymine "T", or a cytosine, "C") or RNA (e.g., an A, a G, an uracil, "U", or a C). The term "nucleic acid" encompasses the terms "oligonucleotide" and "polynucleotide"" each as a subgenus of the term "nucleic acid". The term "oligonucleotide" refers to a molecule of between about 3 and about 100 nucleobases in length. The term "polynucleotide" refers to at least one molecule of greater than about 100 nucleobases in length. The term "nucleic acid" also refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

The terms "polypeptide" and "protein" are used interchangeably to refer to a polymer of amino acid residues, and are not limited to a minimum length. Peptides, oligopeptides, dimers, multimers, and the like, are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational and post-translational modifications of the polypeptide, such as, for example, disulfide-bond formation, glycosylation, acetylation, phosphorylation, proteolytic cleavage (e.g., cleavage by furins or metalloproteases and prohormone convertases (PCs)), and the like. Furthermore, for purposes of the present invention, a "polypeptide" encompasses a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, have a well-defined conformation. Proteins, as opposed to peptides, generally consist of chains of 50 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 50 amino acids in length.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides can exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a GATA3 and/or FOXO1 modulator or a modulator of any one of the one or more gene products as taught herein comprises a GATA3 and/or FOXO1 protein or fragment thereof, or comprises the gene product or fragment thereof, respectively, fused to a Fc fragment, which is comprised of D- or L-amino acid residues, as use of naturally occurring L-amino acid residues has the advantage that any break-down products should be relatively non-toxic to the cell or organism.

In yet a further embodiment, a GATA3 and/or FOXO1 modulator, or a modulator of the one or more gene products as taught herein, which is a peptide or fragments or derivatives thereof can be a retro-inverso peptide. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous a-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C, J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

The term "antibody" is meant to be an immunoglobulin protein that is capable of binding an antigen. Antibody as used herein is meant to include antibody fragments, e.g. F(ab')2, Fab', Fab, capable of binding the antigen or antigenic fragment of interest. Exemplary fragments include Fab, Fab', F(ab')2, Fabc, Fd, dAb, VHH and scFv and/or Fv fragments. As used herein, the term "antibody" is used in its broadest sense and generally refers to any immunologic binding agent, such as a whole antibody, including without limitation a chimeric, humanized, human, recombinant, transgenic, grafted and single chain antibody, and the like, or any fusion proteins, conjugates, fragments, or derivatives thereof that contain one or more domains that selectively bind to an antigen of interest. The term antibody thereby includes a whole immunoglobulin molecule, a monoclonal antibody, a chimeric antibody, a humanized antibody, a human antibody, or an immunologically effective fragment of any of these. The term thus specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro, in cell culture, or in vivo.

The term "humanized antibody" is used herein to describe complete antibody molecules, i.e. composed of two complete light chains and two complete heavy chains, as well as antibodies consisting only of antibody fragments, e.g. Fab, Fab', F(ab')2, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject.

All gene name symbols refer to the gene as commonly known in the art. Gene symbols may be those refered to by the HUGO Gene Nomenclature Committee (HGNC). Any reference to the gene symbol is a reference made to the entire gene or variants of the gene. The HUGO Gene Nomenclature Committee is responsible for providing human gene naming guidelines and approving new, unique human gene names and symbols. All human gene names and symbols can be searched at www.genenames.org, the HGNC website, and the guidelines for their formation are available there (www.genenarnes.org/guidelines). Hence, the gene symbols as used throughout this specification may particularly preferably refer to the respective human genes.

The terms "GATA3" or "Trans-acting T-cell-specific transcription factor GATA-3" are well-known in the art. Exemplary but non-limiting GATA3 genomic sequence includes human GATA3 genomic sequence as annotated under Genbank (www.ncbi.nlm.nih.gov/) accession number NG 015859.1. Exemplary but non-limiting GATA3 mRNA includes human GATA3 mRNA having nucleic acid sequence as annotated under Genbank accession numbers NM 001002295.1 (isoform 1), or NM 002051.2 (isoform 2). Exemplary but non-limiting GATA3 protein includes human GATA3 protein having amino acid sequence as annotated under Genbank accession number NP 001002295.1 (isoform 1) or NP 002042.1 (isoform 2).

The terms "FOXO1" or "forkhead box 01" are well-known in the art. Exemplary but non-limiting FOXO1 genomic sequence includes human FOXO1 genomic sequence as annotated under Genbank accession number NG_023244.1. Exemplary but non-limiting FOXO1 mRNA includes human FOXO1 mRNA having nucleic acid sequence as annotated under Genbank accession number NM 002015.3. Exemplary but non-limiting FOXO1 protein includes human FOXO1 protein having amino acid sequence as annotated under Genbank accession number NP_002006.2.

The terms "POU2AF1" or "POU domain class 2-associating factor 1" are well known in the art. Exemplary but non-limiting POU2AF1 genomic sequence includes human POU2AF1 genomic sequence as annotated under Genbank accession number NM 006235.2. Exemplary but non-limiting POU2AF1 protein includes human POU2AF1 protein having amino acid sequence as annotated under Genbank accession number NP_006226.2.

During persistent immune activation, such as during uncontrolled tumor growth or chronic infections, subpopulations of immune cells, particularly of $CD8^+$ T cells, become compromised to different extents with respect to their cytokine and/or cytolytic capabilities. Such immune cells, particularly $CD8^+$ T cell, are commonly referred to as "dysfunctional" or as "functionally exhausted" or "exhausted". As used herein, the term "dysfunctional" or "functional exhaustion" refer to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation (e.g., in response to a cytokine, such as IFN-gamma) or cell division, entrance into the cell cycle, cytokine production, cytotoxicity, migration and trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type. In some particular embodiments of the aspects described herein, a cell that is dysfunctional is a $CD8^+$ T cell that expresses the $CD8^+$ cell surface marker. Such $CD8^+$ cells normally proliferate and produce cell killing enzymes, e.g., they can release the cytotoxins perforin, granzymes, and granulysin. However, exhausted/dysfunctional T cells do not respond adequately to TCR stimulation, and display poor effector function, sustained expression of inhibitory receptors and a transcriptional state distinct from that of functional effector or memory T cells. Dysfunction/exhaustion of T cells thus prevents optimal control of infection and tumors. Exhausted/dysfunctional immune cells, such as T cells, such as $CD8^+$ T cells, may produce reduced amounts of IFN-gamma, TNF-alpha and/or one or more immunostimulatory cytokines, such as IL-2, compared to functional immune cells. Exhausted/dysfunctional immune cells, such as T cells, such as $CD8^+$ T cells, may further produce (increased amounts of) one or more immunosuppressive transcription factors or cytokines, such as IL-10 and/or Foxp3, compared to functional immune cells, thereby contributing to local immunosuppression.

As used herein, the term "unresponsiveness" also includes refractivity to activating receptor-mediated stimulation. Such refractivity is generally antigen-specific and persists after exposure to the antigen has ceased. Unresponsive immune cells can have a reduction of at least 10%, 20%, 30%, 40%, 50%, 60%, 70%, 80%, 90%, 95%, or even 100% in cytotoxic activity, cytokine production, proliferation (e.g., in response to a cytokine, such as IFN-gamma), migration and trafficking, phagocytotic activity, or any combination thereof, relative to a corresponding control immune cell of the same type.

The Applicants have demonstrated that altering, and more particularly downregulating or abolishing, the expression of GATA3 or FOXO1, or both GATA3 and FOXO1, in dysfunctional immune cells may at least partly counter the observed dysfunction, whereby the immune cell may display an improved tumor- or infection-clearing ability. Without limitation, altering, and more particularly downregulating or abolishing, the expression or activity of GATA3 or FOXO1, or both GATA3 and FOXO1, in dysfunctional immune cells can improve one or more aspects of the immune cell function, such as the immune cell's proliferation (e.g., in response to a cytokine, such as IFN-gamma) or cell division, entrance into the cell cycle, differentiation, cytokine production, cytotoxicity, migration and trafficking, phagocytotic activity, or any combination thereof, preferably at least the immune cell's cytokine production or cytotoxicity or both. Similarly, without limitation, altering, and more particularly downregulating or abolishing, the expression or activity of one or more genes or gene products selected from the group consisting of the genes or gene products listed in Table 3, part "Dysfunction_module", Table 5A or Table 5B, in dysfunctional immune cells can improve one or more aspects of the immune cell function, such as the immune cell's proliferation (e.g., in response to a cytokine, such as IFN-gamma) or cell division, entrance into the cell cycle, differentiation, cytokine production, cytotoxicity, migration and trafficking, phagocytotic activity, or any combination thereof, preferably at least the immune cell's cytokine production or cytotoxicity or both. Further, without limitation, altering, and more particularly upregulating, the expression or activity of one or more genes or gene products selected from the group consisting of the genes or gene products listed in Table 3, part "Activation_module", in immune cells (e.g., dysfunctional or non-dysfunctional) can improve one or more aspects of the immune cell function, such as the immune cell's proliferation (e.g., in response to a cytokine, such as IFN-gamma) or cell division, entrance into the cell cycle, differentiation, cytokine production, cytotoxicity, migration and trafficking, phagocytotic activity, or any combination thereof, preferably at least the immune cell's cytokine production or cytotoxicity or both. As used herein, a "cytokine" is a generic term for proteins released by any of the lymph cells that act on other cells as intercellular mediators and affect cellular activity and control inflammation. Cytokines are typically soluble proteins or peptides which are naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. In some cases, the pro-inflammatory cytokine can also cause apoptosis, such as in chronic heart failure, where TNF has been shown to stimulate cardiomyocyte apoptosis. Non-limiting examples of pro-inflammatory cytokines are tumor necrosis factor (TNF), interleukin (IL)-1.alpha, IL-1.beta, IL-6, IL-8, IL-18, interferon-gamma (INFy), HMG-1, platelet-activating factor (PAF), and macrophage migration inhibitory factor (MIF). Additionally examples of cytokines include, lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and -β; mullerian-inhibiting substance (MIS); mouse gonadotropin-associated peptide; inhibin; activin; vascular endothelial growth factor (VEGF); integrin; thrombopoietin (TPO); nerve growth factors such as NGF-β; platelet-growth factor; transforming growth factors (TGFs) such as TGF-a and TGF-β; insulin-like growth factor-I and -II; erythropoietin (EPO); osteoinductive factors; interferons such as interferon-a, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as, for example and not for limitation, IL-1, IL-1.a, IL-1.beta, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including leukemia inhibitory factor (LIF) and kit ligand (KL). As used herein, when referring to a patient the term "cytokine" refers to on one or more of those produced by the patient.

Hence, in certain embodiments, the immune cell as intended herein, such as a T cell, preferably a CD8$^+$ T cell, may be modified to comprise downregulated or abolished expression or activity of GATA3 and/or FOXO1, or to comprise an agent capable of inducibly downregulating or abolishing expression or activity of GATA3 and/or FOXO1.

In further embodiments, the immune cell as intended herein, such as a T cell, preferably a CD8$^+$ T cell, may be modified to comprise downregulated or abolished expression or activity of the one or more genes or gene products selected from the group consisting of the genes or gene products listed in Table 3, part "Dysfunction_module", Table 5A or Table 5B, or to comprise an agent capable of inducibly downregulating or abolishing expression or activity of the one or more genes or gene products selected from the group consisting of the genes or gene products listed in Table 3, part "Dysfunction_module", Table 5A or Table 5B.

In further embodiments, the immune cell as intended herein, such as a T cell, preferably a CD8$^+$ T cell, may be modified to comprise upregulated expression or activity of the one or more genes or gene products selected from the group consisting of the genes or gene products listed in Table 3, part "Activation_module", or to comprise an agent capable of inducibly upregulating expression or activity of the one or more genes or gene products selected from the group consisting of the genes or gene products listed in Table 3, part "Activation_module".

In further embodiments, the immune cell as intended herein, such as a T cell, preferably a CD8$^+$ T cell, may be modified to comprise downregulated or abolished expression or activity of the one or more genes or gene products selected from the group consisting of the genes or gene products listed in Table 3, part "Dysfunction_module", Table 5A or Table 5B, or to comprise an agent capable of inducibly downregulating or abolishing expression or activity of the one or more genes or gene products selected from the group consisting of the genes or gene products listed in Table 3, part "Dysfunction_module", Table 5A or Table 5B; and further modified to comprise upregulated expression or activity of the one or more genes or gene products selected from the group consisting of the genes or gene products listed in Table 3, part "Activation_module", or to comprise an agent capable of inducibly upregulating expression or activity of the one or more genes or gene products selected from the group consisting of the genes or gene products listed in Table 3, part "Activation_module".

In yet further embodiments, the immune cell as intended herein, such as a T cell, preferably a CD8$^+$ T cell, may be modified to comprise upregulated expression or activity of the one or more genes or gene products selected from the group consisting of the genes or gene products listed in Table 3, part "Dysfunction_module", Table 5A or Table 5B, or to comprise an agent capable of inducibly upregulating expression or activity of the one or more genes or gene products selected from the group consisting of the genes or gene products listed in Table 3, part "Dysfunction_module", Table 5A or Table 5B.

In further embodiments, the immune cell as intended herein, such as a T cell, preferably a CD8⁺ T cell, may be modified to comprise downregulated or abolished expression or activity of the one or more genes or gene products selected from the group consisting of the genes or gene products listed in Table 3, part "Activation_module", or to comprise an agent capable of inducibly downregulating or abolishing expression or activity of the one or more genes or gene products selected from the group consisting of the genes or gene products listed in Table 3, part "Activation_module".

In further embodiments, the immune cell as intended herein, such as a T cell, preferably a CD8⁺ T cell, may be modified to comprise upregulated expression or activity of the one or more genes or gene products selected from the group consisting of the genes or gene products listed in Table 3, part "Dysfunction_module", Table 5A or Table 5B, or to comprise an agent capable of inducibly upregulating expression or activity of the one or more genes or gene products selected from the group consisting of the genes or gene products listed in Table 3, part "Dysfunction_module", Table 5A or Table 5B; and further modified to comprise downregulated or abolished expression or activity of the one or more genes or gene products selected from the group consisting of the genes or gene products listed in Table 3, part "Activation_module", or to comprise an agent capable of inducibly downregulating or abolishing expression or activity of the one or more genes or gene products selected from the group consisting of the genes or gene products listed in Table 3, part "Activation_module".

In certain embodiments, the immune cell as intended herein, such as a T cell, preferably a CD8⁺ T cell, may display tumor specificity. By means of an example, the immune cell, such as a T cell, preferably a CD8⁺ T cell, may have been isolated from a tumor of a subject. More preferably, the immune cell may be a tumor infiltrating lymphocyte (TIL). Generally, "tumor infiltrating lymphocytes" or "TILs" refer to white blood cells that have left the bloodstream and migrated into a tumor. Such T cells typically endogenously express a T cell receptor having specificity to an antigen expressed by the tumor cells (tumor antigen specificity).

In alternative embodiments, an immune cell, such as a T cell, preferably a CD8⁺ T cell, may be engineered to express a T cell receptor having specificity to a desired antigen, such as a tumor cell antigen. For example, the immune cell, such as a T cell, preferably a CD8⁺ T cell, may comprise a chimeric antigen receptor (CAR) having specificity to a desired antigen, such as a tumor-specific chimeric antigen receptor (CAR).

The immune cells of the present invention may be used for adoptive cell transfer. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically redirected peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3-chain, CD97, GDI 1a-CD18, CD2, ICOS, CD27, CD154, CD5, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoreponsive cell, thereby treating or preventing the disease (such as a neoplasia, a pathogen infection, an autoimmune disorder, or an allogeneic transplant reaction).

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional $CD8^+$ T-cells (see PCT Patent Publications:

WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor a-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDLL or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT. In preferred embodiments, the novel genes or gene combinations described herein are targeted or modulated.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

In one embodiment, any of the targets described herein are modulated in CAR T cells before administering to a patient in need thereof, preferably, GATA3 and/or FOXO1, or the one or more genes or gene products as taught herein, such as also preferably the one or more genes or gene products selected from the group consisting of the genes or gene products listed in Table 3, part "Dysfunction_module", Table 5A or Table 5B, or also preferably the one or more genes or gene products selected from the group consisting of the genes or gene products listed in Table 3, part "Activation_module". Not being bound by a theory, modulating the expression or activity of a gene related to dysfunction increases the activity of the T cell. Not being bound by a theory, modulating the expression or activity of a gene related to activation increases the activity of the T cell.

In further embodiments, inhibitors of GATA3 and/or FOXO1, or inhibitors of the one or more genes or gene products as taught herein such as preferably the one or more genes or gene products selected from the group consisting of the genes or gene products listed in Table 3, part "Dysfunction_module", Table 5A or Table 5B, are useful for decreasing $CD8^+$ T-cell exhaustion/dysfunction, e.g., for treatment of a subject with a chronic immune disease, e.g., a chronic infection and/or cancer. In some embodiments, an inhibitor of GATA3 and/or FOXO1, or an inhibitor of the one or more genes or gene products as taught herein such as preferably the one or more genes or gene products selected from the group consisting of the genes or gene products listed in Table 3, part "Dysfunction_module", Table 5A or Table 5B, can be used to increase the activity of dysfunctional/exhausted $CD8^+$ T-cells, e.g., increase the immune cell's proliferation (e.g., in response to a cytokine, such as IFN-gamma) or cell division, entrance into the cell cycle, differentiation, cytokine production, cytotoxicity, migration and trafficking, phagocytotic activity, or any combination thereof.

In some embodiments, an inhibitor of GATA3 and/or FOXO1 is a protein inhibitor, and in some embodiments, the inhibitor is any agent which inhibits the function of GATA3 and/or FOXO1 or the expression of GATA3 and/or FOXO1 from its gene. In some embodiments, an inhibitor of the one or more genes or gene products as taught herein such as preferably the one or more genes or gene products selected from the group consisting of the genes or gene products listed in Table 3, part "Dysfunction_module", Table 5A or Table 5B, is a protein inhibitor, and in some embodiments, the inhibitor is any agent which inhibits the function of the one or more gene products, or the expression of the one or more gene products from its (their) respective gene(s).

Inhibition of a gene, e.g., GATA3 and/or FOXO1 gene, can be by gene silencing RNAi molecules according to methods commonly known by a skilled artisan. For example, a gene silencing siRNA oligonucleotide duplexes targeted specifically to human GATA3 and/or FOXO1 can readily be used to knockdown gene expression. GATA3 and/or FOXO1 mRNA can be successfully targeted using siRNAs; and other siRNA molecules may be readily prepared by those of skill in the art based on the known sequence of the target mRNA.

An inhibitor of GATA3 and/or FOXO1 can be any agent which inhibits the function of GATA3 and/or FOXO1, such as antibodies, gene silencing RNAi molecules and the like. An inhibitor of the one or more genes or gene products as taught herein such as preferably the one or more genes or gene products selected from the group consisting of the genes or gene products listed in Table 3, part "Dysfunction_module", Table 5A or Table 5B, can be any agent which inhibits the function of the one or more gene products, such as antibodies, gene silencing RNAi molecules and the like.

In some embodiments a protein, or protein fragment or polypeptide of a target protein, e.g., GATA3 and/or FOXO1, can be used as an inhibitor of the target protein, e.g., GATA3 and/or FOXO1 in the methods, compositions and kits as disclosed herein. In some embodiments, a protein or protein fragment may be a protein, peptide or protein fragment of at least 10 amino acid sequence of the target protein, e.g., GATA3 and/or FOXO1 protein. In some embodiments, an inhibitor of the target protein, e.g., GATA3 and/or FOXO1, is a fragment or polypeptide of the target protein, e.g., GATA3 and/or FOXO1, which functions as a dominant negative or decoy molecule for transcription factor binding to the endogenous target protein, e.g., endogenous GATA3 and/or FOXO1, and therefore a fragment of the target protein, e.g., GATA3 and/or FOXO1 polypeptide, can inhibit the function of the endogenous target protein, e.g., endogenous GATA3 and/or FOXO1 expressed in cells.

Accordingly, fragment of the target protein, e.g., GATA3 and/or FOXO1 protein can be used to function as a dominant negative protein inhibitor of the target protein, e.g., GATA3 and/or FOXO1, respectively.

In some embodiments of the compositions and methods described herein, an inhibitor or antagonist of a target protein, e.g., GATA3 and/or FOXO1 inhibitor or antagonist, is an antibody fragment or antigen-binding fragment. The terms "antibody fragment", "antigen binding fragment" and "antibody derivative" as used herein, refer to a protein fragment that comprises only a portion of an intact antibody, generally including an antigen binding site of the intact antibody and thus retaining the ability to bind antigen, and as described elsewhere herein.

In some embodiments of the compositions and methods described herein, an inhibitor or antagonist of a target protein, e.g., a GATA3 and/or FOXO1 inhibitor or antagonist, is a chimeric antibody derivative of the antagonist antibody or antigen-binding fragment thereof, e.g., is a chimeric antibody derivative of GATA3 and/or FOXO1 antagonist antibody or antigen-binding fragment thereof.

Inhibitor or antagonist antibodies and antigen-binding fragments thereof described herein, e.g., GATA3 and/or FOXO1 inhibitor or antagonist antibodies and antigen-binding fragments thereof described herein, can also be, in some embodiments, a humanized antibody derivative.

In some embodiments, inhibitor or antagonist antibodies and antigen-binding fragments thereof described herein, e.g., GATA3 and/or FOXO1 inhibitor or antagonist antibodies and antigen-binding fragments thereof described herein, include derivatives that are modified, i.e., by the covalent attachment of any type of molecule to the antibody, provided that the covalent attachment does not prevent the antibody from binding to the target antigen.

In some embodiments of the compositions and methods described herein, completely human antibodies are used, which are particularly desirable for the therapeutic treatment of human patients.

In some embodiments of the compositions and methods described herein, an inhibitor or antagonist of a target gene or gene product, e.g., a GATA3 and/or FOXO1 inhibitor or antagonist is a small molecule inhibitor or antagonist, including, but is not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da. In some embodiments of the compositions and methods described herein, an inhibitor or antagonist of a target gene or gene product, e.g., a GATA3 and/or FOXO1 inhibitor or antagonist comprises a small molecule that binds the target gene or gene product, e.g., GATA3 and/or FOXO1.

In some embodiments of the compositions and methods described herein, an inhibitor or antagonist of a target protein, e.g., a GATA3 and/or FOXO1 inhibitor or antagonist is an RNA or DNA aptamer that binds or physically interacts with the target protein, e.g., GATA3 and/or FOXO1, and blocks interactions between the target protein, e.g., GATA3 and/or FOXO1 and transcription factors.

In some embodiments of the compositions and methods described herein, an inhibitor or antagonist of a target gene or gene product, e.g., a GATA3 and/or FOXO1 inhibitor or antagonist comprises at least one siRNA molecule capable of blocking or decreasing the expression of functional isoforms of the target gene or gene product, e.g., GATA3 and/or FOXO1 by targeting nucleic acids encoding the target gene or gene product, e.g., GATA3 and/or FOXO1 isoforms. It is routine to prepare siRNA molecules that will specifically target one or more target gene mRNAs, e.g., of GATA3 and/or FOXO1 isoforms mRNA without cross-reacting with other polynucleotides. siRNA molecules for use in the compositions and methods described herein can be generated by methods known in the art, such as by typical solid phase oligonucleotide synthesis, and often will incorporate chemical modifications to increase half life and/or efficacy of the siRNA agent, and/or to allow for a more robust delivery formulation. Alternatively, siRNA molecules are delivered using a vector encoding an expression cassette for intracellular transcription of siRNA.

In some embodiments, inhibition of a target gene or gene product, e.g., GATA3 and/or FOXO1 is by an agent. One can use any agent, for example but are not limited to nucleic acids, nucleic acid analogues, peptides, phage, phagemids, polypeptides, peptidomimetics, ribosomes, aptamers, antibodies, small or large organic or inorganic molecules, or any combination thereof.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include, but are not limited to a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues, for example but are not limited to peptide nucleic acid (PNA), pseudo-complementary PNA (pc-PNA), locked nucleic acids (LNA) and derivatives thereof etc. Nucleic acid agents also include, for example, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligo-nucleotides, etc.

In some embodiments, an inhibitor of a target gene or gene product, e.g., GATA3 and/or FOXO1 is a RNAi agent. One of ordinary skill can select a RNAi agent to be used which inhibits the expression of a target gene or gene product, e.g., GATA3 and/or FOXO1 as disclosed herein.

In alternative embodiments, agents useful in the methods as disclosed herein are proteins and/or peptides or fragment thereof, which inhibit the gene expression of a target gene or gene product, e.g., GATA3 and/or FOXO1 or the function of a target protein, e.g., the GATA3 and/or FOXO1 protein. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. As disclosed herein, a protein which inhibit the function of a target protein, e.g., GATA3 and/or FOXO1 may be a soluble dominant negative form of the target protein, e.g., dominant negative GATA3 and/or FOXO1 protein, or a functional fragment or variant thereof which inhibits wild-type full length target protein function, e.g., GATA3 and/or FOXO1 function.

In some embodiments, agents that inhibit a target gene or gene product, e.g., GATA3 and/or FOXO1 is a nucleic acid. Nucleic acid inhibitors of the target gene or gene product, e.g., GATA3 and/or FOXO1 include, for example, but not are limited to, RNA interference-inducing (RNAi) molecules, for example but not limited to siRNA, dsRNA, stRNA, shRNA and modified versions thereof, and CRISPR/Cas systems.

Accordingly, in some embodiments, inhibitors of a target gene or gene product, e.g., GATA3 and/or FOXO1 can inhibit the target gene or gene product, e.g., GATA3 and/or FOXO1 by any "gene silencing" methods commonly known by persons of ordinary skill in the art. In some embodiments, the nucleic acid inhibitor of a target gene or gene product, e.g., GATA3 and/or FOXO1 is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):

9225), thereby inhibiting expression of the target gene. In one embodiment, the RNA is double stranded RNA (dsRNA). This process has been described in plants, invertebrates, and mammalian cells. RNAi can be initiated by the dsRNA-specific endonuclease Dicer, which promotes processive cleavage of long dsRNA into double-stranded fragments termed siRNAs.

siRNAs are incorporated into a protein complex (termed "RNA induced silencing complex" or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. the GATA3 and/or FOXO1 gene sequence. A siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target sequence.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

In certain embodiments, the endogenous GATA3 and/or FOXO1 gene of the immune cell as intended herein, such as a T cell, preferably a $CD8^+$ T cell, may be modified whereby the cell comprises downregulated or abolished expression or activity of GATA3 and/or FOXO1, or the immune cell may be modified to comprise an agent capable of inducibly modifying the endogenous GATA3 and/or FOXO1 gene, such as to inducibly downregulate or abolish expression or activity of GATA3 and/or FOXO1. By means of example, the polypeptide-encoding, non-coding and/or regulatory portions of the GATA3 and/or FOXO1 gene, or any combination thereof, may be modified.

In certain embodiments, the one or more endogenous genes or gene products as taught herein of the immune cell as intended herein, such as a T cell, preferably a $CD8^+$ T cell, may be modified, or the immune cell may be modified to comprise an agent capable of inducibly modifying the one or more endogenous genes or gene products as taught herein. In certain embodiments, the cell may thereby comprise downregulated or abolished (in certain embodiments inducibly downregulated or abolished) expression or activity of the one or more endogenous genes or gene products as taught herein, preferably the one or more genes or gene products selected from the group consisting of the genes or gene products listed in Table 3, part "Dysfunction_module", Table 5A or Table 5B. In certain other embodiments, the cell may thereby comprise upregulated (in certain embodiments inducibly upregulated) expression or activity of the one or more endogenous genes or gene products as taught herein, preferably the one or more genes or gene products selected from the group consisting of the genes or gene products listed in Table 3, part "Activation_module". By means of example, the polypeptide-encoding, non-coding and/or regulatory portions of the one or more genes, or any combination of such portions, may be modified.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. These definitions generally refer to a single-stranded molecule, but in specific embodiments will also encompass an additional strand that is partially, substantially or fully complementary to the single-stranded molecule. Thus, a nucleic acid may encompass a single-stranded molecule or a double-stranded molecule that comprises one or more complementary strand(s) or "complement(s)" of a particular sequence comprising a molecule. As used herein, a single-stranded nucleic acid may be denoted by the prefix "ss", a double stranded nucleic acid by the prefix "ds", and a triple stranded nucleic acid by the prefix "is". The term "gene" may refer to the segment of DNA involved in producing a polypeptide chain, it includes regions preceding and following the coding region as well as intervening sequences (introns and non-translated sequences, e.g., 5'- and 3'-untranslated sequences and regulatory sequences) between individual coding segments (exons). A gene can also be an amplified nucleic acid molecule produced in vitro comprising all or a part of the coding region and/or 5'- or 3'-untranslated sequences linked thereto.

A "promoter" is a region of a nucleic acid sequence at which initiation and rate of transcription are controlled. It may contain elements at which regulatory proteins and molecules may bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and may be upstream or downstream of the promoter.

Hence, the endogenous target gene, e.g., GATA3 and/or FOXO1 gene may be modified or "mutated". Any types of mutations achieving the intended effects are contemplated herein. For example, suitable mutations may include deletions, insertions, and/or substitutions. The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the open reading frame (ORF) encoding the target protein, e.g., GATA3 or FOXO1. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon are apparent to a skilled person. For example but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF encoding the target protein, e.g., GATA3 or FOXO1. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift are apparent to a skilled person. For example but without limitation, a suitable insertion or deletion of one or more (not multiple of 3) nucleotides in the ORF may lead to a frame shift.

In further embodiments, a mutation may delete at least a portion of the ORF encoding the target protein, e.g., GATA3 or FOXO1. Such deletion may lead to production of an N-terminally truncated form, a C-terminally truncated form and/or an internally deleted form of said polypeptide (this may preferably affect, such as diminish or abolish, some or all biological function(s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In further embodiments, a mutation may delete at least a portion of the promoter of the target gene, e.g., GATA3 or FOXO1 promoter, leading to impaired transcription of the target gene, e.g., GATA3 or FOXO1 gene.

In certain other embodiments, a mutation may be a substitution of one or more nucleotides in the ORF encoding the target protein, e.g., GATA3 or FOXO1 resulting in substitution of one or more amino acids of the target protein, e.g., GATA3 or FOXO1. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding the target protein, e.g., GATA3 or FOXO1. In the absence of native splicing, the pre-mRNA may be degraded, or the pre-mRNA may be alternatively spliced, or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing. The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions+2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2.

Typically, mutations which abolish the expression of a target gene or gene product, e.g., GATA3 or FOXO1, e.g., by deleting at least a portion of the ORF, e.g., ORF encoding GATA3 or FOXO1 or the entire ORF, may be referred to as "knock-out" (KO) mutations, e.g., GATA3 or FOXO1 "knock-out" (KO) mutations.

In certain embodiments, the endogenous target gene, e.g., endogenous GATA3 or FOXO1 gene may be modified using a nuclease.

The term "nuclease" as used herein broadly refers to an agent, for example a protein or a small molecule, capable of cleaving a phosphodiester bond connecting nucleotide residues in a nucleic acid molecule. In some embodiments, a nuclease may be a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. Preferably, the nuclease is an endonuclease. Preferably, the nuclease is a site-specific nuclease, binding and/or cleaving a specific phosphodiester bond within a specific nucleotide sequence, which may be referred to as "recognition sequence", "nuclease target site", or "target site". In some embodiments, a nuclease may recognize a single stranded target site, in other embodiments a nuclease may recognize a double-stranded target site, for example a double-stranded DNA target site. Some endonucleases cut a double-stranded nucleic acid target site symmetrically, i.e., cutting both strands at the same position so that the ends comprise base-paired nucleotides, also known as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs", e.g., "5'-overhang" or "3'-overhang", depending on whether the unpaired nucleotide(s) form(s) the 5' or the 5' end of the respective DNA strand.

The nuclease may introduce one or more single-strand nicks and/or double-strand breaks in the endogenous target gene, e.g., endogenous GATA3 or FOXO1 gene, whereupon the sequence of the endogenous target gene, e.g., endogenous GATA3 or FOXO1 gene may be modified or mutated via non-homologous end joining (NHEJ) or homology-directed repair (HDR).

In certain embodiments, the nuclease may comprise (i) a DNA-binding portion configured to specifically bind to the endogenous target gene, e.g., endogenous GATA3 or FOXO1 gene and (ii) a DNA cleavage portion. Generally, the DNA cleavage portion will cleave the nucleic acid within or in the vicinity of the sequence to which the DNA-binding portion is configured to bind.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In certain embodiments, the DNA cleavage portion comprises FokI or variant thereof or DNA cleavage domain of FoId or variant thereof.

In certain embodiments, the nuclease may be an RNA-guided nuclease, such as Cas9 or Cpf1 or any Cas protein described herein.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. application 62/091,462, 12 Dec. 14, DEAD GUIDES FOR CRISPR TRANSCRIPTION FACTORS; U.S. application 62/096,324, 23 Dec. 14, DEAD GUIDES FOR CRISPR TRANSCRIPTION FACTORS; U.S. application 62/091,456, 12 Dec. 14, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTI- MIZED ENZYME AND GUIDE SCAFFOLDS FOR SEQUENCE MANIPULATION; U.S. application 62/098,059, 30 Dec. 14, RNA-TARGETING SYSTEM; U.S. application 62/096,656, 24 Dec. 14, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTIFUNCTIONAL-CRISPR COMPLEXES and/or OPTIMIZED ENZYME LINKED FUNCTIONAL-CRISPR COMPLEXES; U.S. application 62/087,475, 4 Dec. 14, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14, MULTIFUNCTIONAL CRISPR COMPLEXES and/or OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science Dec. 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.ce11.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," Cell 163, 1-13 (Oct. 22, 2015)

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, Attorney Reference 47627.99.2060 and BI-2013/107 entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054, 490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 to 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. In certain embodiments, the guide RNA does not comprise tracr sequence. For example, certain CRISPR-Cas systems and RNA-guided proteins, such as Cpf1, may not require tracr sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al. (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g. the nucleoplasmin bipartite NLS with the sequence KRPAATKKAGQAKKKK) (SEQ ID NO: 2); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKGGNFGGRSSGPYGGGGQYFAK-PRNQGGY (SEQ ID NO: 5); the sequence RMRIZFKNKGKDTAELRRRRVEVSVELRKAKKD-EQILKRRNV (SEQ ID NO: 6) of the IBB domain from importin-alpha; the sequences VSRKRPRP (SEQ ID NO: 16) and PPKKARED (SEQ ID NO: 7) of the myoma T protein; the sequence PQPKKKPL (SEQ ID NO: 8) of human p53; the sequence SALIKKKKMAP (SEQ ID NO: 9) of mouse c-abl IV; the sequences DRLRR (SEQ ID NO: 10) and PKQKKRK (SEQ ID NO: 11) of the influenza virus NS1; the sequence RKLKKKIKKL (SEQ ID NO: 12) of the Hepatitis virus delta antigen; the sequence REKKKFLKRR (SEQ ID NO: 13) of the mouse Mx1 protein; the sequence KRKGDEVDGVDEVAKKKSKK (SEQ ID NO: 14) of the human poly(ADP-ribose) polymerase; and the sequence RKCLQAGMNLEARKTKK (SEQ ID NO: 15) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain embodiments, the DNA-binding portion may comprise a transcription activator-like effector (TALE) protein or DNA-binding domain thereof. Hence, certain embodiments may make use of isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of certain embodiments of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

of sequence that may share identity with only the first 20 amino acids of a repetitive full length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                                  (SEQ ID NO: 17)
M D P I R S R T P S P A R E L L S G P Q P D G V Q P T A D R G V S P

P A G G P L D G L P A R R T M S R T R L P S P P A P S P A F S A D S

F S D L L R Q F D P S L F N T S L F D S L P P F G A H H T E A A T G

E W D E V Q S G L R A A D A P P P T M R V A V T A A R P P R A K P A

P R R R A A Q P S D A S P A A Q V D L R T L G Y S Q Q Q Q E K I K P

K V R S T V A Q H H E A L V G H G F T H A H I V A L S Q H P A A L G

T V A V K Y Q D M I A A L P E A T H E A I V G V G K Q W S G A R A L

E A L L T V A G E L R G P P L Q L D T G Q L L K I A K R G G V T A V

E A V H A W R N A L T G A P L N
```

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch An exemplary amino acid sequence of a C-terminal capping region is:

```
                                                  (SEQ ID NO: 18)
R P A L E S I V A Q L S R P D P A L A A L T N D H L V A L A C L G

G R P A L D A V K K G L P H A P A L I K R T N R R I P E R T S H R

V A D H A Q V V R V L G F F Q C H S H P A Q A F D D A M T Q F G M

S R H G L L Q L F R R V G V T E L E A R S G T L P P A S Q R W D R

I L Q A S G M K R A K P S P T S T Q T P D Q A S L H A F A D S L E

R D L D A P S P M H E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In certain embodiments, the DNA-binding portion may comprise a zinc finger protein or DNA-binding domain thereof.

Artificial zinc-finger (ZF) technology allows to provide programmable DNA-binding domains, and involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79).

In certain embodiments, the expression or activity of the target gene or gene product, e.g., GATA3 or FOXO1 in the immune cell may be (inducibly) altered using a protein comprising a DNA-binding portion configured to specifically bind to the endogenous target gene, e.g., endogenous GATA3 or FOXO1 gene, such as a DNA-binding portion as described above.

In certain embodiments, the protein comprising the DNA-binding portion may further comprise one or more suitable effector portions or domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments, the activity mediated by the effector domain is a biological activity. For example, in some embodiments the effector domain may be a transcriptional inhibitor (i.e., a repressor domain), such as an mSin interaction domain (SID). SID4X domain or a Krüppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

In certain embodiments, the expression or activity of the target gene or gene product, e.g., GATA3 or FOXO1 in the immune cell may thus be (inducibly) altered, in particular downregulated or abolished, using a heterologous repressor protein capable of repressing the transcription of the endogenous target gene, e.g., the endogenous GATA3 or FOXO1 gene. In other embodiments, the expression or activity of the target gene or gene product in the immune cell may thus be (inducibly) altered, in particular upregulated, using a heterologous activator protein capable of activating the transcription of the endogenous target gene.

In certain embodiments, the heterologous repressor protein may comprise at least a DNA-binding portion configured to specifically bind to the endogenous target gene, e.g., the endogenous GATA3 or FOXO1 gene, preferably to the promoter of the endogenous target gene, e.g., the endogenous GATA3 or FOXO1 gene promoter. In certain other embodiments, the heterologous activator protein may comprise at least a DNA-binding portion configured to specifically bind to the endogenous target gene, preferably to the promoter of the endogenous target gene.

In certain embodiments, the heterologous repressor protein may comprise (i) a DNA-binding portion configured to specifically bind to the endogenous target gene, e.g., the endogenous GATA3 or FOXO1 gene, preferably to the promoter of the endogenous target gene, e.g., the endogenous GATA3 or FOXO1 gene promoter, and (ii) a transcription repression portion. In certain other embodiments, the heterologous activator protein may comprise (i) a DNA-binding portion configured to specifically bind to the endogenous target gene, preferably to the promoter of the endogenous target gene, and (ii) a transcription activator portion.

In certain embodiments, the DNA-binding portion comprises a zinc finger protein or DNA-binding domain thereof, TALE protein or DNA-binding domain thereof, or RNA-guided nuclease protein or DNA-binding domain thereof.

In certain embodiments, the DNA-binding portion comprises (i) a Cas protein modified to eliminate its nuclease activity, or (ii) DNA-binding domain of a Cas protein.

In further embodiments, the isolated immune cell as taught herein, such as a T cell, preferably a CD8$^+$ T cell, may be further modified to comprise: (a) an altered expression or activity of any one or more of GATA3, FOXO1, POU2AF1, BTLA, or NRP1; (b) an altered expression or activity of any one or more of PD1, CTLA4, TIGIT, TIM3, LAG3, or PD-L1; (c) an altered expression or activity of any one or more of GATA3, FOXO1, POU2AF1, BTLA, NRP1, PD1, CTLA4, TIGIT, TIM3, LAG3, or PD-L1; (d) an altered expression or activity of any one or more of GPR65, DEC1, PZLP, TCF4, TOSO, or CD5L; (e) an altered expression or activity of any one or more of MINA, PML, POU2AF1, PROCR, SMARCA4, ZEB1, EGR2, CCR6, or FAS; (f) an altered expression or activity of any one or more of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3; (g) an altered expression or activity of any one or more of SP4, IKZF4, or TSC22D3; (h) an altered expression or activity of any one or more of SP4, ETS2, IKZF4, TSC22D3, or IRF1; (i) an altered expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA; (j) an altered expression or activity of any one or more of C1QTNF6 or PROS1; (k) an agent capable of inducibly altering expression or activity of any one or more of GPR65, DEC1, PZLP, TCF4, TOSO, or CD5L; (l) an agent capable of inducibly altering expression or activity of any one or more of GATA3, FOXO1, POU2AF1, BTLA, or NRP1; (m) an agent capable of inducibly altering expression or activity of PD1, CTLA4, TIGIT, TIM3, LAG3, or PD-L1; (n) an agent capable of inducibly altering expression or activity of GATA3, FOXO1, POU2AF1, BTLA, NRP1, PD1, CTLA4, TIGIT, TIM3, LAG3, or PD-L1; (o) an agent capable of inducibly altering expression or activity of any one or more of MINA, PML, POU2AF1, PROCR, SMARCA4, ZEB1, EGR2, CCR6, or FAS; (p) an agent capable of inducibly altering expression or activity of any one or more of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3; (q) an agent capable of inducibly altering expression or activity of any one or more of SP4, IKZF4, or TSC22D3; (r) an agent capable of inducibly altering expression or activity of any one or more of SP4, ETS2, IKZF4, TSC22D3, or IRF1; (s) an agent capable of inducibly altering expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA; or an agent capable of inducibly altering expression or activity of any one or more of C1QTNF6 or_PROS1. Such further modifications include genes present on the surface of a cell and thus may be targeted without entering a cell. Such further modifications include genes that are chromatin regulators, thus may be targeted with agents known in the art for modifying activity of the chromatin regulators. Such agents may include therapeutic antibodies or ligands specific for the target. Such further modifications include genes involved in the complement pathway and have known functions in modifiying an immune response. Such further modifications advantageously improve one or more aspects of the immune cell function, for example, provide for additive or synergistic improvement in one or more aspects of the immune cell function.

In further embodiments, the isolated immune cell as taught herein, such as a T cell, preferably a CD8$^+$ T cell, may be further modified to comprise: (a) an altered expression or activity of a metallothionein or (b) an agent capable of inducibly altering expression or activity of metallothionein. Such further modifications advantageously improve one or more aspects of the immune cell function, for example, provide for additive or synergistic improvement in one or more aspects of the immune cell function. Reference is made to PCT Publication No. WO/2014/172606 published on Oct. 23, 2014, herein incorporated by reference in its entirety.

Metallothioneins (MTs) are a class of ubiquitously occurring low molecular weight cysteine- and metal-rich proteins containing sulfur-based metal clusters. The conservation of these clusters in an increasing number of three-dimensional structures of invertebrate, vertebrate and bacterial MTs signifies the importance of this structural motif. It is becoming increasingly clear that mammalian MTs have diverse functions including involvement in zinc homeostasis, protection against heavy metal toxicity and oxidative damage. Mammalian MTs are single chain polypeptides of 61, 60 or 68 amino acid residues with an N-terminal acetylmethionine and often alanine at the carboxyl terminus. They contain 20 cysteine residues, which are central to the binding of metals. MTs have characteristic C—X—C, C—Y—C, and C—C sequences, where X and Y are non-cysteine amino acids. There are 7 bivalent ions for every 20 cysteines forming metal thiolate complexes in a two domain structure.

There are four MT subgroups, namely MT1, MT2, MT3, and MT4. The MT1 and MT2 isoforms, which differ by only a single negative charge, are the most widely expressed isoforms in different tissues. Human MT genes are clustered at a single locus on chromosome 16, and at least 14 of the 17 genes so far identified, are functional. These encode multiple isoforms of MT1 (MTIA, B, E, F, G, H, I, K, L and X), MT2, MT3 and MT4.

Stimuli that can induce MT expression include metals, hormones (e.g. glucocorticoids), cytokines, a variety of other chemicals, inflammation, and stress. MT degradation takes place mainly in the lysosomes. MT appears less susceptible to proteolysis in the metal bound state. In vivo, metal-MTs have far longer half-lives than apo-MT.

MT1 and MT2 are present throughout the liver, brain and spinal cord, and that the main cell type expressing these MT isoforms is the astrocyte; nevertheless, MT1 and MT2 expression was also found in ependymal cells, epithelial cells of choroid plexus, meningeal cells of the pia mater, and endothelial cells of blood vessels.

MTs are stress-inducible proteins that maintain metal homeostasis and scavenge free radicals. It is generally accepted that the major functions of MTs are related to metal metabolism. Postulated functions include detoxification and storage of heavy metals and the regulation of cellular copper and zinc metabolism in response to dietary and physiological changes. MT1 and MT2 deficient mice showed both increased oxidative stress and neuronal apoptosis during epileptic seizures, experimental autoimmune encephalomyelitis (EAE), and following traumatic brain injury. Likewise, transgenic MT1 overexpressing mice showed significantly reduced oxidative tissue damage and cell death during traumatic brain injury, focal cerebral ischemia, and 6-aminonicotinamide (6-AN)-induced brain stem toxicity. Furthermore, MT1 and MT2 improve the clinical outcome and reduce mortality in different CNS disorders (Penkowa et ah, Biomed Rev, 2002, 13; 1-18). MT has recently been shown to mediate neuroprotection in genetically engineered mouse model of Parkinson's disease (Ebadi et al., 2005, 134; 67-75).

Metallothionein has been documented to bind a wide range of metals including cadmium, zinc, mercury, copper, arsenic, silver, etc. Metallation of MT was previously reported to occur cooperatively but recent reports have provided strong evidence that metal-binding occurs via a sequential, noncooperative mechanism. The observation of partially metallated MT (that is, having some free metal binding capacity) suggest that these species are biologically important.

Metallothioneins likely participate in the uptake, transport, and regulation of zinc in biological systems. Mammalian MT binds three Zn(II) ions in its beta domain and four in the alpha domain. Cysteine is a sulfur-containing amino acid. However, the participation of inorganic sulfide and chloride ions has been proposed for some MT forms. In some MTs, mostly bacterial, histidine participates in zinc binding. By binding and releasing zinc, metallothioneins (MTs) may regulate zinc levels within the body. Zinc, in turn, is a key element for the activation and binding of certain transcription factors through its participation in the zinc finger region of the protein. Metallothionein also carries zinc ions (signals) from one part of the cell to another. When zinc enters a cell, it can be picked up by thionein (which thus becomes "metallothionein") and carried to another part of the cell where it is released to another organelle or protein. In this way the thionein-metallothionein becomes a key component of the zinc signaling system in cells. This system is particularly important in the brain, where zinc signaling is prominent both between and within nerve cells. It also seems to be important for the regulation of the tumor suppressor protein p53.

Where MTs play an important role in transcription factor regulation, problems with MT function or expression may lead to malignant transformation of cells and ultimately cancer. Studies have reported increased expression of MTs in some cancers of the breast, colon, kidney, liver, skin (melanoma), lung, nasopharynx, ovary, prostate, mouth, salivary gland, testes, thyroid and urinary bladder; they have also found lower levels of MT expression in hepatocellular carcinoma and liver adenocarcinoma. There are also reports that higher levels of MT expression may also lead to resistance to chemotherapeutic drugs. Heavy metal toxicity has been proposed as a hypothetical etiology of autism, and dysfunction of MT synthesis and activity may play a role in this. Many heavy metals, including mercury, lead, and arsenic have been linked to symptoms that resemble the neurological symptoms of autism.

Agonists (e.g., activators) and inhibitors (e.g. antagonists) of MT1 can be an agonist (e.g., activator) and inhibitor (e.g. antagonist) of a metallothionein (MT) selected from the group consisting of metallothionein-1 A (MT1A), metallothionein-IB (MT1B), metallothionein IE (MT1E), metallothionein-IF (MT1F), metallothionein-1G (MT1 G), metallothionein-1H (MT1H), metallothionein-II (MT1I), metallothionein-1 K (MT1K), metallothionein-1 L (MT1L), metallothionein-1R (MT1R), metallothionein-IX (MT1 X), metallothionein-2 (MT2), metallothionein-3 (MT3) and metallothionein-4 (MT4). The sequences of the latter mentioned metallothioneins are identified in the Gene Bank under the following Acc. Nos: Q9BQN2, P04731, P07438, P04732, P04733, P13640, P80294, P80295, P80296, Q93083, P80297, P02795, P25713, P47944, respectively. In some embodiments, an agonist (e.g., activator) and inhibitor (e.g. antagonist) of a metallothionein (MT) is an agonist (e.g., activator) and inhibitor (e.g. antagonist) of MT1h and MT1e.

A further aspect provides for a method for generating the modified immune cell as taught herein, the method comprising (i) providing an isolated immune cell, and (ii) modifying said isolated immune cell such as to comprise an altered expression or activity of GATA3 or FOXO1. Further aspects provide a method for generating said modified immune cell, the method comprising (i) providing an isolated immune cell, and (ii) modifying said isolated immune cell such as to comprise an altered expression or activity of:
i) one or more genes or gene products selected from the group consisting of the genes or gene products listed in Table 3, part "Dysfunction_module", Table 5A or Table 5B;
ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like__module".

Another aspect provides for a method for generating the modified immune cell as taught herein, the method comprising (i) providing an isolated immune cell, and (ii) modifying said isolated immune cell such as to comprise an agent capable of inducibly altering expression or activity of GATA3 or FOXO1. Further aspects provide a method for generating said modified immune cell, the method comprising (i) providing an isolated immune cell, and (ii) modifying said isolated immune cell such as to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

In such methods, the step of providing the isolated immune cell may comprise providing the immune cell isolated from a subject, or isolating the immune cell from a subject.

The terms "subject" and "individual" are used interchangeably herein, and refer to an animal, for example a human, to whom treatment, including prophylactic treatment, with a pharmaceutical composition according to the present invention, is provided. The term "subject" as used herein refers to human and non-human animals. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The immune cell as intended herein may be isolated from or originate from an animal, for example a human or a non-human animal, such as a non-human mammal.

The immune cell may be isolated from a tissue of the subject known to comprise, or expected or predicted to comprise said immune cell. The term "tissue" is intended to include intact cells, blood, blood preparations such as plasma and serum, bones, joints, muscles, smooth muscles, and organs. By means of example, the immune cell may be isolated from blood, or lymphatic tissue, or from tumor tissue (e.g., from tumor biopsy or from surgically removed tumor tissue) of a subject.

In certain embodiments, the immune cell isolated from the subject may express GATA3 and/or FOXO1. The expression of GATA3 and/or FOXO1 by the immune cell may indicate that the immune cell is to at least some extent dysfunctional, such that (inducibly) altering, more particularly downregulating or abolishing, the expression or activity of GATA3 or FOXO1 by the immune cell may improve the function of the immune cell and/or prevent further worsening of the dysfunctional phenotype of the cell. In some embodiments, immune cells are expanded and tested for expression of GATA3 and/or FOXO1. Not being bound by a theory, determining the expression of an intracellular factor requires the cell to be killed, thus expansion and testing cells from the expanded population is a predictor that GATA3 and/or FOXO1 is expressed.

In certain embodiments, the immune cell isolated from the subject may be dysfunctional or may not be dysfunctional. (Inducibly) altering, more particularly downregulating or abolishing, the expression of or activity GATA3 or FOXO1 in an immune cell which is dysfunctional may improve the function of the immune cell and/or prevent further worsening of the dysfunctional phenotype of the cell. On the other hand, altering, more particularly downregulating or abolishing, the expression or activity of GATA3 or FOXO1 in an immune cell which is not dysfunctional may prevent that the cell acquires a dysfunctional phenotype when reintroduced into a subject. Similarly, (inducibly) altering, more particularly downregulating or abolishing, the expression or activity of the one or more genes or gene products selected from the group consisting of the genes or gene products listed in Table 3, part "Dysfunction_module", Table 5A or Table 5B, in an immune cell which is dysfunctional may improve the function of the immune cell and/or prevent further worsening of the dysfunctional phenotype of the cell. On the other hand, altering, more particularly downregulating or abolishing, the expression or activity of the one or more genes or gene products selected from the group consisting of the genes or gene products listed in Table 3, part "Dysfunction_module", Table 5A or Table 5B, in an immune cell which is not dysfunctional may prevent that the cell acquires a dysfunctional phenotype when reintroduced into a subject.

Further, (inducibly) altering, more particularly upregulating, the expression or activity of the one or more genes or gene products selected from the group consisting of the genes or gene products listed in Table 3, part "Activation_module", in an immune cell which is dysfunctional may improve the function of the immune cell and/or prevent further worsening of the dysfunctional phenotype of the cell. On the other hand, altering, more particularly upregulating or abolishing, the expression or activity of the one or more genes or gene products selected from the group consisting of the genes or gene products listed in Table 3, part "Activation_module", in an immune cell which is not dysfunctional may ensure persistent activation of the cell when reintroduced into a subject.

In certain embodiments, the immune cell isolated from the subject may express a signature of dysfunction as defined elsewhere in this specification.

The above methods may further comprising the step of expanding the immune cell prior to and/or subsequent to the modification. Any known techniques of propagating immune cells, such as in vitro and ex vivo cell culture techniques, may be used to achieve expansion of the present immune cells.

A further aspect provides a pharmaceutical composition comprising the isolated immune cell or the cell population as taught herein.

A "pharmaceutical composition" refers to a composition that usually contains an excipient, such as a pharmaceutically acceptable carrier that is conventional in the art and that is suitable for administration to cells or to a subject. In addition, compositions for topical (e.g., oral mucosa, respiratory mucosa) and/or oral administration can be in the form of solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21 st Ed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, with which a modulator as described herein is combined in a formulation to be administered to a subject. Each carrier must be "acceptable" in the sense of being compatible with the other ingredients of the formulation, as well as in the sense of not being toxic or provoking undue side effects in an individual. Pharmaceutically acceptable carriers are well known to those of skill in the art.

A further aspect provides the isolated immune cell or the cell population as taught herein for use in therapy.

A further aspect provides the isolated immune cell or the cell population as taught herein for use in immunotherapy or adoptive immunotherapy, preferably immunotherapy or adoptive immunotherapy of a proliferative disease, such as a tumor or cancer, or a chronic infection, such as a chronic viral infection. Certain embodiments provide the isolated immune cell or the cell population as taught herein for use in immunotherapy or adoptive immunotherapy in a subject, wherein the subject has been determined to comprise immune cells which: express GATA3 and/or FOXO1; are dysfunctional, or are not dysfunctional; or express a signature of dysfunction as described herein in this specification.

The term "immunotherapy" broadly encompasses therapeutic or prophylactic treatments aimed at modulating, such as upregulating or downregulating, immune response in a subject.

As used herein, "immune response" refers to a response by a cell of the immune system, such as a B cell, T cell ($CD4^+$ or $CD8^+$), regulatory T cell, antigen-presenting cell, dendritic cell, monocyte, macrophage, NKT cell, NK cell, basophil, eosinophil, or neutrophil, to a stimulus. In some embodiments of the aspects described herein, the response is specific for a particular antigen (an "antigen-specific response"), and refers to a response by a CD4 T cell, CD8 T cell, or B cell via their antigen-specific receptor. In some embodiments of the aspects described herein, an immune response is a T cell response, such as a $CD4^+$ response or a $CD8^+$ response. Such responses by these cells can include, for example, cytotoxicity, proliferation, cytokine or chemokine production, trafficking, or phagocytosis, and can be dependent on the nature of the immune cell undergoing the response.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition, or affliction.

The term "proliferative disease or disorder" generally refers to any disease or disorder characterized by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, premalignant or precancerous lesions, malignant tumors, and cancer.

The terms "tumor" or "tumor tissue" refer to an abnormal mass of tissue resulting from excessive cell division. A tumor or tumor tissue comprises "tumor cells" which are neoplastic cells with abnormal growth properties and no useful bodily function. Tumors, tumor tissue and tumor cells may be benign, pre-malignant or malignant, or may represent a lesion without any cancerous potential. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

The term "cancer" refers to a malignant neoplasm characterized by deregulated or unregulated cell growth. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor. The term "metastatic" or "metastasis" generally refers to the spread of a cancer from one organ or tissue to another non-adjacent organ or tissue. The occurrence of the proliferative disease in the other non-adjacent organ or tissue is referred to as metastasis.

In certain embodiments, the proliferative disease may be selected from the group consisting of squamous cell cancer, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, head cancer and neck cancer.

As well understood by the skilled artisan, autoimmune diseases or autoimmune disorders refer to diseases or disorders caused by an immune response against a self-tissue or tissue component (self-antigen) and include a self-antibody response and/or cell-mediated response. These encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune-associated infertility; autoimmune gastritis; autoimmune hepatitis; autoimmune hemophilia; autoimmune lymphoproliferative syndrome (ALPS); autoimmune thrombocytopenia; autoimmune uveoretinitis; Behcet's disease; bullous pemphigoid; coeliac disease; dermatomyositis; diabetes mellitus type I; glomerulonephritis (e.g., crescentic glomerulonephritis, proliferative glomerulonephritis); Goodpasture's syndrome; Graves' disease; Guillain-Barré syndrome (GBS); Hashimoto's disease; idiopathic thrombocytopenic purpura; inflammatory bowel disease (IBD) including Crohn's disease and ulcerative colitis; insulin resistance; mixed connective tissue disease; multiple sclerosis (MS); myasthenia gravis (MG); opsoclonus myoclonus syndrome (OMS); optic neuritis; Ord's thyroiditis; pemphigus (e.g., pemphigus vulgaris); pernicious anaemia; polyarteritis nodosa; polymyositis; primary biliary cirrhosis; primary myoxedema; psoriasis; rheumatic fever; rheumatoid arthritis; Reiter's syndrome; scleroderma with anti-collagen antibodies; Sjögren's syndrome; systemic lupus erythematosus (SLE); Takayasu's arteritis; temporal arteritis; vitiligo; warm autoimmune hemolytic anemia; or Wegener's granulomatosis. Autoimmune disease has been recognized also to encompass atherosclerosis and Alzheimer's disease.

A further aspect provides a method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising administering to said subject the isolated immune cell or the cell population as taught herein, more particularly administering to said subject a therapeutically or prophylactically effective amount the isolated immune cell or the cell population as taught herein. In certain embodiments, the subject has been determined to comprise immune cells which: express GATA3 and/or FOXO1; are dysfunctional, or are not dysfunctional; or express a signature of dysfunction as described elsewhere in this specification.

As used herein, the terms "treat", "treating" and "treatment" refer to the alleviation or measurable lessening of one or more symptoms or measurable markers of a disease or disorder; while not intending to be limited to such, disease or disorders of particular interest include autoimmune diseases, chronic infection and cancer. Measurable lessening includes any statistically significant decline in a measurable marker or symptom. In some embodiments, treatment is prophylactic treatment.

The term "therapeutically effective amount" refers to an amount effective, at dosages and for periods of time necessary, to achieve the desired therapeutic result, e.g., a diminishment or prevention of effects associated with various disease states or conditions. The term "therapeutically effective amount" refers to an amount of a target gene or gene product modulator, e.g., a GATA3 and/or FOXO1 modulator as disclosed herein effective to treat or prevent a disease or disorder in a mammal. A therapeutically effective amount of a target gene or gene product modulator, e.g., a GATA3 and/or FOXO1 modulator can vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects. In some embodiments, a therapeutically effective amount is an "effective amount", which as used herein refers to the amount of therapeutic agent of pharmaceutical composition to alleviate at least one or some of the symptoms of the disease or disorder. An "effective amount" for purposes herein is thus determined by such considerations as are known in the art and is the amount to achieve improvement including, but not limited to, improved survival rate or more rapid recovery, or improvement or elimination of at least one symptom and other indicator of an immune or autoimmune disease which are appropriate measures by those skilled in the art. It should be noted that a target gene or gene product modulator, e.g., a GATA3 and/or FOXO1 modulator as disclosed herein can be administered as a pharmaceutically acceptable salt and can be administered alone or as an active ingredient in combination with pharmaceutically acceptable carriers, diluents, adjuvants and vehicles.

The term "prophylactically effective amount" refers to an amount of a target gene or gene product modulator, e.g., a GATA3 and/or FOXO1 modulator which is effective, at dosages and for periods of time necessary, to achieve the desired prophylactic result, e.g., the amount of a target gene or gene product modulator, e.g., a GATA3 and/or FOXO1 inhibitor to decrease $CD8^+$ T cell exhaustion/dysfunction to reduce a symptom of a chronic immune disease, e.g., a chronic infection or to treat cancer in the subject. Typically, since a prophylactic dose of a target gene or gene product modulator, e.g., a GATA3 and/or FOXO1 modulator is administered to a subject prior to or at an earlier stage of a disease, and in some embodiments, a prophylactically effective amount is less than the therapeutically effective amount. A prophylactically effective amount of a target gene or gene product modulator, e.g., a GATA3 and/or FOXO1 modulator is also one in which any toxic or detrimental effects of the compound are outweighed by the beneficial effects.

As used herein, the terms "prevent", "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent" "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, the terms "administering" and "introducing" are used interchangeably herein and refer to the placement of the agents of metabolic regulators of the present invention into a subject by a method or route which results in at least partial localization of a target gene or gene product modulator, e.g., a GATA3 and/or FOXO1 modulator at a desired site. The compounds of the present invention can be administered by any appropriate route which results in an effective treatment in the subject. In some embodiments, administering is not systemic administration. In some embodiments, administration includes contacting a specific population of T cells ex vivo with a target gene or gene product modulator, e.g., a GATA3 and/or FOXO1 modulator as disclosed herein, and administering the treated specific T cell population to a subject. For example, in some embodiments, a CD8 T-cell population is contacted with a target gene or gene product modulator, e.g., a GATA3 and/or FOXO1 inhibitor, and the inhibitor treated $CD8^+$ T-cells are administered to a subject, e.g., a subject in need of treatment, such as, for example, a subject with a chronic immune diseases, e.g., a chronic infection and/or cancer.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration", "administered systemically", "peripheral administration" and "administered peripherally" as used herein mean the administration of a GATA3 and/or FOXO1 modulator such that it enters the animal's system and, thus, is subject to metabolism and other like processes, for example, subcutaneous administration.

Methods to deliver agents as intended herein capable of (inducibly) altering expression or activity of a desired target gene or polypeptide, such as expression or activity of GATA3 or FOXO1, into cells, tissues or organs of a subject, for example into cells in vitro or ex vivo, or to a subjects' cells, tissues, or organs in vivo or in situ, are well known in the art.

Exemplary delivery methods for RNA interfering agents may also be used to deliver any of CRISPR/Cas systems, Zinc finger, or Tales. In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs, used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

Methods of delivering RNAi agents, e.g., an siRNA, or vectors containing an RNAi agent, to the target cells (e.g., basal cells or cells of the lung and/or respiratory system or other desired target cells) are well known to persons of ordinary skill in the art. In some embodiments, a RNAi agent can be administered to a subject via aerosol means, for example using a nebulizer and the like. In alternative embodiments, administration of a RNAi agent (e.g. can include, for example (i) injection of a composition containing the RNA interfering agent, e.g., an siRNA, or (ii) directly contacting the cell, e.g., a cell of the respiratory system, with a composition comprising an RNAi agent, e.g., an siRNA. In another embodiment, RNAi agents, e.g., an siRNA can be injected directly into any blood vessel, such as vein, artery, venule or arteriole, via, e.g., hydrodynamic injection or catheterization. In some embodiments an RNAi inhibitor can delivered to specific organs, for example the liver, bone marrow or systemic administration. Administration can be by a single injection or by two or more injections.

In some embodiments, a RNAi agent is delivered in a pharmaceutically acceptable carrier. One or more RNAi agents can be used simultaneously, e.g. one or more gene silencing RNAi agent inhibitors of target gene(s), e.g., GATA3 and/or FOXO1 can be together. The RNA interfering agents, can be delivered singly, or in combination with other RNA interfering agents, e.g., siRNAs, such as, for example siRNAs directed to other cellular genes. A gene silencing-RNAi agent inhibitor of target gene(s), e.g., GATA3 and/or FOXO1 can also be administered in combination with other pharmaceutical agents which are used to treat or prevent diseases or disorders.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNAi effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen which is identified by the antibody. In some embodiments, the antibody can be any antibody which identifies an antigen expressed on cells expressing the target gene or gene product, e.g., expressing GATA3 and/or FOXO1. In some embodiments, the antibody is an antibody which binds to the target gene product antigen, e.g., GATA3 and/or FOXO1 antigen, but where the antibody can or does not inhibit the target gene product function, e.g., GATA3 and/or FOXO1 function. In some embodiments, the siRNA can be conjugated to an antagonist of the target gene product, e.g., a GATA3 and/or FOXO1 antagonist, for example where the antagonist, e.g., GATA3 and/or FOXO1 antagonist is a polypeptide, and where the conjugation with the RNAi does not interrupt the function of the antagonist, e.g., GATA3 and/or FOXO1 antagonist.

In some embodiments, a siRNA or RNAi binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

In some embodiments, a viral-mediated delivery mechanism can also be employed to deliver siRNAs to cells in vitro and in vivo as described in Xia, H. et al. (2002) Nat Biotechnol 20(10): 1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501). Alternatively, in other embodiments, a RNAi agent, e.g., a gene silencing-RNAi agent inhibitor of a target gene, e.g., GATA3 and/or FOXO1 can also be introduced into cells via the vascular or extravascular circulation, the blood or lymph system, and the cerebrospinal fluid.

In general, any method of delivering a nucleic acid molecule can be adapted for use with an RNAi interference molecule (see e.g., Akhtar S. and Julian RL. (1992) Trends Cell. Biol. 2(5): 139-144; WO94/02595, which are incorporated herein by reference in their entirety). However, there are three factors that are important to consider in order to successfully deliver an RNAi molecule in vivo: (a) biological stability of the RNAi molecule, (2) preventing non-specific effects, and (3) accumulation of the RNAi molecule in the target tissue. The non-specific effects of an RNAi molecule can be minimized by local administration by e.g., direct injection into a tissue including, for example, a tumor or topically administering the molecule.

Local administration of an RNAi molecule to a treatment site limits the exposure of the e.g., siRNA to systemic tissues and permits a lower dose of the RNAi molecule to be administered. Several studies have shown successful knockdown of gene products when an RNAi molecule is administered locally. For example, intraocular delivery of a VEGF siRNA by intravitreal injection in cynomolgus monkeys (Tolentino, M J., et al (2004) Retina 24: 132-138) and subretinal injections in mice (Reich, S J., et al (2003) Mol. Vis. 9:210-216) were both shown to prevent neovascularization in an experimental model of age-related macular degeneration. In addition, direct intratumoral injection of an siRNA in mice reduces tumor volume (Pille, J., et al (2005) Mol. Ther. 1 1:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al (2004) Nucleic Acids 32:e49; Tan, P H., et al (2005) Gene Ther. 12:59-66; Makimura, H., et al (2002) BMC Neurosci. 3: 18; Shishkina, G T., et al (2004) Neuroscience 129:521-528; Thakker, E R., et al (2004) Proc. Natl. Acad. Sci. U.S.A. 101: 17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279: 10677-10684; Bitko, V., et al (2005) Nat. Med. 1 1:50-55).

For administering an RNAi molecule systemically for the treatment of a disease, the RNAi molecule can be either be modified or alternatively delivered using a drug delivery system; both methods act to prevent the rapid degradation of the RNAi molecule by endo- and exo-nucleases in vivo. Modification of the RNAi molecule or the pharmaceutical carrier can also permit targeting of the RNAi molecule to the target tissue and avoid undesirable off-target effects.

RNA interference molecules can be modified by chemical conjugation to lipophilic groups such as cholesterol to enhance cellular uptake and prevent degradation. For example, an siRNA directed against ApoB conjugated to a lipophilic cholesterol moiety was injected systemically into mice and resulted in knockdown of apoB mRNA in both the liver and jejunum (Soutschek, J., et al (2004) Nature 432: 173-178). Conjugation of an RNAi molecule to an aptamer has been shown to inhibit tumor growth and mediate tumor regression in a mouse model of prostate cancer (McNamara, J O., et al (2006) Nat. Biotechnol. 24: 1005-1015).

In an alternative embodiment, the RNAi molecules can be delivered using drug delivery systems such as e.g., a nanoparticle, a dendrimer, a polymer, liposomes, or a cationic delivery system. Positively charged cationic delivery systems facilitate binding of an RNA interference molecule (negatively charged) and also enhance interactions at the negatively charged cell membrane to permit efficient uptake of an siRNA by the cell. Cationic lipids, dendrimers, or polymers can either be bound to an RNA interference molecule, or induced to form a vesicle or micelle (see e.g., Kim S H., et al (2008) Journal of Controlled Release 129(2): 107-1 16) that encases an RNAi molecule. The formation of vesicles or micelles further prevents degradation of the RNAi molecule when administered systemically. Methods for making and administering cationic-RNAi complexes are well within the abilities of one skilled in the art (see e.g., Sorensen, D R., et al (2003) J. Mol. Biol 327:761-766; Verma, U N., et al (2003) Clin. Cancer Res. 9: 1291-1300; Arnold, A S et al (2007) J. Hypertens. 25: 197-205, which are incorporated herein by reference in their entirety).

Some non-limiting examples of drug delivery systems useful for systemic administration of RNAi include DOTAP (Sorensen, D R., et al (2003), supra; Verma, U N., et al (2003), supra), Oligofectamine, "solid nucleic acid lipid particles" (Zimmermann, T S., et al (2006) Nature 441: 111-114), cardiolipin (Chien, P Y., et al (2005) Cancer Gene Ther. 12:321-328; Pal, A., et al (2005) Int J. Oncol. 26: 1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16: 1799-1804). In some embodiments, an RNAi molecule forms a complex with cyclodextrin for systemic administration. Methods for administration and pharmaceutical compositions of RNAi molecules and cyclodextrins can be found in U.S. Pat. No. 7,427,605, which is herein incorporated by reference in its entirety. Specific methods for administering an RNAi molecule for the inhibition of angiogenesis can be found in e.g., U.S. Patent Application No. 20080152654, which is herein incorporated by reference in its entirety.

In some embodiments, the siRNA, dsRNA, or shRNA vector can be administered systemically, such as intravenously, e. g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e. g. as described herein and in Gao and Huang, 2008, (Mol. Pharmaceutics, Web publication December 30) and review by Rossi, 2006, Gene Therapy, 13:583-584. The siRNA, dsRNA, or shRNA vector can be formulated in various ways, e. g. conjugation of a cholesterol moiety to one of the strands of the siRNA duplex for systemic delivery to the liver and jejunum (Soutschek J. et. al. 2004, Nature, 432: 173-178), complexing of siRNAs to protamine fused with an antibody fragment for receptor-mediated targeting of siRNAs (Song E, et al. 2005, Nat Biotechnol., 23: 709-717) and the use of a lipid bilayer system by Morrissey et al. 2005 (Nat Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

The dose of the particular RNAi agent will be in an amount necessary to effect RNA interference, e.g., gene silencing of the target gene, e.g., GATA3 and/or FOXO1 gene, thereby leading to a subsequent decrease in the target protein level, e.g., GATA3 and/or FOXO1 protein level.

In another embodiment of the invention, agents which are inhibitors of the target gene or protein, e.g., GATA3 and/or FOXO1 are catalytic nucleic acid constructs, such as, for example ribozymes, which are capable of cleaving RNA transcripts and thereby preventing the production of wild-type protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example for cleavage of the GATA3 and/or FOXO1 proteins or GATA3 and/or FOXO1 genes can be achieved by techniques well known to those skilled in the art (for example Lleber and Strauss, (1995) Mol Cell Biol 15:540.551, the disclosure of which is incorporated herein by reference).

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors".

The term "viral vectors" refers to the use as viruses, or virus-associated vectors as carriers of the nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g. EPV and EBV vectors.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined. Enhancers need not be located in close proximity to the coding sequences whose transcription they enhance. Furthermore, a gene transcribed from a promoter regulated in trans by a factor transcribed by a second promoter may be said to be operatively linked to the second promoter. In such a case, transcription of the first gene is said to be operatively linked to the first promoter and is also said to be operatively linked to the second promoter.

Hence, in certain embodiments the invention involves vectors, e.g. for delivering or introducing in a cell the DNA targeting agent according to the invention as described herein, such as by means of example Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (http://www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals. org/content/34/7/e53. short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

A poly nucleic acid sequence encoding the DNA targeting agent according to the invention as described herein, such as by means of example guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Through this disclosure and the knowledge in the art, the DNA targeting agent as described herein, such as, TALEs, CRISPR-Cas systems, etc., or components thereof or nucleic acid molecules thereof (including, for instance HDR template) or nucleic acid molecules encoding or providing components thereof may be delivered by a delivery system herein described both generally and in detail.

Vector delivery, e.g., plasmid, viral delivery: By means of example, the CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. The DNA targeting agent as described herein, such as Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^{10}$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a DNA targeting agent as described herein, such as a comprising a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver the DNA targeting agent as described herein, such as Cas9 and gRNA (and, for instance, HR repair template) into cells using liposomes or particles. Thus delivery of the CRISPR enzyme, such as a Cas9 and/or delivery of the RNAs of the invention may be in RNA form and via microvesicles, liposomes or particles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to $\alpha$-tocopherol and co-administered with HDL targeted to the brain may be contemplated for humans in the present invention, for example, about 3 nmol to about 3 µmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKC$\gamma$ for in vivo gene silencing in the spinal cord of rats. Zou et al. administered about 10 µl of a recombinant lentivirus having a titer of $1\times10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package nucleic acid molecules, in particular the DNA targeting agent according to the invention as described herein, such as Cas9 coding nucleic acid molecules, e.g., DNA, into vectors, e.g., viral vectors, to mediate genome modification in vivo include:

To achieve NHEJ-mediated gene knockout:
Single virus vector:
  Vector containing two or more expression cassettes:
  Promoter-Cas9 coding nucleic acid molecule-terminator
  Promoter-gRNA1-terminator
  Promoter-gRNA2-terminator
  Promoter-gRNA(N)-terminator (up to size limit of vector)
Double virus vector:
  Vector 1 containing one expression cassette for driving the expression of Cas9
  Promoter-Cas9 coding nucleic acid molecule-terminator
  Vector 2 containing one more expression cassettes for driving the expression of one or more guideRNAs
  Promoter-gRNA1-terminator
  Promoter-gRNA(N)-terminator (up to size limit of vector)

To mediate homology-directed repair.

In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, CAG, CBh, PGK, SV40, Ferritin heavy or light chains, etc.

For brain or other CNS expression, can use promoters: SynapsinI for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.

The promoter used to drive guide RNA can include:
Pol III promoters such as U6 or H1
Use of Pol II promoter and intronic cassettes to express gRNA Adeno Associated Virus (AAV)

The DNA targeting agent according to the invention as described herein, such as by means of example Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of the DNA targeting agent according to the invention as described herein, such as by means of example Cas9 can be driven by a cell-type specific promoter. For example, liver-specific expression might use the Albumin promoter and neuron-specific expression (e.g. for targeting CNS disorders) might use the Synapsin I promoter.

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In terms of in vivo delivery, AAV is advantageous over other viral vectors for a couple of reasons:

Low toxicity (this may be due to the purification method not requiring ultra centrifugation of cell particles that can activate the immune response)

Low probability of causing insertional mutagenesis because it doesn't integrate into the host genome.

AAV has a packaging limit of 4.5 to 4.75 Kb. This means that for instance Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows, by means of example for Cas delivery. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 μl Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 µl of DMEM overnight at 4 C. They were then aliquotted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of $2.5 \times 10^6$ CD34$^+$ cells per kilogram patient weight may be collected and prestimulated for 16 to 20 hours in X-VIVO 15 medium (Lonza) containing 2 µmonglutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm$^2$ tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. US20060281180, US20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The DNA targeting agent according to the invention as described herein, such as the CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (µm). In some embodiments, inventive particles have a greatest dimension of less than 10 µm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of for instance CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

The DNA targeting agent according to the invention as described herein, such as by means of example CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

For example, Su X, Fricke J, Kavanagh D G, Irvine DJ ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured particles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver DNA targeting agents according to the invention as described herein, such as RNA to a cancer cell to stop tumor growth developed by Dan Anderson's lab at MIT may be used/and or adapted to the CRISPR Cas system according to certain embodiments of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the DNA targeting agent according to the invention, such as for instance the CRISPR Cas system according to certain embodiments of the present invention. In one aspect, the aminoalcohol lipidoid compounds are combined with an agent to be delivered to a cell or a subject to form microparticles, particles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the DNA targeting agent according to the invention, such as for instance the CRISPR Cas system according to certain embodiments of the present invention.

In another embodiment, lipid particles (LNPs) are contemplated. An antitransthyretin small interfering RNA has been encapsulated in lipid particles and delivered to humans (see, e.g., Coelho et al., N Engl J Med 2013; 369:819-29), and such a ssystem may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or by means of example CRISPR-Cas RNA in or associated with the LNP may be contemplated, especially for a formulation containing DLinKC2-DMA.

Preparation of LNPs and the DNA targeting agent according to the invention as described herein, such as by means of example CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other particles (particularly gold particles) are also contemplated as a means to deliver the DNA targeting agent according to the invention as described herein, such as by means of example CRISPR-Cas system to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling particles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA particles may be formed by using cyclodextrin-containing polycations. Typically, particles were formed in water at a charge ratio of 3 (+/−) and an siRNA concentration of 0.5 g/liter. One percent of the adamantane-PEG molecules on the surface of the targeted particles were modified with Tf (adamantane-PEG-Tf). The particles were suspended in a 5% (wt/vol) glucose carrier solution for injection.

Davis et al. (Nature, Vol 464, 15 Apr. 2010) conducts a RNA clinical trial that uses a targeted particle-delivery system (clinical trial registration number NCT00689065). Patients with solid cancers refractory to standard-of-care therapies are administered doses of targeted particles on days 1, 3, 8 and 10 of a 21-day cycle by a 30-min intravenous infusion. The particles consist of a synthetic delivery system containing: (1) a linear, cyclodextrin-based polymer (CDP), (2) a human transferrin protein (TF) targeting ligand displayed on the exterior of the particle to engage TF receptors (TFR) on the surface of the cancer cells, (3) a hydrophilic polymer (polyethylene glycol (PEG) used to promote particle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These particles (clinical version denoted as CALAA-01) have been shown to be well tolerated in multi-dosing studies in non-human primates. Although a single patient with chronic myeloid leukaemia has been administered siRNAby liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR Cas system of the present invention. The delivery of the invention may be achieved with particles containing a linear, cyclodextrin-based polymer (CDP), a human transferrin protein (TF) targeting ligand displayed on the exterior of the particle to engage TF receptors (TFR) on the surface of the cancer cells and/or a hydrophilic polymer (for example, polyethylene glycol (PEG) used to promote particle stability in biological fluids).

In terms of this invention, it is preferred to have one or more components of the DNA targeting agent according to the invention as described herein, such as by means of example the CRISPR complex, e.g., CRISPR enzyme or mRNA or guide RNA delivered using particles or lipid envelopes. Other delivery systems or vectors are may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, particles of the invention have a greatest dimension ranging between 35 nm and 60 nm. In other preferred embodiments, the particles of the invention are not nanoparticles.

Particles encompassed in the present invention may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising comprising polymer conjugated to a surfactant, hydrophilic polymer or lipid. U.S. Pat. No. 6,007,845, incorporated herein by reference, provides particles which have a core of a multiblock copolymer formed by covalently linking a multifunctional compound with one or more hydrophobic polymers and one or more hydrophilic polymers, and conatin a biologically active material. U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system. U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system. U.S. Pat. No. 5,543,158, incorporated herein by reference, provides biodegradable injectable particles having a biodegradable solid core containing a biologically active material and poly(alkylene glycol) moieties on the surface. WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). 7C1 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by particle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 μF resulted in the greatest retention of RNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the DNA targeting agent according to the invention as described herein, such as by means of example the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing the DNA targeting agent according to the invention as described herein, such as by means of example CRISPR Cas may be introduced to monocytes and lymphocytes of and autologously reintroduced into a human. Accordingly, delivery or administration according to the invention may beperformed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the DNA targeting agent according to the invention as described herein, such as by means of example the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the DNA targeting agent according to the invention as described herein, such as by means of example the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1, 2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate the DNA targeting agent according to the invention as described herein, such as by means of example CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, di stearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid particles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid particles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The the DNA targeting agent according to the invention as described herein, such as by means of example CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of the DNA targeting agent according to the invention as described herein, such as by means of example CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines): (1) One day before treatment, plate 1×10⁵ cells per well in a 48-well plate. (2) On the day of treatment, dilute purified +36 GFP protein in serumfree media to a final concentration 200 nM. Add RNA to a final concentration of 50 nM. Vortex to mix and incubate at room temperature for 10 min. (3) During incubation, aspirate media from cells and wash once with PBS. (4) Following incubation of +36 GFP and RNA, add the protein-RNA complexes to cells. (5) Incubate cells with complexes at 37° C. for 4h. (6) Following incubation, aspirate the media and wash three times with 20 U/mL heparin PBS. Incubate cells with serum-containing media for a further 48h or longer depending upon the assay for activity. (7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications: (1) One day before treatment, plate 1×10⁵ per well in a 48-well plate. (2) On the day of treatment, dilute purified þ36 GFP protein in serumfree media to a final concentration 2 mM. Add 1 mg of plasmid DNA. Vortex to mix and incubate at room temperature for 10 min. (3) During incubation, aspirate media from cells and wash once with PBS. (4) Following incubation of þ36 GFP and plasmid DNA, gently add the protein-DNA complexes to cells. (5) Incubate cells with complexes at 37 C for 4h. (6) Following incubation, aspirate the media and wash with PBS. Incubate cells in serum-containing media and incubate for a further 24-48h. (7) Analyze plasmid delivery (e.g., by plasmid-driven gene expression) as appropriate. See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in inconjunction with herein teachints can be employed in the delivery of the DNA targeting agent according to the invention as described herein, such as by means of example CRISPR Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the DNA targeting agent according to the invention as described herein, such as by means of example CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, liposomes, chromophores, small molecules and radioactive materials. In aspects of the invention, the cargo may also comprise any component of the the DNA targeting agent according to the invention as described herein, such as by means of example CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and ((R-AhX-R)4) (Ahx=aminohexanoyl) (SEQ ID NO: 19).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the the DNA targeting agent according to the invention as described herein, such as by means of example the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the the DNA targeting agent according to the invention as described herein, such as by means of example CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear-auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the DNA targeting agent according to the invention as described herein, such as by means of example CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the DNA targeting agent according to the invention as described herein, such as by means of example CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, the DNA targeting agent according to the invention as described herein, such as by means of example CRISPR-Cas system or components thereof or nucleic acid molecules thereof or encoding or providing components may be delivered via an implantable device.

The present application also contemplates an inducible CRISPR Cas system. Reference is made to international patent application Serial No. PCT/US13/51418 filed Jul. 21, 2013, which published as WO2014/018423 on Jan. 30, 2014.

In one aspect the invention provides a DNA targeting agent according to the invention as described herein, such as by means of example a non-naturally occurring or engineered CRISPR Cas system which may comprise at least one switch wherein the activity of said CRISPR Cas system is controlled by contact with at least one inducer energy source as to the switch. In an embodiment of the invention the control as to the at least one switch or the activity of said CRISPR Cas system may be activated, enhanced, terminated or repressed. The contact with the at least one inducer energy source may result in a first effect and a second effect.

The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said the DNA targeting agent according to the invention as described herein, such as by means of example CRISPR Cas system. In one embodiment the first effect and the second effect may occur in a cascade.

The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source may be abscisic acid (ABA), doxycycline (DOX), cumate, rapamycin, 4-hydroxytamoxifen (4OHT), estrogen or ecdysone.

The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems.

In one aspect of the invention the inducer energy source is electromagnetic energy.

The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

In a further aspect, the invention provides a method of controlling a the DNA targeting agent according to the invention as described herein, such as by means of example a non-naturally occurring or engineered CRISPR Cas system, comprising providing said CRISPR Cas system comprising at least one switch wherein the activity of said CRISPR Cas system is controlled by contact with at least one inducer energy source as to the switch.

In an embodiment of the invention, the invention provides methods wherein the control as to the at least one switch or the activity of said the DNA targeting agent according to the invention as described herein, such as by means of example CRISPR Cas system may be activated, enhanced, terminated or repressed. The contact with the at least one inducer energy source may result in a first effect and a second effect. The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said CRISPR Cas system. In one embodiment the first effect and the second effect may occur in a cascade.

The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source may be abscisic acid (ABA), doxycycline (DOX), cumate, rapamycin, 4-hydroxytamoxifen (4OHT), estrogen or ecdysone. The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems.

In one aspect of the methods of the invention the inducer energy source is electromagnetic energy. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

In another preferred embodiment of the invention, the inducible effector may be a Light Inducible Transcriptional Effector (LITE). The modularity of the LITE system allows for any number of effector domains to be employed for transcriptional modulation. In yet another preferred embodiment of the invention, the inducible effector may be a chemical. The invention also contemplates an inducible multiplex genome engineering using CRISPR (clustered regularly interspaced short palindromic repeats)/Cas systems.

Useful in the practice of the instant invention, reference is made to the article entitled BCL11A enhancer dissection by Cas9-mediated in situ saturating mutagenesis. Canver, M. C., Smith, E. C., Sher, F., Pinello, L., Sanjana, N. E., Shalem, o., Chen, D. D., Schupp, P. G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI:10.1038/nature15521, published online Sep. 16, 2015, the article is herein incorporated by reference and discussed briefly below:

Canver et al. involves novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

Self-Inactivating Systems

Once all copies of a gene in the genome of a cell have been edited, continued CRISRP/Cas9 expression in that cell is no longer necessary. Indeed, sustained expression would be undesirable in case of off-target effects at unintended genomic sites, etc. Thus time-limited expression would be useful. Inducible expression offers one approach, but in addition Applicants have engineered a Self-Inactivating CRISPR-Cas9 system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self inactivating CRISPR-Cas system includes additional RNA (i.e., guide RNA) that targets the coding sequence for the CRISPR enzyme itself or that targets one or more non-coding guide target sequences complementary to unique sequences present in one or more of the following:

(a) within the promoter driving expression of the non-coding RNA elements,
(b) within the promoter driving expression of the Cas9 gene,
(c) within 100 bp of the ATG translational start codon in the Cas9 coding sequence,
(d) within the inverted terminal repeat (iTR) of a viral delivery vector, e.g., in the AAV genome.

Furthermore, that RNA can be delivered via a vector, e.g., a separate vector or the same vector that is encoding the CRISPR complex. When provided by a separate vector, the CRISPR RNA that targets Cas expression can be administered sequentially or simultaneously. When administered sequentially, the CRISPR RNA that targets Cas expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA/chiRNA capable of hybridizing to a first target, such as a genomic locus or loci of interest and undertakes the function(s) desired of the CRISPR-Cas system (e.g., gene engineering); and subsequently the Cas enzyme may then associate with the second gRNA/chiRNA capable of hybridizing to the sequence comprising at least part of the Cas or CRISPR cassette. Where the gRNA/chiRNA targets the sequences encoding expression of the Cas protein, the enzyme becomes impeded and the system becomes self inactivating. In the same manner, CRISPR RNA that targets Cas expression applied via, for example liposome, lipofection, nanoparticles, microvesicles as explained herein, may be administered sequentially or simultaneously. Similarly, self-inactivation may be used for inactivation of one or more guide RNA used to target one or more targets.

In some aspects, a single gRNA is provided that is capable of hybridization to a sequence downstream of a CRISPR enzyme start codon, whereby after a period of time there is a loss of the CRISPR enzyme expression. In some aspects, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas system. In some aspects of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence. The first and second complexes can use the same tracr and tracr mate, thus differeing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

The first guide RNA can target any target sequence of interest within a genome, as described elsewhere herein. The second guide RNA targets a sequence within the vector which encodes the CRISPR Cas9 enzyme, and thereby inactivates the enzyme's expression from that vector. Thus the target sequence in the vector must be capable of inactivating expression. Suitable target sequences can be, for instance, near to or within the translational start codon for the Cas9 coding sequence, in a non-coding sequence in the promoter driving expression of the non-coding RNA elements, within the promoter driving expression of the Cas9 gene, within 100 bp of the ATG translational start codon in the Cas9 coding sequence, and/or within the inverted terminal repeat (iTR) of a viral delivery vector, e.g., in the AAV genome. A double stranded break near this region can induce a frame shift in the Cas9 coding sequence, causing a loss of protein expression. An alternative target sequence for the "self-inactivating" guide RNA would aim to edit/inactivate regulatory regions/sequences needed for the expression of the CRISPR-Cas9 system or for the stability of the vector. For instance, if the promoter for the Cas9 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenlyation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cas9 systems in order to provide regulation of the CRISPR-Cas9. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas9 shutdown.

In one aspect of the self-inactivating AAV-CRISPR-Cas9 system, plasmids that co-express one or more sgRNA targeting genomic sequences of interest (e.g. 1-2, 1-5, 1-10, 1-15, 1-20, 1-30) may be established with "self-inactivating" sgRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cas9 levels rise in the nucleus. Cas9 complexes with all of the sgRNAs to mediate genome editing and self-inactivation of the CRISPR-Cas9 plasmids.

One aspect of a self-inactivating CRISPR-Cas9 system is expression of singly or in tandem array format from 1 up to 4 or more different guide sequences; e.g. up to about 20 or about 30 guides sequences. Each individual self inactivating guide sequence may target a different target. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter-sgRNA(s)-Pol2 promoter-Cas9.

One aspect of a chimeric, tandem array transcript is that one or more guide(s) edit the one or more target(s) while one or more self inactivating guides inactivate the CRISPR/Cas9 system. Thus, for example, the described CRISPR-Cas9 system for repairing expansion disorders may be directly combined with the self-inactivating CRISPR-Cas9 system described herein. Such a system may, for example, have two guides directed to the target region for repair as well as at least a third guide directed to self-inactivation of the CRISPR-Cas9. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a T cell modulating agent, are used to treat or alleviate a symptom associated with an immune-related disorder or an aberrant immune response. The present invention also provides methods of treating or alleviating a symptom associated with an immune-related disorder or an aberrant immune response. A therapeutic regimen is carried out by identifying a subject, e.g., a human patient suffering from (or at risk of developing) an immune-related disorder or aberrant immune response, using standard methods. For example, T cell modulating agents are useful therapeutic tools in the treatment of cancers.

A therapeutically effective amount of a T cell modulating agent relates generally to the amount needed to achieve a therapeutic objective. The amount required to be administered will furthermore depend on the specificity of the T cell modulating agent for its specific target, and will also depend on the rate at which an administered T cell modulating agent is depleted from the free volume other subject to which it is administered. The T cell modulating agent may be administered in vivo or ex vivo as described herein.

T cell modulating agents can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement:

Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where polypeptide-based T cell modulating agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the a cardiovascular disease, and how the patient responds to the treatment. Additionally, a person having a greater risk of developing a cardiovascular disease (e.g., a person who is genetically predisposed) may receive prophylactic treatment to inhibit or delay symptoms of the disease.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a cardiovascular disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for oral, rectal, intravenous, intramuscular, subcutaneous, inhalation, nasal, topical or transdermal, vaginal, or ophthalmic administration. Thus, the medicament may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

Also envisaged herein are combination therapies, which besides administration of the isolated immune cells or cell populations as defined above further comprise administering to the subject one or more other active pharmaceutical ingredient. Said one or more other active pharmaceutical ingredient may preferably be useful in immunotherapy or adoptive immunotherapy, and/or said one or more other active pharmaceutical ingredient may be useful in the treatment of a proliferative disease, such as a tumour or cancer, or a chronic infection, such as a chronic viral infection.

In certain embodiments, the one or more other active pharmaceutical ingredient may be: an agonist of a cell molecule, such as a cell surface molecule, which when activated is capable of upregulating immune response, such as one or more of an agonist of 4-1BB, an agonist of OX40, an agonist of GITR, an agonist of STING, an agonist of TLR, or an agonist of BTLA; and/or an inhibitor of a cell molecule, such as a cell surface molecule, which when not inhibited is capable of downregulating immune response, such as a checkpoint inhibitor, or such as one or more of an antagonist of PD1, an antagonist of CTLA4, an antagonist of BTLA, an antagonist of TIGIT, an antagonist of TIM3, an antagonist of LAG3, an antagonist of VISTA, an antagonist of LILRB4, an antagonist of NRP1, an antagonist of CD160, an antagonist of CD274, or an antagonist of IDO. Regarding GITR, reference is made to Schaer D A, et al., Anti-GITR antibodies-potential clinical applications for tumor immunotherapy. Current Opinion in Investigational Drugs (London, England: 2000) [2010, 11(12):1378-1386], herein incorporated in its entirety. Regarding OX40, reference is made to Curti B D, et al., OX40 is a potent immune-stimulating target in late-stage cancer patients. Cancer Res. 2013 Dec. 15; 73(24):7189-98], herein incorporated in its entirety.

In some embodiments, the invention provides a method of activating therapeutic immunity by exploiting the blockade of immune checkpoints. The progression of a productive immune response requires that a number of immunological checkpoints be passed. Immunity response is regulated by the counterbalancing of stimulatory and inhibitory signal. The immunoglobulin superfamily occupies a central importance in this coordination of immune responses, and the CD28/cytotoxic T-lymphocyte antigen-4 (CTLA-4):B7.1/B7.2 receptor/ligand grouping represents the archetypal example of these immune regulators (see e.g., Korman A J, Peggs K S, Allison J P, "Checkpoint blockade in cancer immunotherapy." Adv Immunol. 2006; 90:297-339). In part the role of these checkpoints is to guard against the possibility of unwanted and harmful self-directed activities. While this is a necessary function, aiding in the prevention of autoimmunity, it may act as a barrier to successful immunotherapies aimed at targeting malignant self-cells that largely display the same array of surface molecules as the cells from which they derive. The expression of immune-checkpoint proteins can be dysregulated in a disease or disorder and can be an important immune resistance mechanism. Therapies aimed at overcoming these mechanisms of peripheral tolerance, in particular by blocking the inhibitory checkpoints, offer the potential to generate therapeutic activity, either as monotherapies or in synergism with other therapies.

Hence, in one embodiment, the method further comprises administration of one or more additional agents. In another embodiment, the additional agents are selected from the group consisting of: chemotherapeutic agents, anti-angiogenesis agents and agents that reduce immune-suppression. In a further embodiment, the one or more additional agents are one or more anti-glucocorticoid induced tumor necrosis factor family receptor (GITR) agonistic antibodies.

The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, an angiogenesis inhibitor, such as hydroxy angiostatin K1-3, DL-α-Difluoromethyl-ornithine, endostatin, fumagillin, genistein, minocycline, staurosporine, and thalidomide; a DNA intercaltor/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified therapeutic agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The therapeutic agent may be altretamine, amifostine, asparaginase, capecitabine, cladribine, cisapride, cytarabine, dacarbazine (DTIC), dactinomycin, dronabinol, epoetin alpha, filgrastim, fludarabine, gemcitabine, granisetron, ifosfamide, irinotecan, lansoprazole, levamisole, leucovorin, megestrol, mesna, metoclopramide, mitotane, omeprazole, ondansetron, pilocarpine, prochloroperazine, or topotecan hydrochloride. The therapeutic agent may be a monoclonal antibody such as rituximab (Rituxan®), alemtuzumab (Campath®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®), carfilzomib (Kyprolis®), Ramucirumab (Cyramza™) Cabozantinib (Cometriq™), vandetanib (Caprelsa®), Optionally, the therapeutic agent is a neoantigen. The therapeutic agent may be a cytokine such as interferons (INFs), interleukins (ILs), or hematopoietic growth factors. The therapeutic agent may be INF-α, IL-2, Aldesleukin, IL-2, Erythropoietin, Granulocyte-macrophage colony-stimulating factor (GM-CSF) or granulocyte colony-stimulating factor. The therapeutic agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). Aditionally, the therapeutic agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi). For prostate cancer treatment, a preferred chemotherapeutic agent with which anti-CTLA-4 can be combined is paclitaxel (TAXOL).

In certain embodiments, the one or more additional agents are one or more anti-glucocorticoid-induced tumor necrosis factor family receptor (GITR) agonistic antibodies. GITR is a costimulatory molecule for T lymphocytes, modulates innate and adaptive immune system and has been found to participate in a variety of immune responses and inflammatory processes. GITR was originally described by Nocentini et al. after being cloned from dexamethasone-treated murine T cell hybridomas (Nocentini et al. Proc Natl Acad Sci USA 94:6216-6221.1997). Unlike CD28 and CTLA-4, GITR has a very low basal expression on naive CD4$^+$ and CD8$^+$ T cells (Ronchetti et al. Eur J Immunol 34:613-622. 2004). The observation that GITR stimulation has immunostimulatory effects in vitro and induced autoimmunity in vivo prompted the investigation of the antitumor potency of triggering this pathway. A review of Modulation Of Ctla 4 And Gitr For Cancer Immunotherapy can be found in Cancer Immunology and Immunotherapy (Avogadri et al. Current Topics in Microbiology and Immunology 344. 2011). Other agents that can contribute to relief of immune suppression include checkpoint inhibitors targeted at another member of the CD28/CTLA4 Ig superfamily such as BTLA, LAG3, ICOS, PDL1 or KIR (Page et al, Annual Review of Medicine 65:27 (2014)). In further additional embodiments, the checkpoint inhibitor is targeted at a member of the TNFR superfamily such as CD40, OX40, CD137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

In certain embodiments, the one or more additional agents are synergistic in that they increase immunogenicity after treatment. In one embodiment the additional agent allows for lower toxicity and/or lower discomfort due to lower doses of the additional therapeutic agents or any components of the therapy described herein. In another embodiment the additional agent results in longer lifespan due to increased effectiveness of the therapy described herein. Chemotherapeutic treatments that enhance the immunological response in a patient have been reviewed (Zitvogel et al., Immunological aspects of cancer chemotherapy. Nat Rev Immunol. 2008 January; 8(1):59-73). Additionally, chemotherapeutic agents can be administered safely with immunotherapy without inhibiting vaccine specific T-cell responses (Perez et al., A new era in anticancer peptide vaccines. Cancer May 2010). In one embodiment the additional agent is administered to increase the efficacy of the therapy described herein. In one embodiment the additional agent is a chemotherapy treatment. In one embodiment low doses of chemotherapy potentiate delayed-type hypersensitivity (DTH) responses. In one embodiment the chemotherapy agent targets regulatory T-cells. In one embodiment cyclophosphamide is the therapeutic agent. In one embodiment cyclophosphamide is administered prior to treatment with a target gene or gene product modulator, e.g., an GATA3 and/or FOXO1 inhibitor. In one embodiment cyclophosphamide is administered as a single dose before treatment (Walter et al., Multipeptide immune response to cancer vaccine IMA901 after single-dose cyclophosphamide associates with longer patient survival. Nature Medicine; 18:8 2012). In another embodiment, cyclophosphamide is administered according to a metronomic program, where a daily dose is administered for one month (Ghiringhelli et al., Metronomic cyclophosphamide regimen selectively depletes $CD4^+CD25^+$ regulatory T cells and restores T and NK effector functions in end stage cancer patients. Cancer Immunol Immunother 2007 56:641-648). In another embodiment taxanes are administered before treatment to enhance T-cell and NK-cell functions (Zitvogel et al., 2008). In another embodiment a low dose of a chemotherapeutic agent is administered with the therapy described herein. In one embodiment the chemotherapeutic agent is estramustine. In one embodiment the cancer is hormone resistant prostate cancer. A ≥50% decrease in serum prostate specific antigen (PSA) was seen in 8.7% of advanced hormone refractory prostate cancer patients by personalized vaccination alone, whereas such a decrease was seen in 54% of patients when the personalized vaccination was combined with a low dose of estramustine (Itoh et al., Personalized peptide vaccines: A new therapeutic modality for cancer. Cancer Sci 2006; 97: 970-976). In another embodiment glucocorticoids are not administered with or before the therapy described herein (Zitvogel et al., 2008). In another embodiment glucocorticoids are administered after the therapy described herein. In another embodiment Gemcitabine is administered before, simultaneously, or after the therapy described herein to enhance the frequency of tumor specific CTL precursors (Zitvogel et al., 2008). In another embodiment 5-fluorouracil is administered with the therapy described herein as synergistic effects were seen with a peptide based vaccine (Zitvogel et al., 2008). In another embodiment an inhibitor of Braf, such as Vemurafenib, is used as an additional agent. Braf inhibition has been shown to be associated with an increase in melanoma antigen expression and T-cell infiltrate and a decrease in immunosuppressive cytokines in tumors of treated patients (Frederick et al., BRAF inhibition is associated with enhanced melanoma antigen expression and a more favorable tumor microenvironment in patients with metastatic melanoma. Clin Cancer Res. 2013; 19:1225-1231). In another embodiment, an inhibitor of tyrosine kinases is used as an additional agent. In one embodiment the tyrosine kinase inhibitor is used before treatment with the therapy described herein. In one embodiment the tyrosine kinase inhibitor is used simultaneously with the therapy described herein. In another embodiment the tyrosine kinase inhibitor is used to create a more immune permissive environment. In another embodiment the tyrosine kinase inhibitor is sunitinib or imatinib mesylate. It has previously been shown that favorable outcomes could be achieved with sequential administration of continuous daily dosing of sunitinib and recombinant vaccine (Farsaci et al., Consequence of dose scheduling of sunitinib on host immune response elements and vaccine combination therapy. Int J Cancer; 130: 1948-1959). Sunitinib has also been shown to reverse type-1 immune suppression using a daily dose of 50 mg/day (Finke et al., Sunitinib Reverses Type-1 Immune Suppression and Decreases T-Regulatory Cells in Renal Cell Carcinoma Patients. Clin Cancer Res 2008; 14(20)). In another embodiment additional targeted therapies are administered in combination with the therapy described herein. Doses of targeted therapies has been described previously (Alvarez, Present and future evolution of advanced breast cancer therapy. Breast Cancer Research 2010, 12(Suppl 2):S1). In another embodiment temozolomide is administered with the therapy described herein. In one embodiment temozolomide is administered at 200 mg/day for 5 days every fourth week of the therapy described herein. Results of a similar strategy have been shown to have low toxicity (Kyte et al., Telomerase Peptide Vaccination Combined with Temozolomide: A Clinical Trial in Stage IV Melanoma Patients. Clin Cancer Res; 17(13) 2011). In another embodiment the target gene or gene product modulator therapy, e.g., GATA3 and/or FOXO1 therapy is administered with an additional therapeutic agent that results in lymphopenia. In one embodiment the additional agent is temozolomide. An immune response can still be induced under these conditions (Sampson et al., Greater chemotherapy-induced lymphopenia enhances tumor-specific immune responses that eliminate EGFRvIII-expressing tumor cells in patients with glioblastoma. Neuro-Oncology 13(3):324-333, 2011).

In one embodiment the method may comprise administering the target gene or gene product modulator therapy, e.g., GATA3 and/or FOXO1 therapy within a standard of care for a particular cancer. In another embodiment the target gene or gene product modulator therapy, e.g., GATA3 and/or FOXO1 therapy is administered within a standard of care where addition of the therapy is synergistic with the steps in the standard of care.

In another aspect, the combination therapy described herein provides selecting the appropriate point to administer the target gene or gene product modulator therapy, e.g., GATA3 and/or FOXO1 therapy in relation to and within the standard of care for the cancer being treated for a patient in need thereof. The therapy can be effectively administered even within the standard of care that includes surgery, radiation, or chemotherapy. The standards of care for the most common cancers can be found on the website of National Cancer Institute (http://www.cancer.gov/cancer-topics). The standard of care is the current treatment that is accepted by medical experts as a proper treatment for a certain type of disease and that is widely used by healthcare professionals. Standard or care is also called best practice, standard medical care, and standard therapy. Standards of Care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. The therapy described herein can be incorporated within the standard of care. The therapy described herein may also be administered where the standard of care has changed due to advances in medicine.

Incorporation of the target gene or gene product modulator therapy, e.g., GATA3 and/or FOXO1 therapy described herein may depend on a treatment step in the standard of care that can lead to activation of the immune system.

Treatment steps that can activate and function synergistically with the therapy have been described herein. The therapy can be advantageously administered simultaneously or after a treatment that activates the immune system.

Incorporation of the therapy described herein may depend on a treatment step in the standard of care that causes the immune system to be suppressed. Such treatment steps may include irradiation, high doses of alkylating agents and/or methotrexate, steroids such as glucosteroids, surgery, such as to remove the lymph nodes, imatinib mesylate, high doses of TNF, and taxanes (Zitvogel et al., 2008). The target gene or gene product modulator therapy, e.g., GATA3 and/or FOXO1 therapy may be administered before such steps or may be administered after. Advantageously, the treatment is administered as part of adoptive T-cell therapy.

In one embodiment the therapy may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "minitransplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy with the therapy described herein can take advantage of this by increasing immunity after a transplant.

In one embodiment the therapy is administered to a patient in need thereof with a cancer that requires surgery. In one embodiment the combination therapy described herein is administered to a patient in need thereof in a cancer where the standard of care is primarily surgery followed by treatment to remove possible micro-metastases, such as breast cancer. Breast cancer is commonly treated by various combinations of surgery, radiation therapy, chemotherapy, and hormone therapy based on the stage and grade of the cancer. Adjuvant therapy for breast cancer is any treatment given after primary therapy to increase the chance of long-term survival. Neoadjuvant therapy is treatment given before primary therapy. Adjuvant therapy for breast cancer is any treatment given after primary therapy to increase the chance of long-term disease-free survival. Primary therapy is the main treatment used to reduce or eliminate the cancer. Primary therapy for breast cancer usually includes surgery, a mastectomy (removal of the breast) or a lumpectomy (surgery to remove the tumor and a small amount of normal tissue around it; a type of breast-conserving surgery). During either type of surgery, one or more nearby lymph nodes are also removed to see if cancer cells have spread to the lymphatic system. When a woman has breast-conserving surgery, primary therapy almost always includes radiation therapy. Even in early-stage breast cancer, cells may break away from the primary tumor and spread to other parts of the body (metastasize). Therefore, doctors give adjuvant therapy to kill any cancer cells that may have spread, even if they cannot be detected by imaging or laboratory tests.

In one embodiment the target gene or gene product modulator therapy, e.g., GATA3 and/or FOXO1 therapy is administered consistent with the standard of care for Ductal carcinoma in situ (DCIS). The standard of care for this breast cancer type is:
1. Breast-conserving surgery and radiation therapy with or without tamoxifen.
2. Total mastectomy with or without tamoxifen.
3. Breast-conserving surgery without radiation therapy.

The therapy may be administered before breast conserving surgery or total mastectomy to shrink the tumor before surgery. In another embodiment the therapy can be administered as an adjuvant therapy to remove any remaining cancer cells.

In another embodiment patients diagnosed with stage I, II, IIIA, and Operable IIIC breast cancer are treated with the therapy as described herein. The standard of care for this breast cancer type is:
1. Local-regional treatment:
   Breast-conserving therapy (lumpectomy, breast radiation, and surgical staging of the axilla).
   Modified radical mastectomy (removal of the entire breast with level I-II axillary dissection) with or without breast reconstruction.
   Sentinel node biopsy.
2. Adjuvant radiation therapy postmastectomy in axillary node-positive tumors:
   For one to three nodes: unclear role for regional radiation (infra/supraclavicular nodes, internal mammary nodes, axillary nodes, and chest wall).
   For more than four nodes or extranodal involvement: regional radiation is advised.
3. Adjuvant systemic therapy In one embodiment the therapy is administered as a neoadjuvant therapy to shrink the tumor. In another embodiment the therapy is administered as an adjuvant systemic therapy.

In another embodiment patients diagnosed with inoperable stage IIIB or IIIC or inflammatory breast cancer are treated with the therapy as described herein. The standard of care for this breast cancer type is:
1. Multimodality therapy delivered with curative intent is the standard of care for patients with clinical stage IIIB disease.
2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by postoperative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the therapy is administered as part of the various components of multimodality regimens. In another embodiment the therapy is administered before, simultaneously with, or after the multimodality regimens. In another embodiment the therapy is administered based on synergism between the modalities. In another embodiment the therapy is administered after treatment with anthracycline-based chemotherapy and/or taxane-based therapy (Zitvogel et al., 2008). The therapy may also be administered after radiation.

In another embodiment the therapy described herein is used in the treatment in a cancer where the standard of care is primarily not surgery and is primarily based on systemic treatments, such as Chronic Lymphocytic Leukemia (CLL).

In another embodiment patients diagnosed with stage I, II, III, and IV Chronic Lymphocytic Leukemia are treated with the therapy as described herein. The standard of care for this cancer type is:
1. Observation in asymptomatic or minimally affected patients
2. Rituximab
3. Ofatumomab
4. Oral alkylating agents with or without corticosteroids
5. Fludarabine, 2-chlorodeoxyadenosine, or pentostatin
6. Bendamustine
7. Lenalidomide
8. Combination chemotherapy.
    combination chemotherapy regimens include the following:
    Fludarabine plus cyclophosphamide plus rituximab.
    Fludarabine plus rituximab as seen in the CLB-9712 and CLB-9011 trials.
    Fludarabine plus cyclophosphamide versus fludarabine plus cyclophosphamide plus rituximab.
    Pentostatin plus cyclophosphamide plus rituximab as seen in the MAYO-MC0183 trial, for example.
    Ofatumumab plus fludarabine plus cyclophosphamide.
    CVP: cyclophosphamide plus vincristine plus prednisone.
    CHOP: cyclophosphamide plus doxorubicin plus vincristine plus prednisone.
    Fludarabine plus cyclophosphamide versus fludarabine as seen in the E2997 trial [NCT00003764] and the LRF-CLL4 trial, for example.
    Fludarabine plus chlorambucil as seen in the CLB-9011 trial, for example.
9. Involved-field radiation therapy.
10. Alemtuzumab
11. Bone marrow and peripheral stem cell transplantations are under clinical evaluation.
12. Ibrutinib In one embodiment the therapy is administered before, simultaneously with or after treatment with Rituximab or Ofatumomab. As these are monoclonal antibodies that target B-cells, treatment with the combination therapy may be synergistic. In another embodiment the therapy is administered after treatment with oral alkylating agents with or without corticosteroids, and Fludarabine, 2-chlorodeoxyadenosine, or pentostatin, as these treatments may negatively affect the immune system if administered before. In one embodiment bendamustine is administered with the therapy in low doses based on the results for prostate cancer described herein. In one embodiment the therapy is administered after treatment with bendamustine.

In embodiments where the present therapies would be adopted for downregulating the immune response, such therapies may be combined with one or more immunosuppressive agents. As used herein, the term "immunosuppressive agents" is meant any composition capable of suppressing the immune system, and includes analogs, hydrolysis products, metabolites, and precursors of an immunosuppressive agent unless the context precludes it. In some embodiments, immunosuppressive agents useful in the compositions and methods as disclosed herein can be selected from one of the following compounds: mycophenolic acid, cyclosporin, azathioprine, tacrolimus, cyclosporin A, FK506, rapamycin, leflunomide, deoxyspergualin, prednisone, azathioprine, mycophenolate mofetil, OKT3, ATAG or mizoribine. One example of such a composition is cyclosporine.

A further aspect thus provides a method of treating a subject in need thereof, preferably a subject in need of immunotherapy or adoptive immunotherapy, more preferably immunotherapy or adoptive immunotherapy of a proliferative disease, such as a tumour or cancer, or a chronic infection, such as a chronic viral infection, comprising: (a) providing an isolated immune cell from the subject, or isolating an immune cell from a subject; (b) modifying said isolated immune cell such as to comprise an altered expression of GATA3 and/or FOXO1, or modifying said isolated immune cell such as to comprise an agent capable of inducibly altering expression or activity of GATA3 and/or FOXO1; and (c) reintroducing the modified isolated immune cell to the subject. Further aspects provide a method of treating a subject in need thereof, comprising: (a) providing an isolated immune cell from the subject, or isolating an immune cell from a subject; (b) modifying said isolated immune cell such as to comprise an altered expression or activity of, or modifying said isolated immune cell such as to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module"; and (c) reintroducing the modified isolated immune cell to the subject.

In certain embodiments, the immune cell isolated from the subject may express GATA3 and/or FOXO1. In certain embodiments, the immune cell isolated from the subject may be dysfunctional or may not be dysfunctional. In certain embodiments, the immune cell isolated from the subject may express a signature of dysfunction as defined elsewhere in this specification.

The method may further comprise the step of expanding the isolated immune cell prior to and/or subsequent to the modification, and before reintroduction to the subject.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8$^+$ cells via intravenous infusion is appropriate.

Effective, cytotoxic amounts of the activated CD8$^+$ cells can vary between in vitro and in vivo uses, as well as with the amount and type of cells that are the ultimate target of these killer cells. The amount can also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^6$-$5\times10^7$ cells used in mice.

In one embodiment, the administration of the therapeutic composition is initiated following tumor resection. In another embodiment, administration is initiated 1-15 weeks after tumor resection. In another further embodiment, administration of the therapeutic composition is initiated 4-12 weeks after tumor resection.

The present invention features methods of treating or preventing a neoplasia comprising the steps of administering to a subject the target gene or gene modulator, e.g., a GATA3 and/or FOXO1 inhibitor, as described herein, and at least one checkpoint inhibitor. Accordingly, 1, 2, 3, 4, 5, or more checkpoint inhibitors may be administered. In certain exemplary embodiments, one checkpoint inhibitor is administered. In other exemplary embodiments, 2 checkpoint inhibitors are administered.

Page et al. (Annu. Rev. Med. 2014.65) summarizes published trials investigating checkpoint modulators in solid tumors. Mullard, A. (Nature Reviews, Drug Discovery. Vol. 12, July 2013) provides a review of checkpoint inhibitors. In one embodiment, a checkpoint inhibitor is administered at a dose of about 0.1-1 mg per 70 kg individual. According to certain exemplary embodiments, the checkpoint inhibitor is administered at a dose of about 1 mg/kg-3 mg/kg. For example, in certain exemplary embodiments, anti-CTLA4 antibody, Nivolumab isgin dosing at the standard single agent dosing level of 3 mg/kg.

A further aspect provides a method of detecting dysfunctional immune cells comprising detection of a gene expression signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14.

A related aspect provides a method of detecting dysfunctional immune cells comprising detection of a gene expression signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14. A further aspect provides a method of detecting dysfunctional immune cells comprising detection of a gene expression signature comprising one or more markers of dysfunction selected from the group consisting of NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, and LYZ2. A related aspect provides a method of detecting dysfunctional immune cells comprising detection of a gene expression signature comprising one or more markers of dysfunction selected from the group consisting of the markers listed in Table 3, part "Dysfunction_module", Table 5A or Table 5B. Preferably, the immune cell may be a T cell, more preferably a CD8$^+$ T cell.

In certain embodiments, the signature may comprise at least two markers, or at least three markers, or at least four markers, or at least five markers, or six or more markers, e.g., 7, 8, 9, 10 or more markers. In certain embodiments, the signature may consists of two markers, three markers, four markers, or five markers, e.g., 6, 7, 8, 9 or 10 markers.

In certain embodiments, the signature may comprise one or more markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4. In certain embodiments, the signature may comprise one or more markers selected from the group consisting of GATA3, FOXO1, POU2AF1, BTLA, and NRP1.

In certain embodiments, the signature may comprise two or more markers, wherein: (a) one of said two or more markers is GATA3; (b) one of said two or more markers is FOXO1; or (c) two of said two or more markers are GATA3 and FOXO1.

In certain embodiments, the signature may comprise (a) at least one transcription factor or intracellular marker; (b) at least one transcription factor or intracellular marker and at least one or at least two or at least three co-inhibitory receptors; (c) at least one transcription factor or intracellular marker and at least one or at least two or at least three co-stimulatory receptors; (d) at least one transcription factor or intracellular marker, at least one or at least two or at least three co-inhibitory receptors and at least one or at least two or at least three co-stimulatory receptors; (e) at least two transcription factors or intracellular markers and at least one or at least two or at least three co-inhibitory receptors; (f) at least two transcription factors or intracellular markers and at least one or at least two or at least three co-stimulatory receptors; (g) at least two transcription factors or intracellular markers, at least one or at least two or at least three co-inhibitory receptors and at least one or at least two or at least three co-stimulatory receptors; (h) at least three transcription factors or intracellular markers and at least one or at least two or at least three co-inhibitory receptors; (i) at least three transcription factors or intracellular markers and at least one or at least two or at least three co-stimulatory receptors; or (j) at least three transcription factors or intracellular markers, at least one or at least two or at least three co-inhibitory receptors and at least one or at least two or at least three co-stimulatory receptors.

In certain embodiments the at least one, at least two or at least three transcription factors or intracellular markers are selected from the group consisting of NOTCH2, RELB, KLF3, POU2AF1, GATA3, PIAS2, FOXO1, RARA, CRTC3, BCL6, MYB, BCL3, KDM5B, KDM4B, KDM3A, PCGF5, SPRY1, NR4A1, PNRC1, IKZF2, ZFP62, MT1, MT2, WTAP, HDAC8, UBE2D3, and BRD4. In certain embodiments the at least one, at least two or at least three transcription factors or intracellular markers are selected from the group consisting of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, and MT2.

In certain embodiments, the least one or at least two or at least three co-inhibitory receptors are selected from the group consisting of PD1, CTLA4, TIGIT, TIM3, LAG3, KLRC1, BTLA, NRP1, CD160, CD274, IDO, CD200, CD244, KLRD1, LAIR1, CEACAM1, KLRA7, FAS, GPR132, CD74, SLAMF6, CD5, GPR35, CD28, CD44, and PTGER4. In certain embodiments, the least one or at least two or at least three co-inhibitory receptors are selected from the group consisting of PD1, CTLA4, TIGIT, TIM3, LAG3, KLRC1, BTLA, NRP1, CD160, CD274, IDO, CD200, CD244, KLRD1, LAIR1, CEACAM1, and KLRA7.

In certain embodiments, the least one or at least two or at least three co-stimulatory receptors are selected from the group consisting of TNFRSF9, TNFRSF4, TNFSF4, TNFRSF18, TNFSF11, TNFRSF13C, CD27, CD28, CD86, ICOS, TNFSF14. In certain embodiments, the least one or at least two or at least three co-stimulatory receptors are selected from the group consisting of TNFRSF9, TNFRSF4, TNFSF4, TNFRSF18, TNFSF11, CD27, CD28, CD86, ICOS, TNFSF14.

Hence, in certain embodiments, the signature may comprise: (a) at least one or at least two or at least three markers selected from the marker group "A"; (b) at least one or at least two or at least three markers selected from the marker group "A" and at least one or at least two or at least three markers selected from the marker group "B"; (c) at least one or at least two or at least three markers selected from the marker group "A" and at least one or at least two or at least three markers selected from the marker group "C"; (d) at least one or at least two or at least three markers selected from the marker group "A", at least one or at least two or at least three markers selected from the marker group "B", and at least one or at least two or at least three markers selected from the marker group "C"; wherein group "A" consists of markers NOTCH2, RELB, KLF3, POU2AF1, GATA3, PIAS2, FOXO1, RARA, CRTC3, BCL6, MYB, BCL3, KDM5B, KDM4B, KDM3A, PCGF5, SPRY1, NR4A1, PNRC1, IKZF2, ZFP62, MT1, MT2, WTAP, HDAC8, UBE2D3, and BRD4, group "B" consists of markers PD1, CTLA4, TIGIT, TIM3, LAG3, KLRC1, BTLA, NRP1, CD160, CD274, IDO, CD200, CD244, KLRD1, LAIR1, CEACAM1, KLRA7, FAS, GPR132, CD74, SLAMF6, CD5, GPR35, CD28, CD44, and PTGER4, and group "C" consists of markers TNFRSF9, TNFRSF4, TNFSF4, TNFRSF18, TNFSF11, TNFRSF13C, CD27, CD28, CD86, ICOS, TNFSF14. Hence, in certain embodiments, the signature may comprise: (a) at least one or at least two or at least three markers selected from the marker group "A"; (b) at least one or at least two or at least three markers selected from the marker group "A" and at least one or at least two or at least three markers selected from the marker group "B"; (c) at least one or at least two or at least three markers selected from the marker group "A" and at least one or at least two or at least three markers selected from the marker group "C"; (d) at least one or at least two or at least three markers selected from the marker group "A", at least one or at least two or at least three markers selected from the marker group "B", and at least one or at least two or at least three markers selected from the marker group "C"; wherein group "A" consists of markers NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, and MT2, group "B" consists of markers PD1, CTLA4, TIGIT, TIM3, LAG3, KLRC1, BTLA, NRP1, CD160, CD274, IDO, CD200, CD244, KLRD1, LAIR1, CEACAM1, and KLRA7, and group "C" consists of markers TNFRSF9, TNFRSF4, TNFSF4, TNFRSF18, TNFSF11, CD27, CD28, CD86, ICOS, TNFSF14.

In certain embodiments, the signature of dysfunction as taught herein comprises:
(a) one or more markers selected from the group consisting of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62;
(b) one or more markers selected from the group consisting of BTLA, CD160, CD274, and CD200; or
(c) one or more markers selected from the group consisting of CD28, TNFSF11, ICOS, and TNFSF14.

In certain embodiments, the signature of dysfunction further comprises one or more additional markers of dysfunction. In certain embodiments, the one or more additional markers of dysfunction is selected from the group consisting of PD1, CTLA4, TIGIT, TIM3, LAG3, and KLRC1.

In certain embodiments, the signature comprises two or more markers, wherein:
(a) one of said two or more markers is GATA3;
(b) one of said two or more markers is FOXO1;
(c) one of said two or more markers is POU2AF1;
(d) one of said two or more markers is BTLA;
(e) one of said two or more markers is NRP1;
(f) one of said two or more markers is GATA3 and another one of said two or more markers is selected from the group consisting of FOXO1, POU2AF1, BTLA, NRP1, PD1, CTLA4, TIGIT, TIM3, LAG3, and KLRC1;
(g) one of said two or more markers is FOXO1 and another one of said two or more markers is selected from the group consisting of GATA3, POU2AF1, BTLA, NRP1, PD1, CTLA4, TIGIT, TIM3, LAG3, and KLRC1;
(h) one of said two or more markers is POU2AF1 and another one of said two or more markers is selected from the group consisting of GATA3, FOXO1, BTLA, NRP1, PD1, CTLA4, TIGIT, TIM3, LAG3, and KLRC1;
(i) one of said two or more markers is BTLA and another one of said two or more markers is selected from the group consisting of GATA3, FOXO1, POU2AF1, NRP1, PD1, CTLA4, TIGIT, TIM3, LAG3, and KLRC1; or
(j) one of said two or more markers is NRP1 and another one of said two or more markers of dysfunction is selected from the group consisting of GATA3, FOXO1, POU2AF1, BTLA, PD1, CTLA4, TIGIT, TIM3, LAG3, and KLRC1.

In certain embodiments, the signature comprises:
(a) at least one marker selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14, and at least one or at least two or at least three markers selected from the group consisting of PD1, CTLA4, TIGIT, TIM3, LAG3, and KLRC1;
(b) at least two markers selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14, and at least one or at least two or at least three markers selected from the group consisting of PD1, CTLA4, TIGIT, TIM3, LAG3, and KLRC1;
(c) at least three markers selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, and CACNB3, and at least one or at least two or at least three markers selected from the group consisting of PD1, CTLA4, TIGIT, TIM3, LAG3, and KLRC1;
(d) at least one marker selected from the group consisting of GATA3, FOXO1, POU2AF1, BTLA, and NRP1, and at least one or at least two or at least three markers selected from the group consisting of PD1, CTLA4, TIGIT, TIM3, LAG3, and KLRC1;

(e) at least two markers selected from the group consisting of GATA3, FOXO1, POU2AF1, BTLA, and NRP1, and at least one or at least two or at least three markers selected from the group consisting of PD1, CTLA4, TIGIT, TIM3, LAG3, and KLRC1; or
(f) at least three markers selected from the group consisting of GATA3, FOXO1, POU2AF1, BTLA, and NRP1, and at least one or at least two or at least three markers selected from the group consisting of PD1, CTLA4, TIGIT, TIM3, LAG3, and KLRC1.

In certain embodiments, the signature comprises:
(a) at least one marker selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4,MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14, and at least one or at least two or at least three markers selected from the group consisting of PD1, CTLA4, TIGIT, TIM3, LAG3, and KLRC1;
(b) at least two markers selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4,MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14, and at least one or at least two or at least three markers selected from the group consisting of PD1, CTLA4, TIGIT, TIM3, LAG3, and KLRC1;
(c) at least three markers selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, and PTGER4, and at least one or at least two or at least three markers selected from the group consisting of PD1, CTLA4, TIGIT, TIM3, LAG3, and KLRC1;

(d) at least one marker selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4 (preferably said marker being selected from the group consisting of GATA3, FOXO1, POU2AF1, BTLA, and NRP1), and at least one or at least two or at least three markers selected from the group consisting of PD1, CTLA4, TIGIT, TIM3, LAG3, and KLRC1;

(e) at least two markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4 (preferably said marker being selected from the group consisting of GATA3, FOXO1, POU2AF1, BTLA, and NRP1), and at least one or at least two or at least three markers selected from the group consisting of PD1, CTLA4, TIGIT, TIM3, LAG3, and KLRC1; or (f) at least three markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4 (preferably said marker being selected from the group consisting of GATA3, FOXO1, POU2AF1, BTLA, and NRP1), and at least one or at least two or at least three markers selected from the group consisting of PD1, CTLA4, TIGIT, TIM3, LAG3, and KLRC1.

In certain embodiments, upregulation of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, or MT2 may be indicative of dysfunction. In certain embodiments, upregulation of PD1, CTLA4, TIGIT, TIM3, LAG3, KLRC1, BTLA, NRP1, CD160, CD274, IDO, or CD200 may be indicative of dysfunction. In certain embodiments, downregulation of CD244, KLRD1, LAIR1, CEACAM1, or KLRA7 may be indicative of dysfunction. In certain embodiments, upregulation of TNFRSF9, TNFRSF4, TNFSF4, TNFRSF18, TNFSF11, CD27, CD28, CD86, ICOS, or TNFSF14 may be indicative of dysfunction.

The invention provides T cell related gene signatures for use in a variety of diagnostic and/or therapeutic indications. For example, the invention provides CD8$^+$ T cell related signatures that are useful in a variety of diagnostic and/or therapeutic indications. "Signatures" in the context of the present invention encompasses, without limitation nucleic acids, together with their polymorphisms, mutations, variants, modifications, subunits, fragments, and other analytes or sample-derived measures.

In one aspect, the genes present within the gene expression signature are modulated with an inhibitor or activator or agonist or antagonist as described herein, such that gene expression or activity of the gene is modulated. In one embodiment, any of the genes in the signature are targeted singularly or in combination. In preferred embodiments, BTLA is targeted with an agonist singularly, or BTLA is targeted with an agonist and another target selected from the gene signature is targeted by an antagonist. Not being bound by a theory, Applicants have shown the BTLA gene to be a marker for dysfunctional CD8$^+$ T cells, however it also has been shown to be a pro-survival gene involved in expanded T cells and memory cells. Not being bound by a theory, increasing expression of BTLA in CD8$^+$ T cells in combination with another gene in the gene expression signature that is a marker for a dysfunctional phenotype as described herein leads to an improved immune response. In one embodiment, the T cells are treated ex vivo as described herein. In another embodiment, NRP1 gene expression is modulated singularly or in combination with any of the genes described in the gene expression signature. In preferred embodiments, GATA3 and/or FOXO1 and/or the one or more genes or gene products selected from the group consisting of the genes or gene products listed in Table 3, part "Dysfunction_module", Table 5A or Table 5B, is treated with an antagonist in combination with an agonist of BTLA activity or expression, or GATA3 and/or FOXO1 and/or the one or more genes or gene products selected from the group consisting of the genes or gene products listed in Table 3, part "Dysfunction_module", Table 5A or Table 5B, is treated with an antagonist in immune cells stratified such as to select immune cell with comparatively higher expression of BTLA. In another preferred embodiment, GATA3 and/or FOXO1 and/or the one or more genes or gene products selected from the group consisting of the genes or gene products listed in Table 3, part "Dysfunction_module", Table 5A or Table 5B, is modulated with an antagonist in combination with an antagonist of NRP1. As NRP1 and BTLA are surface markers, antagonists or agonists may be administered directly to the surface of a T cell, in addition to or in combination with an agent that targets gene expression. In one embodiment, MT1 and/or MT2 inhibitors are used in combination with any target in the gene expression signature described herein.

In one embodiment, the therapy comprises decreasing expression or activity or function of a transcription factor or intracellular target. The transcription factor or intracellular target may be any target or combination of targets including NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, and MT2. In one embodiment, the therapy comprises decreasing function of a surface receptor or any combination of surface receptors including PD-1, Tim-3, TIGIT, Lag-3, CTLA-4, Lilrb4, NRP-1, CD160, BTLA, CD274, and IDO. In one embodiment, the therapy comprises decreasing function/expression with a small molecule targeting any combination of targets including OX-40, GITR, 4-1BB, STING, and TLR agonists. In preferred embodiments, a therapy includes any combination of inhibitors of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, and MT2, with any combination of inhibitor of PD-1, Tim-3, TIGIT, Lag-3, CTLA-4, Lilrb4, NRP-1, CD160, BTLA, CD274, and IDO, with any combination of agonist of OX-40, GITR, 4-1BB, STING, and TLR.

Accordingly, the present specification also discloses aspects set forth in the following numbered paragraphs (1') to (41'):

(1') An isolated immune cell modified to comprise an altered expression or activity of any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(2') The isolated immune cell according to (1'), wherein the immune cell is a T cell, preferably a CD8$^+$ T cell.

(3') The isolated immune cell according to any one of (1') or (2'), wherein the immune cell displays tumor specificity.

(4') The isolated immune cell according to (3'), wherein the immune cell has been isolated from a tumor of a subject, preferably wherein the immune cell is a tumor infiltrating lymphocyte.

(5') The isolated immune cell according to (3'), wherein the immune cell comprises a tumor-specific chimeric antigen receptor (CAR).

(6') The isolated immune cell according to any one of (1') to (5'), modified to comprise: (a) downregulated or abolished expression or activity of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1; (b) upregulated expression or activity of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1; or (c) each independently, downregulated or abolished expression or activity of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1, and upregulated expression or activity of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(7') The isolated immune cell according to (6'), wherein the endogenous gene of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1 has been modified, whereby the cell comprises downregulated or abolished expression or activity of said one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(8') The isolated immune cell according to (7'), wherein the endogenous gene(s) has been modified using a nuclease.

(9') The isolated immune cell according to (8'), wherein the nuclease comprises (i) a DNA-binding portion configured to specifically bind to the endogenous gene(s) and (ii) a DNA cleavage portion.

(10') The isolated immune cell according to (9'), wherein the DNA-binding portion comprises a zinc finger protein or DNA-binding domain thereof, a transcription activator-like effector (TALE) protein or DNA-binding domain thereof, or an RNA-guided protein or DNA-binding domain thereof.

(11') The isolated immune cell according to (10'), wherein the DNA-binding portion comprises (i) a Cas protein modified to eliminate its nuclease activity, or (ii) DNA-binding domain of a Cas protein.

(12') The isolated immune cell according to any one of (9') to (11'), wherein the DNA cleavage portion comprises FokI or variant thereof or DNA cleavage domain of FokI or variant thereof.

(13') The isolated immune cell according to claim 8'), wherein the nuclease is an RNA-guided nuclease, such as a Cas protein.

(14') The isolated immune cell according to (6'), wherein the cell comprises a protein comprising a DNA-binding portion configured to specifically bind to the endogenous gene(s).

(15') The isolated immune cell according to (14'), wherein: (a) the protein is a heterologous repressor protein capable of repressing the transcription of the endogenous gene(s), or (b) the protein is a heterologous activator protein capable of activating the transcription of the endogenous gene(s).

(16') The isolated immune cell according to (15'), wherein: (a) the heterologous repressor protein comprises at least a DNA-binding portion configured to specifically bind to the endogenous gene(s), preferably to the endogenous gene(s) promoter, or (b) the heterologous activator protein comprises at least a DNA-binding portion configured to specifically bind to the endogenous gene(s), preferably to the endogenous gene(s) promoter.

(17') The isolated immune cell according to any one of (15') or (16'), wherein: (a) the heterologous repressor protein comprises (i) a DNA-binding portion configured to specifically bind to the endogenous gene(s), preferably to the endogenous gene(s) promoter, and (ii) a transcription repression portion, or (b) the heterologous activator protein comprises (i) a DNA-binding portion configured to specifically bind to the endogenous gene(s), preferably to the endogenous gene(s) promoter, and (ii) a transcription activation portion.

(18') The isolated immune cell according to any one of (16') or (17'), wherein the DNA-binding portion comprises a zinc finger protein or DNA-binding domain thereof, TALE protein or DNA-binding domain thereof, or RNA-guided nuclease protein or DNA-binding domain thereof.

(19') The isolated immune cell according to any one of (16') or (17'), wherein the DNA-binding portion comprises (i) a Cas protein modified to eliminate its nuclease activity, or (ii) DNA-binding domain of a Cas protein.

(20') An isolated immune cell modified to comprise an agent capable of inducibly altering expression or activity of any one or more of, e.g., any two of or any three of, of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(21') The isolated immune cell according to (20'), wherein the agent comprises: (a) nuclease capable of modifying the endogenous gene of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1, such as to downregulate or abolish expression or activity of GATA3 or FOXO1, such as the nuclease as defined in any one of (9') to (13'); or (b) a heterologous repressor or activator protein capable of repressing or activating the transcription of the endogenous gene of any one or more of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1, such as the heterologous repressor or activator protein as defined in any one of (15') to (18').

(22') The isolated immune cell according to any one of (1') to (21'), further modified to comprise: (a) an altered expression of any one or more of PD1, CTLA4, TIGIT, TIM3, LAG3, or PD-L1; (b) an altered expression any one or more of GPR65, DEC1, PZLP, TCF4, TOSO, or CD5L; (c) an altered expression any one or more of MINA, PML, PROCR, SMARCA4, ZEB1, EGR2, CCR6, or FAS; (d) an altered expression any one or more of MINA, MYC, NKFB1, NOTCH, PML, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3; (e) an altered expression any one or more of SP4, IKZF4, or TSC22D3; (f) an altered expression any one or more of SP4, ETS2, IKZF4, TSC22D3, or IRF1; (g) an agent capable of inducibly altering expression of any one or more of GPR65, DEC1, PZLP, TCF4, TOSO, or CD5L; (h) an agent capable of inducibly altering expression of any one or more of PD1, TIGIT, TIM3, LAG3, or PD-L1; (i) an agent capable of inducibly altering expression any one or more of MINA, PML, PROCR, SMARCA4, ZEB1, EGR2, CCR6, or FAS; (j) an agent capable of inducibly altering expression any one or more of MINA, MYC, NKFB1, NOTCH, PML, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3; (k) an agent capable of inducibly altering expression any one or more of SP4, IKZF4, or TSC22D3; or (l) an agent capable of inducibly altering expression any one or more of SP4, ETS2, IKZF4, TSC22D3, or IRF1.

(23') A cell population of immune cells as defined in any one of (1') to (22').

(24') A method for generating the modified immune cell as defined in any one of (1') to (19'), the method comprising (i) providing an isolated immune cell, and (ii) modifying said isolated immune cell such as to comprise an altered expression or activity of any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(25') A method for generating the modified immune cell as defined in any one of (20') or (21'), the method comprising (i) providing an isolated immune cell, and (ii) modifying said isolated immune cell such as to comprise an agent capable of inducibly altering expression or activity of any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(26') The method according to any one of (24') or (25'), wherein the step of providing the isolated immune cell comprises providing the immune cell isolated from a subject, or isolating the immune cell from a subject.

(27') The method according to (26'), wherein the immune cell isolated from the subject expresses any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(28') The method according to (26'), wherein the immune cell isolated from the subject is dysfunctional or is not dysfunctional.

(29') The method according to (26'), wherein the immune cell isolated from the subject expresses a signature of dysfunction as defined elsewhere in this specification.

(30') The method of any one of (24') to (29'), further comprising the step of expanding the isolated immune cell prior to and/or subsequent to the modification.

(31') A pharmaceutical composition comprising the isolated immune cell according to any one of (1') to (22'), or the cell population according to (23').

(32') The isolated immune cell according to any one of (1') to (22'), or the cell population according to (23'), for use in therapy.

(33') The isolated immune cell according to any one of (1') to (22'), or the cell population according to (23'), for use in immunotherapy or adoptive immunotherapy, preferably immunotherapy or adoptive immunotherapy of a proliferative disease, such as a tumor or cancer, or a chronic infection, such as a chronic viral infection.

(34') The isolated immune cell or cell population for use according to (33') in a subject, wherein the subject has been determined to comprise immune cells which:
 express any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1;
 are dysfunctional, or are not dysfunctional; or
 express a signature of dysfunction as defined elsewhere in this specification.

(35') A method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising administering to said subject the isolated immune cell according to any one of (1') to (22'), or the cell population according to (23').

(36') The method according to (35'), further comprising administering to said subject one or more other active pharmaceutical ingredient, preferably wherein said one or more other active pharmaceutical ingredient is useful in immunotherapy or adoptive immunotherapy, or wherein said one or more other active pharmaceutical ingredient is useful in the treatment of a proliferative disease, such as a tumor or cancer, or a chronic infection, such as a chronic viral infection.

(37') The method according to (36'), wherein the one or more other active pharmaceutical ingredient is: (a) an agonist of a cell molecule, such as a cell surface molecule, which when activated is capable of upregulating immune response, such as one or more of an agonist of 4-1BB, an agonist of OX40, an agonist of GITR, an agonist of STING or an agonist of TLR; and/or (b) an inhibitor of a cell molecule, such as a cell surface molecule, which when not inhibited is capable of downregulating immune response, such as a checkpoint inhibitor, or such as one or more of an antagonist of PD1, an antagonist of CTLA4, an antagonist of TIGIT, an antagonist of TIM3, an antagonist of LAG3, an antagonist of VISTA, an antagonist of LILRB4, an antagonist of CD160, an antagonist of CD274, or an antagonist of IDO.

(38') The method according to any one of (35') to (37'), wherein the subject has been determined to comprise immune cells which:

express any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1;
are dysfunctional or are not dysfunctional; or
express a signature of dysfunction as defined elsewhere in this specification.

(39') A method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising: (a) providing an isolated immune cell from the subject, or isolating an immune cell from a subject; (b) modifying said isolated immune cell such as to comprise an altered expression or activity of any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1, or modifying said isolated immune cell such as to comprise an agent capable of inducibly altering expression or activity of any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1; and (c) reintroducing the modified isolated immune cell to the subject.

(40') The method according to (39'), wherein the immune cell isolated from the subject: (a) expresses any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1; (b) is dysfunctional or is not dysfunctional; or (c) expresses a signature of dysfunction as defined elsewhere in this specification.

(41') The method of any one of (39') or (40'), further comprising the step of expanding the isolated immune cell prior to and/or subsequent to the modification, and before reintroduction to the subject.

Further, the present specification also discloses aspects set forth in the following numbered paragraphs (1*) to (41*):

(1*) An isolated immune cell modified to comprise an altered expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

(2*) The isolated immune cell according to (1*), wherein the immune cell is a T cell, preferably a CD8$^+$ T cell.

(3*) The isolated immune cell according to any one of (1*) or (2*), wherein the immune cell displays tumor specificity.

(4*) The isolated immune cell according to (3*), wherein the immune cell has been isolated from a tumor of a subject, preferably wherein the immune cell is a tumor infiltrating lymphocyte.

(5*) The isolated immune cell according to (3*), wherein the immune cell comprises a tumor-specific chimeric antigen receptor (CAR).

(6*) The isolated immune cell according to any one of (1*) to (5*), modified to comprise downregulated or abolished expression or activity of said one or more genes or gene products, or upregulated expression or activity of said one or more genes or gene products; for example to comprise downregulated or abolished expression or activity of said one or more genes selected from the group consisting of the genes or gene products listed in Table 3, part "Dysfunction_module", Table 5A or Table 5B and/or upregulated expression or activity of said one or more genes selected from the group consisting of the genes or gene products listed in Table 3, part "Activation_module"; or for example for example to comprise upregulated expression or activity of said one or more genes selected from the group consisting of the genes or gene products listed in Table 3, part "Dysfunction_module", Table 5A or Table 5B and/or downregulated or abolished expression or activity of said one or more genes selected from the group consisting of the genes or gene products listed in Table 3, part "Activation_module".

(7*) The isolated immune cell according to (6*), wherein the endogenous gene of said one or more genes has been modified.

(8*) The isolated immune cell according to (7*), wherein the endogenous gene(s) has been modified using a nuclease.

(9*) The isolated immune cell according to (8*), wherein the nuclease comprises (i) a DNA-binding portion configured to specifically bind to the endogenous gene(s) and (ii) a DNA cleavage portion.

(10*) The isolated immune cell according to (9*), wherein the DNA-binding portion comprises a zinc finger protein or DNA-binding domain thereof, a transcription activator-like effector (TALE) protein or DNA-binding domain thereof, or an RNA-guided protein or DNA-binding domain thereof.

(11*) The isolated immune cell according to (10*), wherein the DNA-binding portion comprises (i) a Cas protein modified to eliminate its nuclease activity, or (ii) DNA-binding domain of a Cas protein.

(12*) The isolated immune cell according to any one of (9*) to (11*), wherein the DNA cleavage portion comprises FokI or variant thereof or DNA cleavage domain of FokI or variant thereof.

(13*) The isolated immune cell according to claim 8*), wherein the nuclease is an RNA-guided nuclease, such as a Cas protein.

(14*) The isolated immune cell according to (6*), wherein the cell comprises a protein comprising a DNA-binding portion configured to specifically bind to the endogenous gene(s).

(15*) The isolated immune cell according to (14*), wherein: (a) the protein is a heterologous repressor protein capable of repressing the transcription of the endogenous gene(s), or (b) the protein is a heterologous activator protein capable of activating the transcription of the endogenous gene(s).

(16*) The isolated immune cell according to (15*), wherein: (a) the heterologous repressor protein comprises at least a DNA-binding portion configured to specifically bind to the endogenous gene(s), preferably to the endogenous gene(s) promoter, or (b) the heterologous activator protein comprises at least a DNA-binding portion configured to specifically bind to the endogenous gene(s), preferably to the endogenous gene(s) promoter.

(17*) The isolated immune cell according to any one of (15*) or (16*), wherein: (a) the heterologous repressor protein comprises (i) a DNA-binding portion configured to specifically bind to the endogenous gene(s), preferably to the endogenous gene(s) promoter, and (ii) a transcription repression portion, or (b) the heterologous activator protein comprises (i) a DNA-binding portion configured to specifically bind to the endogenous gene(s), preferably to the endogenous gene(s) promoter, and (ii) a transcription activation portion.

(18*) The isolated immune cell according to any one of (16*) or (17*), wherein the DNA-binding portion comprises a zinc finger protein or DNA-binding domain thereof, TALE protein or DNA-binding domain thereof, or RNA-guided nuclease protein or DNA-binding domain thereof.

(19*) The isolated immune cell according to any one of (16*) or (17*), wherein the DNA-binding portion comprises (i) a Cas protein modified to eliminate its nuclease activity, or (ii) DNA-binding domain of a Cas protein.

(20*) An isolated immune cell modified to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

(21*) The isolated immune cell according to (20*), wherein the agent comprises: (a) nuclease capable of modifying the endogenous gene of said one or more genes; or (b) a heterologous repressor or activator protein capable of repressing or activating the transcription of the endogenous gene of said one or more genes.

(22*) The isolated immune cell according to any one of (1*) to (21*), further modified to comprise: an altered expression or activity of any one or more of GATA3, FOXO1, POU2AF1, BTLA, or NRP1; (a) an altered expression or activity of any one or more of PD1, CTLA4, TIGIT, TIM3, LAG3, or PD-L1; (b) an altered expression or activity of any one or more of GATA3, FOXO1, POU2AF1, BTLA, NRP1, PD1, CTLA4, TIGIT, TIM3, LAG3, or PD-L1; (c) an altered expression or activity of any one or more of GPR65, DEC1, PZLP, TCF4, TOSO, or CD5L; (d) an altered expression or activity of any one or more of MINA, PML, POU2AF1, PROCR, SMARCA4, ZEB1, EGR2, CCR6, or FAS; (e) an altered expression or activity of any one or more of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3; (f) an altered expression or activity of any one or more of SP4, IKZF4, or TSC22D3; (g) an altered expression or activity of any one or more of SP4, ETS2, IKZF4, TSC22D3, or IRF1; (h) an altered expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA; (i) an altered expression or activity of any one or more of C1QTNF6 or_PROS1; (j) an agent capable of inducibly altering expression or activity of any one or more of GPR65, DEC1, PZLP, TCF4, TOSO, or CD5L; (k) an agent capable of inducibly altering expression or activity of any one or more of GATA3, FOXO1, POU2AF1, BTLA, or NRP1; (l) an agent capable of inducibly altering expression or activity of PD1, CTLA4, TIGIT, TIM3, LAG3, or PD-L1; (m) an agent capable of inducibly altering expression or activity of GATA3, FOXO1, POU2AF1, BTLA, NRP1, PD1, CTLA4, TIGIT, TIM3, LAG3, or PD-L1; (n) an agent capable of inducibly altering expression or activity of any one or more of MINA, PML, POU2AF1, PROCR, SMARCA4, ZEB1, EGR2, CCR6, or FAS; (o) an agent capable of inducibly altering expression or activity of any one or more of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3; (q) an agent capable of inducibly altering expression or activity of any one or more of SP4, IKZF4, or TSC22D3; (r) an agent capable of inducibly altering expression or activity of any one or more of SP4, ETS2, IKZF4, TSC22D3, or IRF1; (s) an agent capable of inducibly altering expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA; or (t) an agent capable of inducibly altering expression or activity of any one or more of C1QTNF6 or PROS1.

(23*) A cell population of immune cells as defined in any one of (1*) to (22*).

(24*) A method for generating the modified immune cell as defined in any one of (1*) to (19*), the method comprising (i) providing an isolated immune cell, and (ii) modifying said isolated immune cell such as to comprise an altered expression or activity of any one or more of, e.g., any two of or any three of, NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62, MT1, MT2, BTLA, or NRP1.

(25*) A method for generating the modified immune cell as defined in any one of (20*) or (21*), the method comprising (i) providing an isolated immune cell, and (ii) modifying said isolated immune cell such as to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

(26*) The method according to any one of (24*) or (25*), wherein the step of providing the isolated immune cell comprises providing the immune cell isolated from a subject, or isolating the immune cell from a subject.

(27*) The method according to (26*), wherein the immune cell isolated from the subject expresses: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module".

(28*) The method according to (26*), wherein the immune cell isolated from the subject is dysfunctional or is not dysfunctional.

(29*) The method according to (26*), wherein the immune cell isolated from the subject expresses a signature of dysfunction as defined elsewhere in this specification.

(30*) The method of any one of (24*) to (29*), further comprising the step of expanding the isolated immune cell prior to and/or subsequent to the modification.

(31*) A pharmaceutical composition comprising the isolated immune cell according to any one of (1*) to (22*), or the cell population according to (23*).

(32*) The isolated immune cell according to any one of (1*) to (22*), or the cell population according to (23*), for use in therapy.

(33*) The isolated immune cell according to any one of (1*) to (22*), or the cell population according to (23*), for use in immunotherapy or adoptive immunotherapy, preferably immunotherapy or adoptive immunotherapy of a proliferative disease, such as a tumor or cancer, or a chronic infection, such as a chronic viral infection.

(34*) The isolated immune cell or cell population for use according to (33*) in a subject, wherein the subject has been determined to comprise immune cells which:
express: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_ module";
are dysfunctional, or are not dysfunctional; or
express a signature of dysfunction as defined elsewhere in this specification.

(35*) A method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising administering to said subject the isolated immune cell according to any one of (1*) to (22*), or the cell population according to (23*).

(36*) The method according to (35*), further comprising administering to said subject one or more other active pharmaceutical ingredient, preferably wherein said one or more other active pharmaceutical ingredient is useful in immunotherapy or adoptive immunotherapy, or wherein said one or more other active pharmaceutical ingredient is useful in the treatment of a proliferative disease, such as a tumor or cancer, or a chronic infection, such as a chronic viral infection.

(37*) The method according to (36*), wherein the one or more other active pharmaceutical ingredient is: (a) an agonist of a cell molecule, such as a cell surface molecule, which when activated is capable of upregulating immune response, such as one or more of an agonist of 4-1BB, an agonist of OX40, an agonist of GITR, an agonist of STING or an agonist of TLR; and/or (b) an inhibitor of a cell molecule, such as a cell surface molecule, which when not inhibited is capable of downregulating immune response, such as a checkpoint inhibitor, or such as one or more of an antagonist of PD1, an antagonist of CTLA4, an antagonist of TIGIT, an antagonist of TIM3, an antagonist of LAG3, an antagonist of VISTA, an antagonist of LILRB4, an antagonist of CD160, an antagonist of CD274, or an antagonist of IDO.

(38*) The method according to any one of (35*) to (37*), wherein the subject has been determined to comprise immune cells which:
express: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_ module";
are dysfunctional or are not dysfunctional; or
express a signature of dysfunction as defined elsewhere in this specification.

(39*) A method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising: (a) providing an isolated immune cell from the subject, or isolating an immune cell from a subject; (b) modifying said isolated immune cell such as to comprise an altered expression or activity of, or modifying said isolated immune cell such as to comprise an agent capable of inducibly altering expression or activity of: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/ Activation Module"; and/or iv) one or more genes or gene products selected from the group consisting of the genes or gene products listed in Table 3, part "Näive/Memory_like_ module".

(40*) The method according to (39*), wherein the immune cell isolated from the subject: (a) expresses: i) one or more genes or gene products selected from the group consisting of the genes or gene products listed in Table 3, part "Dysfunction_module", Table 5A or Table 5B; ii) one or more genes or gene products selected from the group consisting of the genes or gene products listed in Table 3, part "Activation_module"; iii) one or more genes or gene products selected from the group consisting of the genes or gene products listed in Table 3, part "Dysfunction/Activation Module"; and/or iv) one or more genes or gene products selected from the group consisting of the genes or gene products listed in Table 3, part "Näive/Memory_like_module"; (b) is dysfunctional or is not dysfunctional; or (c) expresses a signature of dysfunction as defined elsewhere in this specification.

(41*) The method of any one of (39*) or (40*), further comprising the step of expanding the isolated immune cell prior to and/or subsequent to the modification, and before reintroduction to the subject.

Another aspect provides a kit of parts comprising means for detection of the above signature of immune cell dysfunction. In an aspect, the invention provides kits containing any one or more of the elements discussed herein to allow administration of the therapy. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more delivery or storage buffers. Reagents may be provided in a form that is usable in a particular process, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more of the vectors, proteins and/or one or more of the polynucleotides described herein. The kit may advantageously allow the provision of all elements of the systems of the invention. Kits can involve vector(s) and/or particle(s) and/or nanoparticle(s) containing or encoding RNA(s) to be administered to an animal, mammal, primate, rodent, etc., with such a kit including instructions for administering to such a eukaryote; and such a kit can optionally include any of the anti-cancer agents described herein. The kit may include any of the components above (e.g. vector(s) and/or particle(s) and/or nanoparticle(s) containing or encoding RNA(s) and/or proteins and/or checkpoint inhibitors) as well as instructions for use with any of the methods of the present invention.

In another aspect, the invention provides kits containing any one or more of the elements discussed herein to allow detection of the gene expression signature. The kits may include antibodies, microarrays, PCR primers, sequencing primers. The kit may also include all buffers and enzymes useful in the detection method, with such a kit including instructions.

The present invention also comprises a kit with a detection reagent that binds to one or more signature nucleic acids. Also provided by the invention is an array of detection reagents, e.g., oligonucleotides that can bind to one or more signature nucleic acids. Suitable detection reagents include nucleic acids that specifically identify one or more signature nucleic acids by having homologous nucleic acid sequences, such as oligonucleotide sequences, complementary to a portion of the signature nucleic acids packaged together in the form of a kit. The oligonucleotides can be fragments of the signature genes. For example the oligonucleotides can be 200, 150, 100, 50, 25, 10 or fewer nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or DNA chips or a sandwich ELISA or any other method as known in the art. Alternatively, the kit contains a nucleic acid substrate array comprising one or more nucleic acid sequences.

A further aspect provides a method for determining whether or not an immune cell has a dysfunctional immune phenotype and/or whether or not an immune cell would benefit from upregulation of an immune response, said method comprising: (a) determining in said immune cell the expression of GATA3 and/or FOXO1, whereby expression of GATA3 and/or FOXO1 indicates that the immune cell has a dysfunctional immune phenotype and/or would benefit from upregulation of an immune response; or (b) determining in said immune cell the expression of the above signature of immune cell dysfunction, whereby expression of the signature indicates that the immune cell has a dysfunctional immune phenotype and/or would benefit from upregulation of an immune response.

Another aspect provides a method for determining whether or not a patient would benefit from a therapy aimed at reducing dysfunction of immune cells or a therapy aimed at upregulating of an immune response, the method comprising: (a) determining, in immune cells from said patient the expression of GATA3 and/or FOXO1, whereby expression of GATA3 and/or FOXO1 indicates that the patient will benefit from the therapy; or (b) determining, in immune cells from said patient the expression of the above signature of immune cell dysfunction, whereby expression of the signature indicates the patient will benefit from the therapy.

In certain embodiments, the therapy may comprise treatment with the isolated immune cells or cell populations as described elsewhere in this specification.

In certain embodiments, the therapy may comprise treatment with one or more checkpoint inhibitors.

A further aspect provides a method for determining the efficacy of a treatment of a patient with a therapy, particularly immune therapy, more particularly therapy or immune therapy aimed at reducing dysfunction of immune cells or a therapy aimed at upregulating of an immune response, said method comprising: (a) determining in immune cells from said patient the expression of GATA3 and/or FOXO1 before and after said treatment and determining the efficacy of said therapy based thereon, whereby unchanged or increased expression of GATA3 and/or FOXO1 indicates that the treatment should be adjusted; or (b) determining in immune cells from said patient the expression of the above signature of immune cell dysfunction before and after said treatment and determining the efficacy of said therapy based thereon, whereby unchanged or increased expression of the signature indicates that the treatment should be adjusted.

In certain embodiments, the therapy may comprise treatment with the isolated immune cells or cell populations as described elsewhere in this specification.

In certain embodiments, the therapy may comprise: (a) activation of one or more cell molecules, such as cell surface molecules, which when activated are capable of upregulating immune response, such as activation of one or more of 4-1BB, OX40, GITR, STING or TLR; and/or (b) inhibition of one or more cell molecules, such as cell surface molecules, which when not inhibited are capable of downregulating immune response, such as treatment with one or more checkpoint inhibitors, or such as treatment with one or more of an antagonist of PD1, an antagonist of CTLA4, an antagonist of BTLA, an antagonist of TIGIT, an antagonist of TIM3, an antagonist of LAG3, an antagonist of VISTA, an antagonist of LILRB4, an antagonist of NRP1, an antagonist of CD160, an antagonist of CD274, or an antagonist of IDO.

A further aspect provides a method for determining the suitability of a compound as a checkpoint inhibitor, said method comprising: (a) contacting an immune cell expressing GATA3 and/or FOXO1 with said compound and determining whether or not said compound can affect the expression of GATA3 and/or FOXO1 by said cell, whereby decreased expression indicates that the compound is suitable as a checkpoint inhibitor; or (b) contacting an immune cell expressing the above signature of immune cell dysfunction with said compound and determining whether or not said compound can affect the expression of the signature by said cell, whereby decreased expression indicates that the compound is suitable as a checkpoint inhibitor.

Another aspect provides a method for determining the suitability of a compound for reducing a dysfunctional immune phenotype and/or upregulating of an immune response, said method comprising: (a) contacting an immune cell expressing GATA3 and/or FOXO1 with said compound and determining whether or not said compound can affect the expression of GATA3 and/or FOXO1 by said cell, whereby decreased expression indicates that the compound is suitable for reducing dysfunctional immune phenotype and/or upregulating of an immune response; or (b) contacting an immune cell expressing the above signature of immune cell dysfunction with said compound and determining whether or not said compound can affect the expression of the signature by said cell, whereby decreased expression indicates that the compound is suitable for reducing dysfunctional immune phenotype and/or upregulating of an immune response.

A further aspect provides a method for stratification of immune cells into one or more cell populations comprising at least a first cell population having a comparatively more dysfunctional immune phenotype and a second population having a comparatively less dysfunctional immune phenotype, comprising: (a) determining in said immune cells the expression of GATA3 and/or FOXO1, and allotting cells having no or comparatively lower expression of GATA3 and/or FOXO1 into said second population, and cells having comparatively higher expression of GATA3 and/or FOXO1 into said first population; or determining in said immune cells the expression of the above signature of immune cell dysfunction, and allotting cells having no or comparatively lower expression of said signature into said second population, and cells having comparatively higher expression of said signature into said first population.

The above stratification process may allow to select for comparatively less dysfunctional immune cells. Such comparatively less dysfunctional immune cells may be particularly suitable for adoptive cell therapy, with or without further alteration of GATA3 and/or FOXO1 expression as taught herein. Alternatively, the above stratification process may allow to select for comparatively more dysfunctional immune cells. Such comparatively more dysfunctional immune cells may particularly benefit from alteration of GATA3 and/or FOXO1 expression as taught herein. Where the stratification process relies on determination of an intracellularly localised polypeptide, such polypeptide may be preferably determined by detecting a surrogate cell surface polypeptide, i.e., a polypeptide, the expression of which on the surface of the cells depends on (e.g., is controlled or regulated by) the expression of the intracellularly localised polypeptide.

Further, the present specification also discloses aspects set forth in the following numbered paragraphs (1#) to (39#):

(1#) A method of detecting dysfunctional immune cells comprising detection of a gene expression signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14.

(2#) The method according to (1#), wherein the signature comprises one or more markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4.

(3#) The method according to (1#), wherein the signature comprises:
 (a) one or more markers selected from the group consisting of NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, ZFP62;
 (b) one or more markers selected from the group consisting of BTLA, CD160, CD274, and CD200; or
 (c) one or more markers selected from the group consisting of CD28, TNFSF11, ICOS, and TNFSF14.

(4#) The method according to any one of (1#) to (3#), wherein the signature further comprises one or more additional markers of dysfunction.

(5#) The method according to (4#), wherein the one or more additional markers of dysfunction is selected from the group consisting of PD1, CTLA4, TIGIT, TIM3, LAG3, and KLRC1.

(6#) The method according to any one of (1#) to (5#), wherein the signature comprises at least two markers, or at least three markers, or at least four markers, or at least five markers, or six or more markers, such as wherein the signature consists of two markers, three markers, four markers, or five markers.

(7#) The method according to any one of (1#) to (6#), wherein the signature comprises two or more markers, and wherein:
  (a) one of said two or more markers is GATA3;
  (b) one of said two or more markers is FOXO1;
  (c) one of said two or more markers is POU2AF1;
  (d) one of said two or more markers is BTLA;
  (e) one of said two or more markers is NRP1;
  (f) one of said two or more markers is GATA3 and another one of said two or more markers is selected from the group consisting of FOXO1, POU2AF1, BTLA, NRP1, PD1, CTLA4, TIGIT, TIM3, LAG3, and KLRC1;
  (g) one of said two or more markers is FOXO1 and another one of said two or more markers is selected from the group consisting of GATA3, POU2AF1, BTLA, NRP1, PD1, CTLA4, TIGIT, TIM3, LAG3, and KLRC1;
  (h) one of said two or more markers is POU2AF1 and another one of said two or more markers is selected from the group consisting of GATA3, FOXO1, BTLA, NRP1, PD1, CTLA4, TIGIT, TIM3, LAG3, and KLRC1;
  (i) one of said two or more markers is BTLA and another one of said two or more markers is selected from the group consisting of GATA3, FOXO1, POU2AF1, NRP1, PD1, CTLA4, TIGIT, TIM3, LAG3, and KLRC1; or
  (j) one of said two or more markers is NRP1 and another one of said two or more markers of dysfunction is selected from the group consisting of GATA3, FOXO1, POU2AF1, BTLA, PD1, CTLA4, TIGIT, TIM3, LAG3, and KLRC1.

(8#) The method according to any one of (1#) to (6#), wherein the signature comprises:
  (a) at least one marker selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4,MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14, and at least one or at least two or at least three markers selected from the group consisting of PD1, CTLA4, TIGIT, TIM3, LAG3, and KLRC1;
  (b) at least two markers selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4,MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14, and at least one or at least two or at least three markers selected from the group consisting of PD1, CTLA4, TIGIT, TIM3, LAG3, and KLRC1;
(c) at least three markers selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, and PTGER4, and at least one or at least two or at least three markers selected from the group consisting of PD1, CTLA4, TIGIT, TIM3, LAG3, and KLRC1;
(d) at least one marker selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4 (preferably said marker being selected from the group consisting of GATA3, FOXO1, POU2AF1, BTLA, and NRP1), and at least one or at least two or at least three markers selected from the group consisting of PD1, CTLA4, TIGIT, TIM3, LAG3, and KLRC1;
(e) at least two markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4 (preferably said marker being selected from the group consisting of GATA3, FOXO1, POU2AF1, BTLA, and NRP1), and at least one or at least two or at least three markers selected from the group consisting of PD1, CTLA4, TIGIT, TIM3, LAG3, and KLRC1;
(f) at least three markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4 (preferably said marker being selected from the group consisting of GATA3, FOXO1, POU2AF1, BTLA, and NRP1), and at least one or at least two or at least three markers selected from the group consisting of PD1, CTLA4, TIGIT, TIM3, LAG3, and KLRC1.

(9#) A method for determining whether or not an immune cell has a dysfunctional immune phenotype and/or whether or not an immune cell would benefit from upregulation of an immune response, said method comprising determining in said immune cell the expression of the signature of dysfunction as defined in any one of (1#) to (8#), whereby expression of the signature indicates that the immune cell has a dysfunctional immune phenotype and/or would benefit from upregulation of an immune response.

(10#) A method for determining whether or not a patient would benefit from a therapy aimed at reducing dysfunction of immune cells or a therapy aimed at upregulating of an immune response, the method comprising determining, in immune cells from said patient the expression of the signature of dysfunction as defined in any one of (1#) to (8#), whereby expression of the signature indicates the patient will benefit from the therapy.

(11#) The method according to (104 wherein the therapy comprises treatment with one or more checkpoint inhibitors.

(12#) A method for determining the efficacy of a treatment of a patient with a therapy, particularly immune therapy, more particularly therapy or immune therapy aimed at reducing dysfunction of immune cells or a therapy aimed at upregulating of an immune response, said method comprising determining in immune cells from said patient the expression of the signature of dysfunction as defined in any one of (1#) to (8#) before and after said treatment and determining the efficacy of said therapy based thereon, whereby unchanged or increased expression of the signature indicates that the treatment should be adjusted.

(13#) The method according to (12#), wherein the therapy comprises:
(a) activation of one or more cell surface molecules which when activated are capable of upregulating immune response, such as activation of one or more of 4-1BB, OX40, GITR, STING or TLR; and/or
(b) inhibition of one or more cell surface molecules which when not inhibited are capable of downregulating immune response, such as treatment with one or more checkpoint inhibitors, such as one or more checkpoint inhibitors selected from the group consisting of an antagonist of PD1, an antagonist of CTLA4, an antagonist of BTLA, an antagonist of TIGIT, an antagonist of TIM3, an antagonist of LAG3, and an antagonist of VISTA.

(14#) A method for determining the suitability of a compound as a checkpoint inhibitor, said method comprising contacting an immune cell expressing the signature of dysfunction as defined in any one of (1#) to (8#) with said compound and determining whether or not said compound can affect the expression of the signature by said cell, whereby decreased expression indicates that the compound is suitable as a checkpoint inhibitor.

(15#) A method for determining the suitability of a compound for reducing a dysfunctional immune phenotype and/or upregulating of an immune response, said method comprising contacting an immune cell expressing the signature of dysfunction as defined in any one of (1#) to (8#) with said compound and determining whether or not said compound can affect the expression of the signature by said cell, whereby decreased expression indicates that the compound is suitable for reducing dysfunctional immune phenotype and/or upregulating of an immune response.

(16#) A method of detecting activated immune cells comprising detection of a gene expression signature comprising one or more markers of activation selected from the group consisting of TMCO1, PRMT5, EXOC4, TYR, HDHD2, RCN1, LMNB2, TCTEX1D2, VMA21, HCFC2, MRPS27, DUSP19, CD200R4, SRSF10, NAP1L4, ZADH2, ERGIC1, STARD3NL, RCC1, CD38, ZFP142, METTL10, MOGS, S100PBP, AREG, 1700052N19RIK, NDUFA13, RFT1, TAF12, ELP2, TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BCO26590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127 and KPNB1.

(17#) The method according to (16#), wherein the signature comprises one or more markers selected from the group consisting of METTL3 and MINA.

(18#) The method according to (16#) or (17#), wherein the signature further comprises one or more additional markers.

(19#) The method according to (18#), wherein the one or more additional markers is selected from the group consisting of PD1, CTLA4, TIGIT, TIM3, LAG3, and KLRC1.

(20#) The method according to any one of (16#) to (19#), wherein the signature comprises:
(a) at least one marker selected from the group consisting of TMCO1, PRMT5, EXOC4, TYR, HDHD2, RCN1, LMNB2, TCTEX1D2, VMA21, HCFC2, MRPS27, DUSP19, CD200R4, SRSF 10, NAP1L4, ZADH2, ERGIC1, STARD3NL, RCC1, CD38, ZFP142, METTL10, MOGS, S100PBP, AREG, 1700052N19RIK, NDUFA13, RFT1, TAF12, ELP2, TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BCO26590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127 and KPNB1, and at least one or at least two or at least three markers selected from the group consisting of PD1, CTLA4, TIGIT, TIM3, LAG3, and KLRC1;
(b) at least two markers selected from the group consisting of TMCO1, PRMT5, EXOC4, TYR, HDHD2, RCN1, LMNB2, TCTEX1D2, VMA21, HCFC2, MRPS27, DUSP19, CD200R4, SRSF 10, NAP1L4, ZADH2, ERGIC1, STARD3NL, RCC1, CD38, ZFP142, METTL10, MOGS, S100PBP, AREG, 1700052N19RIK, NDUFA13, RFT1, TAF12, ELP2, TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BCO26590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127 and KPNB1, and at least one or at least two or at least three markers selected from the group consisting of PD1, CTLA4, TIGIT, TIM3, LAG3, and KLRC1; or (c) at least three markers selected from the group consisting of TMCO1, PRMT5, EXOC4, TYR, HDHD2, RCN1, LMNB2, TCTEX1D2, VMA21, HCFC2, MRPS27, DUSP19, CD200R4, SRSF 10, NAP1L4, ZADH2, ERGIC1, STARD3NL, RCC1, CD38, ZFP142, METTL10, MOGS, S100PBP, AREG, 1700052N19RIK, NDUFA13, RFT1, TAF12, ELP2, TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BCO26590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127 and KPNB1, and at least one or at least two or at least three markers selected from the group consisting of PD1, CTLA4, TIM3, LAG3, and KLRC1.

(21#) The method according to any one of (16#) to (20#), wherein the signature comprises at least two markers, or at least three markers, or at least four markers, or at least five markers, or six or more markers, such as wherein the signature consists of two markers, three markers, four markers, or five markers.

(22#) A method of detecting dysfunctional and/or activated immune cells comprising detection of a gene expression signature comprising one or more markers selected from the group consisting of SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, and TOPBP1.

(23#) The method according to (22#), wherein the signature comprises one or more markers selected from the group consisting of C1QTNF6, PROS1, TNFRSF4 and TNFRSF9.

(24#) The method according to (22#) or (23#), wherein the signature further comprises one or more additional markers.

(25#) The method according to (24#), wherein the one or more additional markers is selected from the group consisting of PD1, CTLA4, TIGIT, TIM3, LAG3, and KLRC1.

(26#) The method according to any one of (22#) to (25#), wherein the signature comprises:

(a) at least one marker selected from the group consisting of SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, and TOPBP1, and at least one or at least two or at least three markers selected from the group consisting of PD1, CTLA4, TIGIT, TIM3, LAG3, and KLRC1;

(b) at least two markers selected from the group consisting of SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, and TOPBP1, and at least one or at least two or at least three markers selected from the group consisting of PD1, CTLA4, TIGIT, TIM3, LAG3, and KLRC1; or (c) at least three markers selected from the group consisting of SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, and TOPBP1, and at least one or at least two or at least three markers selected from the group consisting of PD1, CTLA4, TIGIT, TIM3, LAG3, and KLRC1.

(27#) The method according to any one of (22#) to (26#), wherein the signature comprises at least two markers, or at least three markers, or at least four markers, or at least five markers, or six or more markers, such as wherein the signature consists of two markers, three markers, four markers, or five markers.

(28#) A method of detecting naïve-memory-like immune cells comprising detecting of a gene expression signature comprising one or more markers selected from the group consisting of GPR183, THA1, TREML2, ZNRF3, CDK2AP2, CREB3, RPS16, BLOC1S2A, ATP1B3, BLNK, RPS29, SHARPIN, TSC22D1, KLRA1, HSD11B1, RPS15, AKAP8L, PHC1, RPL31, S1PR1, GM5547, SRSF5, ACSS2, ADK, AMICA1, ATP1B1, CNP, SNHG8, FCRLA, H2-T23, RAB33B, TLR12, RPF1, SP140, SH3GL1, CTSL, RPGRIP1, 5430417L22RIK, CXXC5, RABGGTA, KCNJ8, DYM, FRAT1, SPIB, ADRB2, COX6A2, TMEM219, GPR18, CCPG1, PLCB2, CALM2, KYNU, CRLF3, IDNK, TNFRSF26, DNAJB9, TXNIP, UPB1, GM11346, PHF1, RPL18A, DNTT, HAAO, PIM2, RABAC1, APOPT1, BIN2, OXR1, GPR171, RASGRP2, SLC9A9, 5830411N06RIK, PIAS1, PYDC3, ZCCHC18, TCSTV3, KLRA7, NPC2, CD180, SMIM14, P2RY14, PDLIM1, MYLIP, PDE2A, PPIF, KLRA17, FBXO32, DIRC2, ELOVL6, PJA1, SP110, KLRA6, USP7, HCST, KLRA23, GAB3, TOM1, ACP5, PBLD1, SMPD5, EVI2A, KLF13, MFSD11, IFNGR1, POU6F1, USE1, HDAC4, SMIM5, MAF1, 1810034E14RIK, TSC22D3, GAS5, RPL21, RELL1, SERTAD2, BC147527, KMO, SKAP1, TCF4, SP100, RNF167, TMEM59, IRGM1, CD69, DNAJC7, PIK3IP1, TAZ, HAVCR1, LY6D, RPL23, DAPP1, FLT3, ITM2B, NUCB2, RPS14, GIMAP9, HBP1, MAN2A2, RNF122, SOCS3, CD7, PNCK, 2610019F03RIK, SLC27A1, BPTF, H2-Q9, KLHL6, RPL17, SEMA4B, LDLRAD4, TCEA2, GM14207, CIRBP, FAM189B, ZFP707, ATP10D, RNASET2A, ATP2A1, BST2, EYA2, IRF7, ITPR2, STK17B, CYBASC3, TRIM11, KLK1B27, ZMYND8, LEF1, RNASE6, EIF4A2, HS3ST1, NIPBL, STX4A, UGCG, CAMK1D, PPFIA4, UVRAG, CDKN2D, ZBTB21, LEFTY1, APBB1IP, GIMAP3, H13, RGS10, RNF138, RPL12, SLC7A6OS, FADS2, SELPLG, CXCR4, GPR146, ZFP386, BCL11A, TRIM34A, RPS7, TLR9, PACSIN1, PAIP1, PGAM2, and JAKMIP1.

(29#) (28#) at least three markers, or at least four markers, or at least five markers, or six or more markers, such as wherein the signature consists of two markers, three markers, four markers, or five markers.

(30#) A method of isolating an immune cell as defined by any one of (1#) to (29#) comprising binding of an affinity ligand to a signature gene expressed on the surface of the immune cell.

(31#) A method of treating a subject in need thereof, comprising administering to said subject an agent capable of modulating the immune cell as defined in any one of (1#) to (29#).

(32#) The method according to (31#), wherein the agent is capable of reducing the dysfunction of the immune cell, or is capable of increasing the dysfunction of the immune cell, or is capable of reducing the activation of the immune cell, or is capable of increasing the activation of the immune cell.

(33#) The method according to any one of (31#) or (32#), wherein the agent is capable of modulating expression or activity of one or more genes or gene products comprised by the signature of dysfunction, activation, activation and/or dysfunction, or memory as defined in any one of (1#) to (32#).

(34#) The method according to (34#), wherein:
(a) the agent is capable of downregulating or abolishing expression or activity of one or more genes or gene products comprised by the signature of dysfunction as defined in any one of (1#) to (8#), thereby reducing dysfunction of the immune cell;
(b) the agent is capable of upregulating expression or activity of one or more genes or gene products comprised by the signature of dysfunction as defined in any one of (1#) to (8#), thereby increasing dysfunction of the immune cell;
(c) the agent is capable of upregulating expression or activity of one or more genes or gene products comprised by the signature of activation as defined in (16#), thereby increasing the activation of the immune cell; or
(d) the agent is capable of downregulating or abolishing expression or activity of one or more genes or gene products comprised by the signature of activation as defined in (16#), thereby reducing activation of the immune cell.

(35#) A method of treatment comprising administering one or more checkpoint inhibitors to a patient in need thereof, wherein immune cells obtained from the patient have a gene signature as defined in any one of (1#) to (29#), such as the gene signature of dysfunction as defined in any one of (1#) to (8#).

(36#) The method according to any of (1#) to (35#), wherein said immune cells comprise T cells, preferably CD8$^+$ T cells.

(37#) The method according to any of (1#) to (36#), wherein determining whether or not an immune cell expresses a signature comprises cell sorting.

(38#) A kit of parts comprising means for detection of the signature of dysfunction, activation, activation and/or dysfunction, or memory as defined in any one (1#) to (37#).

(39#) The kit of (38#), wherein means for detection comprises primers, probes, or antibodies.

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R. I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Transcriptional Signatures for CD8$^+$ T Cell Dysfunction and Activation are Intertwined CD8$^+$ tumor-infiltrating lymphocytes (TILs) exhibit distinct functional phenotypes that Applicants (Sakuishi et al., 2010, J Exp Med., vol. 207(10), 2187-94) and others (Baitsch et al., 2011, J Clin Invest 121, 2350-2360; Fourcade et al., 2010, The Journal of experimental medicine 207, 2175-2186; Matsuzaki et al., 2010, Proceedings of the National Academy of Sciences of the United States of America 107, 7875-7880; Zhou et al., 2011, Blood 117, 4501-4510) have previously defined using a combination of co-inhibitory receptors as markers. Specifically, T cell immunoglobin and mucin domain-containing-3 (Tim-3) and Programmed cell death-1 (PD-1) can be used to distribute CD8$^+$ TILs into three different groups that are Tim-3$^-$PD-1$^-$ (DN; double negative), Tim-3$^-$PD-1$^+$ (SP; single positive), and Tim-3$^+$PD-1$^+$ (DP; double positive). The DN TILs exhibit full effector function, the SP TILS exhibit partial dysfunction, and DP TILs exhibit severe dysfunction, as reflected by the respective differences in their ability to produce effector cytokines (Sakuishi et al., 2010). Tumor infiltrating lymphocytes (TILs) are frequently found to be in a state of dysfunction (also termed "exhaustion"), consisting of a spectrum of phenotypes in which pro-inflammatory cytokine-secretion and cytolytic function are compromised.).

To gain insight into the molecular programs underlying the broad spectrum of functional phenotypes in CD8+ TILs Applicants generated transcriptional profiles for the CD8+ DP, SP and DN TILs (FIG. 1A) (Johnson et al., 2007, Biostatistics 8, 118-127; Reich et al., 2006, Nature genetics 38, 500-501; Subramanian et al., 2005, Proceedings of the National Academy of Sciences of the United States of America 102, 15545-15550)). CD8+ Tim-3+PD1- TILs were not examined as these cells are rarely observed in growing tumors. Additionally, for comparison Applicants profiled CD8+ CD44$^{hi}$CD62$^{Low}$ effector/memory (EffMem) and naïve CD8+ CD44$^{low}$ CD62L$^{high}$ T cells from non-tumor bearing mice.

Figure 1B:
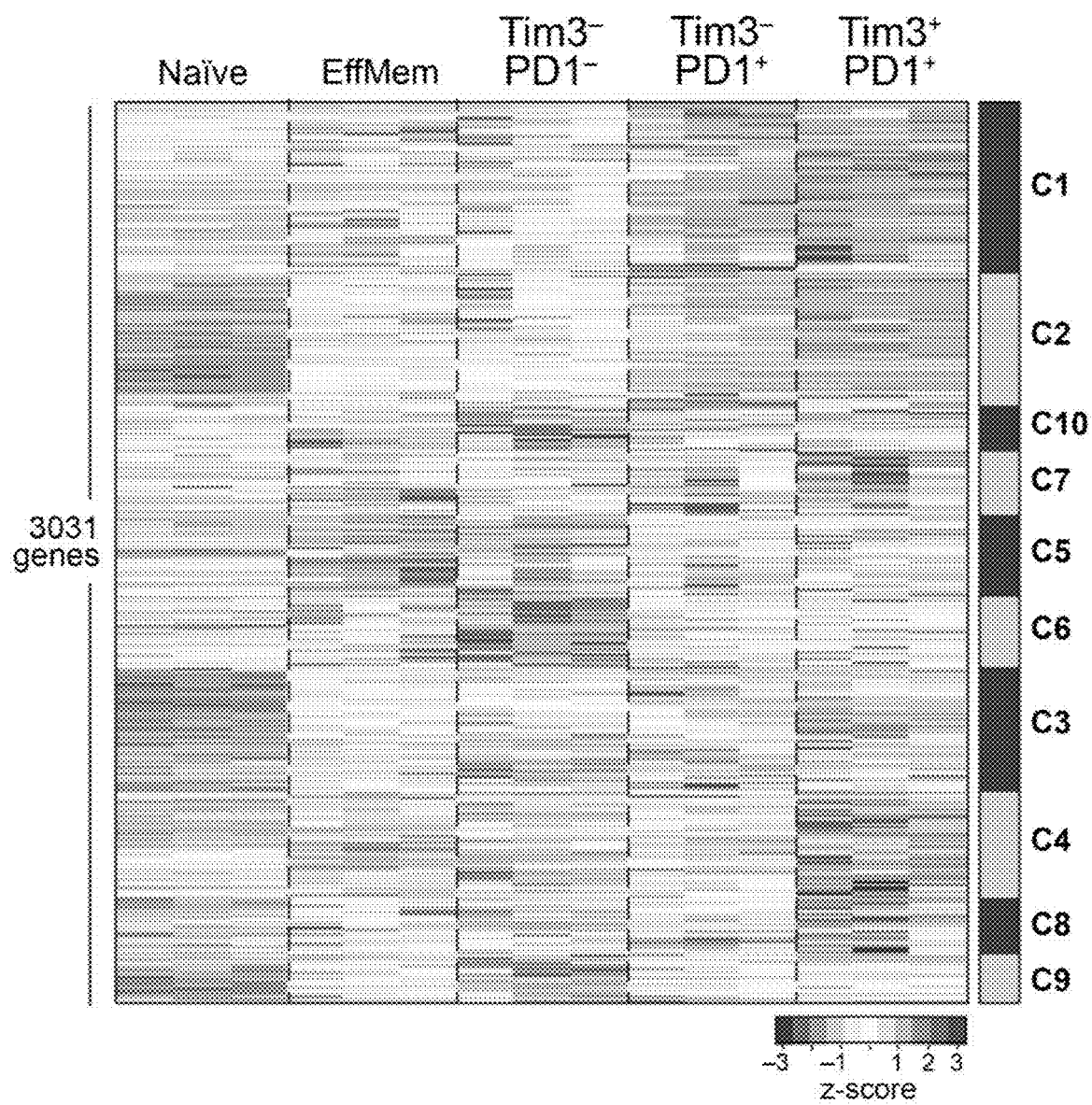
Figure 1C:
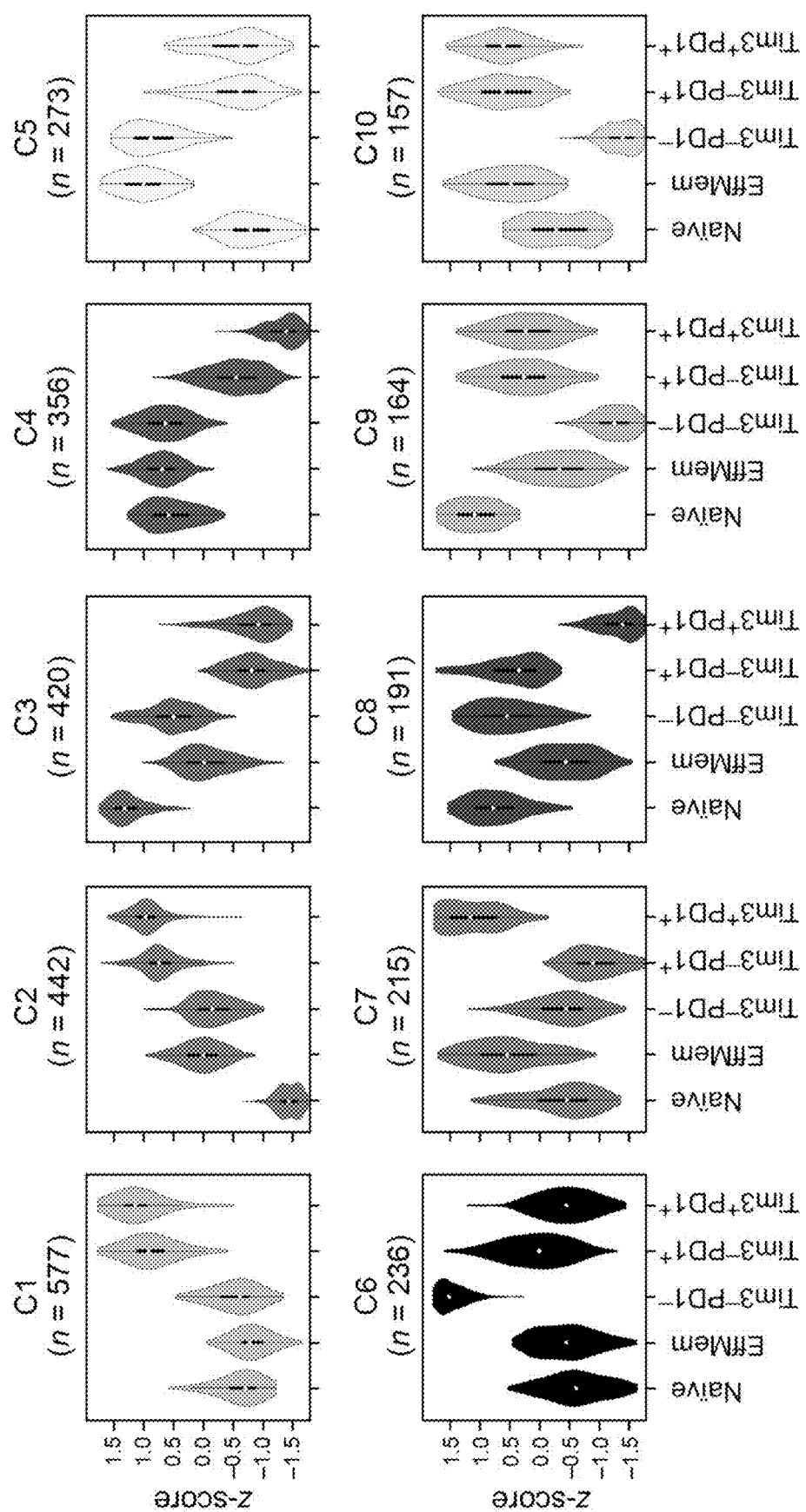
Figure 1D:
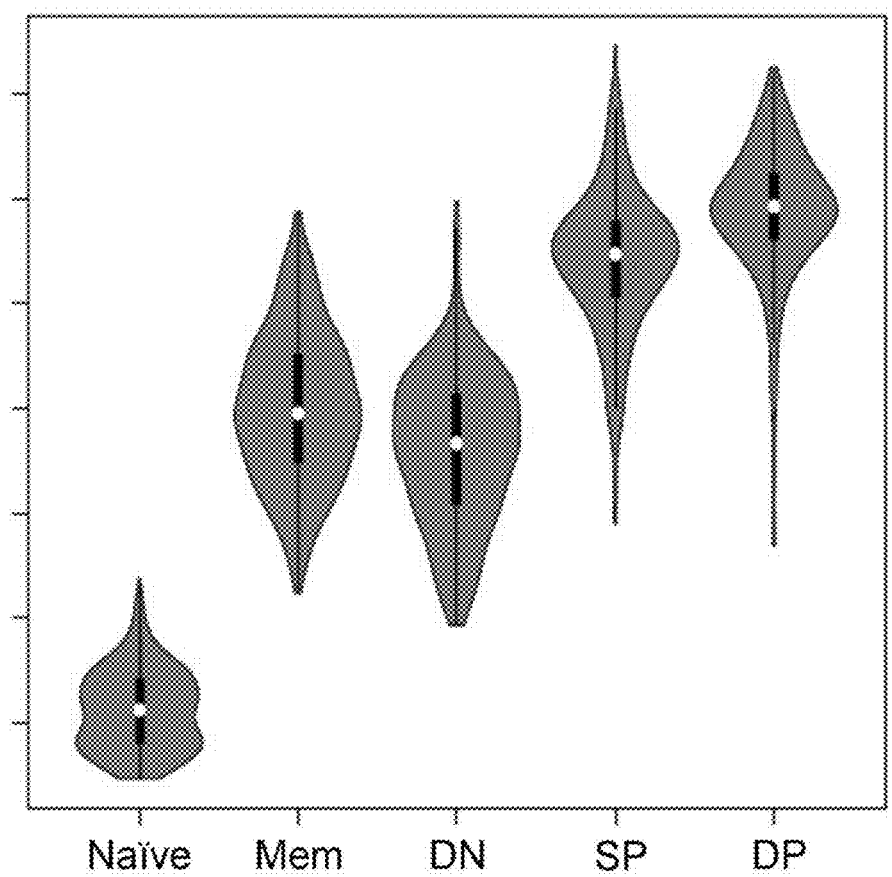
Figure 1E:
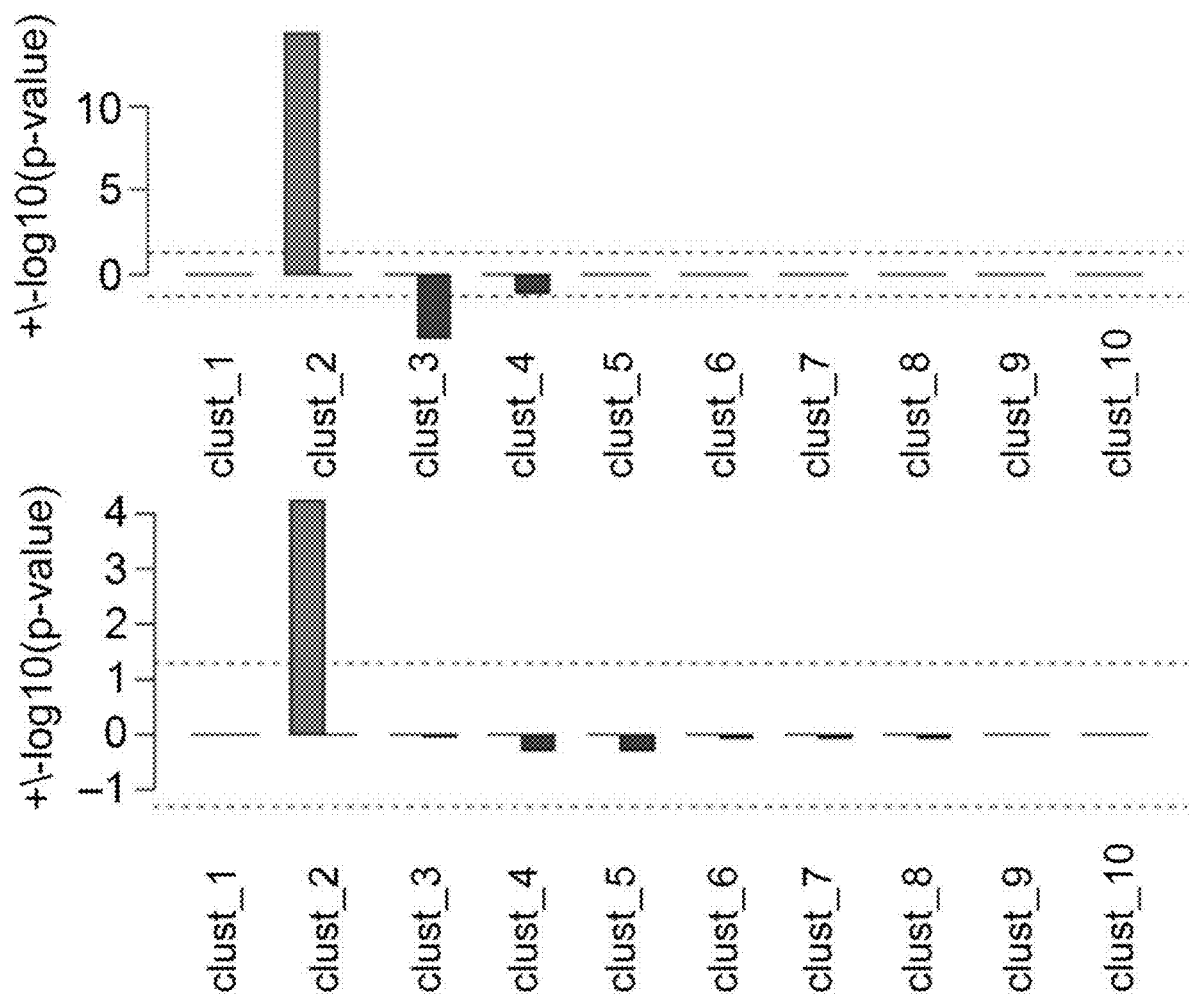

To identify a signature specific for CD8+ dysfunctional TILs, Applicants first identified genes that were differentially expressed across the three TILs subpopulations. Appli- memory CD8+ T cells (FIG. 1B). Among others, co-inhibitory and co-stimulatory receptors were upregulated in the dysfunctional DP subpopulation (FIG. 1J). Subsequent clustering of the expression patterns across the profiled populations showed that the large majority of differentially expressed (DE) genes are part of an expression profile involving 10 clusters (k-means clustering; C1-C10) with distinct gene expression patterns across DN, SP and DP TILs (FIG. 1B,C,D,F). Some of these clusters showed either gradually increased or decreased expression in TILs across the DP, SP, and DN populations, suggesting a possible association with the functional differences observed in these populations. TABLE 1 set forth below lists the top-ranking genes and enrichments in the each of the clusters shown in FIG. 1C.

TABLE 1

Top-ranking genes and enrichments for the different clusters. Enrichments from MSigDB KEGG Reactome/Metabolism, C5 or C7.

| Cluster | Gene count | Top-ranking genes* | Top Enrichments |
|---|---|---|---|
| 1 | 577 | 2900026A02RIK, STYK1, GZMD, GZMF, GZMG, DSC2, SERPINB9B, SPP1, GZME, SPIN4 | None (insignificant association with CD8 Effector, Treg Fat) |
| 2 | 442 | MT1, SERPINE2, GZMC, DUSP4, OSBPL3, NRN1, CDKN3, CSF1, PLSCR1, CDKN2B | Cell cycle, Glucose metabolism, PLK1 pathway, NFAT Pathway, Metabolism of Carbohydrates Effector CD8, Chronic LCMV infection, Tregs in Thymus, Memory CD8, in vitro stim CD8 |
| 3 | 420 | CARD6, ATP10D, GBP2, IL1RL2, IL6RA, UNC5CL, GM1060, C230085N15RIK, ENC1, NME4 | CD4 conventional (vs. Treg), downregulation in Tregs, Naïve CD8 |
| 4 | 356 | LOC100048338.PDLIM1, 5730508B09RIK, ID3, RXRA, EMB, AB124611, FGF13, ITGB7, RTN4RL1, TLR1 | WNT_signaling (top but not significant) Naive CD8, Acute LCMV infection (vs. chronic), CD4 (vs. Treg) |
| 5 | 273 | KLK1.KLK1B5, TUBB2B, ST3GAL6, D13ERTD608E, 9130004J05RIK, CD7, DMRTA1, TSHZ3, KLK1B22.KLK1B9, CXCR3, | Myeloid cells (vs. cd4) |
| 6 | 236 | PMEPA1, HEMGN, IFIT1, IFIT3, RTP4, EGLN3, WHRN, TCF12, PTCRA, PLTP | Cytokine signaling in the immune system, Interferon signaling, JAK-STAT pathway, protein kinase cascade |
| 7 | 215 | HAVCR2, ADAM8, GPR56, ALOX5, TMEM119, RIPPLY3, IGF2BP2, ITLN1, C920021A13, CCL9, MMP12 | Complement and coagulaGon cascades, extracellular space, integral to plasma membrane, lipoprotein binding, G protein coupled receptor |
| 8 | 191 | IL7R, KRT10, TNFSF8, PDE4B, SSBP2, A630057N01RIK, PKD1, ZFP365, GRAMD3, MACROD1 | DNA repair (top but not significant) |
| 9 | 164 | SLFN10, FAM110C, PABPC1L, LHFPL2, 4933437N03RIK, D3ERTD740E, USP40, C130068B02RIK, 4930518I15RIK, SYNGR3 | WNT signaling (top but not significant) |
| 10 | 157 | 2310001H17RIK, NSL1, TMBIM4, ENO3, EEA1, TBC1D7, GAS2L1, GNG11, MTMR1, CCDC99 | None |

*Whereas the present examples describe experiments performed in mice as suitable and informative model organisms, and therefore the genes listed throughout the present examples have been identified in mice, the skilled person can routinely identify orthologs of mouse genes from other species, such as in particular human orthologs thereof, inter alia by reference to HGCN guidelines for gene symbols formation and using publically available databases. By means of further guidance, HGCN prescribes to assign equivalent gene symbols to human/mouse ortholog pairs, using only distinctive capitalization to indicate the origin of the gene (e.g., all uppercase letters indicate human genes). Furthermore, complete list of human and mouse homologs are available from online sources, such as from the Mouse Genome Informatics (MGI) database (www.informatics.jax.org/homology.shtml). Also, routine homology searches can be employed to identify putative gene orthologs where such have not been annotated in available databases.

cants identified 3031 genes that were significantly differentially expressed across the TILs subpopulations, and clear expression patterns were observed distinguishing the Tim3$^{-PD-}$1+ (SP) and Tim3+PD-1+ (DP) subpopulations from those of the Tim3$^{-PD-}$1- (DN), naïve, and effector- Any one or a combination of two or more genes or polypeptides listed in TABLE 1 may be employed in therapeutic and/or diagnostic applications as disclosed in this specification for GATA3, FOXO1 or any other genes or polypeptides mutatis mutandis, instead of or in addition to GATA3, FOXO1 or any such other genes or polypeptides.

Figure 1F:
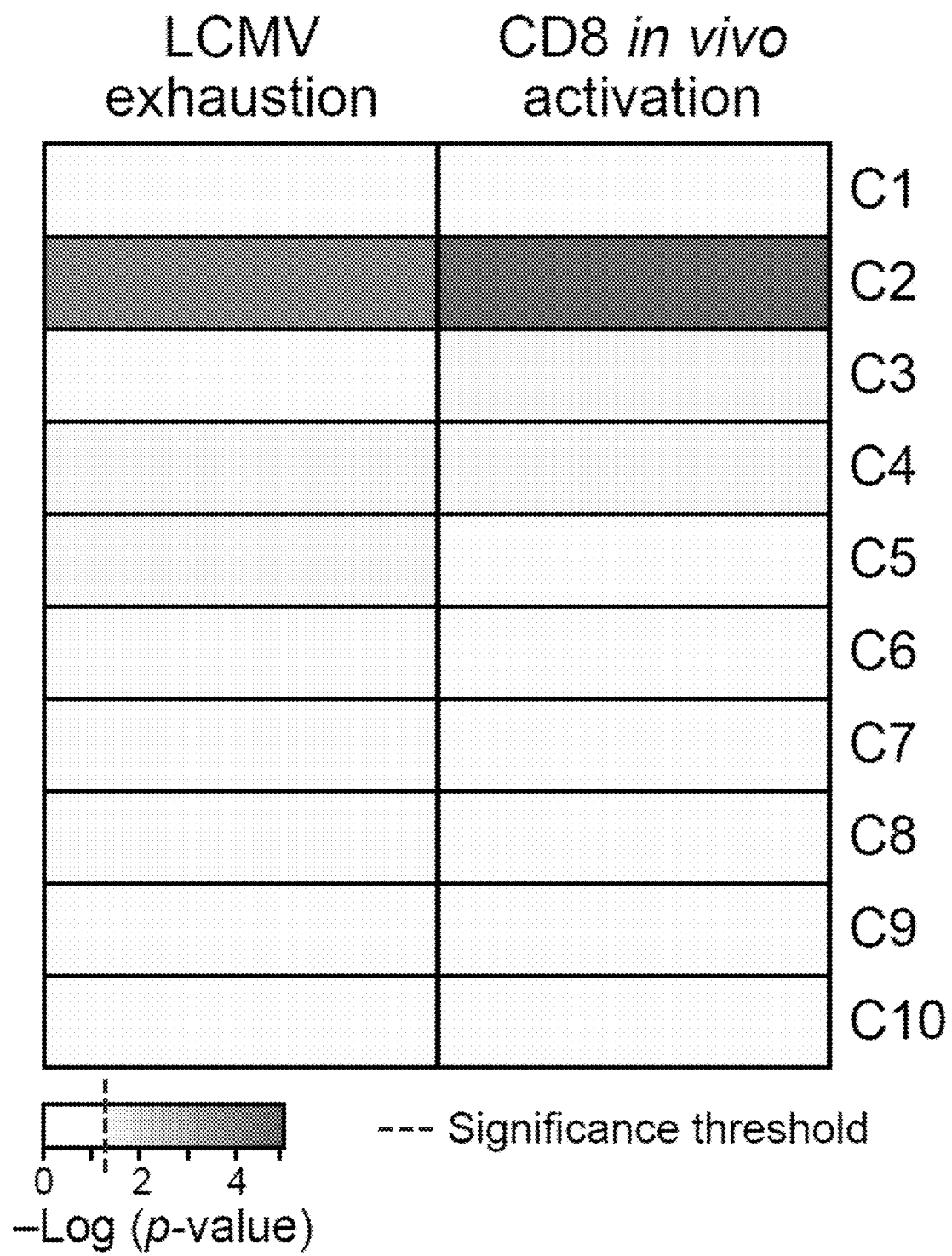
Figure 1G:
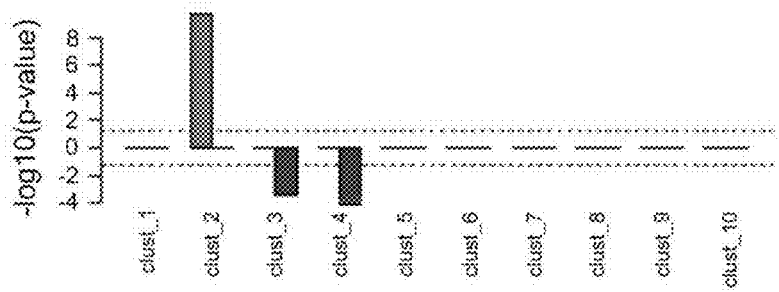
Figure 1G:
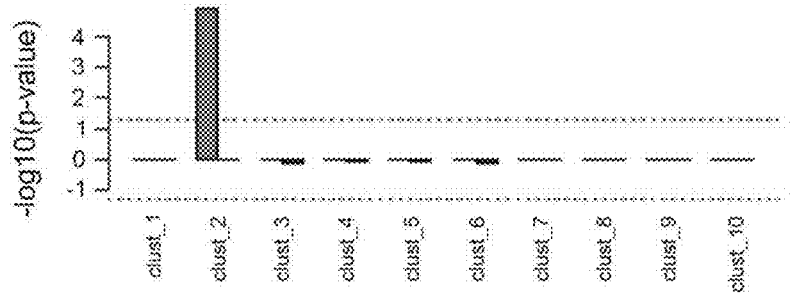
Figure 1G:
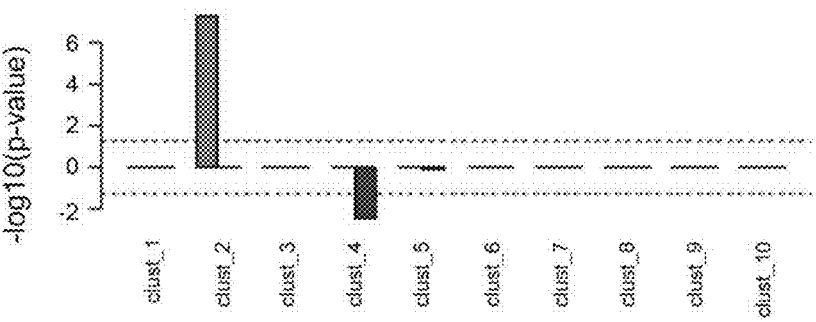
Figure 1G:
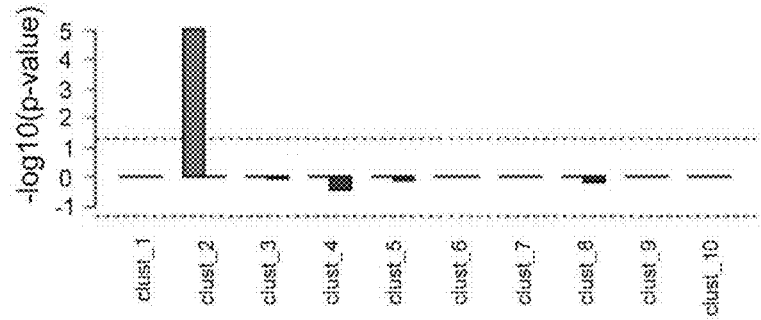
Figure 1H:
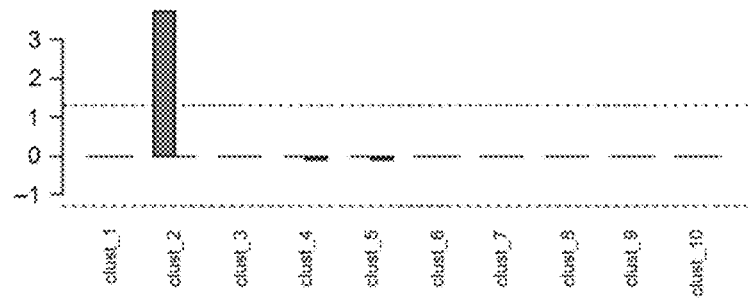
Figure 1H:
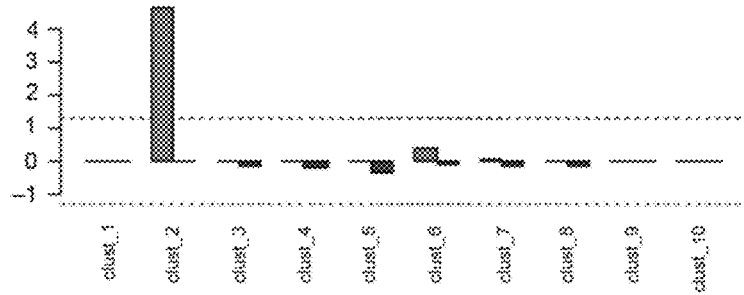

Of the 10 gene expression clusters, only cluster 2 (C2) showed significant enrichment for genes up-regulated in a viral CD8+ T cell exhaustion signature (Doering et al., 2012, supra) (FIG. 1F). However, cluster 2 also showed strong enrichment for genes up-regulated in an in vivo CD8+ T cell activation signature (Sarkar et al., 2008, supra) (FIG. 1F). Conversely, clusters 3 and 4 showed enrichment for genes down-regulated in the in vivo CD8+ T cell activation signature (FIG. 1F) and genes highly expressed in naïve T cells (FIG. 1B). The following provides a complete ranked list of genes that were differentially expressed across the three TILs subpopulations and belonged to cluster C2: MT1 (which was the top-ranking gene), SERPINE2, GZMC, DUSP4, OSBPL3, NRN1, CDKN3, CSF1, PLSCR1, CDKN2B, TOX, ARSB, TNFRSF9, CCRL2, C1QTNF6, CD81, SERPINA3G, CD244, LOC677008, ITGA1, FASL, CREB3L2, D630039A03RIK, GEM, TBX21, KIT, STK39, DUSP14, ETV5, SYNPO, MDFIC, PHACTR2, TRPS1, ATXN1, RAP2A, CASP4, SERPINB9, TIAM1, NDRG1, SYTL2, SERPINB6B, STX11, EMILIN2, ASNS, CCL3, CASP3, LITAF, TUBB6, TPX2, CD244, GM10786, CD200, SPRY2, ANXA2, CCNB1, CTLA4, TNFRSF4, PRDM1, CCNB1, GM5593, GM8416, CISD3, ASPM, GRK5, GPM6B, ABI2, GINS1, UGT1A1, UGT1A10, UGT1A2, UGT1A5, UGT1A6A, UGT1A6B, UGT1A7C, UGT1A9, 2610029101RIK, SAMSN1, KDELC2, NR4A2, DUSP3, RASGEF1B, FAM72A, EPDR1, NCAPH, ENTPD1, TMBIM1, 2010002N04RIK, KLRA3, KLRA9, IL2RA, AA467197, SLC2A3, CD38, GABARAPL1, IFNG, ZBTB32, DUSP6, PDCD1LG2, CCDC50, TNFSF10, CENPN, HIP1, ALCAM, GCNT1, LPXN, CHN2, TMCC3, LAG3, ADAMS, PHLPP1, BUB1B, MND1, PRSS2, HSPA13, FGL2, KCTD17, BHLHE40, ADRB1, PGLYRP1, SH3BGRL, CDCA2, CST7, PGM2, BUB1, E2F8, PLXDC2, LANCL3, JDP2, LAT2, NRGN, DENND3, LOC100046643, SPRY1, CD14, SRGAP3, ANXA4, LCLAT1, DAPK2, MS4A6D, SLC25A24, FCER1G, BCAT1, GMEB2, ZDHHC2, TNFSF11, CAPG, IL18RAP, HSPA2, HIST1H2BC, 1300014106RIK, IFITM2, BCL2A1A.BCL2A1B.BCL2A1D, PLEK, LYZ1, S100A1, TMEM126A, CYP20A1, SELM, LYZ2, TNFSF9, UBE2C, ENDOD1, ID2, COBLL1, 1110067D22RIK, CCDC109B, EXO1, LGALS3, LAMC1, 0610010B08RIK, GM14295, LOC627901, PTGS2, EHD4, RHOC, FAM176B, SESTD1, PTTG1, C030046G05, SLC35F5, 4933413G19RIK, FOXM1, PEBP1, 6330503K22RIK, SLC43A3, TACC3, DKKL1, OLFM1, STIL, FLYWCH1, NUF2, ARF2, STARD3NL, CSDA, BIRC5, EFHD2, CDCA3, NCAPG2, LOC100046168, NDFIP1, NAIP2, HTATIP2, ZFP511, NRP1, LOC100046232, NFIL3, PRR11, CDC27, TCRGV2, TCRGV3, GSTO1, MID1IP1, TK1, GDAP2, IFITM3, CHSY1, LOC100047167, PLEKHF1, ESCO2, TCTEX1D2, TFG, GM12397, KDM2B, S100A4, TMEM49, FAH, MRPS6, NDC80, NKG7, VAMP8, STK24, ZEB2, D2ERTD750E, UNC119B, NEK7, FOS, 4921509J17RIK, CDCA8, CUGBP2, PGK1, TRIB3, EGR1, LOC100047091, TMEM163, ATP6V0E2, XCL1, NEK2, S100A11, CCL4, PF4, BST1, GATA3, ERN1, CDCA5, AI747699, IKZF2, 3110073H01RIK, KLF10, SCD2, PRC1, AP1S2, ERMP1, GM10397, FOSL2, ACOT7, KRT18, DYNLT3, SLFN3, GAPDH, GM10284, GM10358, GM12969, GM2076, GM2308, GM2451, GM2606, GM3222, GM5674, GM6283, GM6322, GM8349, LOC100044981, LOC100045908, LOC100047352, LOC100048329, MYST4, CTLA2A, PIK3CG, CD160, SPOCK2, CSRNP1, CTLA2A.CTLA2B, ATRNL1, XDH, DIAP3, CDC2A, IRF4, CDKN1A, ALDOA, SAT1, 4930551013RIK, CWC15, DDX28, GPT2, ANXA1, ZFP52, 2410127L17RIK, LOC677553, NT5DC2, ERO1L, UTF1, CMTM7, TBC1D8B, ALDOC, CALU, INO80C, PMAIP1, NLRX1, SERPINB1A, NEBL, NIPA2, TMEM48, 1700025K23RIK, SLCO4A1, CLIP3, ICOS, CCNB2, SLC35B1, GLRX, TSGA10, CNIH, HIF1A, CARHSP1, KIF2C.LOC631653, GPR174, GM9790, HIGD1A, LOC100045763, KDM2B, ABHD14A, TNF, AXL, EHBP1, SNRNP25, DCTN4, ECT2, KDM4D, PXMP2, ECE1, RFC3, LOC677224, UBASH3B, ZDHHCS, S100A8, SEC23A, MTHFD2, KCNQS, PPAP2C, TPI1, PKM2, FAM98B, ALAD, LOC100046072, CASP1, TIRAP, ZC3H6, CCL5, FAM92A, 2510009E07RIK, LPGAT1, SH2D2A, CYSLTR2, FAM162A, UGP2, 2610027H17RIK, PPP3CB, PTPN11, AW555464, WBPS, IPO8, NOL7, TMSB15B1, TMSB15B2, TMSB15B2, B3GALTL, 2810417H13RIK, UCHL5, DTL, ZWILCH, GCSH, RRAGC, TTC39C, SDC1, 2700097009RIK, RGS16, A430093F15RIK, ERGIC1, TYMS, TYMS.PS, PTGFRN, GBE1, ENO1, GM4735, GM5506, LOC100047043, TRAM1, PPFIBP1, C330027C09RIK, TCRG.V4, ARL6, 1110004F10RIK, ARL3, CARSB, SMC2, LASS6, PYGL, KIF22, RAB31, PLS3, CX3CR1, S100A9, LRRK1, PLEKHO2, ARPC1A, ZFP316, CALM3, PTPN13, CENPH, ADM, SEPN1, METTL7A1, SLC25A13, NQO2, DPY19L4, FZDS, ABHD4, FAM124B, MYADM, PAQR4, PROS1, 2600001M11RIK, CEP55, HIST1H2AD, KPNA2, CRYZ, CYTSB, 2610318NO2RIK, ANXA3, SH3RF1, ARHGAP18, CCR5, FAM83D, IER3, ZCCHC24, PHACTR4, LCMT1, PLEKHB2, RABLS, LOH12CR1, E2F3, DUT, UNC119, ZC3H12A, GEMIN8, DCXR, ATAD5, 1500009L16RIK, CYP4V3, PTGER2, MXRA7, PLK1, ACADL, A630035D09RIK, TMEM38B, D1ERTD83E, MID2, MEST, AI847670, SDC4, 4930547N16RIK, LOC676654, LYN, SLC15A3, RAD51, KIF20A, SHCBP1, FBXO45, SNX9, CENPF, RNF216, PTGR1, MRC1. Any one or a combination of two or more of said genes or polypeptides may be employed in therapeutic and/or diagnostic applications as disclosed in this specification for GATA3, FOXO1 or any other genes or polypeptides mutatis mutandis, instead of or in addition to GATA3, FOXO1 or any such other genes or polypeptides.

Additionally, Cluster 7 is enriched for complement genes. 13 complement genes overlap with the initial set of 3031 differentially expressed genes (shown FIG. 1B). In single cell analysis described herein the complement genes are statistically enriched in the co-inhibitory cluster. Cluster 7 includes PLAU, C5AR1, C4B, C3AR1, C1QA and C1QC. Cluster 6 includes F2R, PLAT, PLAUR. Cluster 5 includes C1QB. Cluster 3 includes CD55. Cluster 2 includes C1QTNF6, PROS1. Cluster 1 includes F13A1. Any one or a combination of two or more of said genes or polypeptides may be employed in therapeutic and/or diagnostic applications as disclosed in this specification for GATA3, FOXO1 or any other genes or polypeptides mutatis mutandis, instead of or in addition to GATA3, FOXO1 or any such other genes or polypeptides.

Applicants found several characteristic features of the defined signature that reflect the complexity of dysfunctional T cells. Applicants observed that cell-cycle progression was the most significantly-associated attribute with the dysfunctional CD8+ TILs population (FIG. 1C, cluster C2, enlarged representation in FIG. 1D).

Dysfunctional CD8+ T cells have been previously profiled at the whole-transcriptome level in the setting of chronic infection with lymphocytic choriomeningitis virus (LCMV) (Doering et al., 2012, Immunity, vol. 37(6), 1130-44). Applicants found there to be a highly significant overlap between the dysfunctional signature and the viral exhaustion signature (FIG. 1E).

A significant characteristic of the CD8$^+$ dysfunctional signature defined by cluster C2 was a strong association with an "effector-like" activated CD8$^+$ state (FIG. 1E-H, TABLE 1). Both inhibitory and stimulatory receptors were upregulated in the dysfunctional signature. This feature coincides with the upregulation of a substantial number of cytokines associated with activation. This transcriptome profile does not appear to be in accordance with cytokine production at the protein level. These observations could support a hypothesis that while the exhausted CD8$^+$ T cells are primed for activation, they lack critical components for carrying out a proper effector response.

Example 2: Metallothioneins (MT) are Differentially Expressed in CD8 Exhaustion in Cancer The coupling of T cell activation and dysfunction at the transcription level has been observed previously (Doering et al., 2012, supra; Tirosh et al., 2016) and is expected given that T cell dysfunction/exhaustion arises from chronic T cell activation due to antigen persistence. However, the underlying molecular mechanisms that drive this association have not been identified. This raises the fundamental question of whether a distinct gene module for T cell dysfunction exists and if so is it exclusively expressed by a subset of CD8$^+$ TILs.

Figure 1I:
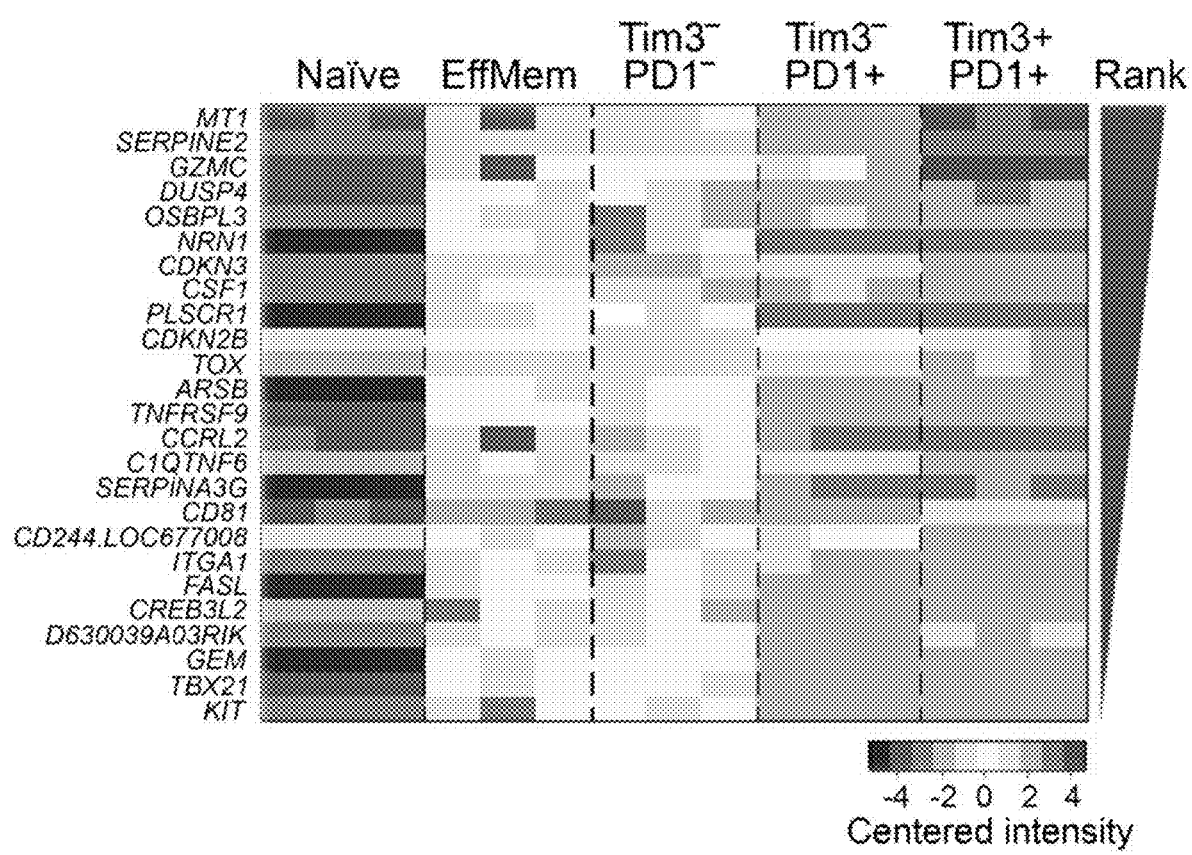
Figure 1J:
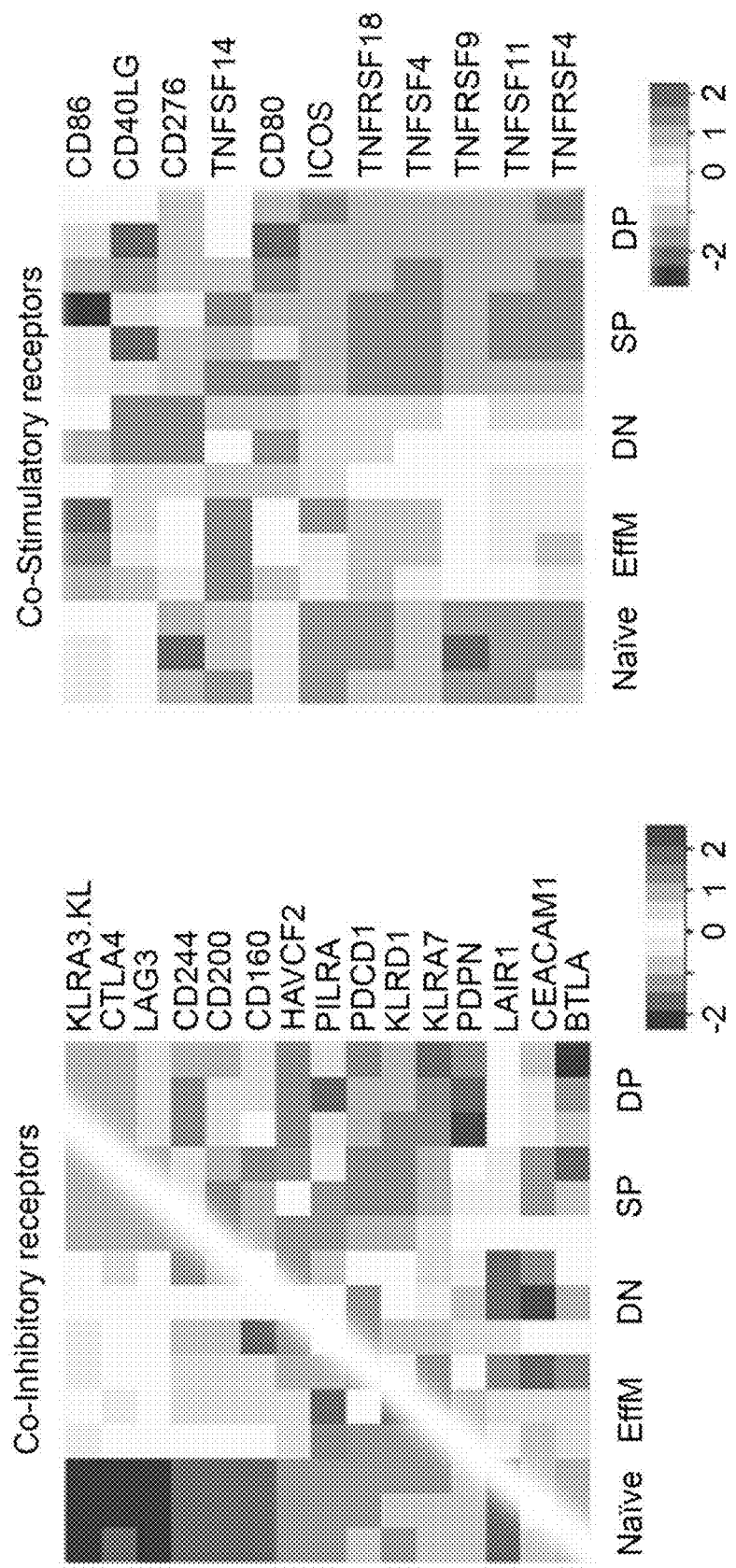
Figure 2A:
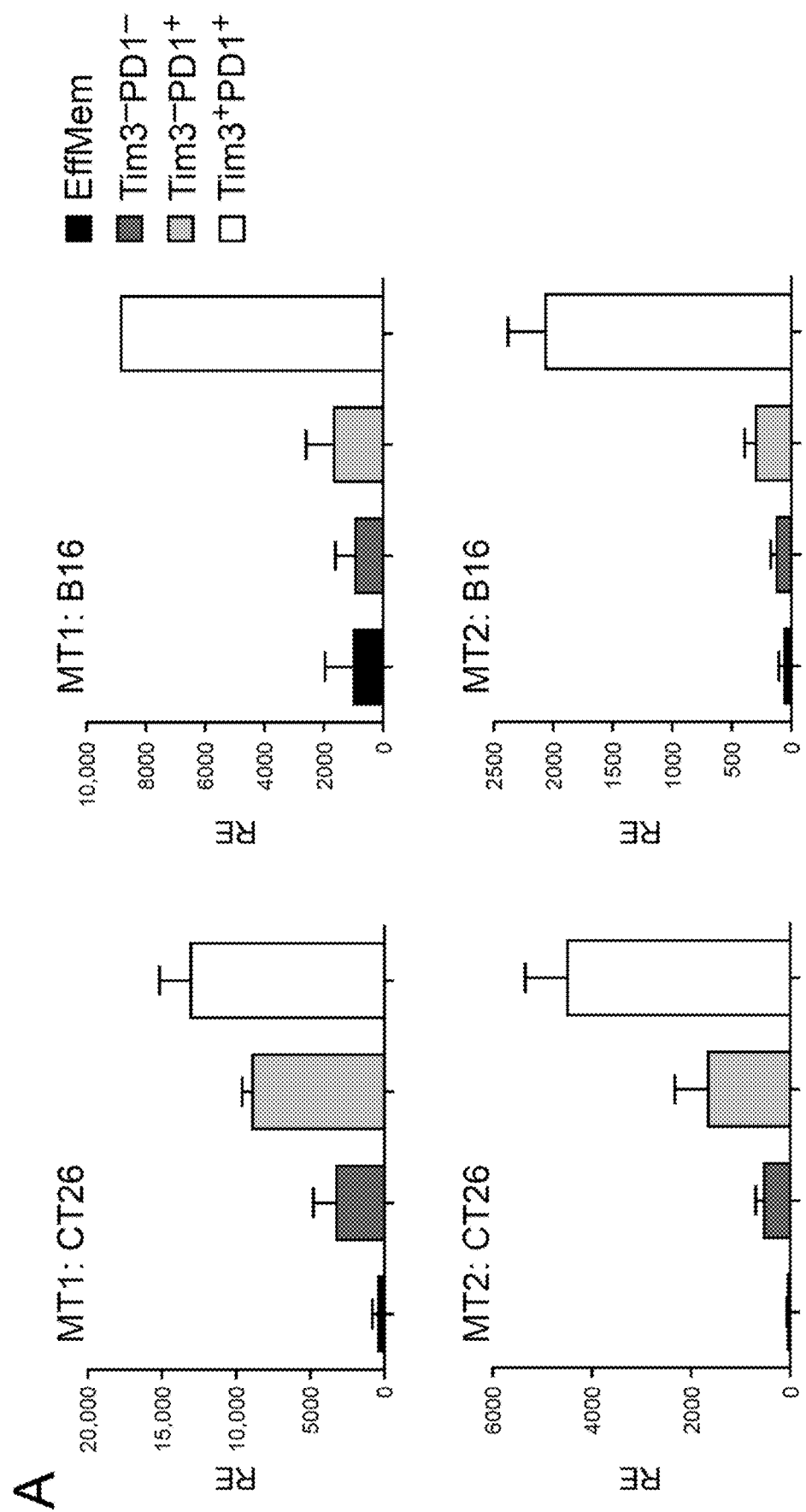

To identify putative molecular regulators of the CD8$^+$ T cell state might enable refinement of the dysfunction program signature. Applicants therefore focused on the genes of cluster 2. To identify putative molecular regulators of the CD8$^+$ T cell dysfunction program Applicants ranked the Cluster 2 genes by their differential expression across the three TIL subpopulations, and Applicants observed that the gene encoding metallothionein 1 (MT1) ranked highest in C2, the cluster best associated with the dysfunctional CD8$^+$ signature (FIG. 1I, TABLE 1). MT1 is coordinately regulated with its paralog MT2 and Applicants confirmed up-regulation of both of these metallothioneins in DP CD8$^+$ TILs in each of the two different mouse tumor models (FIG. 2A).

Metallothioneins are cysteine-rich intracellular proteins with high affinity for zinc that play a key role in regulating zinc availability, more particularly serve as zinc chaperones and regulate zinc metabolism. Given that zinc is essential to the proper functioning of several transcription factors and kinases (Bonaventura et al., 2015 Autoimmun Rev 14, 277-285; Hamer, 1986, Annu Rev Biochem 55, 913-951), the Applicants hypothesized, without any limitation to such hypothesis, that regulatory mechanisms driven by zinc associated factors could be perturbed during the initiation and maintenance of CD8$^+$ exhaustion in tumor. Applicants confirmed that both MT1 and its co-regulated paralog MT2 are consistently up-regulated in highly dysfunctional CD8$^+$ DP TILs in two different mouse tumor models (FIG. 2A).

The Applicants examined whether zinc availability is modulated in the present TILs populations and found that the availability of intracellular zinc closely parallels the up-regulation of MT1 and MT2 in DP CD8$^+$ TILs (FIG. 2D), evidencing that the expression of MT1 and MT2 and elevated zinc status directly correlate with loss of effector function and acquisition of dysfunctional phenotype. Applicants therefore hypothesized, without any limitation to such hypothesis, that MT1 and 2 may regulate CD8$^+$ T cell dysfunction and impact anti-tumor immunity.

Figure 2B:
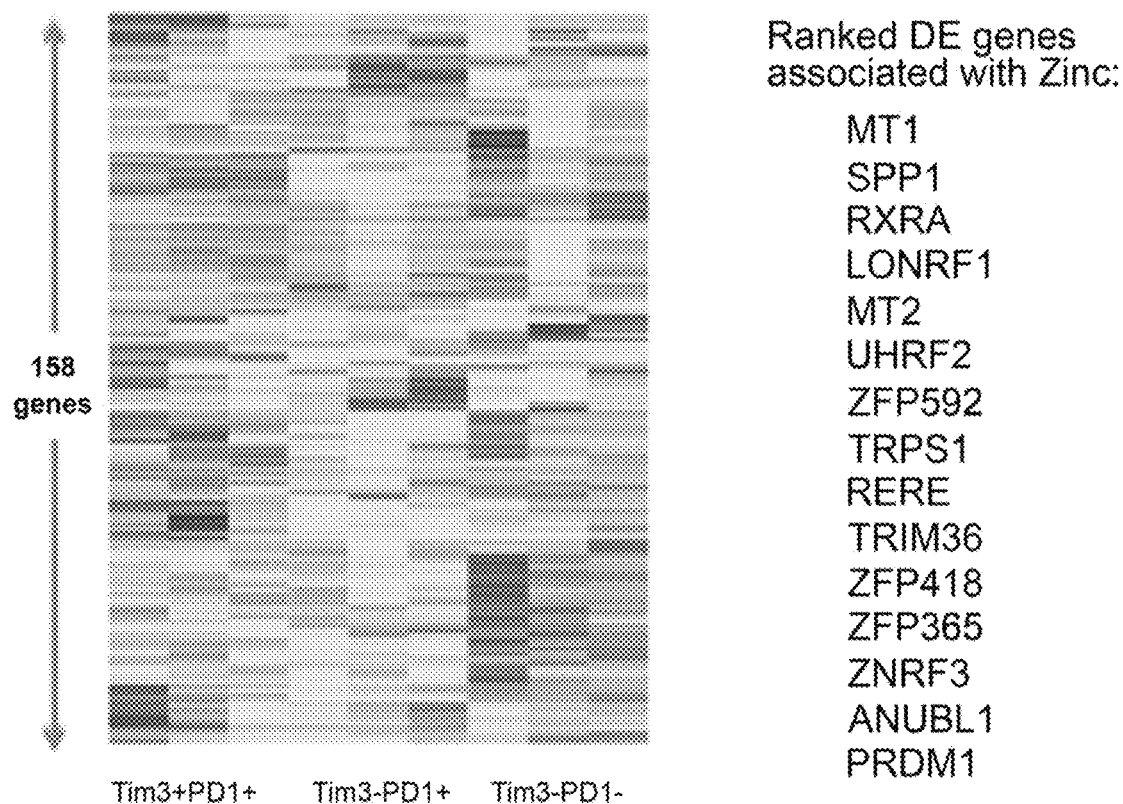

The Applicants constructed a list of zinc-associated genes and tested for their enrichment in the differentially expressed gene set. The genes downregulated in the dysfunctional CD8 TILs were significantly enriched for genes in the "zinc list" (p=0.003, FIG. 2B), indicating zinc dysregulation in the CD8 dysfunctional setting in tumor, in which pathways associated with zinc are generally downregulated. Further preliminary experiments indicated that an enrichment for zinc-associated genes was not observed in the viral set of differentially expressed genes upon exhaustion, suggesting that zinc dysregulation may be a unique feature of dysfunction in the cancer environment.

Dysregulation of Zinc was further tested by measuring zinc availability. Zinc levels varied significantly across the Tim3 and PD1 expressing subpopulations in CD8 TILs, with the most dysfunctional subpopulation of Tim3$^+$PD$^+$ (DP) having the highest zinc levels. Labeled zinc measurements in CD4$^+$ TILs and CD8$^+$ from draining lymph nodes showed that the higher zinc levels were a unique feature of the Tim3+PD1$^+$ (DP) and Tim3$^{-PD}$1$^+$ (SP) populations in CD8$^+$ TILs cancer (FIG. 2C). The higher levels of zinc in DP and SP paralleled the upregulation of metallothionein 1 and 2 in these subpopulations, thus linking metallotionein up-regulation to increased zinc availability within the cell. Applicants thus hypothesized, without any limitation, that zinc regulation has a causal relationship with the dysfunction of CD8$^+$ TILs, and that MT1 is a driver of this regulation.

Figure 2D:
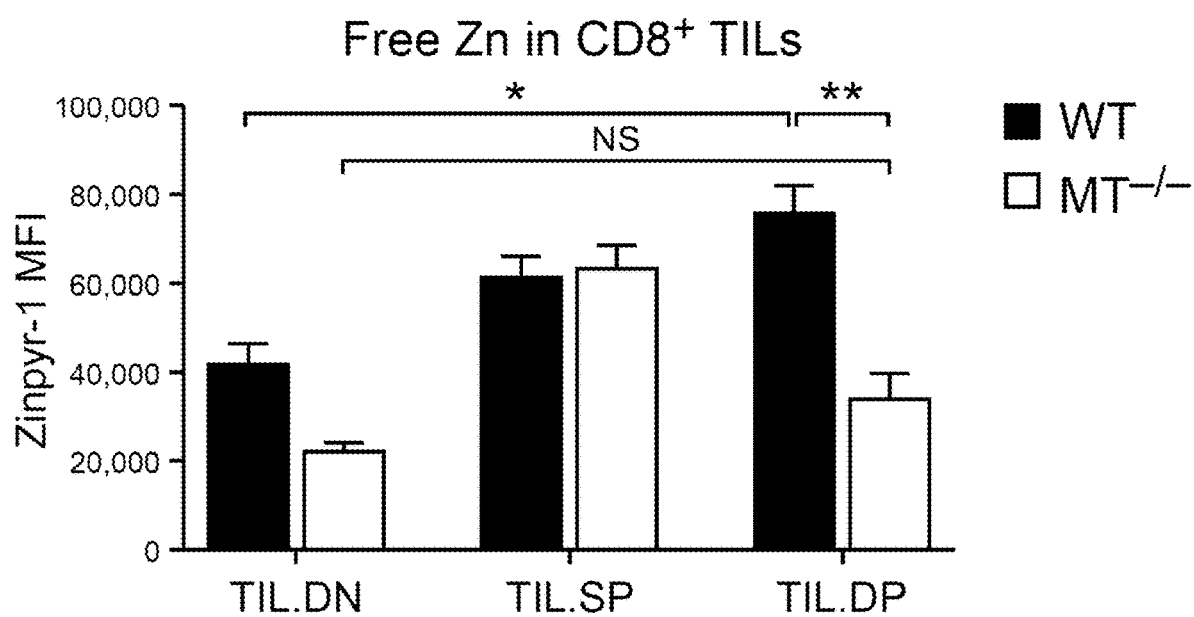
Figure 3B:
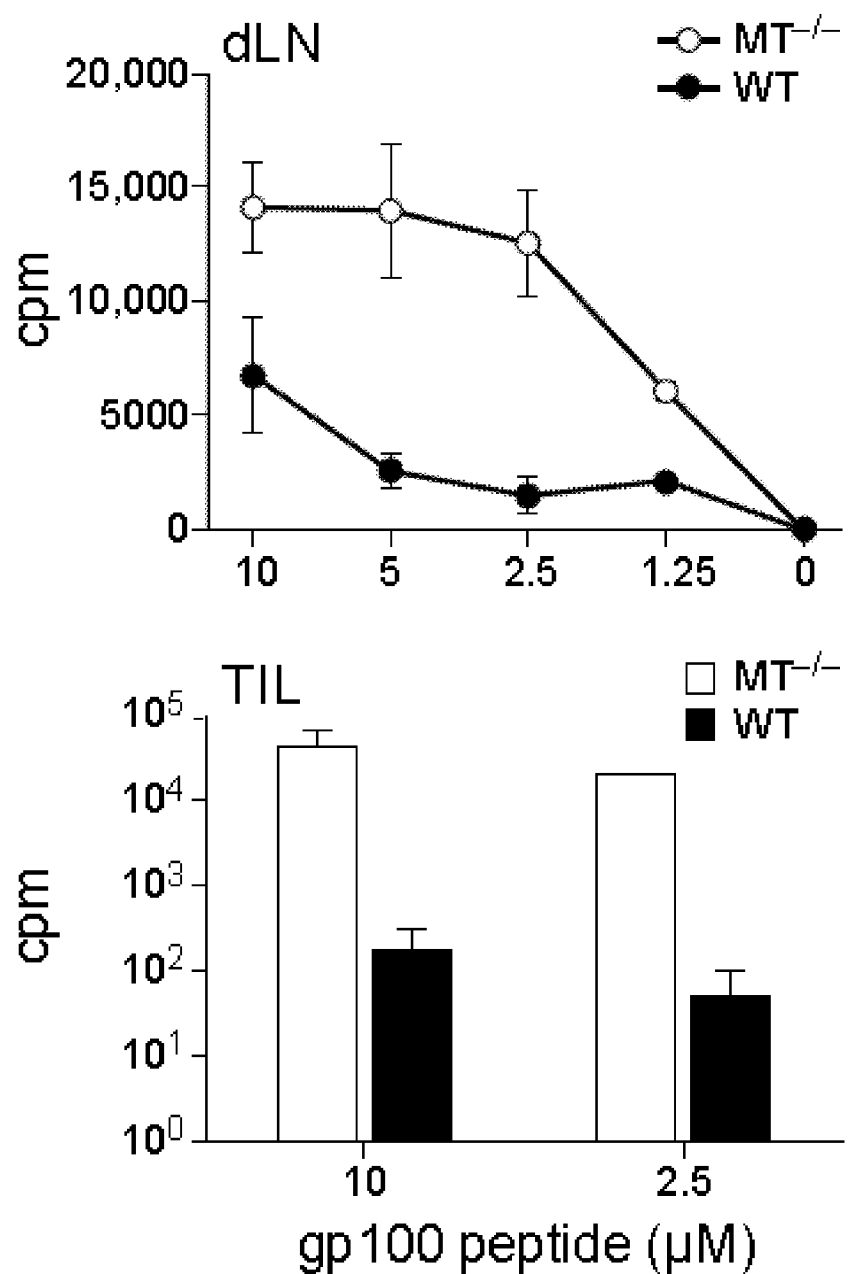

Example 3: Metallothionein Deficiency Improves Tumor Control and CD8$^+$ T Cell Function in DP TILs Without wishing to be bound by any theory, the Applicants hypothesized that metallothioneins and zinc metabolism could regulate T cell dysfunction directly. Several complementary approaches were used to determine the effect of perturbation of metallothionein on anti-tumor immunity. Firstly, the effect of total MT deficiency on tumor progression was examined. Mice deficient in both MT1 and MT2 (i.e., MT$^{-/-}$ mice) and wild type (WT) littermate controls were implanted subcutaneously with B16F10 melanoma. A significant delay in growth of B16F10 melanoma in MT$^{-/-}$ mice compared to littermate controls was observed (FIG. 3A). Consistent with an improved CD8$^+$ T cell response, increased proliferation in response to stimulation with tumor specific antigen in CD8$^+$ cells isolated from the tumor draining lymph node (dLN) and tumor (TIL) of MT$^{-/-}$ mice was observed, supporting an improved anti-tumor CD8$^+$ T cell response (FIG. 3B). MT1 and MT2 deficiency also reversed the increased zinc observed in DP CD8$^+$ TILs (FIG. 2D).

Figure 3C:
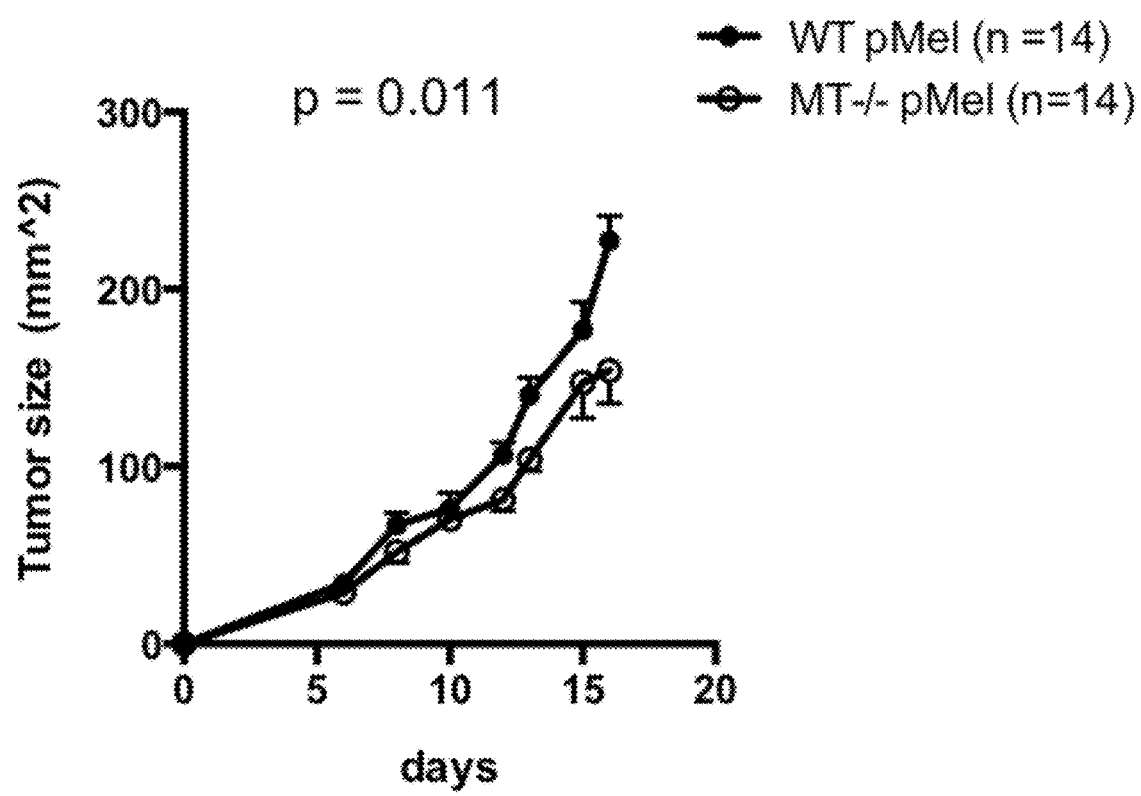

Next, Applicants showed that the effect of MT was CD8$^+$ T cell intrinsic. Applicants crossed MT$^{-/-}$ with pmel transgenic mice with a specific T cell receptor (TCR) to the mouse homologue of human premelanosome protein. Wild type recipients of MT$^{-/-}$ pmel CD8$^+$ T cells resulted in slower tumor growth as compared to those transferred with wild type pmel CD8$^+$ T cells, indicating a CD8$^+$ T cell intrinsic role of MT (FIG. 3C). To confirm a T cell intrinsic role of metallothioneins in regulating anti-tumor responses, Applicants used a system in which adoptive transfer of Ova-specific OT1 CD8$^+$ T cells to mice bearing MC38 tumors that express Ova (MCA38-Ova) shows tumor growth control. Applicants overexpressed MT1 in OT1 CD8$^+$ T cells and transferred these cells or control OT-1 CD8+ T cells into wildtype (WT) mice bearing MC38-Ova tumors. Recipients of MTOT1 CD8+ T cells failed to exhibit tumor growth control compared to recipients of control OT-1 CD8+ T cells (FIG. 3D). Thus, ectopic expression of MT1 in ova-specific OT1 CD8+ T cells (OT1 TCR mouse transgenic line produces MHC class I-restricted, ovalbumin-specific, CD8+ T cells, i.e., OT1 CD8+ T cells) using retroviral gene transduction resulted in a failure to control growth of MC38 colon carcinoma expressing ovalbumin (OVA) in wild type mice bearing MC38-Ova tumors relative to wild type OT1 CD8+ T cells (FIG. 3D). Indeed, the tumor growth in recipients of MT-OT1 CD8+ T cells resembled that of mice that did not receive any tumor antigen-specific CD8+ T cells. These results indicate a CD8+ T cell intrinsic role of MT. Collectively, these data support the premise that expression of metallothioneins in CD8+ T cells plays a critical role in suppressing anti-tumor T cell responses.

Figure 3E:
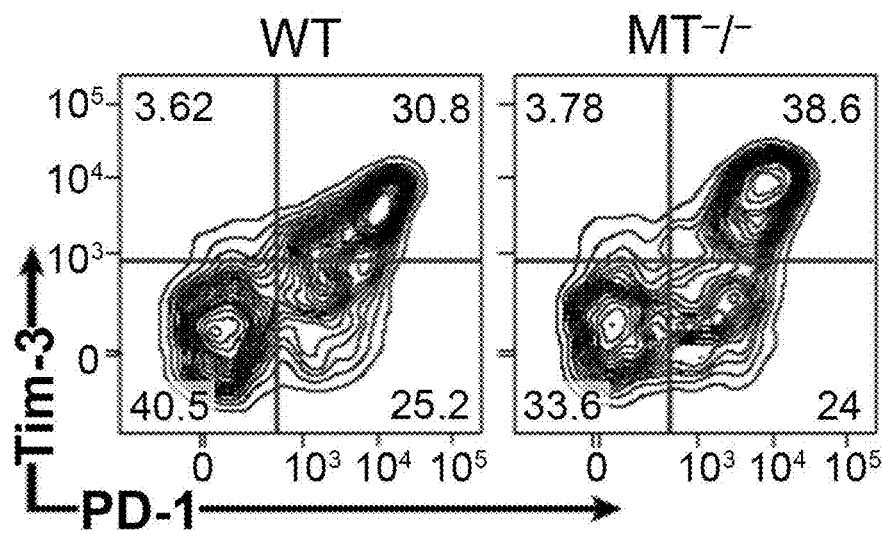
Figure 3E:
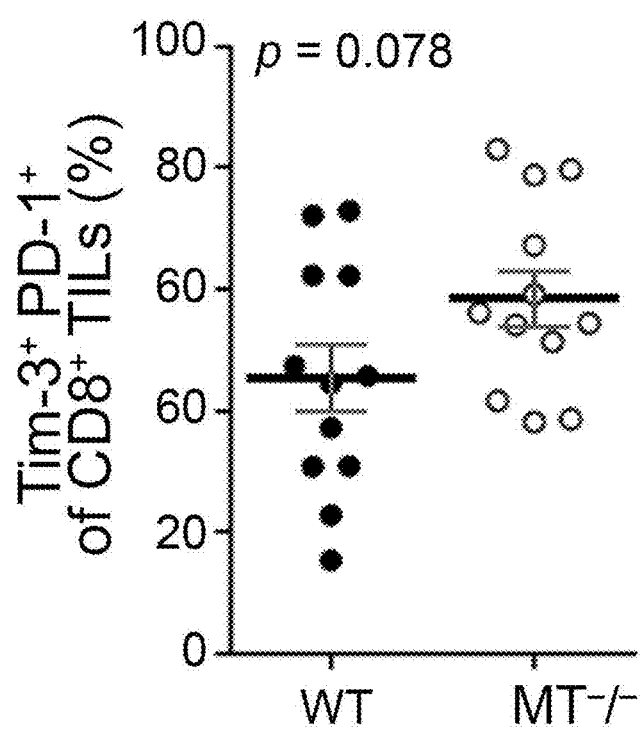
Figure 3F:
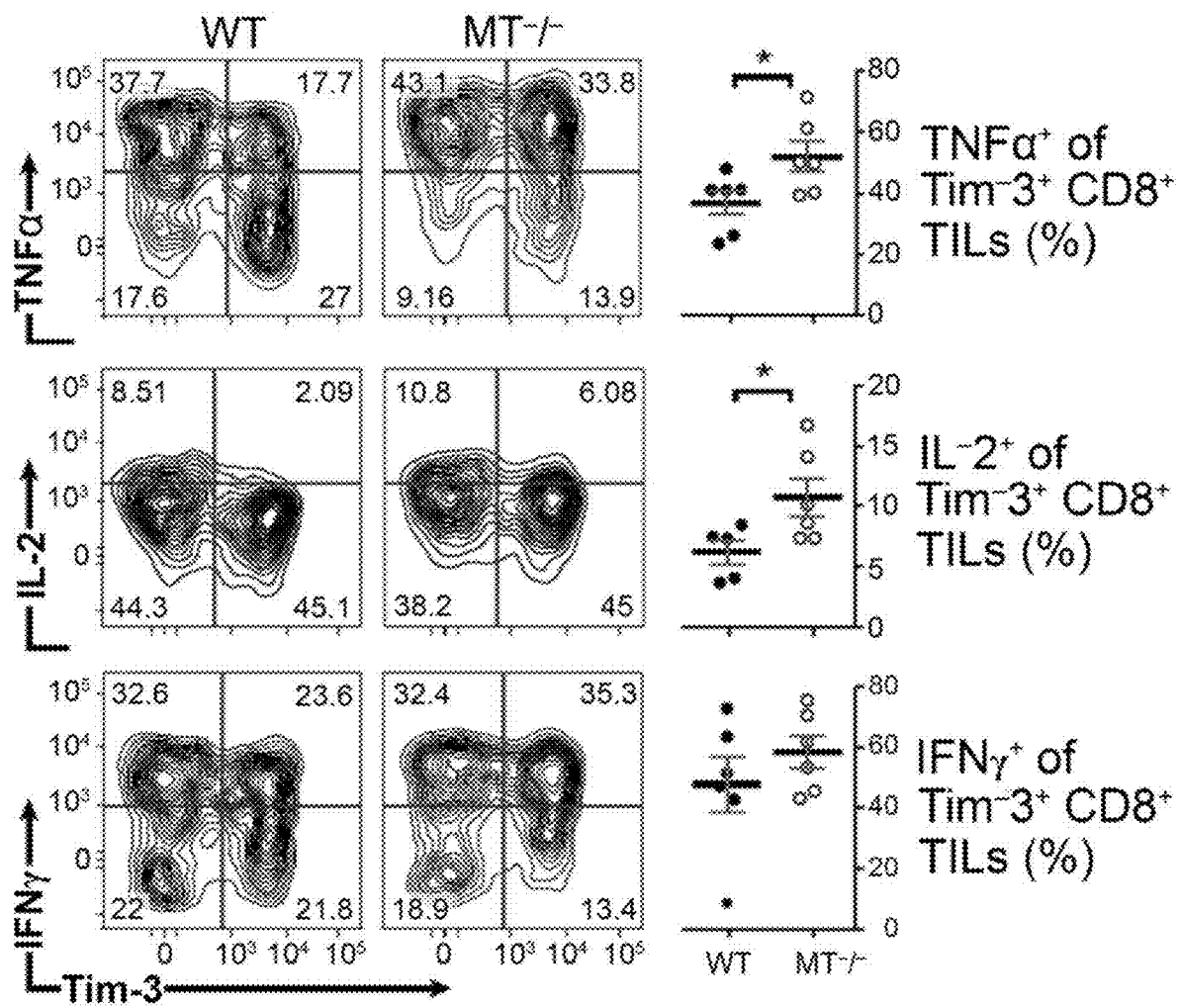
Figure 3G:
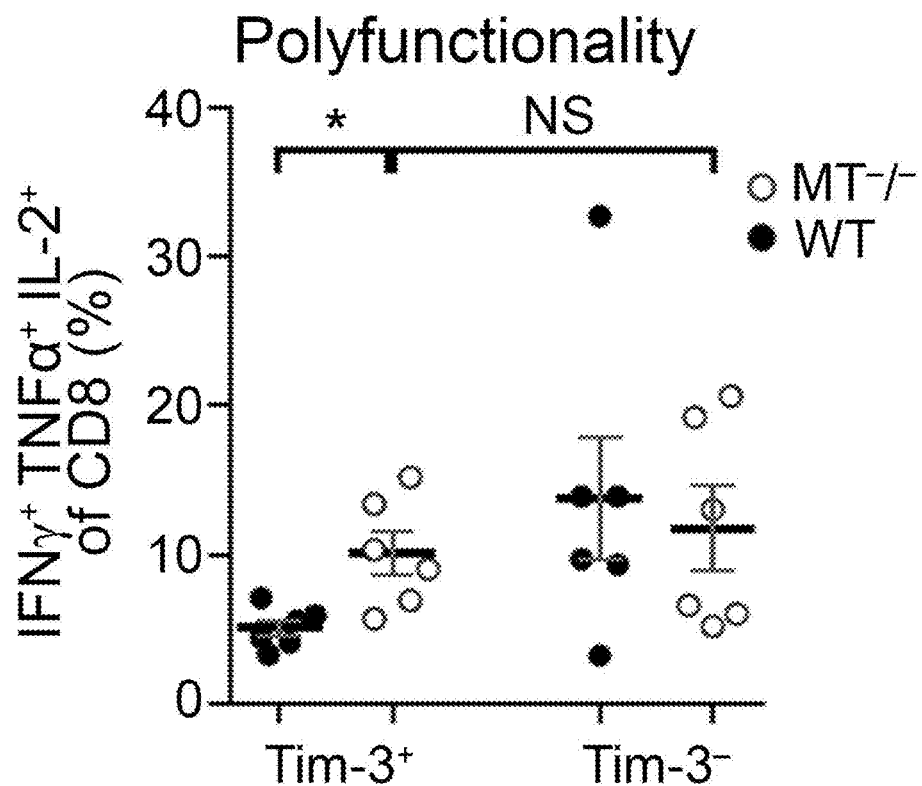

The Applicants next analyzed the phenotype of TILs isolated from wild type and $MT^{-/-}$ tumor-bearing mice. Cytokine production and co-inhibitory receptor expression was measured using flow cytometry. Interestingly, the expression of Tim3 and PD-1 was either not significantly altered or even increased in $MT^{-/-}$ mice (FIG. 3E). However, the effector function of Tim-3+ $MT^{-/-}$ CD8+ TILs was significantly improved, showing higher production of IL-2, TNF-alpha (FIG. 3F) and granzyme B (FIG. 3I), consistent with slower tumor growth (FIG. 3A). Notably, the increase of IL-2 and TNF-alpha was most significant on the Tim3+ TILs. It has been reported that polyfunctional effector CD8+ T cells with the ability to simultaneously produce multiple cytokines are associated with protective immunity in patients with controlled chronic viral infections, as well as cancer patients responsive to immune therapy (Spranger et al., 2014, J. Immunother. Cancer, vol. 2, 3). In this regard, Applicants noted that $MT^{-/-}$ TILs also contained a higher percentage of polyfunctional T cells, specifically in the Tim3+ subpopulation (FIG. 3G), also consistent with slower tumor growth (FIG. 3A). These results suggest that MT plays a role in restraining CD8+ T cell function particularly in the DP population without dramatically influencing the PD-1 and Tim3 subpopulation structure, such that PD-1 and Tim3 no longer mark dysfunctional CD8+ TILs in the $MT^{-/-}$ setting. Hence, in the above experiments, metallothionein deficiency improved T cell dysfunction without affecting coinhibitory receptor expression. Thus, in the setting of metallothionein deficiency, Tim3 and PD-1 expression are no longer associated with dysfunctional T cell phenotype but rather with activated T cell phenotype. This uncoupling of co-inhibitory receptor expression from dysfunctional T cell phenotype suggested that co-inhibitory receptors are part of a transcriptional program that is associated with T cell activation and is separable from the transcriptional program that drives the dysfunctional CD8+ T cell phenotype.

Without wishing to be bound to any theory, the Applicants postulate that the present results, which are seemingly in contrast to the established association of Tim-3 and PD-1 with CD8 dysfunction, may suggest a model where metallothioneins function either independently or downstream of co-inhibitory receptors to restrain the effector functions of T cells, and thus their knockout decouples the expression of co-inhibitory receptors from the cell's downstream phenotype.

Figure 3H:
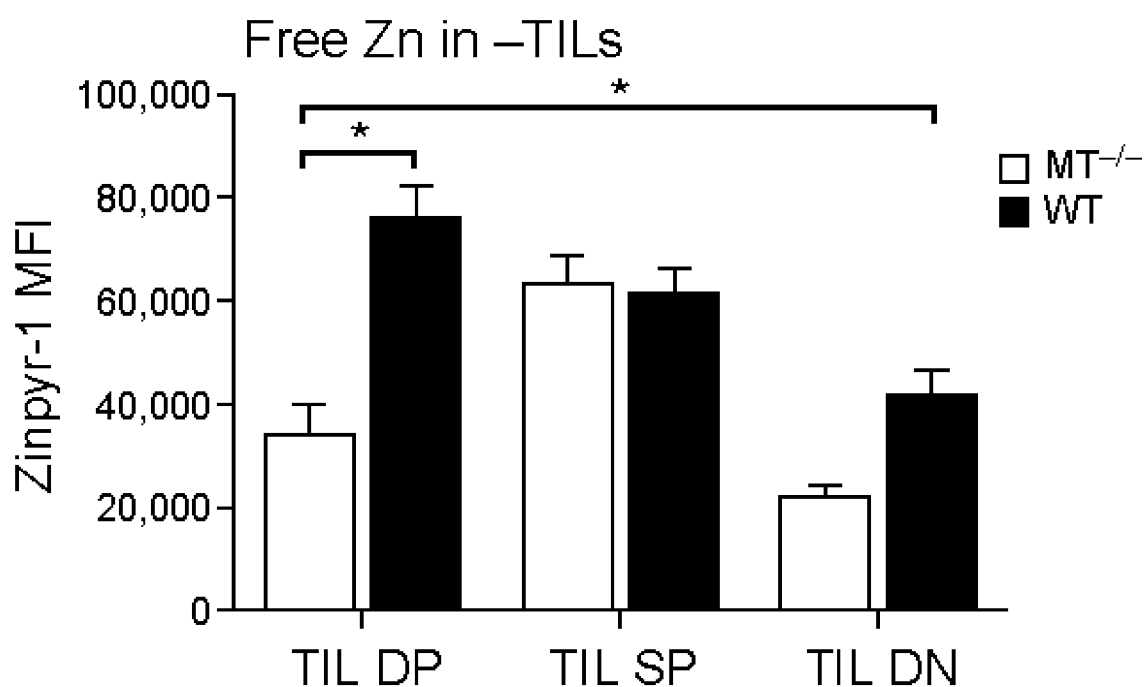
Figure 3I:
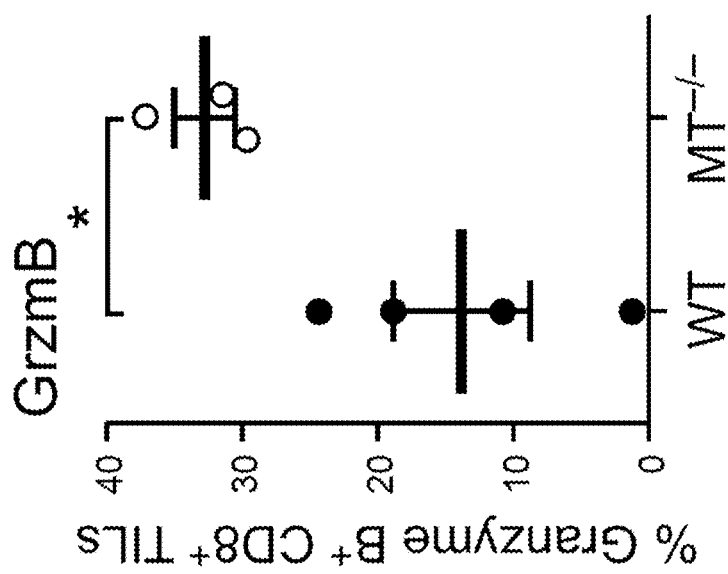
Figure 3I:
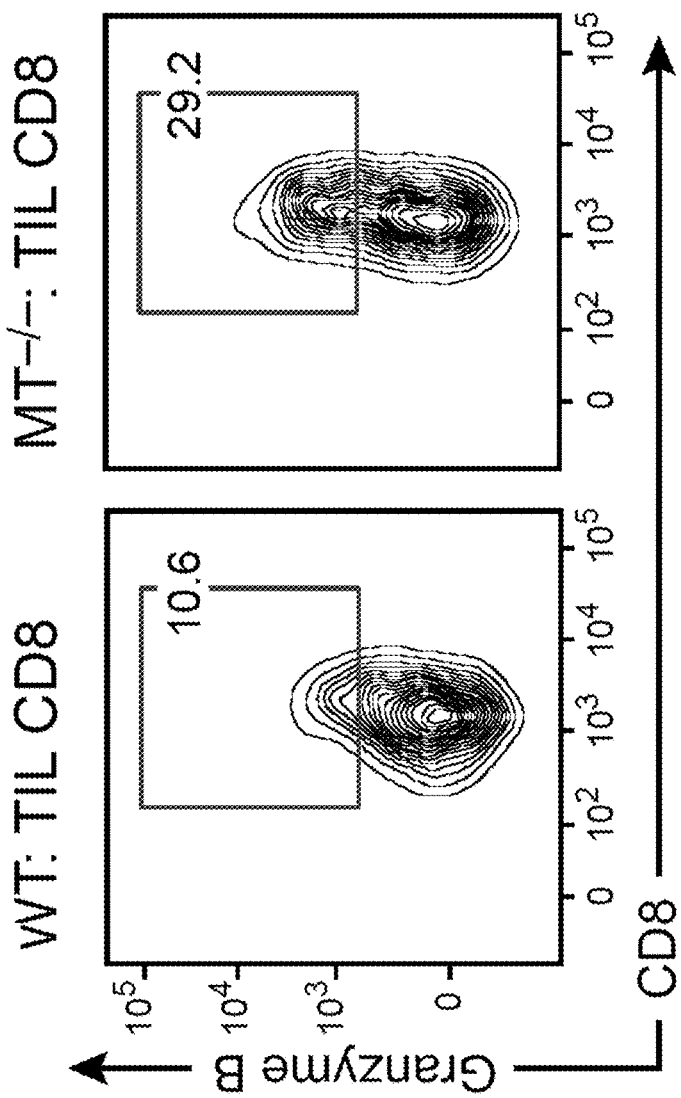

Finally, the Applicants addressed whether zinc metabolism had a role in the observed MT-induced regulation of CD8+ T cell function and tumor growth. If so, a change in the zinc status within the TILs in $MT^{-/-}$ vs. wild type mice should be observed. Indeed, a significantly reduced zinc level in DP TILs in $MT^{-/-}$ as compared to WT was observed (FIG. 3H). This result supports the notion that MT plays a role in regulating zinc metabolism and that the zinc status of CD8+ T cells correlates with T cell dysfunction.

Example 4: Expression Profiling of MT-/- TILs Identifies Distinct Programs for T Cell Activation and T Cell Dysfunction and T Cell Dysfunction The Applicants further realized that the unexpected observation that the dysfunctional phenotype of DP CD8+ TILs was lost in the absence of MT1 and MT2 (FIG. 3F,G, I), even though co-inhibitory receptors were expressed, provided a system allowing to gain an insight into the specific characteristics of T cell dysfunction in cancer by comparing the transcriptome of dysfunctional and non-dysfunctional CD8+ Tim3+PD+ subpopulations. More particularly, transcriptional profiling of $MT^{-/-}$ TILs can decouple signatures of T cell activation and T cell dysfunction, allowing to distinguish within the dysfunction signature of Tim3+PD1+ TILs the gene module associated with T cell activation from the gene module that is only related to T cell dysfunction, leading to identification of the respective components of the activation and dysfunction programs. The Applicants hypothesized that both modules should be expressed in the CD8+ Tim3+PD1+ population in WT (dysfunctional) cells, but only the (upstream) activation module should be expressed in the $MT^{-/-}$ (functional) cells.

Figure 4A:
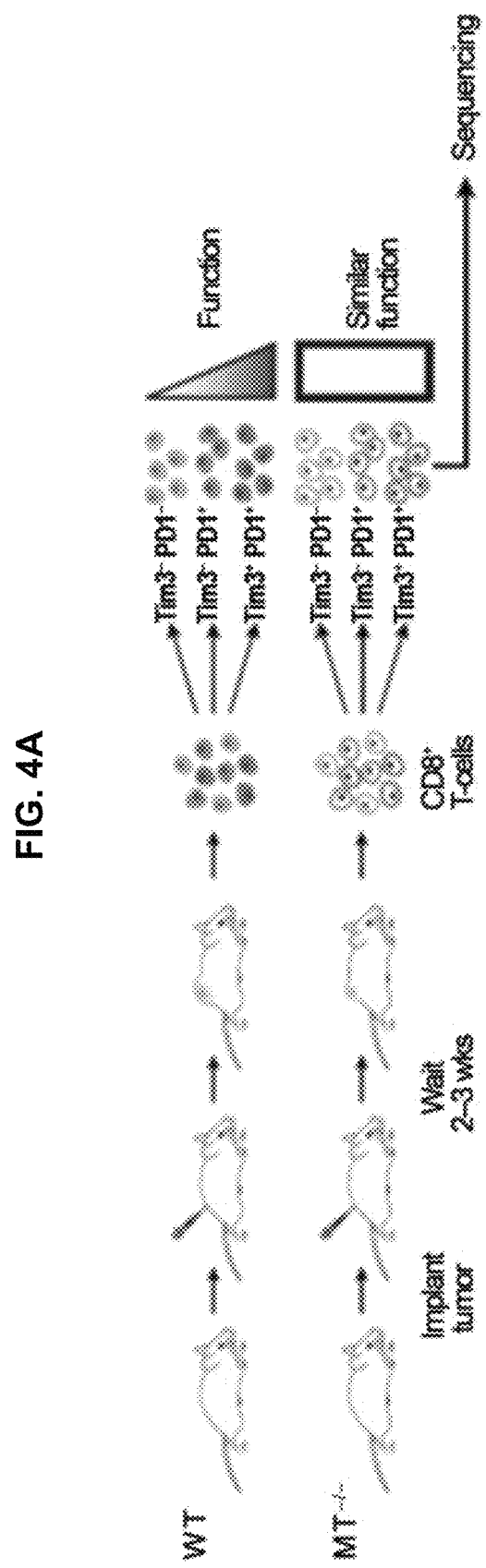
FIG. 4A-4F show that $MT^{-/-}$ transcriptome enables decoupling of activation and dysfunction in $CD8^+$ TILs.
Figure 4B:
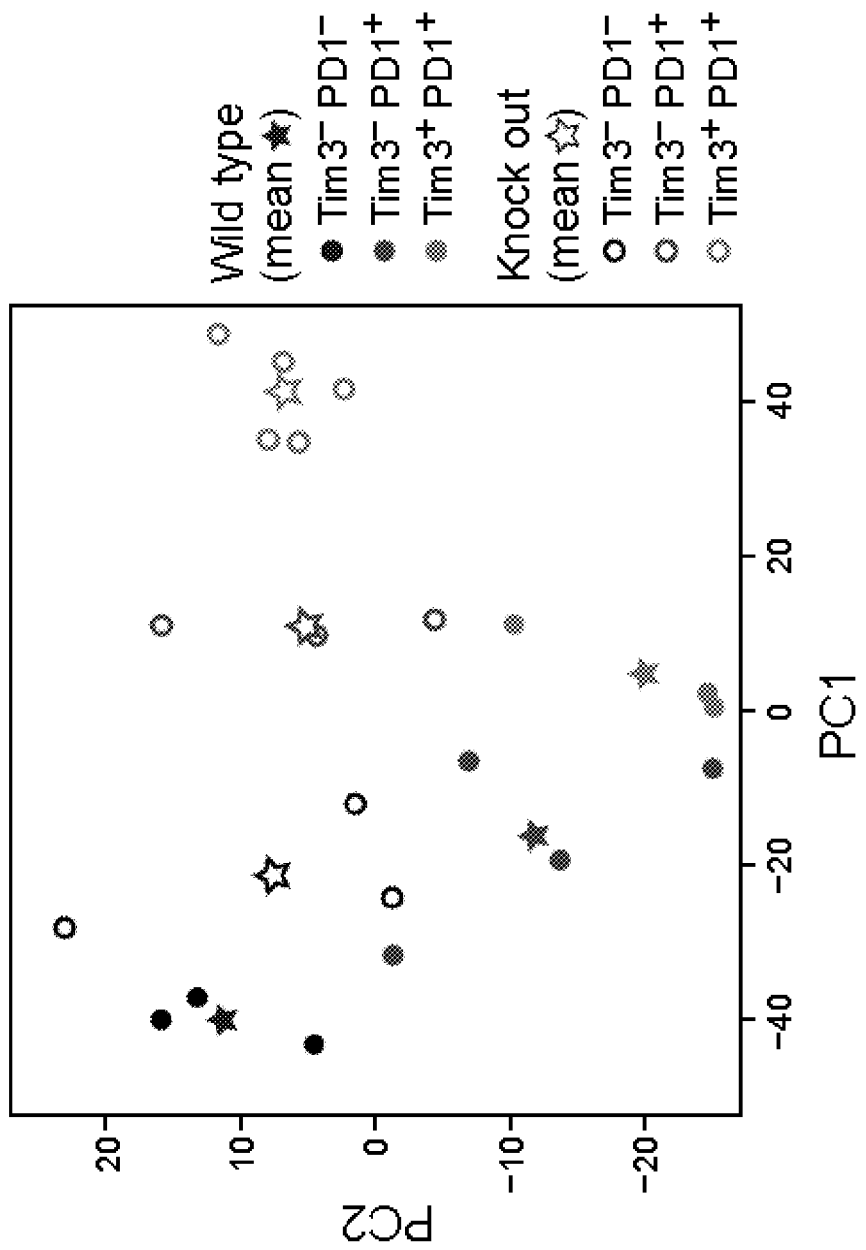
Figure 4C:
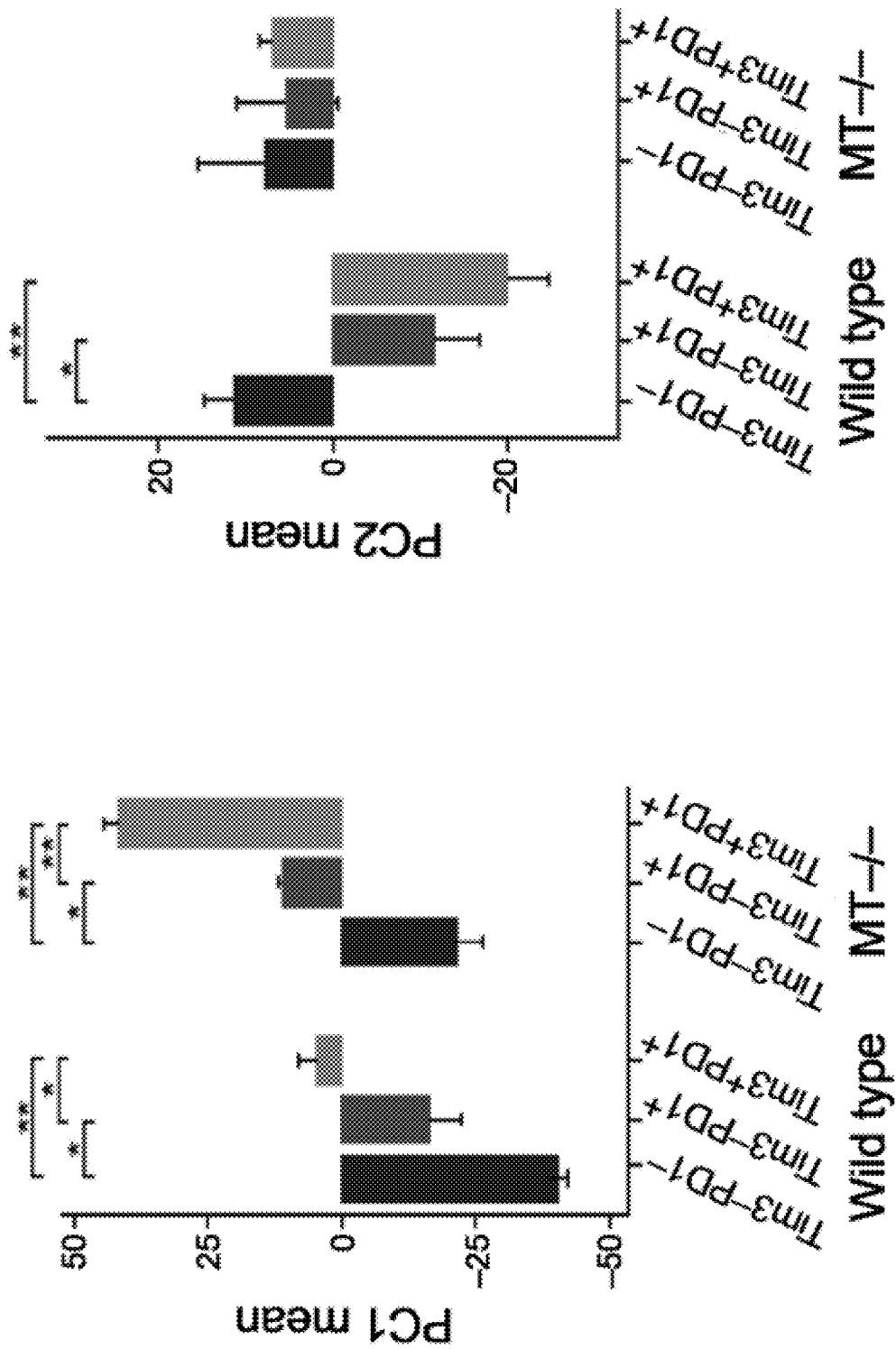

The Applicants therefore isolated the three subpopulations (DP/SP/DN) of CD8+ TILs from $MT^{-/-}$ tumor-bearing mice and wild type littermate tumor-bearing controls and performed unbiased whole-transcriptome analysis (FIG. 4A). To extract the major determinants of variability across the samples Applicants conducted a principle-component analysis (PCA), incorporating the 4,155 genes that were both highly expressed and variable across the CD8+ TIL subsets (FIG. 4B) (Langmead et al., 2009, Genome Biol 10, R25; Li and Dewey, 2011, BMC Bioinformatics 12, 323; Picelli et al., 2013, Nat Methods 10, 1096-1098)). Applicants found that first principle component (PC1; 38% of variance) clearly separated the DN/SP/DP subpopulations of CD8+ TILs from both the WT and $MT^{-/-}$ and in a manner reflecting their transcriptional activation status (FIG. 4B,C). In each of WT or $MT^{-/-}$, the DN, SP, and DP profiles had respectively increasing scores on PC1, with DP populations scoring highest (FIG. 4C). $MT^{-/-}$ DPs scored higher than WT DPs, and had the strongest association with PC1. Thus, Applicants inferred that PC1 separated cells based on their activation status, with high activation associated with high PC1 scores. Indeed, cell cycle associated signatures were highly enriched for the PC1 loadings ($P<10^{-3}$, GSEA Preranked test); a signature for CD8+ in vivo activation (Sarkar et al., 2008, supra) was positively correlated with PC1. A ranked Gene Set Enrichment Analysis (GSEA) showed strong association of PC1 with T-cell activation, cell-cycle, and T cell dysfunction/exhaustion signatures both from previous studies and in the Cluster 2. PC1 KEGG Enrichments (FDR<0.01):
1. KEGG_CELL_CYCLE
2. KEGG_DNA_REPLICATION
3. KEGG_OOCYTE_MEIOSIS
4. KEGG_PROGESTERONE_MEDIATED_OOCYTE_MATURATION.

Figure 4D:
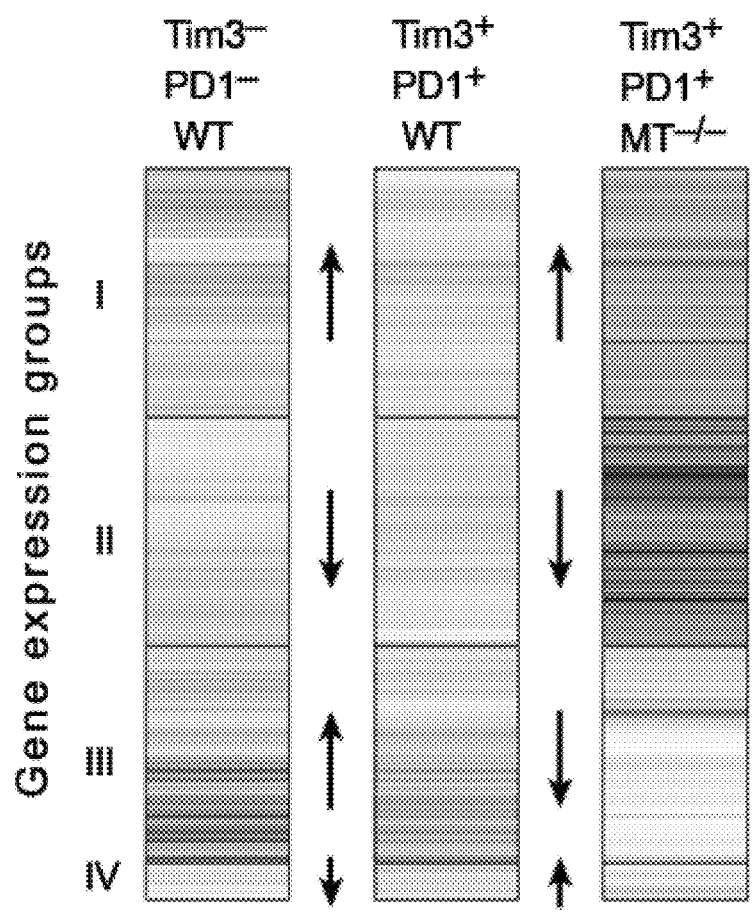
Figure 4E:
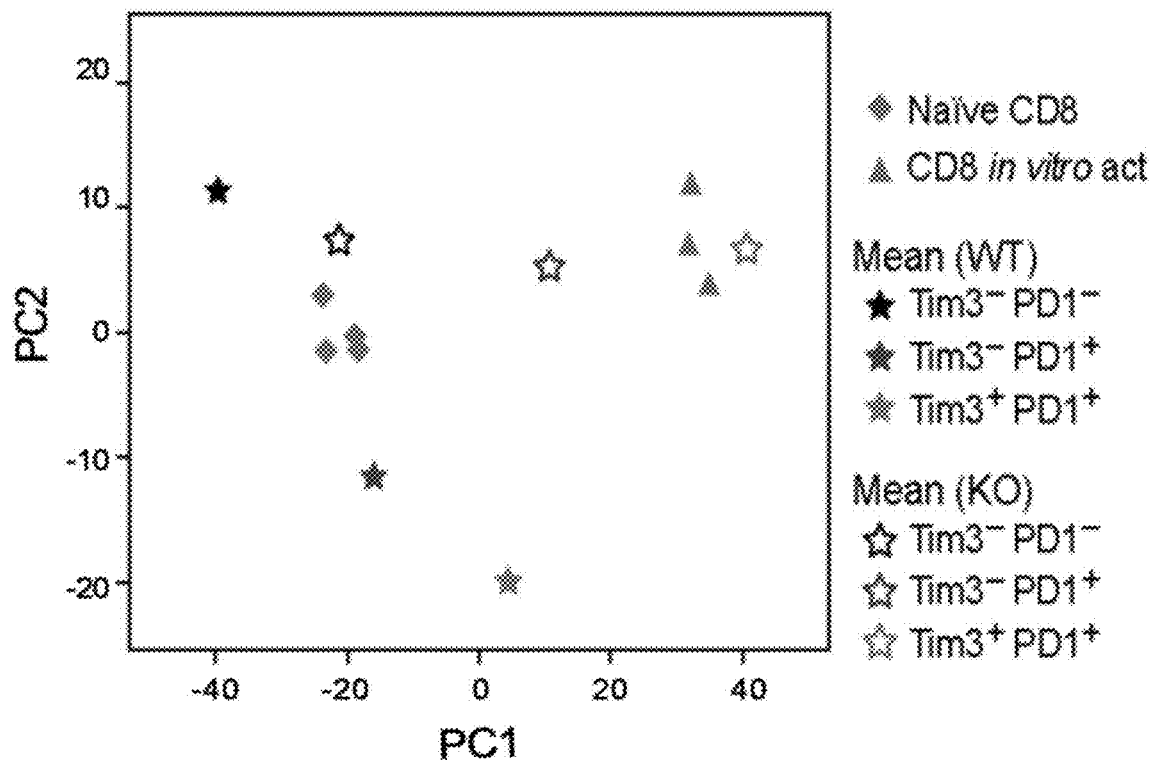
Figure 4F:
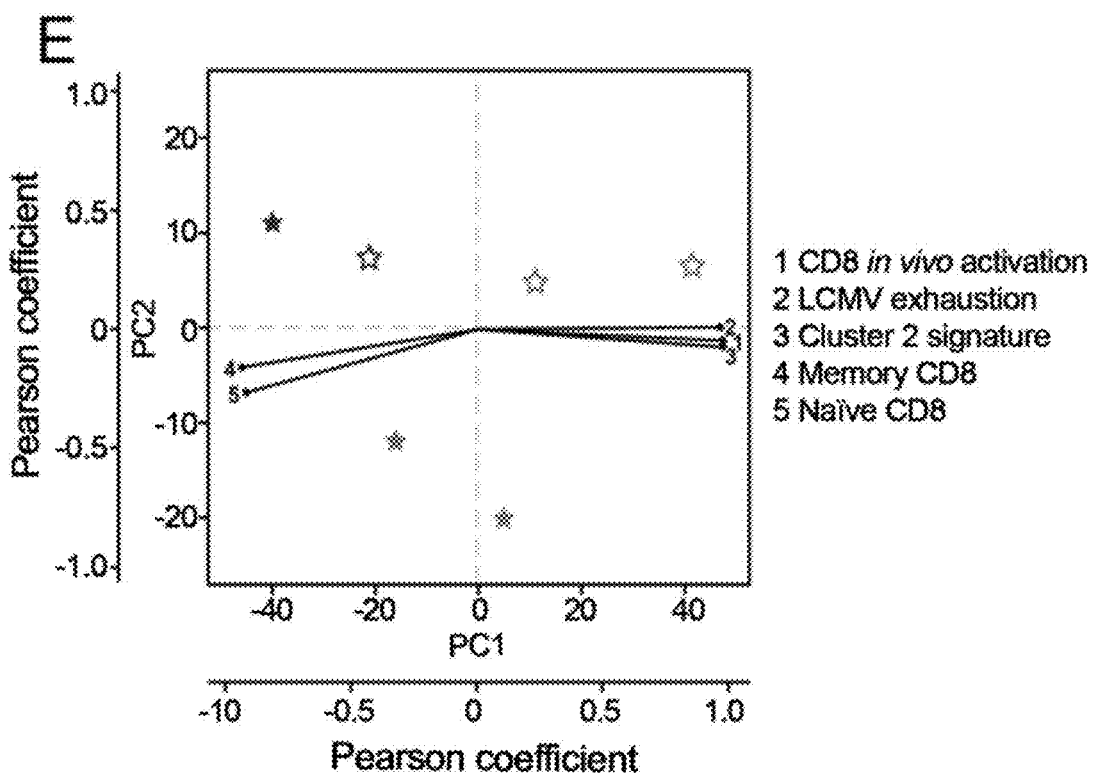

Indeed, naïve and in vitro activated CD8+ T cell profiles from cells isolated from non-tumor bearing WT mice had low and high scores, respectively, on PC1 (FIG. 4F). Thus, PC1 captures a healthy CD8+ T cell activation transcriptional signature. Interestingly, PC1 also showed enrichment for previously annotated signatures of T cell dysfunction/exhaustion (Doering et al., 2012, supra) as well as the cluster 2 gene signature (FIG. 4F). Collectively, these data indicate that PC1 captures a transcriptional signature for CD8+ T cell activation and that the enrichment of previously annotated T cell exhaustion signatures with PC1 genes likely reflects the coupling of the T cell activation and dysfunction gene modules.

PC2 reflected the unique contribution of the T cell dysfunction program. PC2 (8.4% of variance) distinguished clearly between the DN/SP/DP CD8+ TILs populations from WT but not MT$^{-/-}$ mice (FIG. 4C), but did not separate naïve and in vitro activated T cells (FIG. 4F). Since T cell dysfunction is observed in WT SP and DP cells but not MT$^{-/-}$ SP and DP cells, this suggests that PC2 (and any associated genes) represents the activity of the downstream module in the exhaustion program and could contribute to the dysfunctional phenotype WT CD8+ TILs., which expression depends on MT, and is absent otherwise.

Thus, while the WT subpopulations are separated by independent contributions from both PC1 and PC2 (FIG. 5C), previous annotated signatures of T cell dysfunction account only for the separation observed on PC1, likely because of the larger proportion of variance it explains, and the strong association in WT TILs between the upstream activation program and the downstream dysfunction program.

Interestingly, PC2 genes showed no significant association with known signatures of T cell activation, previously annotated signatures of T cell dysfunction/exhaustion, or other features of T cell biology.

TABLE 2

GSEA enrichments for gene loadings of PC1 and PC2.

| NAME | GS<br> follow link to MSigDB | GS DETAILS | SIZE | ES | NES | NOM p-val |
|---|---|---|---|---|---|---|
| KEGG_MAPK_SIGNALING_PATHWAY | KEGG_MAPK_SIGNALING_PATHWAY | Details . . . | 72 | 0.6424006 | 2.3417175 | 0 |
| KEGG_B_CELL_RECEPTOR_SIGNALING_PATHWAY | KEGG_B_CELL_RECEPTOR_SIGNALING_PATHWAY | Details . . . | 34 | 0.70799434 | 2.2316542 | 0 |
| KEGG_CYTOKINE_CYTOKINE_RECEPTOR_INTERACTION | KEGG_CYTOKINE_CYTOKINE_RECEPTOR_INTERACTION | Details . . . | 64 | 0.59601074 | 2.1291182 | 0 |
| KEGG_HEMATOPOIETIC_CELL_LINEAGE | KEGG_HEMATOPOIETIC_CELL_LINEAGE | Details . . . | 18 | 0.75382715 | 2.022664 | 0 |
| KEGG_FC_GAMMA_R_MEDIATED_PHAGOCYTOSIS | KEGG_FC_GAMMA_R_MEDIATED_PHAGOCYTOSIS | Details . . . | 28 | 0.66880953 | 2.020188 | 0 |
| KEGG_LEUKOCYTE_TRANSENDOTHELIAL_MIGRATION | KEGG_LEUKOCYTE_TRANSENDOTHELIAL_MIGRATION | Details . . . | 26 | 0.67029366 | 1.9933354 | 0.001510 57 |
| KEGG_ADHERENS_JUNCTION | KEGG_ADHERENS_JUNCTION | Details . . . | 16 | 0.733344 | 1.95144985 7 | 0 |
| KEGG_FC_EPSILON_RI_SIGNALING_PATHWAY | KEGG_FC_EPSILON_RI_SIGNALING_PATHWAY | Details . . . | 22 | 0.6713664 | 1.9294703 | 0.001579 78 |
| KEGG_PATHWAYS_IN_CANCER | KEGG_PATHWAYS_IN_CANCER | Details . . . | 89 | 0.510569 7 | 1.905192 7 | 0 |
| KEGG_PHOSPHATIDYLINOSITOL_SIGNALING_SYSTEM | KEGG_PHOSPHATIDYLINOSITOL_SIGNALING_SYSTEM | Details . . . | 26 | 0.6318883 | 1.874481 3 | 0 |
| KEGG_CHEMOKINE_SIGNALING_PATHWAY | KEGG_CHEMOKINE_SIGNALING_PATHWAY | Details . . . | 55 | 0.5339553 | 1.8723699 | 0 |
| KEGG_NEUROTROPHIN_SIGNALING_PATHWAY | KEGG_NEUROTROPHIN_SIGNALING_PATHWAY | Details . . . | 37 | 0.5732551 | 1.8374879 | 0.001522 07 |
| KEGG_REGULATION_OF_ACTIN_CYTOSKELETON | KEGG_REGULATION_OF_ACTIN_CYTOSKELETON | Details . . . | 38 | 0.5717748 | 1.8181554 | 0 |
| KEGG_VEGF_SIGNALING_PATHWAY | KEGG_VEGF_SIGNALING_PATHWAY | Details . . . | 21 | 0.646476 2 | 1.817689 8 | 0.001547 99 |
| KEGG_PROGESTERONE_MEDIATED_OOCYTE_MATURATION | KEGG_PROGESTERONE_MEDIATED_OOCYTE_MATURATION | Details . . . | 29 | 0.578361 3 | 1.776087 8 | 0.001483 68 |
| KEGG_COLORECTAL_CANCER | KEGG_COLORECTAL_CANCER | Details . . . | 29 | 0.576902 | 1.754214 8 | 0.003072 2 |
| KEGG_LEISHMANIA_INFECTION | KEGG_LEISHMANIA_INFECTION | Details . . . | 23 | 0.591793 5 | 1.732933 4 | 0.012269 94 |

TABLE 2-continued

GSEA enrichments for gene loadings of PC1 and PC2.

| Name | Name | | | | | | |
|------|------|------|---|---|---|---|---|
| KEGG_GAP_JUNCTION | KEGG_GAP_JUNCTION | Details... | 16 | 0.655819 | 1.716728 | 0.00195 | 0.006464 |
| KEGG_GNRH_SIGNALING_PATHWAY | KEGG_GNRH_SIGNALING_PATHWAY | Details... | 200 | 0.6001545 | 1.6995355 | 0.013910036 | |
| KEGG_ENDOCYTOSIS | KEGG_ENDOCYTOSIS | Details... | 48 | 0.50726146 | 1.6951907 | 0.002801212 | |
| KEGG_WNT_SIGNALING_PATHWAY | KEGG_WNT_SIGNALING_PATHWAY | | 300 | 0.54864216 | 1.6717725 | 0.00294985 | |
| KEGG_INSULIN_SIGNALING_PATHWAY | KEGG_INSULIN_SIGNALING_PATHWAY | | 372 | 0.50553552 | 1.6294372 | 0.01044776 | |
| KEGG_ALZHEIMERS_DISEASE | KEGG_ALZHEIMERS_DISEASE | | 333 | 0.51445156 | 1.6194717 | 0.01689708 | |
| KEGG_CHRONIC_MYELOID_LEUKEMIA | KEGG_CHRONIC_MYELOID_LEUKEMIA | | 285 | 0.5424945 | 1.6112645 | 0.01820941 | |
| KEGG_ERBB_SIGNALING_PATHWAY | KEGG_ERBB_SIGNALING_PATHWAY | | 26 | 0.5160332 | 1.576521 | 0.02556391 | |
| KEGG_APOPTOSIS | KEGG_APOPTOSIS | | 36 | 0.48434055 | 1.5470847 | 0.01923077 | |
| KEGG_TOLL_LIKE_RECEPTOR_SIGNALING_PATHWAY | KEGG_TOLL_LIKE_RECEPTOR_SIGNALING_PATHWAY | | 41 | 0.47326176 | 1.541886 | 0.02496329 | |
| KEGG_SMALL_CELL_LUNG_CANCER | KEGG_SMALL_CELL_LUNG_CANCER | | 26 | 0.50380874 | 1.5050162 | 0.04113924 | |
| KEGG_NOD_LIKE_RECEPTOR_SIGNALING_PATHWAY | KEGG_NOD_LIKE_RECEPTOR_SIGNALING_PATHWAY | | 19 | 0.5392119 | 1.4911547 | 0.06079027 | |
| KEGG_ACUTE_MYELOID_LEUKEMIA | KEGG_ACUTE_MYELOID_LEUKEMIA | | 22 | 0.5146318 | 1.4875253 | 0.05434782 | |
| KEGG_GLYCEROPHOSPHOLIPID_METABOLISM | KEGG_GLYCEROPHOSPHOLIPID_METABOLISM | | 15 | 0.5642713 | 1.4783891 | 0.06220096 | |
| KEGG_OOCYTE_MEIOSIS | KEGG_OOCYTE_MEIOSIS | | 33 | 0.4672855 | 1.4661755 | 0.05547226 | |
| KEGG_CALCIUM_SIGNALING_PATHWAY | KEGG_CALCIUM_SIGNALING_PATHWAY | | 277 | 0.4874947 | 1.4565356 | 0.060882 8 | |
| KEGG_GLUTATHIONE_METABOLISM | KEGG_GLUTATHIONE_METABOLISM | | 15 | 0.548904 | 1.453085 | 0.06885246 | |
| KEGG_MTOR_SIGNALING_PATHWAY | KEGG_MTOR_SIGNALING_PATHWAY | | 225 | 0.5030085 | 1.4492611 | 0.07570978 | |
| KEGG_FOCAL_ADHESION | KEGG_FOCAL_ADHESION | | 34 | 0.45582932 | 1.439669 | 0.06278027 | |
| KEGG_PANCREATIC_CANCER | KEGG_PANCREATIC_CANCER | | 27 | 0.47110844 | 1.427469 | 0.083582309 | |
| KEGG_P53_SIGNALING_PATHWAY | KEGG_P53_SIGNALING_PATHWAY | | 31 | 0.4590733 | 1.421358 | 0.0735298242 | |
| KEGG_RENAL_CELL_CARCINOMA | KEGG_RENAL_CELL_CARCINOMA | | 21 | 0.4992554 | 1.4102653 | 0.07763975 | |
| KEGG_GLIOMA | KEGG_GLIOMA | | 16 | 0.5452685 | 1.408405 | 0.10172144 | |
| KEGG_ALDOSTERONE_REGULATED_SODIUM_REABSORPTION | KEGG_ALDOSTERONE_REGULATED_SODIUM_REABSORPTION | | 15 | 0.528262855 | 1.3959928 | 0.11256117 | |
| KEGG_IOSITOL_PHOSPHATE_METABOLISM | KEGG_IOSITOL_PHOSPHATE_METABOLISM | | 17 | 0.52720153 | 1.3953542 | 0.10737279 | |
| KEGG_TYPE_II_DIABETES_MELLITUS | KEGG_TYPE_II_DIABETES_MELLITUS | | 17 | 0.5018920 | 1.3946338 | 0.10010181 | |

TABLE 2-continued

GSEA enrichments for gene loadings of PC1 and PC2.

| Name | Name | Count | Value 1 | Value 2 | Value 3 |
|---|---|---|---|---|---|
| KEGG_NON_SMALL_CELL_LUNG_CANCER | KEGG_NON_SMALL_CELL_LUNG_CANCER | 16 | 0.5352725 | 1.3922657 | 0.0912 |
| KEGG_NATURAL_KILLER_CELL_MEDIATED_CYTOTOXICITY | KEGG_NATURAL_KILLER_CELL_MEDIATED_CYTOTOXICITY | 41 | 0.41863474 | 1.3774581 | 0.08333334 |
| KEGG_VASCULAR_SMOOTH_MUSCLE_CONTRACTION | KEGG_VASCULAR_SMOOTH_MUSCLE_CONTRACTION | 16 | 0.50117517 | 1.3372933 | 0.15031646 |
| KEGG_EPITHELIAL_CELL_SIGNALING_IN_HELICOBACTER_PYLORI_INFECTION | KEGG_EPITHELIAL_CELL_SIGNALING_IN_HELICOBACTER_PYLORI_INFECTION | 24 | 0.44272485 | 1.2918754 | 0.14495113 |
| KEGG_PROSTATE_CANCER | KEGG_PROSTATE_CANCER | 23 | 0.44710904 | 1.279609 | 0.17272727 |
| KEGG_T_CELL_RECEPTOR_SIGNALING_PATHWAY | KEGG_T_CELL_RECEPTOR_SIGNALING_PATHWAY | 38 | 0.38582063 | 1.2371033 | 0.16395864 |
| KEGG_NEUROACTIVE_LIGAND_RECEPTOR_INTERACTION | KEGG_NEUROACTIVE_LIGAND_RECEPTOR_INTERACTION | 16 | 0.46010584 | 1.2206852 | 0.21103896 |
| KEGG_TGF_BETA_SIGNALING_PATHWAY | KEGG_TGF_BETA_SIGNALING_PATHWAY | 19 | 0.42516205 | 1.1783327 | 0.25827813 |
| KEGG_UBIQUITIN_MEDIATED_PROTEOLYSIS | KEGG_UBIQUITIN_MEDIATED_PROTEOLYSIS | 44 | 0.34863842 | 1.1760381 | 0.23579545 |
| KEGG_CELL_CYCLE | KEGG_CELL_CYCLE | 55 | 0.33941835 | 1.162439 | 0.21840659 |
| KEGG_AMYOTROPHIC_LATERAL_SCLEROSIS_ALS | KEGG_AMYOTROPHIC_LATERAL_SCLEROSIS_ALS | 18 | 0.42941752 | 1.1573184 | 0.28209192 |
| KEGG_BASE_EXCISION_REPAIR | KEGG_BASE_EXCISION_REPAIR | 18 | 0.42478803 | 1.1554246 | 0.29605263 |
| KEGG_JAK_STAT_SIGNALING_PATHWAY | KEGG_JAK_STAT_SIGNALING_PATHWAY | 44 | 0.34720463 | 1.1458596 | 0.261348 |
| KEGG_AXON_GUIDANCE | KEGG_AXON_GUIDANCE | 24 | 0.38434517 | 1.1316112 | 0.28661418 |
| KEGG_ENDOMETRIAL_CANCER | KEGG_ENDOMETRIAL_CANCER | 19 | 0.4051678 | 1.1224884 | 0.31748468 |
| KEGG_SPHINGOLIPID_METABOLISM | KEGG_SPHINGOLIPID_METABOLISM | 15 | 0.43023482 | 1.1021138 | 0.34810126 |
| KEGG_ADIPOCYTOKINE_SIGNALING_PATHWAY | KEGG_ADIPOCYTOKINE_SIGNALING_PATHWAY | 19 | 0.38475955 | 1.0544876 | 0.40924093 |
| KEGG_CYTOSOLIC_DNA_SENSING_PATHWAY | KEGG_CYTOSOLIC_DNA_SENSING_PATHWAY | 19 | 0.3746188 | 1.0387726 | 0.43209878 |
| KEGG_CELL_ADHESION_MOLECULES_CAMS | KEGG_CELL_ADHESION_MOLECULES_CAMS | 19 | 0.36824366 | 1.026336 | 0.434375 |
| KEGG_TIGHT_JUNCTION | KEGG_TIGHT_JUNCTION | 22 | 0.33711565 | 0.9644612 | 0.5386997 |
| KEGG_HUNTINGTONS_DISEASE | KEGG_HUNTINGTONS_DISEASE | 18 | 0.32967693 | 0.9167991 | 0.5820189 |
| KEGG_DNA_REPLICATION | KEGG_DNA_REPLICATION | 25 | 0.28674263 | 0.83589387 | 0.7098284 |
| KEGG_PURINE_METABOLISM | KEGG_PURINE_METABOLISM | 44 | 0.24416003 | 0.8003361 | 0.76933897 |
| KEGG_AMINOACYL_TRNA_BIOSYNTHESIS | KEGG_AMINOACYL_TRNA_BIOSYNTHESIS | 17 | 0.23202989 | 0.6257108 | 0.9234528 |
| KEGG_GLYCOLYSIS_GLUCONEOGENESIS | KEGG_GLYCOLYSIS_GLUCONEOGENESIS | 21 | 0.21082664 | 0.6062998 | 0.9476117 |

TABLE 2-continued

GSEA enrichments for gene loadings of PC1 and PC2.

| | | | | | | |
|---|---|---|---|---|---|---|
| KEGG_RIG_I_LIKE_RECEPTOR_SIGNALING_PATHWAY | KEGG_RIG_I_LIKE_RECEPTOR_SIGNALING_PATHWAY | 21 | 781707 | 16599 | 457326 | 0.19 0.56 0.96 |

| NAME | FDR q-val | FWER p-val | RANK AT MAX | LEADING EDGE |
|---|---|---|---|---|
| KEGG_MAPK_SIGNALING_PATHWAY | 0 | 0 | 686 | tags = 49%, list = 17%, signal = 57% |
| KEGG_B_CELL_RECEPTOR_SIGNALING_PATHWAY | 0 | 0 | 832 | tags = 62%, list = 20%, signal = 77% |
| KEGG_CYTOKINE_CYTOKINE_RECEPTOR_INTERACTION | 0 | 0 | 656 | tags = 44%, list = 16%, signal = 51% |
| KEGG_HEMATOPOIETIC_CELL_LINEAGE | 0.00304926 | 0.009 | 437 | tags = 56%, list = 11%, signal = 62% |
| KEGG_FC_GAMMA_R_MEDIATED_PHAGOCYTOSIS | 0.00243941 | 0.009 | 635 | tags = 57%, list = 15%, signal = 67% |
| KEGG_LEUKOCYTE_TRANSENDOTHELIAL_MIGRATION | 0.00420962 | 0.019 | 1159 | tags = 81%, list = 28%, signal = 111% |
| KEGG_ADHERENS_JUNCTION | 0.00626209 | 0.033 | 533 | tags = 50%, list = 13%, signal = 57% |
| KEGG_FC_EPSILON_RI_SIGNALING_PATHWAY | 0.00776455 | 0.047 | 635 | tags = 59%, list = 15%, signal = 69% |
| KEGG_PATHWAYS_IN_CANCER | 0.00804935 | 0.055 | 641 | tags = 40%, list = 15%, signal = 47% |
| KEGG_PHOSPHATIDYLINOSITOL_SIGNALING_SYSTEM | 0.01059278 | 0.079 | 1024 | tags = 62%, list = 25%, signal = 81% |
| KEGG_CHEMOKINE_SIGNALING_PATHWAY | 0.00986896 | 0.081 | 832 | tags = 49%, list = 20%, signal = 61% |
| KEGG_NEUROTROPHIN_SIGNALING_PATHWAY | 0.01219352 | 0.108 | 635 | tags = 38%, list = 15%, signal = 44% |
| KEGG_REGULATION_OF_ACTIN_CYTOSKELETON | 0.01383754 | 0.13 | 1078 | tags = 58%, list = 26%, signal = 77% |
| KEGG_VEGF_SIGNALING_PATHWAY | 0.01296649 | 0.131 | 832 | tags = 62%, list = 20%, signal = 77% |
| KEGG_PROGESTERONE_MEDIATED_OOCYTE_MATURATION | 0.01857779 | 0.193 | 1024 | tags = 52%, list = 25%, signal = 68% |
| KEGG_COLORECTAL_CANCER | 0.02096668 | 0.231 | 641 | tags = 48%, list = 15%, signal = 57% |
| KEGG_LEISHMANIA_INFECTION | 0.02304902 | 0.262 | 600 | tags = 43%, list = 14%, signal = 51% |
| KEGG_GAP_JUNCTION | 0.0257399 | 0.295 | 926 | tags = 56%, list = 22%, signal = 72% |
| KEGG_GNRH_SIGNALING_PATHWAY | 0.02883266 | 0.34 | 595 | tags = 40%, list = 14%, signal = 46% |
| KEGG_ENDOCYTOSIS | 0.02873599 | 0.352 | 517 | tags = 33%, list = 12%, signal = 38% |
| KEGG_WNT_SIGNALING_PATHWAY | 0.03428804 | 0.416 | 1293 | tags = 70%, list = 31%, signal = 101% |
| KEGG_INSULIN_SIGNALING_PATHWAY | 0.04885082 | 0.56 | 1271 | tags = 54%, list = 31%, signal = 77% |
| KEGG_ALZHEIMERS_DISEASE | 0.05159632 | 0.597 | 539 | tags = 27%, list = 13%, signal = 31% |
| KEGG_CHRONIC_MYELOID_ | 0.05 | | | tags = 64%, |

TABLE 2-continued

GSEA enrichments for gene loadings of PC1 and PC2.

| Pathway | Col2 | Col3 | Col4 | Stats |
|---|---|---|---|---|
| LEUKEMIA | 243528 | 0.618 | 1246 | list = 30%, signal = 91% |
| KEGG_ERBB_SIGNALING_PATHWAY | 751728 | 0.063 0.72 | 1246 | tags = 65%, list = 30%, signal = 93% |
| KEGG_APOPTOSIS | 300969 | 0.08 0.805 | 902 | tags = 39%, list = 22%, signal = 49% |
| KEGG_TOLL_LIKE_RECEPTOR_SIGNALING_PATHWAY | 344293 | 0.08 0.818 | 635 | tags = 29%, list = 15%, signal = 34% |
| KEGG_SMALL_CELL_LUNG_CANCER | 574963 | 0.10 0.903 | 1082 | tags = 54%, list = 26%, signal = 72% |
| KEGG_NOD_LIKE_RECEPTOR_SIGNALING_PATHWAY | 276245 | 0.11 0.923 | 609 | tags = 37%, list = 15%, signal = 43% |
| KEGG_ACUTE_MYELOID_LEUKEMIA | 122104 | 0.11 0.928 | 1196 | tags = 59%, list = 29%, signal = 83% |
| KEGG_GLYCEROPHOSPHOLIPID_METABOLISM | 460439 | 0.11 0.947 | 812 | tags = 47%, list = 20%, signal = 58% |
| KEGG_OOCYTE_MEIOSIS | 074395 | 0.12 0.959 | 1293 | tags = 48%, list = 31%, signal = 70% |
| KEGG_CALCIUM_SIGNALING_PATHWAY | 50328 | 0.12 0.964 | 539 | tags = 37%, list = 13%, signal = 42% |
| KEGG_GLUTATHIONE_METABOLISM | 409273 | 0.12 0.966 | 531 | tags = 27%, list = 13%, signal = 30% |
| KEGG_MTOR_SIGNALING_PATHWAY | 388269 | 0.12 0.967 | 1196 | tags = 55%, list = 29%, signal = 76% |
| KEGG_FOCAL_ADHESION | 74161 | 0.12 0.968 | 635 | tags = 38%, list = 15%, signal = 45% |
| KEGG_PANCREATIC_CANCER | 342862 | 0.13 0.975 | 902 | tags = 48%, list = 22%, signal = 61% |
| KEGG_P53_SIGNALING_PATHWAY | 252711 | 0.13 0.976 | 827 | tags = 39%, list = 20%, signal = 48% |
| KEGG_RENAL_CELL_CARCINOMA | 978119 | 0.13 0.986 | 635 | tags = 43%, list = 15%, signal = 50% |
| KEGG_GLIOMA | 80615 | 0.13 0.987 | 1024 | tags = 56%, list = 25%, signal = 74% |
| KEGG_ALDOSTERONE_REGULATED_SODIUM_REABSORPTION | 552094 | 0.14 0.991 | 1420 | tags = 73%, list = 34%, signal = 111% |
| KEGG_IOSITOL_PHOSPHATE_METABOLISM | 250086 | 0.14 0.991 | 951 | tags = 41%, list = 23%, signal = 53% |
| KEGG_TYPE_II_DIABETES_MELLITUS | 986328 | 0.13 0.991 | 1166 | tags = 59%, list = 28%, signal = 81% |
| KEGG_NON_SMALL_CELL_LUNG_CANCER | 831544 | 0.13 0.992 | 1024 | tags = 56%, list = 25%, signal = 74% |
| KEGG_NATURAL_KILLER_CELL_MEDIATED_CYTOTOXICITY | 678319 | 0.14 0.992 | 635 | tags = 41%, list = 15%, signal = 48% |
| KEGG_VASCULAR_SMOOTH_MUSCLE_CONTRACTION | 70671 | 0.17 0.999 | 549 | tags = 38%, list = 13%, signal = 43% |
| KEGG_EPITHELIAL_CELL_SIGNALING_IN_HELICOBACTER_PYLORI_INFECTION | 832672 | 0.21 1 | 609 | tags = 29%, list = 15%, signal = 34% |
| KEGG_PROSTATE_CANCER | 679089 | 0.22 1 | 635 | tags = 30%, list = 15%, signal = 36% |
| KEGG_T_CELL_RECEPTOR_SIGNALING_PATHWAY | 221712 | 0.27 1 | 1293 | tags = 55%, list = 31%, signal = 79% |

TABLE 2-continued

GSEA enrichments for gene loadings of PC1 and PC2.

| Pathway | Value | | Rank | Stats |
|---|---|---|---|---|
| KEGG_NEUROACTIVE_LIGAND_RECEPTOR_INTERACTION | 0.285624 06 | 1 | 122 | tags = 19%, list = 3%, signal = 19% |
| KEGG_TGF_BETA_SIGNALING_PATHWAY | 0.334677 52 | 1 | 1510 | tags = 68%, list = 36%, signal = 107% |
| KEGG_UBIQUITIN_MEDIATED_PROTEOLYSIS | 0.330685 76 | 1 | 1312 | tags = 48%, list = 32%, signal = 69% |
| KEGG_CELL_CYCLE | 0.343045 06 | 1 | 1331 | tags = 40%, list = 32%, signal = 58% |
| KEGG_AMYOTROPHIC_LATERAL_SCLEROSIS_ALS | 0.343413 08 | 1 | 902 | tags = 44%, list = 22%, signal = 57% |
| KEGG_BASE_EXCISION_REPAIR | 0.339758 96 | 1 | 1163 | tags = 39%, list = 28%, signal = 54% |
| KEGG_JAK_STAT_SIGNALING_PATHWAY | 0.346033 1 | 1 | 1159 | tags = 50%, list = 28%, signal = 69% |
| KEGG_AXON_GUIDANCE | 0.359362 24 | 1 | 897 | tags = 46%, list = 22%, signal = 58% |
| KEGG_ENDOMETRIAL_CANCER | 0.365277 7 | 1 | 1082 | tags = 42%, list = 26%, signal = 57% |
| KEGG_SPHINGOLIPID_METABOLISM | 0.388068 08 | 1 | 104 | tags = 13%, list = 3%, signal = 14% |
| KEGG_ADIPOCYTOKINE_SIGNALING_PATHWAY | 0.446880 3 | 1 | 1159 | tags = 42%, list = 28%, signal = 58% |
| KEGG_CYTOSOLIC_DNA_SENSING_PATHWAY | 0.462233 3 | 1 | 1 | tags = 5%, list = 0%, signal = 5% |
| KEGG_CELL_ADHESION_MOLECULES_CAMS | 0.472122 46 | 1 | 1583 | tags = 74%, list = 38%, signal = 118% |
| KEGG_TIGHT_JUNCTION | 0.558621 5 | 1 | 1233 | tags = 45%, list = 30%, signal = 64% |
| KEGG_HUNTINGTONS_DISEASE | 0.626950 9 | 1 | 790 | tags = 33%, list = 19%, signal = 41% |
| KEGG_DNA_REPLICATION | 0.743636 97 | 1 | 1269 | tags = 44%, list = 31%, signal = 63% |
| KEGG_PURINE_METABOLISM | 0.784432 2 | 1 | 1324 | tags = 39%, list = 32%, signal = 56% |
| KEGG_AMINOACYL_TRNA_BIOSYNTHESIS | 0.967195 4 | 1 | 829 | tags = 24%, list = 20%, signal = 29% |
| KEGG_GLYCOLYSIS_GLUCONEOGENESIS | 0.965507 15 | 1 | 793 | tags = 19%, list = 19%, signal = 23% |
| KEGG_RIG_I_LIKE_RECEPTOR_SIGNALING_PATHWAY | 0.973004 4 | 1 | 609 | tags = 19%, list = 15%, signal = 22% |

A ranked GSEA analysis of PC2 identified factors as enriched in the ranking of PC2 but not enriched in PC1. PC2 KEGG Enrichments (FDR <0.01):
1. KEGG_B_CELL_RECEPTOR_SIGNALING_PATHWAY
2. KEGG_CYTOKINE_CYTOKINE_RECEPTOR_INTERACTION
3. KEGG_MAPK_SIGNALING_PATHWAY
4. KEGG_LEUKOCYTE_TRANSENDOTHELIAL_MIGRATION
5. KEGG_HEMATOPOIETIC_CELL_LINEAGE
6. KEGG_FC_GAMMA_R_MEDIATED_PHAGOCYTOSIS
7. KEGG_ADHERENS_JUNCTION
8. KEGG_FC_EPSILON_RI_SIGNALING_PATHWAY
9. KEGG_PATHWAYS_IN_CANCER
10. KEGG_NEUROTROPHIN_SIGNALING_PATHWAY
11. KEGG_PHOSPHATIDYLINOSITOL_SIGNALING_SYSTEM
12. KEGG_CHEMOKINE_SIGNALING_PATHWAY
13. KEGG_VEGF_SIGNALING_PATHWAY
14. KEGG_REGULATION_OF_ACTIN_CYTOSKELETON.

To assess the connection between PCI and PC2 with trends in differential expression across the WT and MT$^{-/-}$ CD8+ T cells, two sets of differentially expressed genes that exhibit opposite trends were annotated: (1) an "enhanced set" (FIG. 4D, groups I and II) consisting of genes that were differentially expressed when comparing WT DN vs. WT DP and that showed significant further up or down regulation in MT$^{-/-}$ DP and (2) a "reversed set" (FIG. 4D, groups III and IV) consisting of genes that were differentially expressed when comparing WT DN vs. WT DP and whose directionality of expression was opposite in MT$^{-/-}$ DP (see Experimental procedures below and FIG. 4D). The "enhanced set" was strongly enriched for genes highly ranked in PC1, and the "reversed set" was strongly enriched for genes highly ranked in PC2 (FIG. 4D). Hence, genes with high PC2 loadings are enriched for those whose expression in WT DN cells is similar to that in MT$^{-/-}$ DP cells, but different from WT DP cells (FIG. 4D, groups III, IV), suggesting that PC2 genes indeed reflect a "reversal" of expression patterns from one characterizing the exhausted state (WT DP) to one characterizing a functional effector state (WT DN).

These data support the notion that PC1 captures aspects of dysfunctional CD8+ populations that are also present, and enhanced, in healthy activated T-cells, while PC2 captures aspects that are unique to the dysfunctional phenotype and are not present in healthy activated T-cells.

To further test the hypothesis that PC1 is associated with a healthy CD8+ T cell activation signature and that PC2 is independent of activation, the transcriptome of naïve CD8+ T cells isolated from non-tumor bearing WT mice before and after activation in vitro was profiled. The transcriptomic profiles of the naïve and activated CD8+ cells revealed a strong association with PC1, but no such association with PC2 (FIG. 4E), confirming the conclusion that PC1 is strongly associated with general CD8+ T cell activation and that PC2 is not.

Figure 5A:
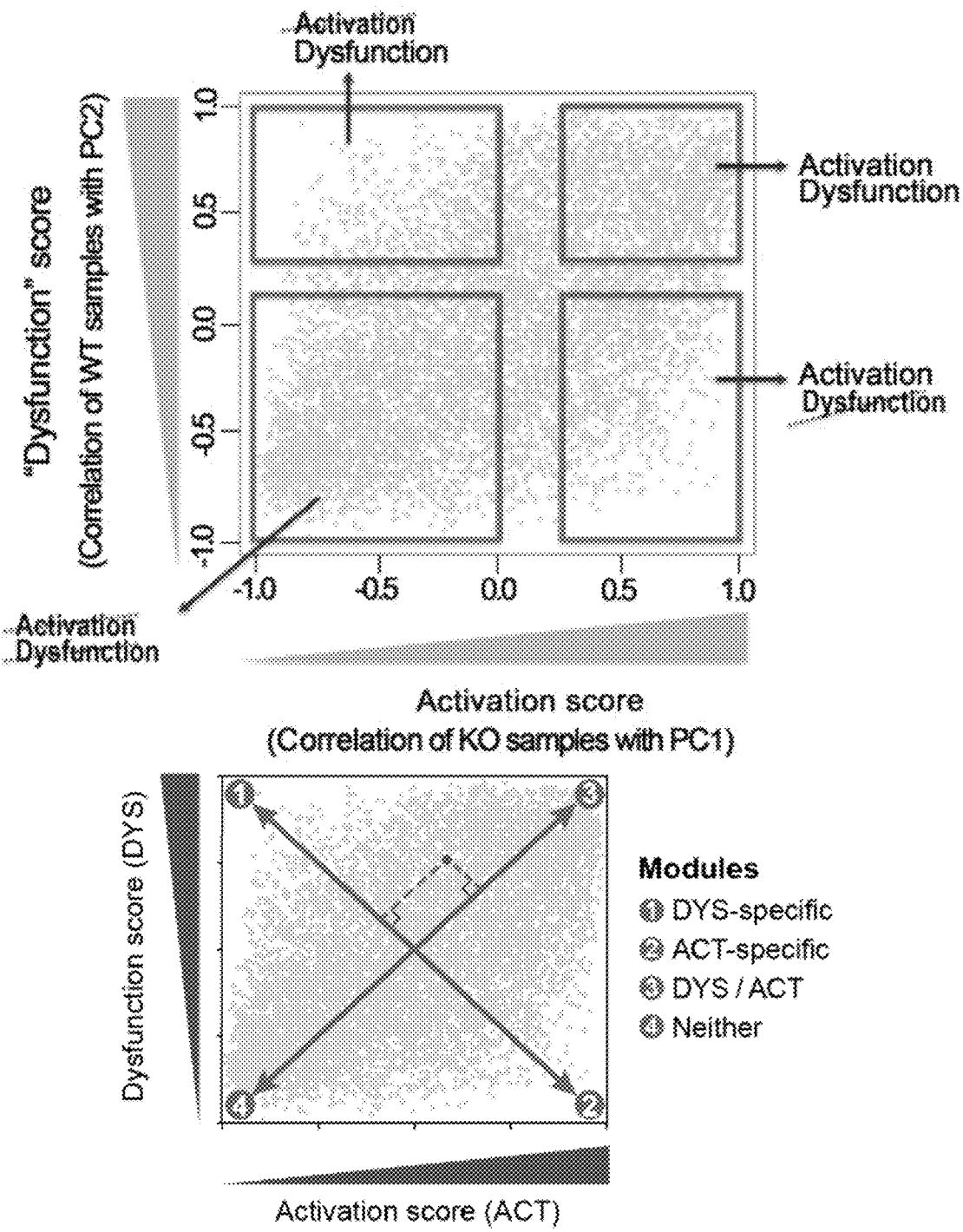

The association of PC2 with the dysfunctional phenotype but not the activation phenotype of CD8+ T cells enables the deco upling of each gene's association with dysfunction from its association with pure activation. The Applicants thus next scored each gene for its association with the downstream T cell dysfunction and upstream T cell activation programs. Since only WT TILs are dysfunctional, Applicants compute a "dysfunction score" only from the WT subpopulation samples as (−1) times the Pearson correlation coefficient between the gene's expression profile across the WT samples and those samples' PC2 scores (FIG. 5A, Y axis). Since the MT$^{-/-}$ TILs have the least dysfunction and separate best on PC1, Applicants compute an "activation score" as the Pearson correlation coefficient between the gene's expression profile across the MT$^{-/-}$ samples, and those samples' PC1 scores (FIG. 5A, X axis). Finally, Applicants ranked the genes with respect to the four corners of the plot, by ranking each gene by its distance from each of the two diagonals (x=y and x=−y; FIG. 5A), to identify those associated with a downstream dysfunction module (upper-left corner), activation-only module (lower-right corner), upstream dysfunction-activation module (upper right corner), and neither (bottom-left corner). Finally, Applicants generated gene signatures for each of these four modules (Methods and Resources, Table 3). Applicants observed that many genes were strongly associated with dysfunction but inversely correlated with activation, supporting the presence of a dysfunction-specific signature (FIG. 5A, upper left region).

TABLE 3

| Top ranking Genes |
|---|
| Dysfunction module |
| NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, BTLA |
| Activation module |
| TMCO1, PRMT5, EXOC4, TYR, HDHD2, RCN1, LMNB2, TCTEX1D2, VMA21, HCFC2, MRPS27, DUSP19, CD200R4, SRSF10, NAP1L4, ZADH2, ERGIC1, STARD3NL, RCC1, CD38, ZFP142, METTL10, MOGS, S100PBP, AREG, 1700052N19RIK, NDUFA13, RFT1, TAF12, ELP2, TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BC026590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127, KPNB1 |
| Dysfunction/Activation Module |
| SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, |

TABLE 3-continued

Top ranking Genes

NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, TOPBP1

Naïve/Memory like module

GPR183, THA1, TREML2, ZNRF3, CDK2AP2, CREB3, RPS16, BLOC1S2A, ATP1B3, BLNK, RPS29, SHARPIN, TSC22D1, KLRA1, HSD11B1, RPS15, AKAP8L, PHC1, RPL31, S1PR1, GM5547, SRSF5, ACSS2, ADK, AMICA1, ATP1B1, CNP, SNHG8, FCRLA, H2-T23, RAB33B, TLR12, RPF1, SP140, SH3GL1, CTSL, RPGRIP1, 5430417L22RIK, CXXC5, RABGGTA, KCNJ8, DYM, FRAT1, SPIB, ADRB2, COX6A2, TMEM219, GPR18, CCPG1, PLCB2, CALM2, KYNU, CRLF3, IDNK, TNFRSF26, DNAJB9, TXNIP, UPB1, GM11346, PHF1, RPL18A, DNTT, HAAO, PIM2, RABAC1, APOPT1, BIN2, OXR1, GPR171, RASGRP2, SLC9A9, 5830411N06RIK, PIAS1, PYDC3, ZCCHC18, TCSTV3, KLRA7, NPC2, CD180, SMIM14, P2RY14, PDLIM1, MYLIP, PDE2A, PPIF, KLRA17, FBXO32, DIRC2, ELOVL6, PJA1, SP110, KLRA6, USP7, HCST, KLRA23, GAB3, TOM1, ACP5, PBLD1, SMPD5, EVI2A, KLF13, MFSD11, IFNGR1, POU6F1, USE1, HDAC4, SMIM5, MAF1, 1810034E14RIK, TSC22D3, GAS5, RPL21, RELL1, SERTAD2, BC147527, KMO, SKAP1, TCF4, SP100, RNF167, TMEM59, IRGM1, CD69, DNAJC7, PIK3IP1, TAZ, HAVCR1, LY6D, RPL23, DAPP1, FLT3, ITM2B, NUCB2, RPS14, GIMAP9, HBP1, MAN2A2, RNF122, SOCS3, CD7, PNCK, 2610019F03RIK, SLC27A1, BPTF, H2-Q9, KLHL6, RPL17, SEMA4B, LDLRAD4, TCEA2, GM14207, CIRBP, FAM189B, ZFP707, ATP10D, RNASET2A, ATP2A1, BST2, EYA2, IRF7, ITPR2, STK17B, CYBASC3, TRIM11, KLK1B27, ZMYND8, LEF1, RNASE6, EIF4A2, HS3ST1, NIPBL, STX4A, UGCG, CAMK1D, PPFIA4, UVRAG, CDKN2D, ZBTB21, LEFTY1, APBB1IP, GIMAP3, H13, RGS10, RNF138, RPL12, SLC7A6OS, FADS2, SELPLG, CXCR4, GPR146, ZFP386, BCL11A, TRIM34A, RPS7, TLR9, PACSIN1, PAIP1, PGAM2, JAKMIP1

Genes previously associated with T cell dysfunction such as co-inhibitory receptors (e.g., PD-1, Tim-3, TIGIT, and CTLA-4) scored highly for both axes, i.e., for the dysfunction-activation module, as did the majority of co-stimulatory receptors that belong to the TNF receptor family, including TNFRSF9 (4-1BB), TNFRSF4 (OX-40), and TNFRSF18 (GITR) (FIG. 5B). Indeed, these data further support the co-regulation of co-inhibitory and co-stimulatory receptors Applicants have observed on T cells that are marked for the development of dysfunctional phenotype (see Chihara et al.). The presence of TNF receptor family co-stimulatory receptors together with co-inhibitory receptors in this module could reflect shared regulatory mechanisms for these receptors.

Figure 5D:
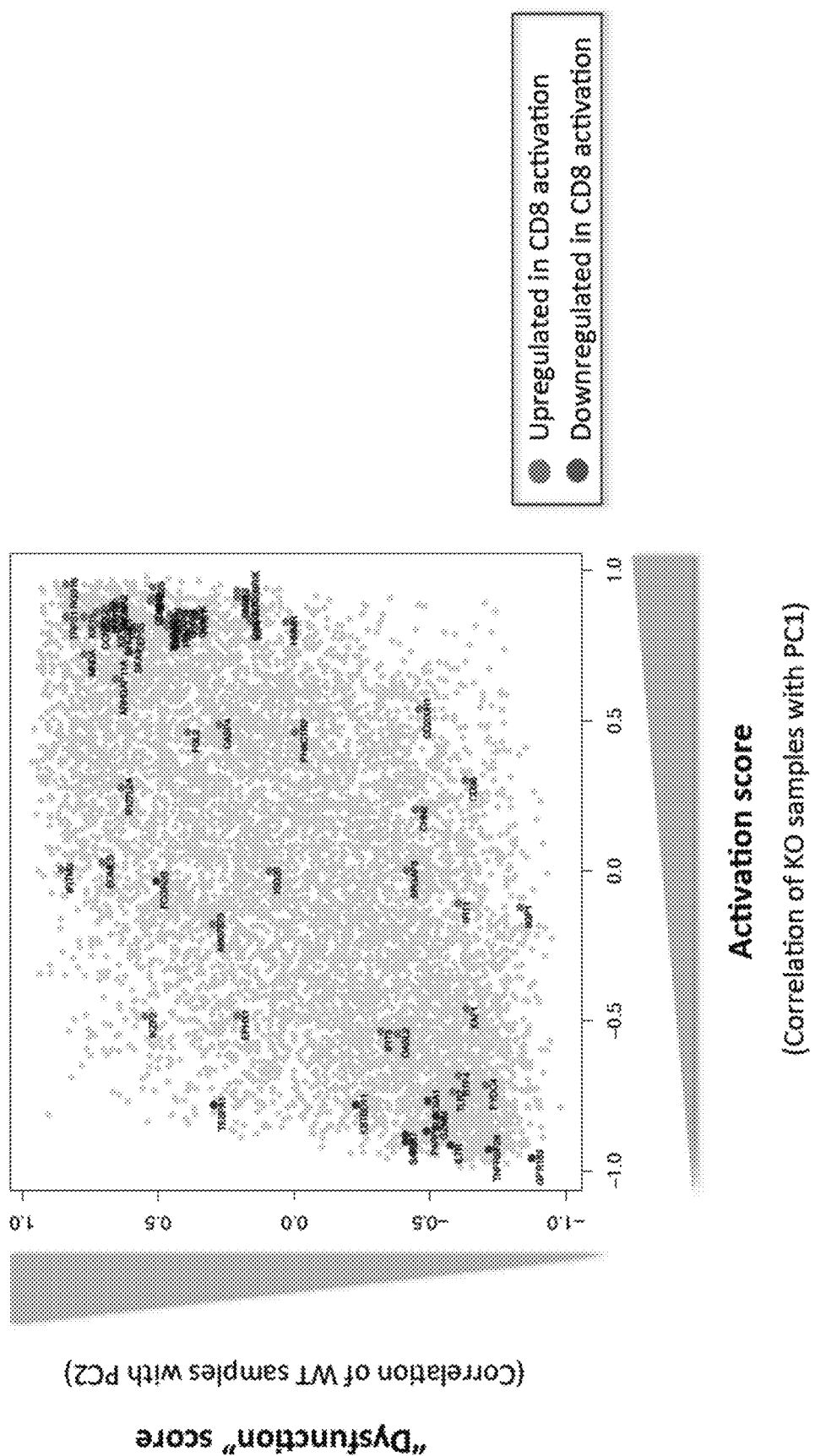

Also, numerous genes that are either upregulated or downregulated in CD8 activation (CD8 activation signature) were distributed on "Activation axis", and were more broadly distributed across the "Dysfunction axis" (FIG. 5C), validating the present approach. FIG. 5D further shows the placement of genes reported as constituting the viral LCMV exhaustion signature (Doering et al. 2012, supra) in the "Activation-Dysfunction space".

Figure 5E:
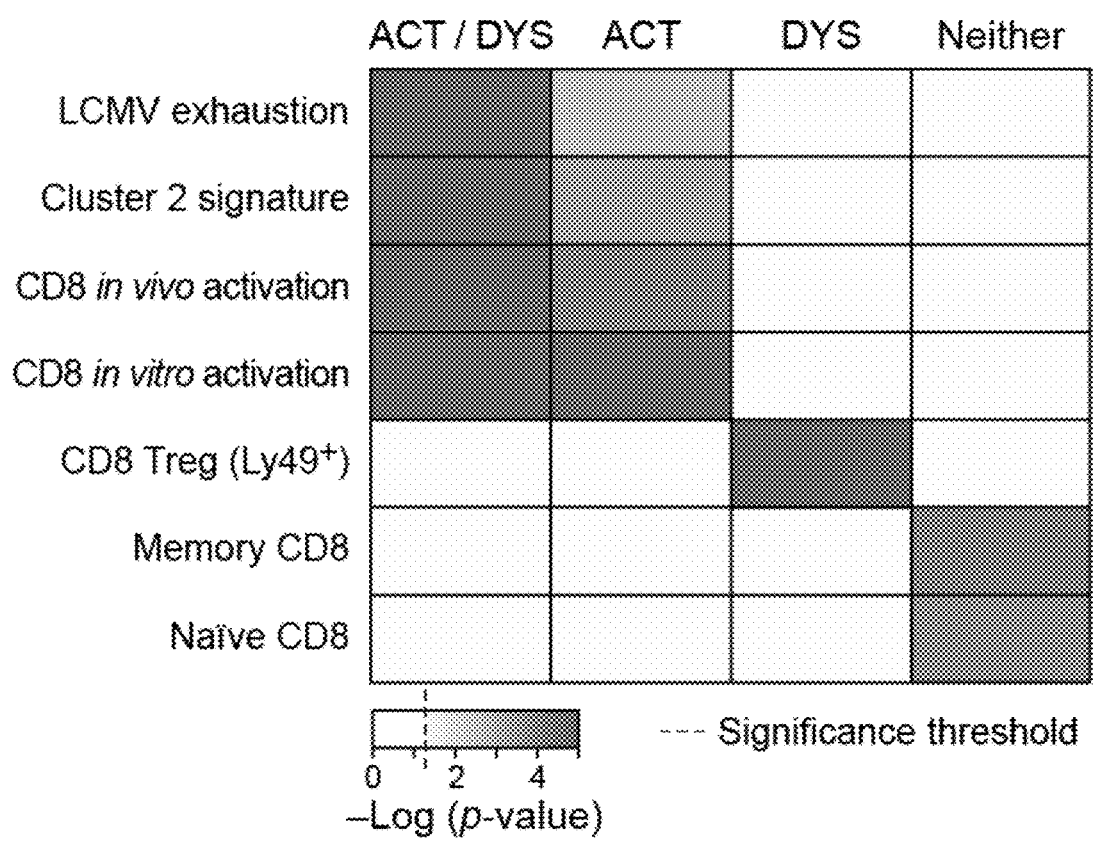

Each of the four modules was significantly associated with distinct signatures (mHG ranked test; FIG. 5E). As expected, the activation/dysfunction module was enriched for signatures of in vivo and in vitro CD8 activation as well as previously annotated signatures for T cell dysfunction (Doering et al., 2012, supra) and the cluster 2 gene signature (FIG. 1I). The activation module was also enriched for the same set of signatures, being most significantly associated with in vitro activation. The module with neither high activation nor high dysfunction scores was enriched for naïve $CD8^+$ T cell signatures and memory $CD8^+$ T cell signatures (Methods and Resources, (Eden et al., 2007; Wagner, 2015)), and Applicants therefore determined it to be a naïve/memory-like module. The dysfunction module was enriched for a $CD8^+$ Treg signature (Kim et al., 2015, Science 350, 334-339), suggesting that mechanisms present within the dysfunctional $CD8^+$ T cell population are shared with T cells that exhibit regulatory functions.

Figure 5F:
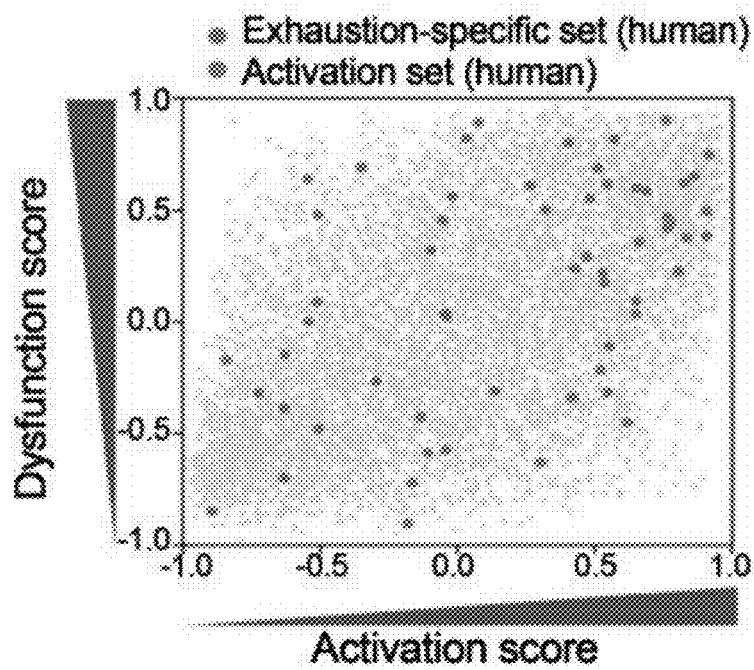
Figure 5F:
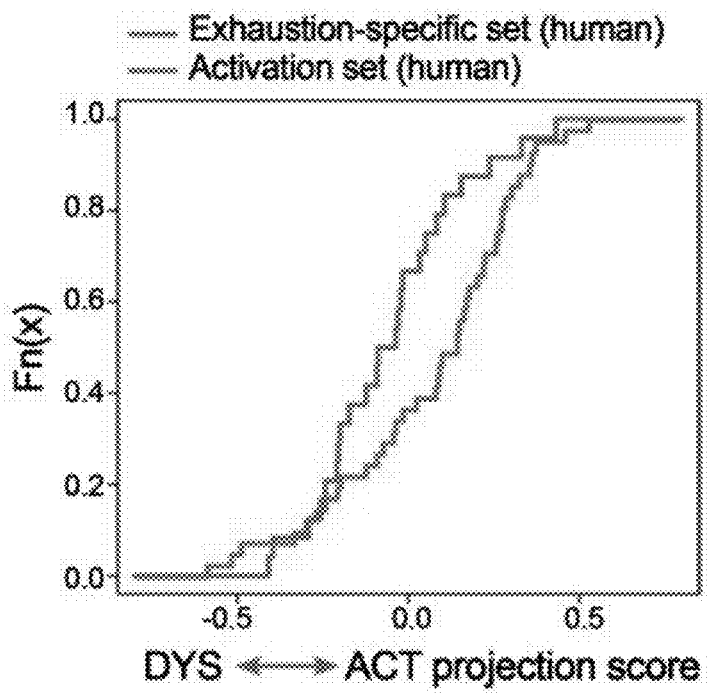

The relevance of the newly identified modules to human tumors, is further underscored by a comparison of the module scores to two signatures obtained from $CD8^+$ TILs from melanoma patients Applicants recently analyzed by single cell RNA-Seq (Tirosh et al. 2016, Science, vol. 352(6282), 189-96). In human melanoma TILs, Applicants found evidence for a similar phenomenon: while most gene expression associated with dysfunction is correlated to the extent of the expression of the activation program, variation between single cells can help identify an activation independent signature. Interestingly, genes in the dysfunction module in human TILs have higher scores for the dysfunction module in the mouse TILs analysis compared to genes in the activation module ($P<0.007$, KS test) (FIG. 5F). This corroborates that the dysfunction only module is also distinguishable in human tumors and is therefore diagnostically and therapeutically relevant.

Among others, the dysfunction signature included Gata3, Foxo1, Pou2af1, CD160, CD274, PTGER4 and BTLA. Furthermore, this signature included NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, and CACNB3. Hence, the signature included the transcription factors NOTCH2, RELB, KLF3, POU2AF1, GATA3, PIAS2, FOXO1, RARA, CRTC3, BCL6, MYB, BCL3, KDM5B, KDM4B, PCGF5, SPRY1, NR4A1, PNRC1, IKZF2, and ZFP62. Hence the signature also included the surface secreted factors and chromatin regulators NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA. Not being bound by a theory, surface markers may be used to isolate specific dysfunctional T cells and may be drug targets. Drugs targeting chromatin factors are also well known. The following Table 5A provides a ranked list of top 100 genes comprised in the dysfunction module.

followed for tumor growth. The transfer of Nrp1$^{-/-}$ pmel CD8$^+$ T cells is expected to significantly delay tumor growth in WT mice.

Further markers of interest associated with dysfunction and found in the "Dyfunction" region of the "Activation-Dysfunction space" included metallothionein 1 (MT1) and 2 (MT2), the co-inhibitory receptors CD160, CD274, CD200, and CD244; and the co-stimulatory receptors CD28, TNFSF11, ICOS, TNFSF14, and TNFRSF9.

The following provides a ranked list of top 200 genes comprised in the activation module: TMCO1, PRMT5, EXOC4, TYR, HDHD2, RCN1, LMNB2, TCTEX1D2, VMA21, HCFC2, MRPS27, DUSP19, CD200R4, SRSF10, NAP1L4, ZADH2, ERGIC1, STARD3NL, RCC1, CD38,

TABLE 5A

Ranked list of top 100 genes comprised in the dysfunction module.

NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3

The following Table 5B provides a ranked list of top 200 genes comprised in the dysfunction module.

ZFP142, METTL10, MOGS, S100PBP, AREG, 1700052N19RIK, NDUFA13, RFT1, TAF12, ELP2,

TABLE 5B

Ranked list of top 200 genes comprised in the dysfunction module.

NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, POU2AF1, GATA3, B3GNT2, FAS, PIAS2, FOXO1, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2

Figure 5G:
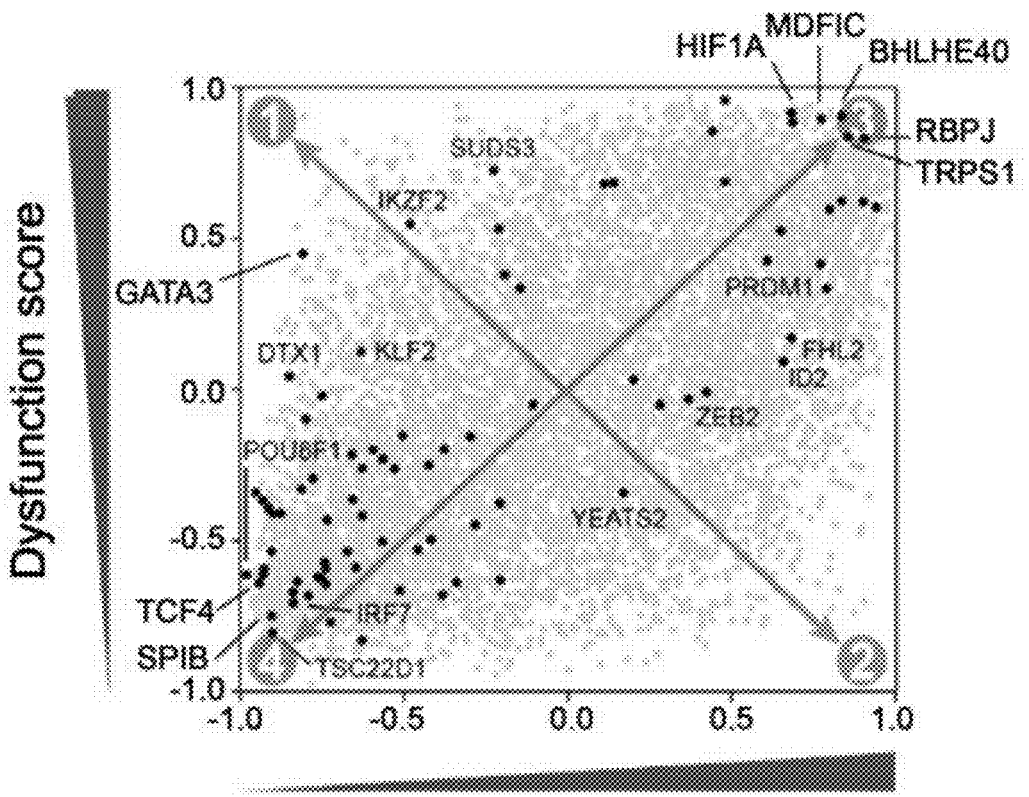
Figure 5G:
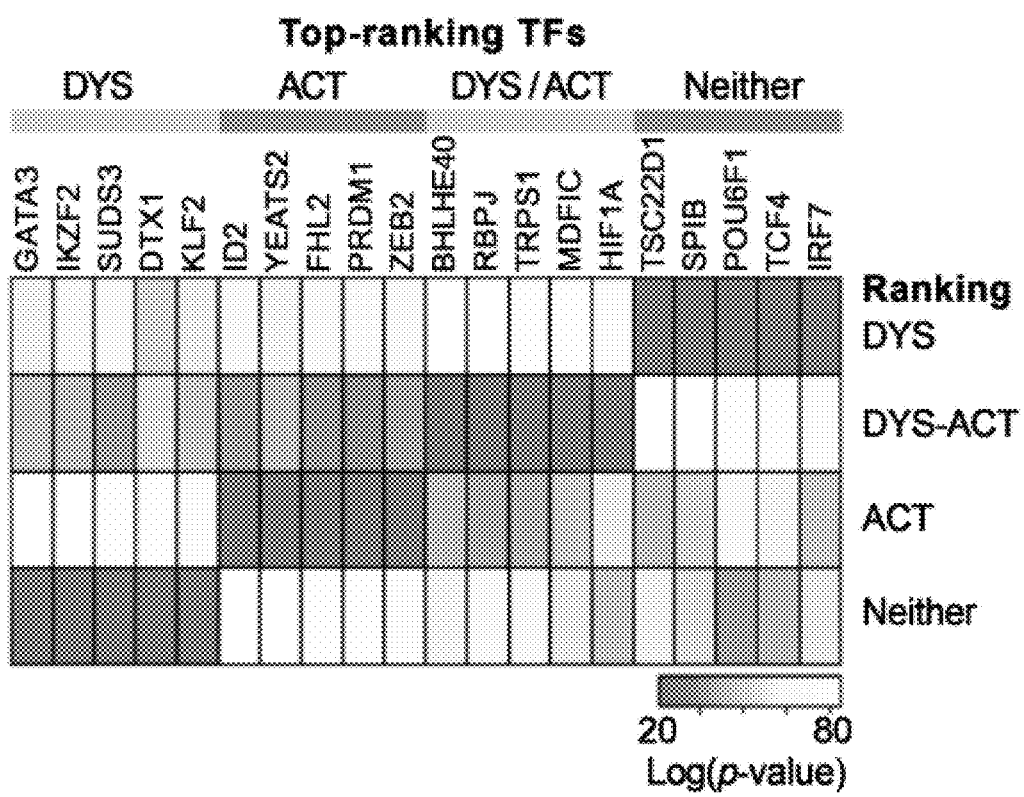
Figure 5H:
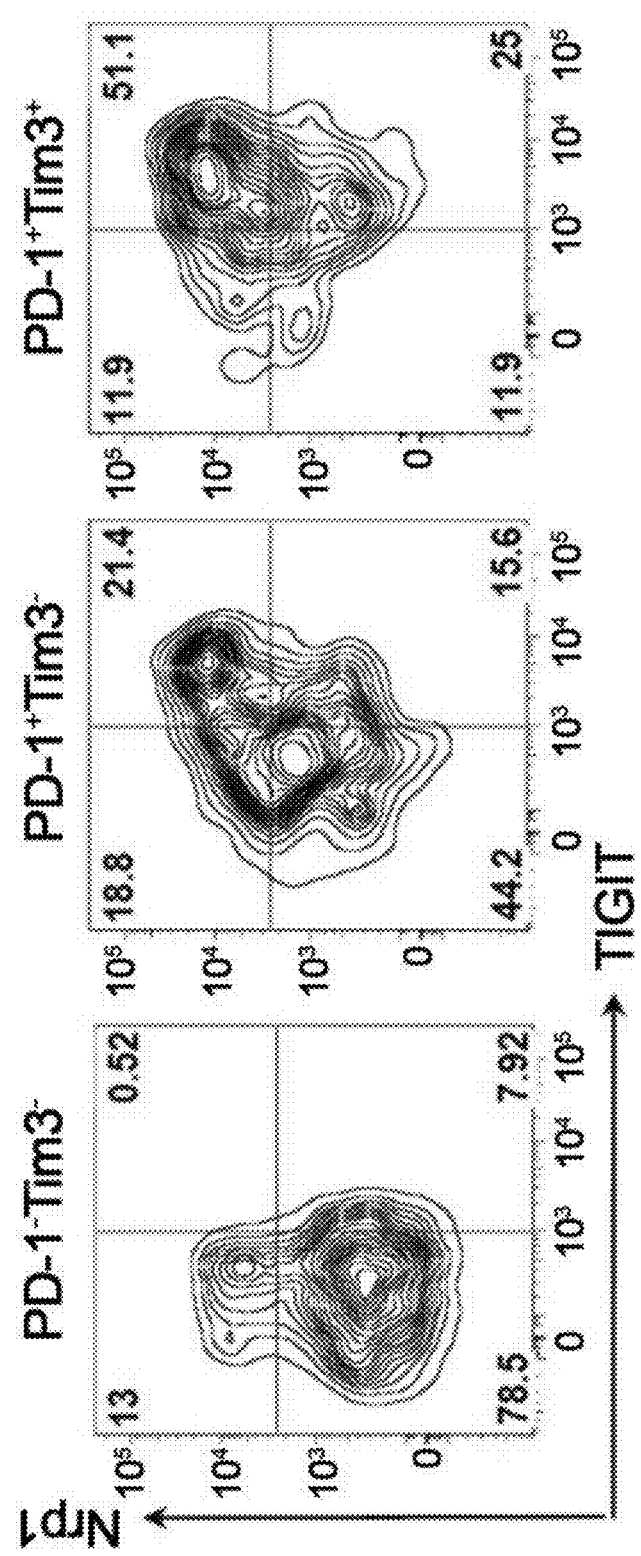

Furthermore, the Applicants analyzed KEGG pathways enriched in the ranking of PC2, and thereby identified VEGF signaling pathway. The Applicants demonstrated that the NRP1 receptor was differentially expressed in the dataset, and that NRP1 was highly expressed in PD-1$^+$ Tim3$^+$ CD8 TILs (FIG. 5H). Accordingly, NRP1 can also be a valuable constituent of a dysfunction-specific signature as taught herein.

Further, a lentiviral CRISPR/cas9 targeting approach is used to knockout Nrp1 in pmel CD8$^+$ T cells. CRISPR targeted pmel CD8$^+$ T cells (Nrp1$^{-/-}$) are transferred to WT mice bearing B16F10 melanoma tumors; the mice are then TONSL, FANCG, PIGF, GNG2, HIST1H1E, MINA, NDUFAB1, AP1M1, DYNLT1C, JAGN1, CERS4, METTL3, GCDH, RBX1, HAUS4, TFIP11, BCO26590, PSMB9, PTPN23, PIAS3, TMEM129, DPYSL2, TMEM209, CALU, EXOSC1, PQLC3, ACO1, PDIA4, POLR3K, NTAN1, PSMB3, ARFIP1, PHF11B, MYEF2, TIMM50, ACAD8, RDM1, CCNH, TMEM41A, PLAA, MEAF6, EXOSC3, QRSL1, UPF1, ANXA6, FTSJD2, PRPSAP1, ARSB, GM11127, HNRNPA2B1, NUP35, RPRD1B, NCBP2, HIST1H3E, KIFC1, MLH1, CD200R1, CPSF6, CDT1, PPM1G, MRPS33, PRADC1, GBP3, RAD17, MTHFSD, FOXRED1, TAX1BP3, C1D, TPM3, D16ERTD472E, SARS2, 0610009O20RIK, ARPP19, ASRGL1, SDF2L1, TBCC, MYG1, SEPHS1, DYNC1LI1, ZBTB38, TARDBP, SLC9A8, TYK2, THUMPD3, MRPL16, ACOT8, LRRK1, HMGB1, HSPA1B, TCEA1, MAVS, POFUT2, VPS53, RIT1, SNAPC1, DNAAF2, COMMD10, PMPCB, EHBP1L1, ADAT3, DOHH, LSM4, PTCD1, GMPPB, LAMTOR1, DRG2, CDCA7L, SSBP1, ANAPC15, NAGLU, AKR1B3, PAOX, EIF4E2, GPAA1, RAD50, STX18, GRPEL1, VMP1, REXO2, HIST1H1C, ZFP429, GGH, TAF6, COMMD3, PARL, RBM18, 2700029M09RIK, EXOSC4, ABHD10, DNAJC14, DPCD, ATPBD4, SERPINA3F, CTCF, LMAN1, NEU3, EIF2D, HAUS5, USF1, AAR2, FARSB, COG4, COG2, FKBP2, SLC35A1, DPY30, ALDH3A2, 1110008P14RIK, KLRE1, ZDHHC6, RAD18, TSPAN4, METTL20, NUDT16L1, TMEM167, IPP, INIP, REEP4, ERP44, GIMAP7, CYB5B, ACAT2, ANAPC5, PEX19, PUF60, SLBP, MTG1, ACTR10, CCDC127, KPNB1.

Among others, the activation signature included METTL3 involved in the posttranscriptional methylation of internal adenosine residues in eukaryotic mRNAs, forming N6-methyladenosine. The signature also included MINA, a gene previously shown to be a positive regulator of Th17 differentiation (WO/2014/134351).

The following provides a ranked list of top 200 genes comprised in the dysfunction/activation module: SEC23A, ACTN4, MTMR1, TIGIT, TRIP13, NCOR2, CCDC50, LPCAT1, GMNN, CCR8, FLNA, CIAPIN1, TK1, E430025E21RIK, ENDOD1, RGS8, SLC35A3, ARL6IP1, CALM3, MCM3, MKI67, SLC25A13, SUOX, AP3S1, NAA38, NUCKS1, CDCA8, UHRF2, RAD54L, PSAT1, FEM1B, MCM5, CCNB2, CX3CR1, SH3BGRL, HIST1H1B, CASP3, DNMT3A, CCNA2, DUT, STMN1, MEMO1, WHSC1, BUB1B, FKBP1A, CCT7, ATP6V1A, POLA1, GTDC1, RPPH1, NR4A2, AP2M1, FUT7, CDCA3, STRN, CHAF1A, IL18RAP, ST14, ADAMTS14, ACTG1, KIF13B, PTPN5, RAB8B, SERPINE2, CSTF2, EIF4H, GM5069, TMEM48, CTLA4, GM9855, EZH2, MMS22L, RAD51, TPX2, METRN, TMEM126A, HIF1A, MSH6, NCAPD2, UHRF1, ALCAM, HMGN2, MAP4, POLD1, DGKZ, LCP1, AURKB, MRPS22, 2810417H13RIK, WDR76, GALNT3, IPO5, GM5177, NAB2, CISH, ARF5, CENPH, STAP1, KIF15, HIST1H2AG, CDC45, PTPN11, GINS1, TFDP1, MLF2, PGP, POLE, HIST1H2AO, IL10RA, LDHA, SERPINB6A, ASNSD1, LCLAT1, CALR, LGALS1, NDFIP2, GPD2, RRM1, TPI1, DUSP14, MAD2L1, MLEC, CRMP1, DTL, PDCD1, INTS7, WDR3, MED14, EEA1, UAP1, FAR1, GAPDH, YWHAH, MMD, CSF1, HN1L, MDFIC, DUSP4, IL2RA, ALDOA, HIST2H3B, ENO1, SIVA1, TNFRSF4, TNFRSF9, CSRP1, IGFBP7, MCM6, RDX, KIF2C, RBL2, BCL2A1B, HIST1H3C, ATP5B, CIT, B4GALT5, HELLS, TRPS1, FAM129A, TXN1, HSP90AB1, H2AFZ, METAP2, DESI1, FIGNL1, LIN54, CAPG, SYNE3, AI836003, LIG1, HCFC1, GARS, SMARCA5, PGK1, PPP2R4, BCL2A1D, PPP1CA, RBPJ, BHLHE40, SLC16A3, DNMT1, S100A4, PKM, PRELID1, KIF20A, ITGAV, TWSG1, TACC3, ATP5F1, RQCD1, ANKRD52, RGS16, ANXA2, TMPO, ATP10A, PRIM1, ZFP207, STX11, RPS2, TOPBP1.

The following provides a ranked list of top 200 genes comprised in the Näive/Memory_like_module: GPR183, THA1, TREML2, ZNRF3, CDK2AP2, CREB3, RPS16, BLOC1S2A, ATP1B3, BLNK, RPS29, SHARPIN, TSC22D1, KLRA1, HSD11B1, RPS15, AKAP8L, PHC1, RPL31, S1PR1, GM5547, SRSF5, ACSS2, ADK, AMICA1, ATP1B1, CNP, SNHG8, FCRLA, H2-T23, RAB33B, TLR12, RPF1, SP140, SH3GL1, CTSL, RPGRIP1, 5430417L22RIK, CXXC5, RABGGTA, KCNJ8, DYM, FRAT1, SPIB, ADRB2, COX6A2, TMEM219, GPR18, CCPG1, PLCB2, CALM2, KYNU, CRLF3, IDNK, TNFRSF26, DNAJB9, TXNIP, UPB1, GM11346, PHF1, RPL18A, DNTT, HAAO, PIM2, RABAC1, APOPT1, BIN2, OXR1, GPR171, RASGRP2, SLC9A9, 5830411N06RIK, PIAS1, PYDC3, ZCCHC18, TCSTV3, KLRA7, NPC2, CD180, SMIM14, P2RY14, PDLIM1, MYLIP, PDE2A, PPIF, KLRA17, FBXO32, DIRC2, ELOVL6, PJA1, SP110, KLRA6, USP7, HCST, KLRA23, GAB3, TOM1, ACP5, PBLD1, SMPD5, EVI2A, KLF13, MFSD11, IFNGR1, POU6F1, USE1, HDAC4, SMIM5, MAF1, 1810034E14RIK, TSC22D3, GAS5, RPL21, RELL1, SERTAD2, BC147527, KMO, SKAP1, TCF4, SP100, RNF167, TMEM59, IRGM1, CD69, DNAJC7, PIK3IP1, TAZ, HAVCR1, LY6D, RPL23, DAPP1, FLT3, ITM2B, NUCB2, RPS14, GIMAP9, HBP1, MAN2A2, RNF122, SOCS3, CD7, PNCK, 2610019F03RIK, SLC27A1, BPTF, H2-Q9, KLHL6, RPL17, SEMA4B, LDLRAD4, TCEA2, GM14207, CIRBP, FAM189B, ZFP707, ATP10D, RNASET2A, ATP2A1, BST2, EYA2, IRF7, ITPR2, STK17B, CYBASC3, TRIM11, KLK1B27, ZMYND8, LEF1, RNASE6, EIF4A2, HS3ST1, NIPBL, STX4A, UGCG, CAMK1D, PPFIA4, UVRAG, CDKN2D, ZBTB21, LEFTY1, APBB1IP, GIMAP3, H13, RGS10, RNF138, RPL12, SLC7A6OS, FADS2, SELPLG, CXCR4, GPR146, ZFP386, BCL11A, TRIM34A, RPS7, TLR9, PACSIN1, PAIP1, PGAM2, JAKMIP1.

Example 5: Gata3 Regulates Dysfunction in CD8$^+$ TILs and Marks a Novel Population with an Altered Functional Phenotype To validate that members of the dysfunctional signature perform important functions and to identify candidate transcription factors (TFs) that may be critical for inducing T cell dysfunction independent of activation, Applicants scored each TF that was consistently differentially expressed across the datasets for its rank in the four modules (FIG. 5G). In the dysfunction only module, Gata3, a zinc-finger transcription factor, was the top ranking transcription factor, followed by IKZF2, another zinc-finger TF, from a TF family known to regulate lymphocyte development (Kim et al., 2015, supra), then SUDS3. and others (FIG. 5G). Since Gata3, a zinc finger TF, was the top ranking TF for the downstream, dysfunction-only module, and is a member of Cluster 2, the Applicants postulated that it may be involved, together with MT1 and MT2, in regulating CD8$^+$ T cell dysfunction.

Figure 11A:
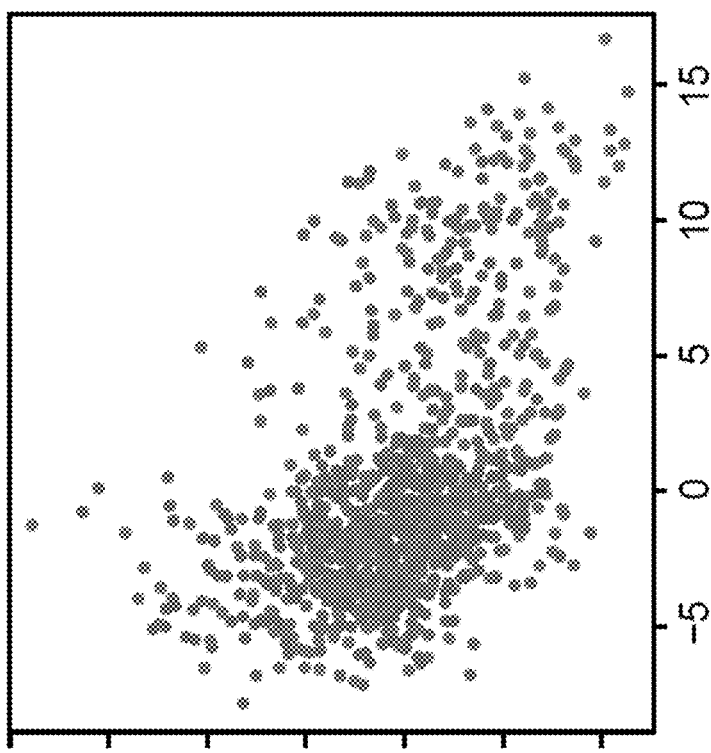
FIG. 11A-11G, The dysfunction and activation transcriptional programs are anti-correlated at the single-cell level.
Figure 11A:
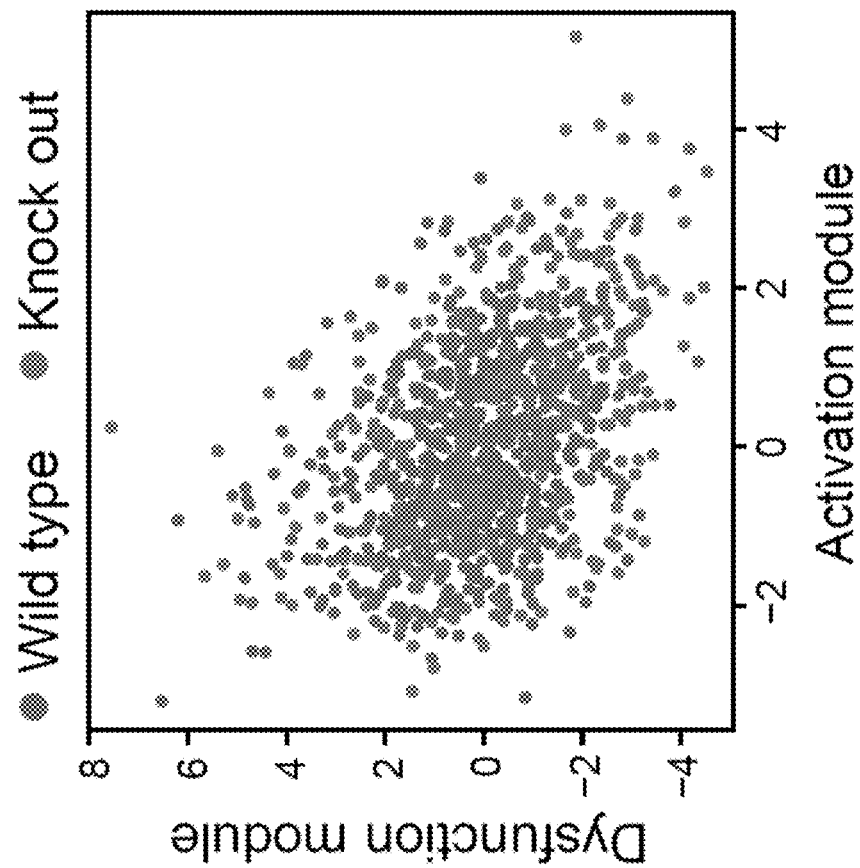

Several lines of evidence supported a role for Gata-3 in regulating CD8$^+$ TIL dysfunction. Genes bound by Gata-3 in nTregs are enriched in both the dysfunction (P=0.013, hypergeometric test) and activation/dysfunction (P=0.0056) modules; it is the top ranking TF member of the dysfunction module (FIG. 11A); and it is a member of cluster 2 (FIG. 1). Applicants therefore hypothesized that Gata-3 may be involved, together with MT1 and MT2, in regulating CD8$^+$ T cell dysfunction.

Based on the foregoing data, the Applicants thus further experimentally corroborated the involvement of Gata3 in regulating CD8 T cell dysfunction in cancer.

Figure 6A:
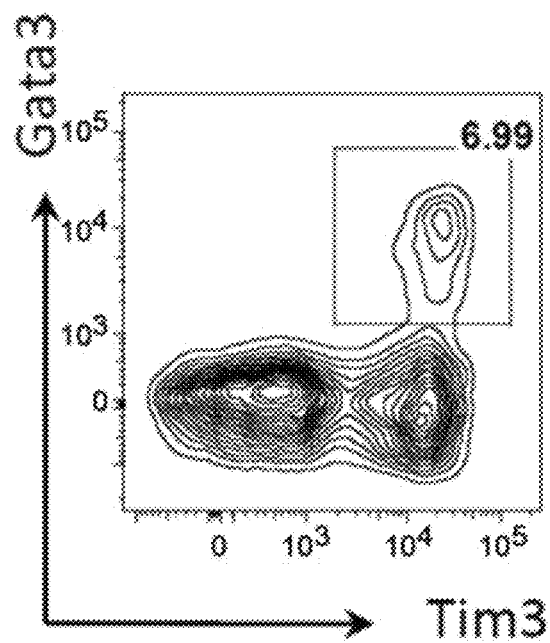

First, the Applicants characterized Gata3 expression and its associated function in CD8$^+$ WT tumor-bearing mice, and found that Gata3 was expressed on a subpopulation of Tim3$^{-PD-}$1$^+$ CD8 T cells in TILs (FIG. 6A), but not in tumor draining lymph node.

Figure 6B:
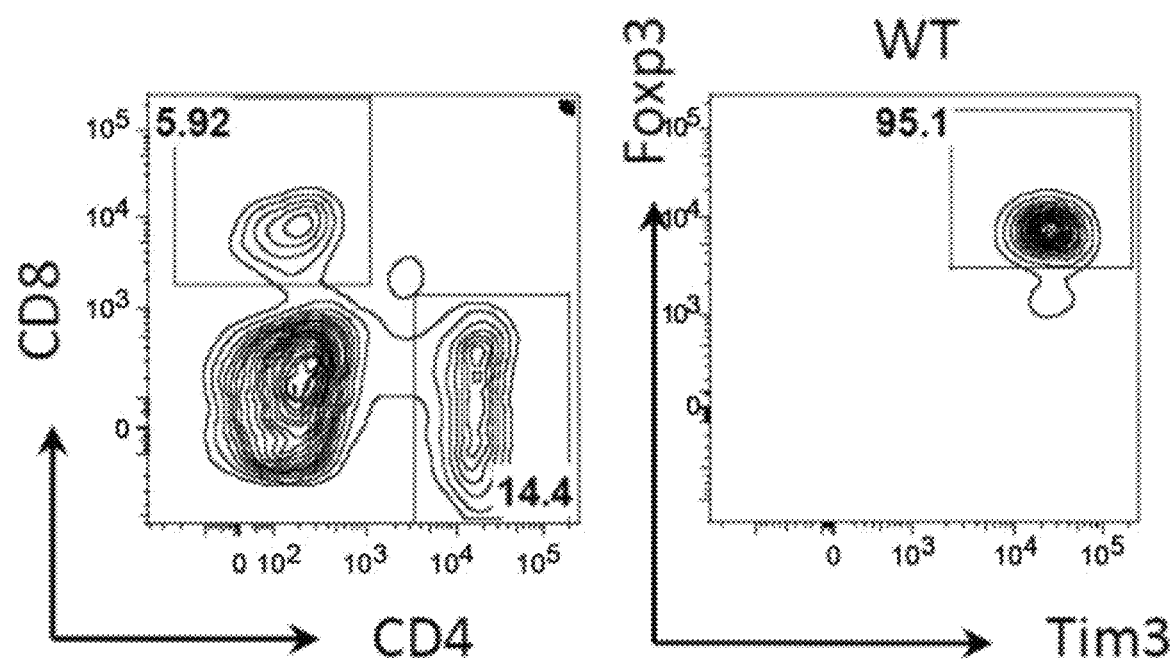

Further, cytokine expression in Gata3-expressing CD8$^+$ TILs was examined to determine whether the Gata3 expression correlates with CD8+ T cell function. Gata3+CD8 TILs expressed significantly lower levels of IFNg and IL-2, and significantly higher levels of IL-10 compared to Gata-3− CD8+ TILs upon stimulation (FIG. 6C). This result suggests that Gata3+ CD8 TILs are not only poorly functional as measured by traditional effector molecules associated with protective T cell function, they also actively produce the suppressive cytokine IL-10 and thus may contribute to suppression locally in the tumor microenvironment. Given that Gata3 has been recently associated with regulatory T cells that are Foxp3+ (Yu et al., 2015, Nat Immunol., vol. 16(2), 197-206), Applicants assessed Foxp3 expression in CD8+ Gata3+ TILs and found that a substantial proportion of Gata3+ CD8+ T cells expressed the suppressive transcription factor Foxp3 (FIG. 6B).

Figure 6D:
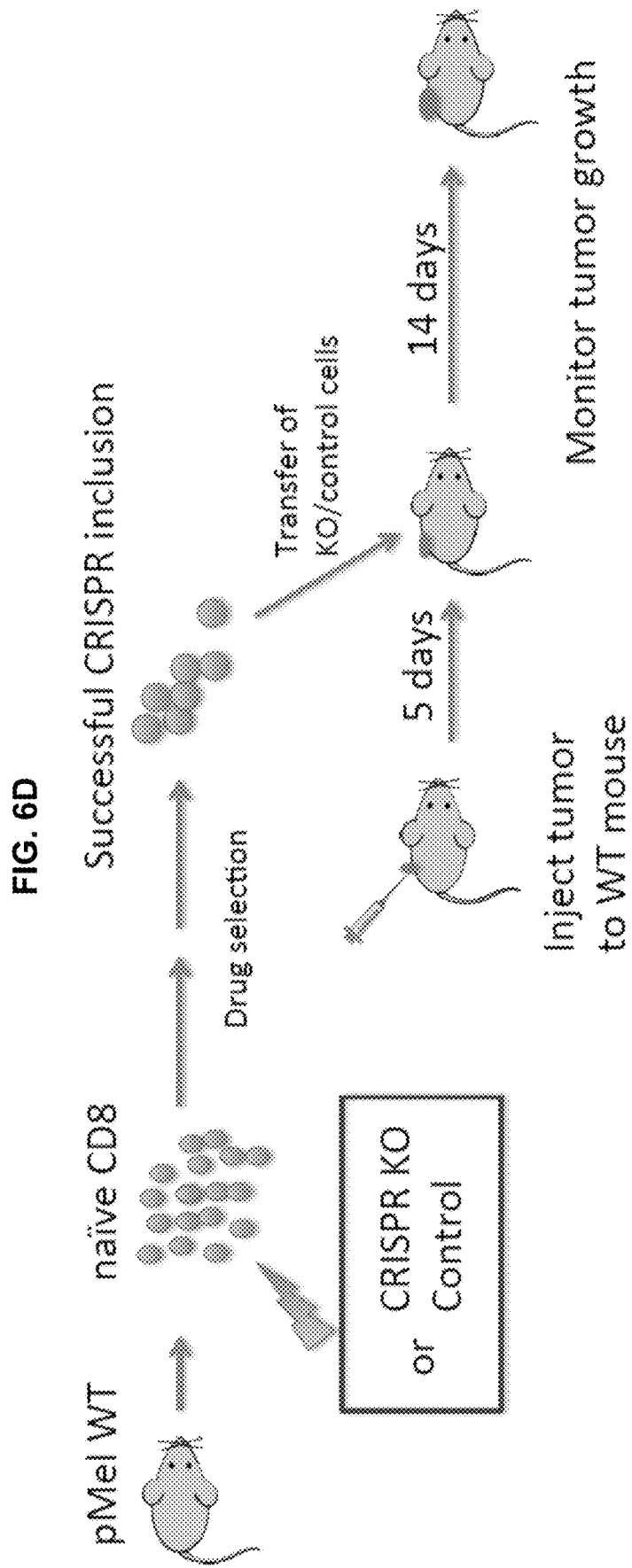

To directly analyze the functional role of Gata3 in regulating CD8+ T cell dysfunction, a lentiviral CRISPR/cas9 targeting approach was used to knockout Gata3 in naïve transgenic pmel CD8+ T cells. Control or Gata3 CRISPR lentiviruses were transduced into CD8+ T cells isolated from PMEL transgenic mice in which all T cells have a single tumor antigen specific TCR with specificity for the mouse homologue of the human premelanosome protein. PMEL CD8+ T cells are normally ineffective at controlling growth of B16F10 melanoma tumors, such that perturbations that promote tumor clearance can be readily discerned. Control or Gata3-targeted (deleted, i.e., Gata3$^{-/-}$) pmel CD8+ T cells were activated and equal numbers of cells were transferred into WT mice with established B16F10 melanoma tumor. Mice were then followed for tumor growth. This approach is schematically set forth in FIG. 6D. Efficiency of Gata3 deletion was determined by quantitative real time PCR (FIG. 6H).

Figure 6E:
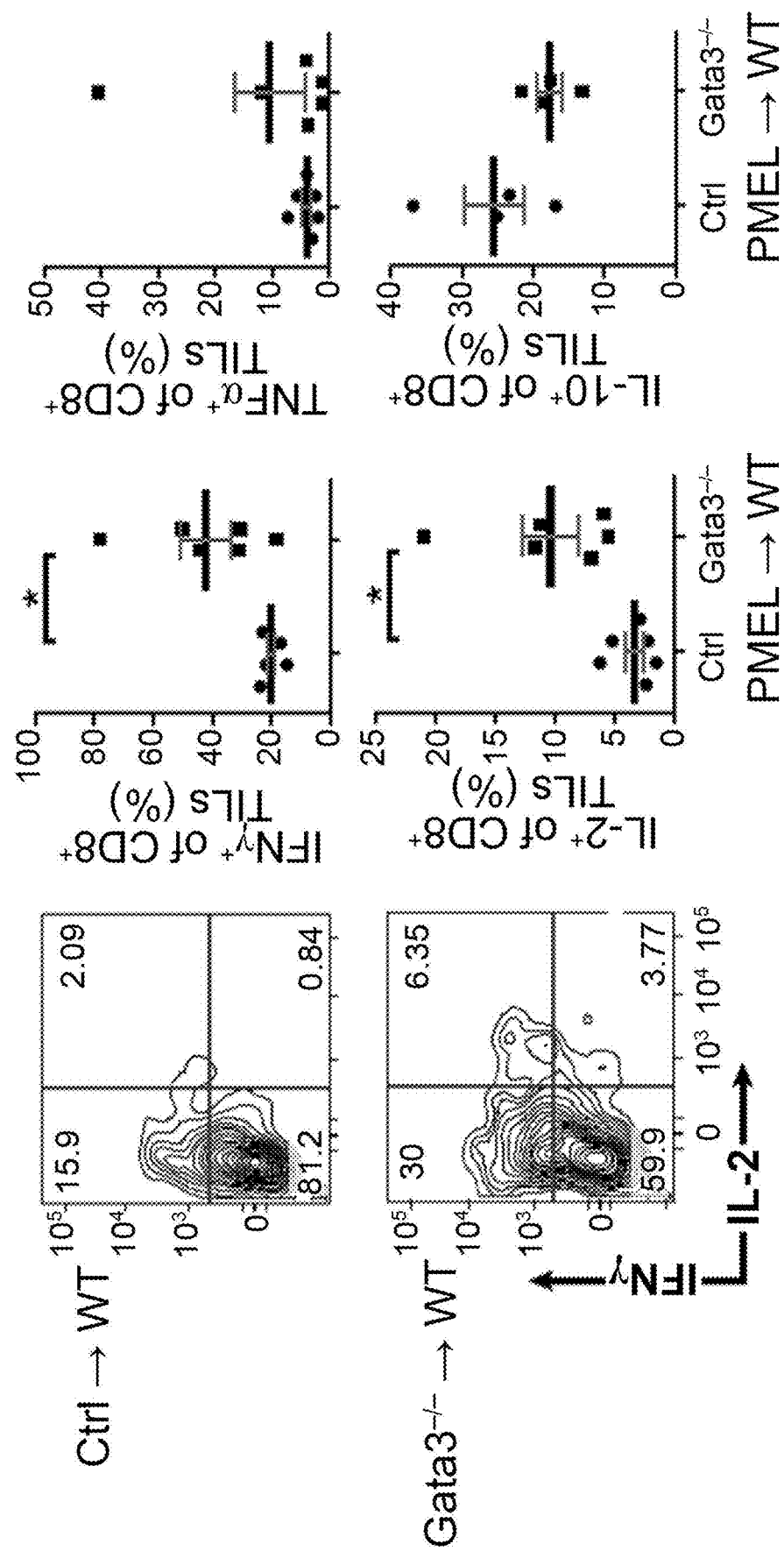
Figure 6F:
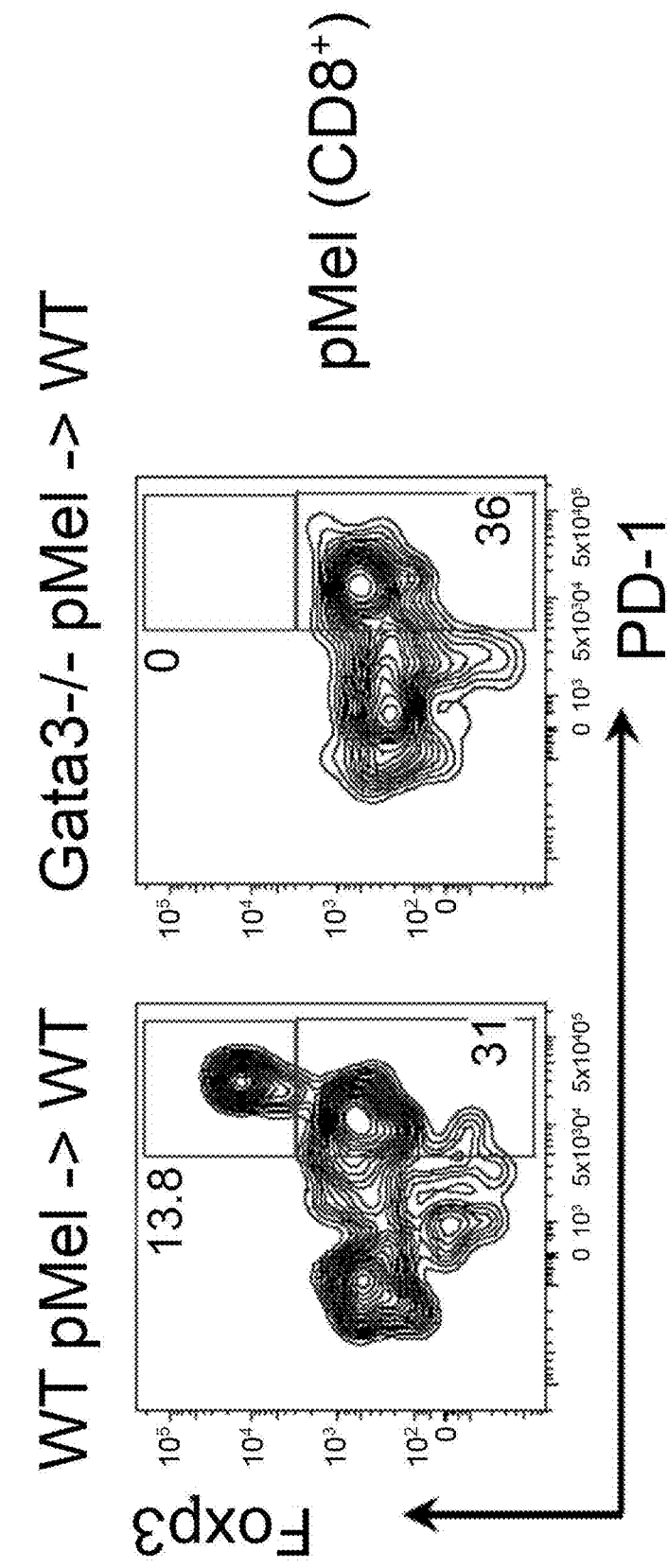
Figure 6G:
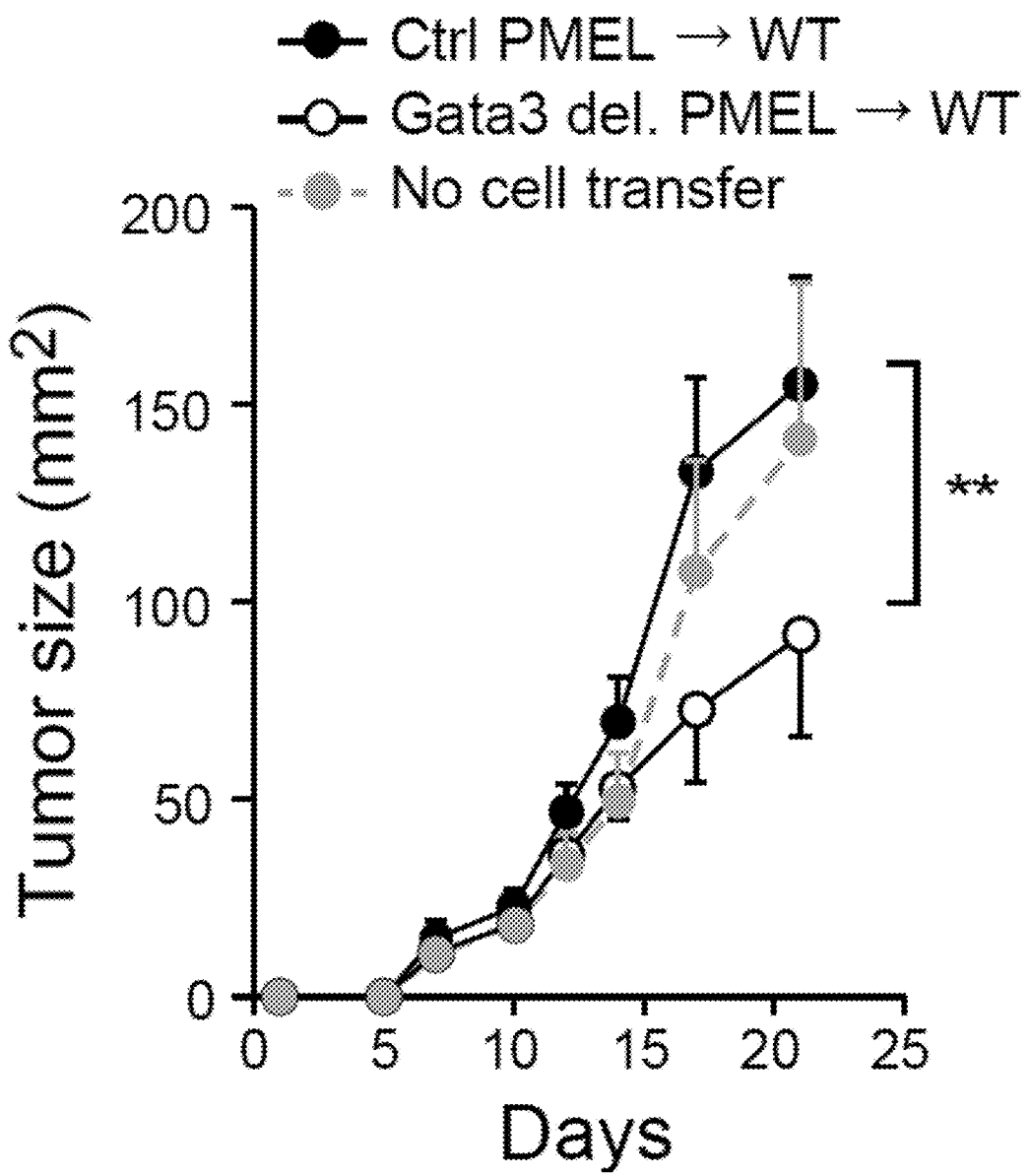

Upon transfer into WT hosts, Gata3$^{-/-}$ pmel CD8+ T cells produced significantly higher percent of poly-functional IL-2 and IFNg-producing cells(FIG. 6E), consistent with a less dysfunctional phenotype compared to control WT pmel CD8+ T cells. Similar to MT$^{-/-}$ CD8+ T cells, the loss of Gata3$^{-/-}$ CD8+ cells did not alter the expression of Tim-3 and PD-1 on CD8+ TILs (FIG. 6I). Interestingly, while a significant proportion of WT pmel CD8+ T cells acquired Foxp3 expression, none of the Gata3$^{-/-}$ T cells did (FIG. 6F). Accordingly, the transfer of Gata3$^{-/-}$ pmel CD8+ T cells significantly delayed tumor growth in WT mice (FIG. 6G). Together these data support a role for Gata3 as a regulator of CD8+ T cell dysfunction program that contributes to poor tumor control.

Example 6: MT and Gata3 Cooperatively Promote a Suppressive Phenotype of Dysfunctional CD8+ T Cells in Tumor The expression of suppression associated genes (IL-10 and Foxp3) in CD8+ T cells in tumor prompted the Applicants to test the hypothesis that dysfunctional CD8+ T cells are not only unable to exert effective tumor control but also negatively affect other T cells in tumor microenvironment and that Gata3 and metallothioneins may regulate such effects.

Figure 7A:
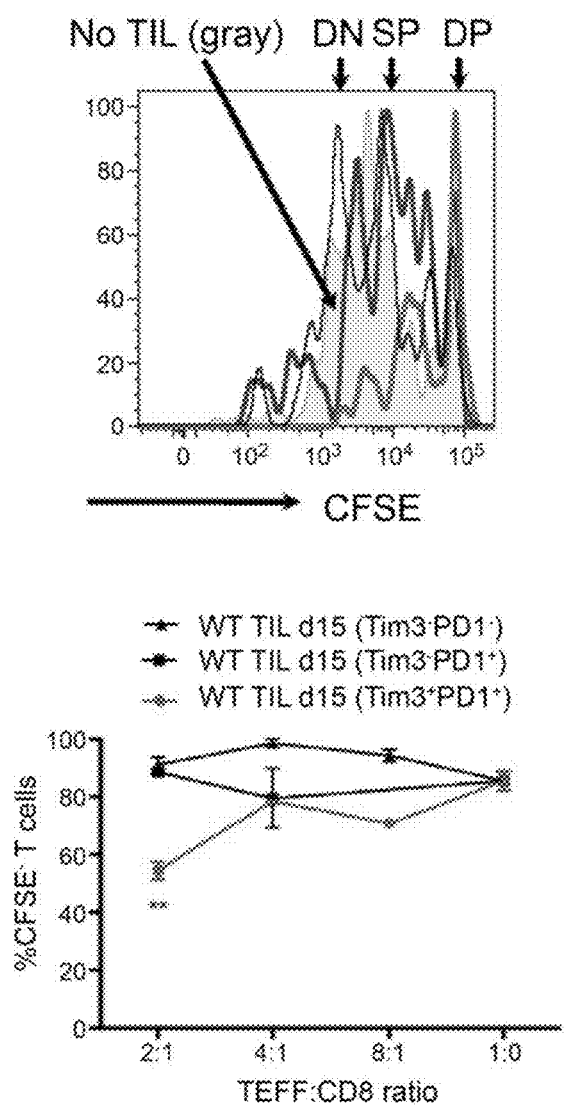
FIG. 7A-7E illustrate that MT and Gata3 cooperatively promote a suppressive phenotype of dysfunctional $CD8^+$ T cells in tumor.

WT DP, SP, and DN CD8+ CD4− T cells were isolated from TILs and assessed for their ability to influence effector T cell proliferation using a suppression assay. The addition of SP or DN CD8+ TILs did not interfere with effector cell proliferation, however, the addition of DP CD8+ TILs significantly inhibited the proliferation of effector T cells (FIG. 7A). These results corroborate that dysfunctional CD8+ T cells are not only poor CD8+ effector cells but also can exhibit a suppressive phenotype.

Figure 7B:
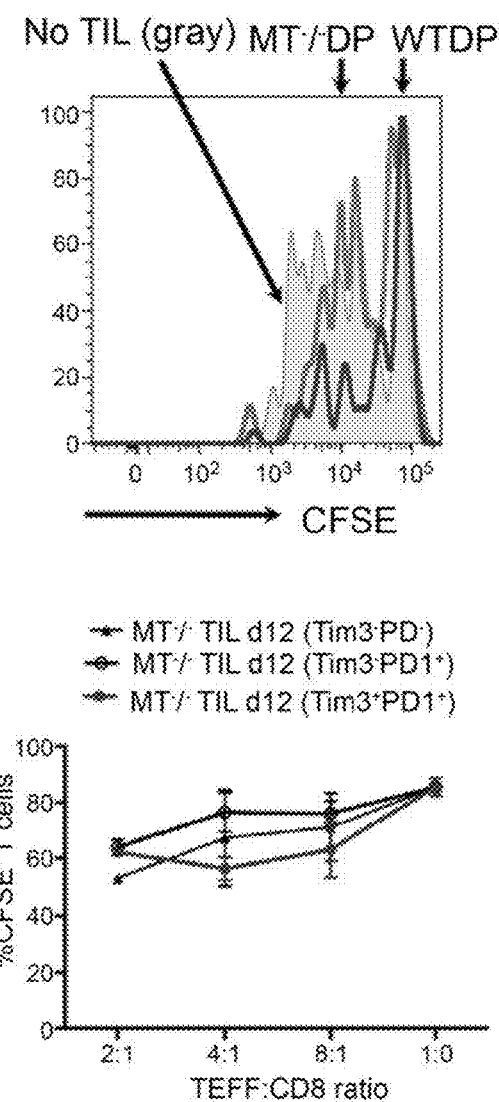
Figure 7C:
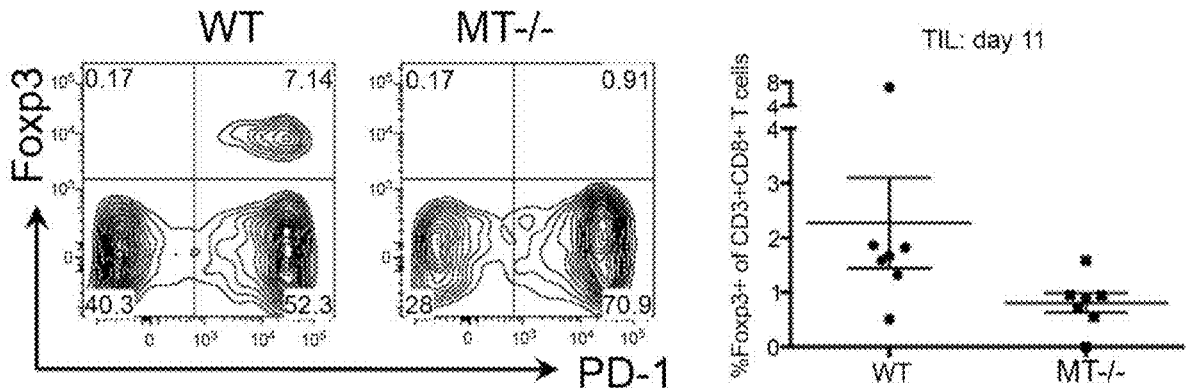

The Applicants next investigated whether MT and Gata3 were regulators of the suppressive function of dysfunctional CD8+ T cells in cancer. Since Gata3$^{-/-}$ CD8+ T cells have decreased Foxp3 expression (FIG. 6F), the Applicants postulated that the suppressive phenotype of dysfunctional CD8 T cells may depend on Gata3 expression. Further, the Applicants observed that MT$^{-/-}$ DP TILs failed to suppress effector T cell proliferation compared to WT DP TILs and that the MT$^{-/-}$ DP/SP/DN populations showed indistinguishable impact on Teff proliferation (FIG. 7B) in contrast to that of the WT TILs subpopulations. Consistent with a reduced suppressive function of MT deficient CD8+ TILs, there was a significant reduction of Foxp3 expression in MT$^{-/-}$ TILs (FIG. 7C). Thus both Gata3 and MT are key regulators of the suppressive phenotype of dysfunctional CD8+ T cell subpopulation in cancer.

Figure 7D:
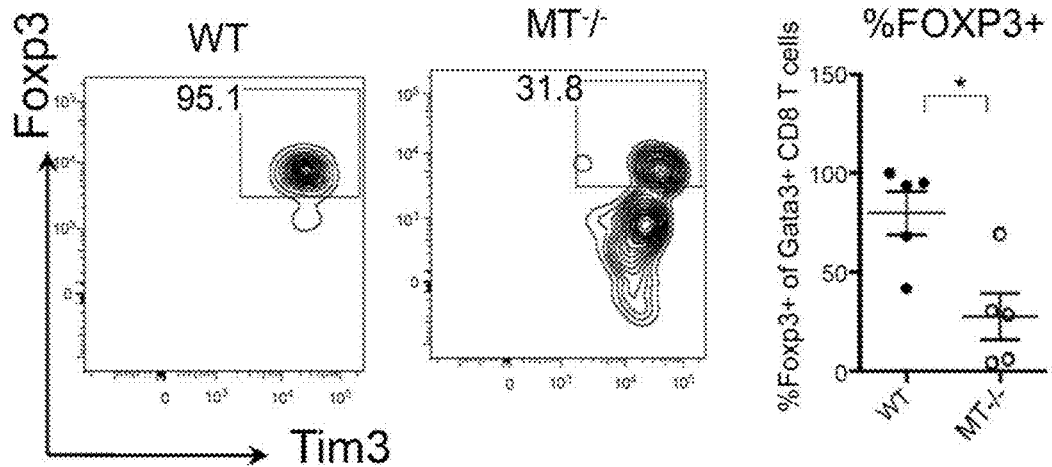

Gata3 is a zinc-finger containing transcription factor and MT regulates intracellular zinc, and Gata3 and MT could thus potentially collaborate to regulate the suppressive phenotype of dysfunctional CD8+ TILs. The Applicants tested whether MT$^{-/-}$ CD8+ TIL exhibit altered Gata3 expression or function, and did not see a significant change in Gata3 expression in CD8+ TILs, however, the Foxp3 expression in the Gata3+ population was dramatically reduced in MT$^{-/-}$ TILs, consistent with the reduced suppressive phenotype of MT$^{-/-}$ CD8+ TILs (FIG. 7D). As Gata3 was previously shown to directly regulate foxp3 expression through binding to its promoter, the present observations indicate that metallothionein-driven regulation of zinc may in turn regulate Gata3 function (FIG. 7D).

Figure 7E:
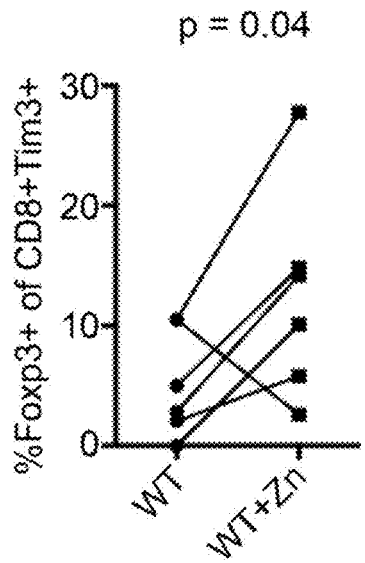

The Applicants further investigated whether MT regulated the function of Gata3, a zinc-finger transcription factor, by shuttling Zinc. If the availability of Zinc indeed regulated Gata3 function in TILs, adding exogenous Zinc may regulate Foxp3 expression in a Gata3 dependent manner. TILs were treated ex vivo with Zinc, leading to significantly increased frequency of Foxp3+ CD8 T cells (FIG. 7E). The Applicants further investigate whether Gata3 deficiency alters the effect of Zinc on Foxp3 expression, and whether Zinc alters the suppressive phenotype of WT vs. Gata3$^{-/-}$ dysfunctional CD8 TILs.

Example 7: Involvement of Pou2af1 in Dysfunction of CD8+ TILs

Figure 8A:
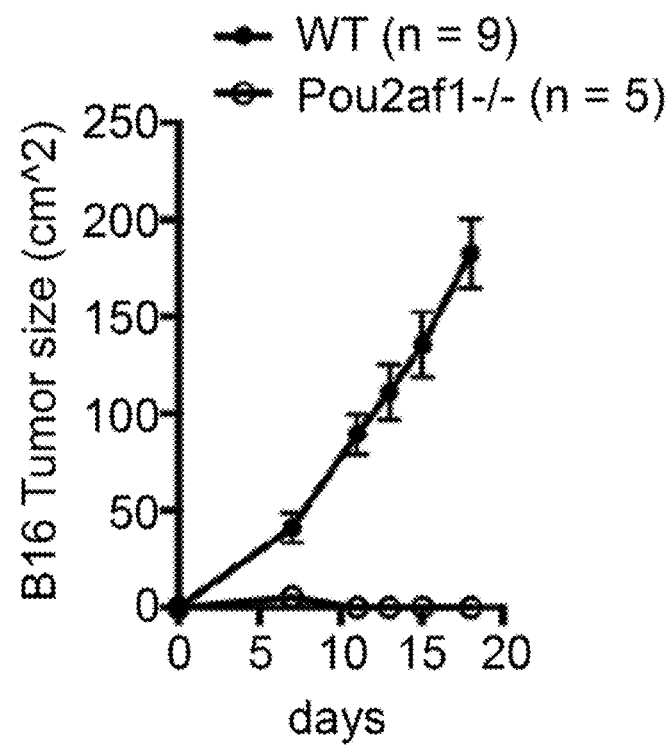
FIG. 8A-8B illustrate experiments corroborating involvement of Pou2af1 in dysfunction of $CD8^+$ TILs.
Figure 8B:
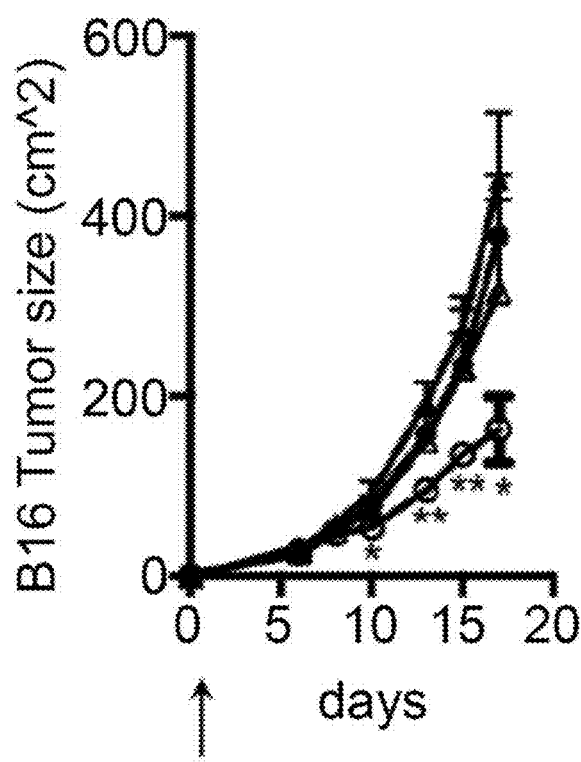

The Applicants further demonstrated that the tumor growth was significantly reduced or abolished in Pou2af1$^{-/-}$ KO mice (FIG. 8A), and that splenic Pou2af1$^{-/-}$ CD8+ T cells from Pou2af1$^{-/-}$ KO mice harboring a tumor led to reduction in tumor size when transferred into tumor harboring wild type animals (FIG. 8B). In particular, WT or Pou2af1$^{-/-}$ mice were implanted with B16-F10 tumor subcutaneously. At day 18, CD8 and CD4 T cells were isolated from spleens of WT and Pou2af1$^{-/-}$ mice and transferred into WT host mice which was subsequently injected with B16-F10 tumor subcutaneously. Tumor growth was followed as indicated in FIG. 8B.

Further, a lentiviral CRISPR/cas9 targeting approach is used to knockout Pou2af1 in pmel CD8+ T cells. CRISPR targeted pmel CD8+ T cells (Pou2af1$^{-/-}$) are transferred to WT mice bearing B16F10 melanoma tumors; the mice are then followed for tumor growth. The transfer of Pou2af1$^{-/-}$ pmel CD8+ T cells is expected to significantly delay tumor growth in WT mice.

Example 8: Foxo1 Regulates Dysfunction in CD8+ TILs

Figure 10:
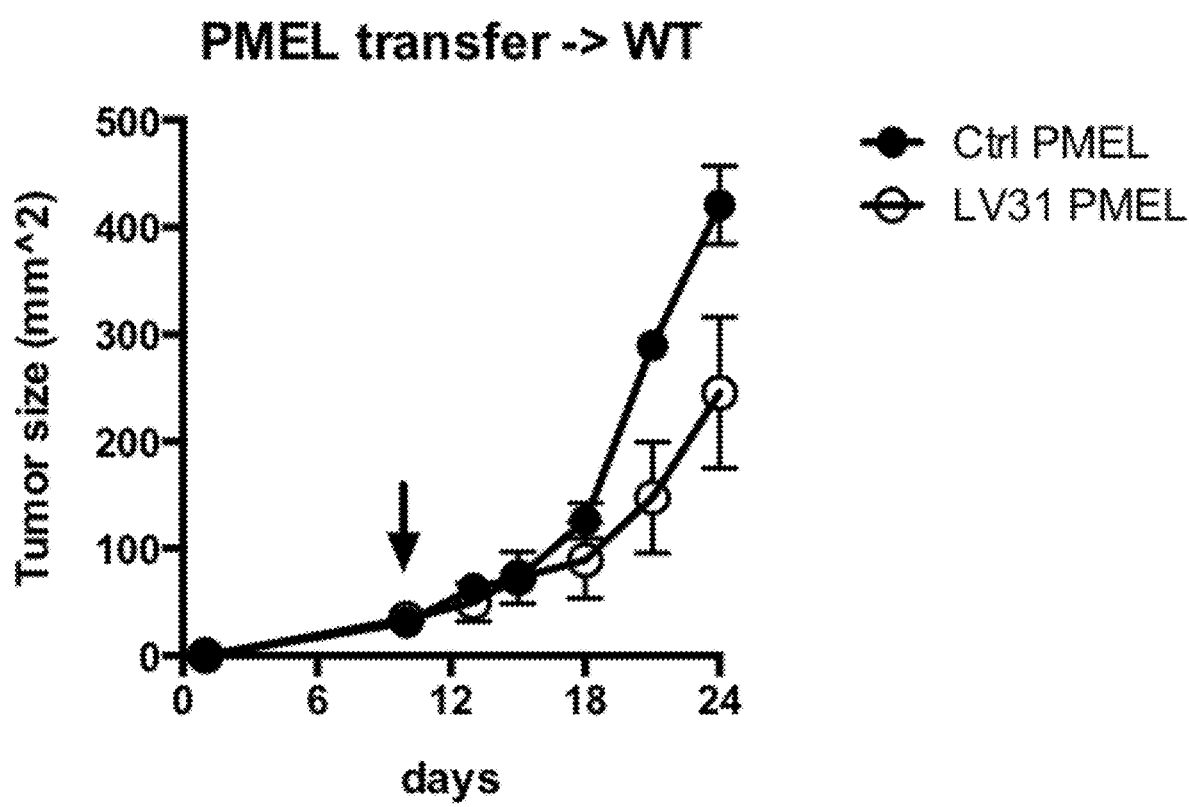
FIG. 10, CRISPR targeted pmel CD8+ T cells (Foxo1−/−; denoted LV31 in the figure) were transferred to WT mice bearing B16F10 melanoma tumors on the indicated day. Mean tumor growth is shown.

To directly analyze the functional role of Foxo1 in regulating CD8+ T cell dysfunction, a lentiviral CRISPR/cas9 targeting approach was used to knockout Foxo1 in pmel CD8+ T cells. CRISPR targeted pmel CD8+ T cells (Foxo1$^{-/-}$) were transferred to WT mice bearing B16F10 melanoma tumors; the mice were then followed for tumor growth. The transfer of Foxo1$^{-/-}$ pmel CD8+ T cells significantly delayed tumor growth in WT mice (FIG. 10).

Example 9: Further Factors Regulating Dysfunction in CD8+ TILs

A lentiviral CRISPR/cas9 targeting approach is used to knockout any one or a combination of any two or more genes selected from the following group in pmel CD8+ T cells: BTLA, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, and PTGER4.

In a certain example, a lentiviral CRISPR/cas9 targeting approach is used to knockout any one or a combination of any two or more genes (transcription factors) selected from the following group in pmel CD8+ T cells: NOTCH2, RELB, KLF3, PIAS2, RARA, CRTC3, BCL6, MYB, BCL3, KDM5B, KDM4B, PCGF5, SPRY1, NR4A1, PNRC1, IKZF2, and ZFP62.

In a certain example, a lentiviral CRISPR/cas9 targeting approach is used to knockout any one or a combination of any two or more genes selected from the following group in pmel CD8+ T cells: CD160, CD274, CD200, CD244, CD28, TNFSF11, ICOS, TNFSF14, and TNFRSF9.

CRISPR targeted pmel CD8+ T cells are transferred to WT mice bearing B16F10 melanoma tumors; the mice are then followed for tumor growth. The transfer of KO CD8+ T cells is expected to significantly delay tumor growth in WT mice.

Figure 11B:
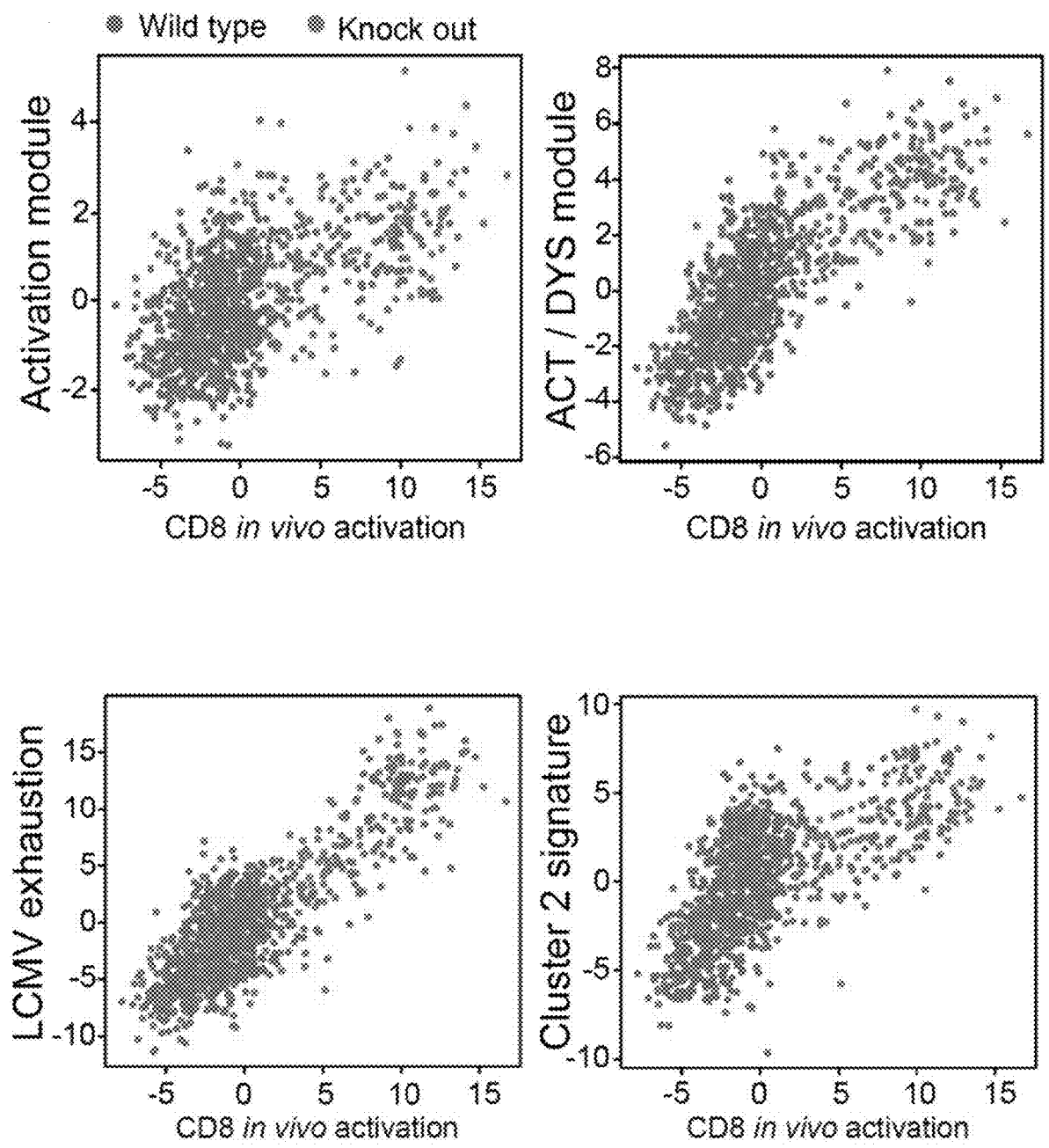

Example 10 the Dysfunction and Activation Transcriptional Programs Gene Modules are Anti-Correlated and Uncoupled at the Single-Cell Level The difference in transcriptional states of the bulk DN, SP, and DP populations between WT and MT-/- could stem from either changes in cell intrinsic states or from changes in the proportion of cells exhibiting different transcriptional states. To test whether the CD8+ TILs in vivo include cells that express only the dysfunction module but not the activation module, Applicants analyzed 1,061 CD8+ TILs with single-cell RNA-seq (516 WT and 545 MT$^{-/-}$ cells that passed QC thresholds from 1,504 processed cells. Applicants then assigned each cell with "signature scores" based on the relative extent to which it expressed the different module signatures (while controlling for the cell's profile complexity, a measure of quality, Experimental Procedures). The activation and dysfunction module scores were negatively correlated across cells (FIG. 11A), such that a higher expression of one module's genes by a cell predicts lower expression of the other module's genes in the same cell. Similarly, the dysfunction module score was also negatively correlated with the in vivo CD8+ activation signature (Sarkar et al., 2008, The Journal of experimental medicine 205, 625-640). In contrast (FIG. 11B), the expression of the in vivo CD8+ activation signature (Sarkar et al., 2008, supra) positively correlated with that of the annotated activation and activation/dysfunction signatures, as well as with the expression of a previously annotated signature of viral exhaustion (Doering et al., 2012, supra) and the cluster 2 signature (FIG. 1I). These observed trends were present in both the WT and MT$^{-/-}$ cells.

Figure 11C:
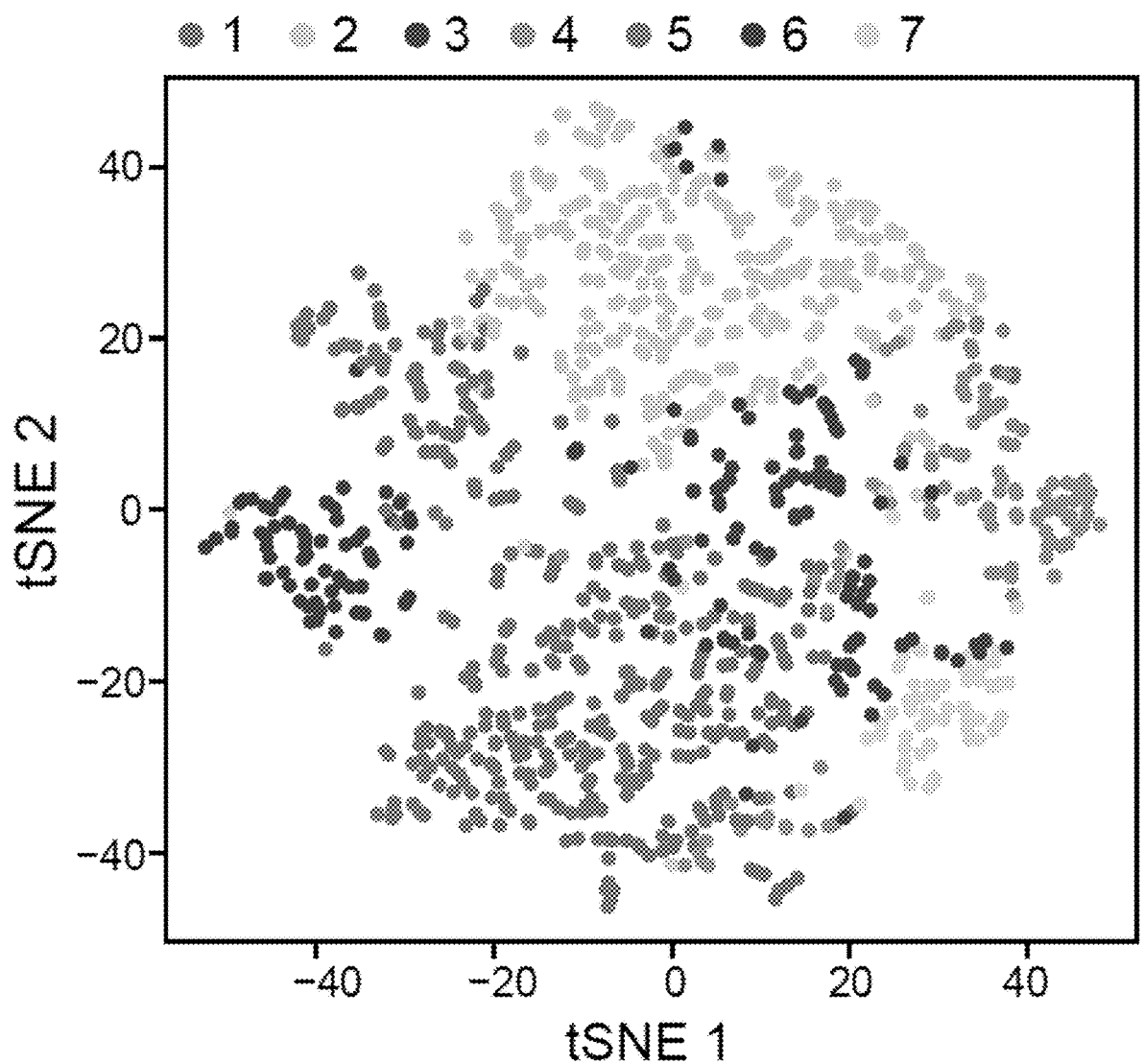
Figure 11D:
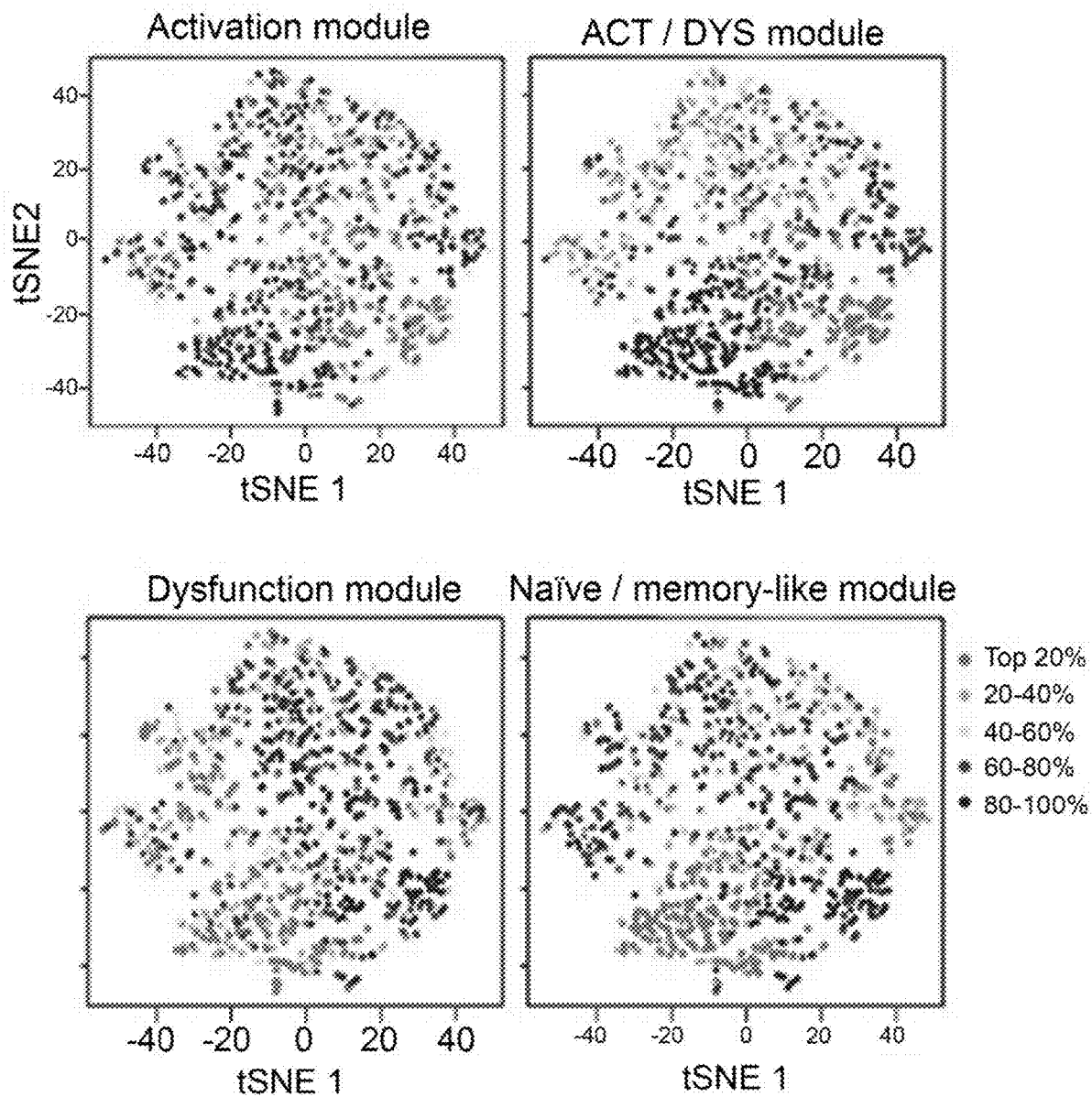
Figures 11E, 11F, 11G:
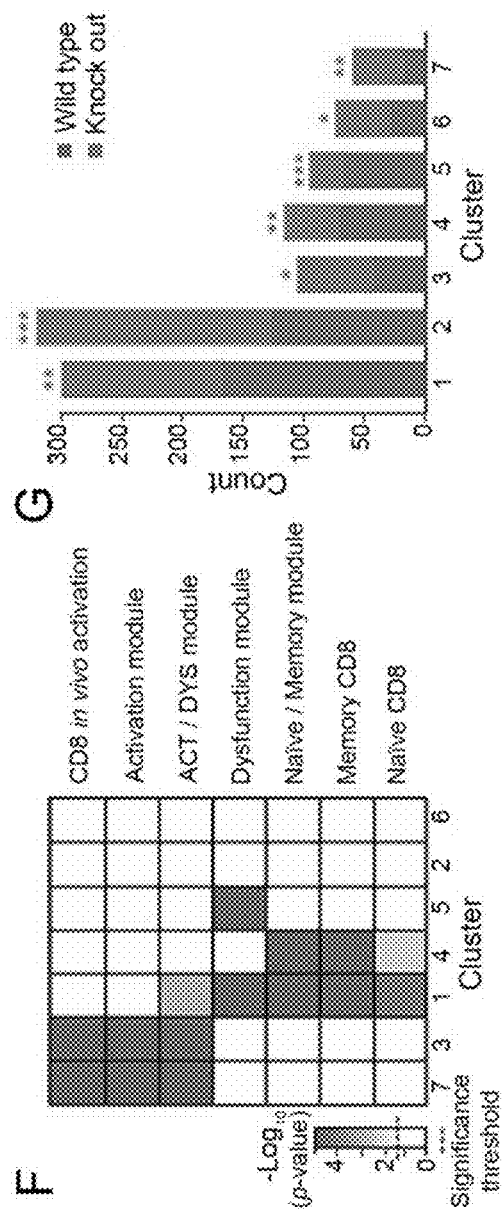
Figure 12:
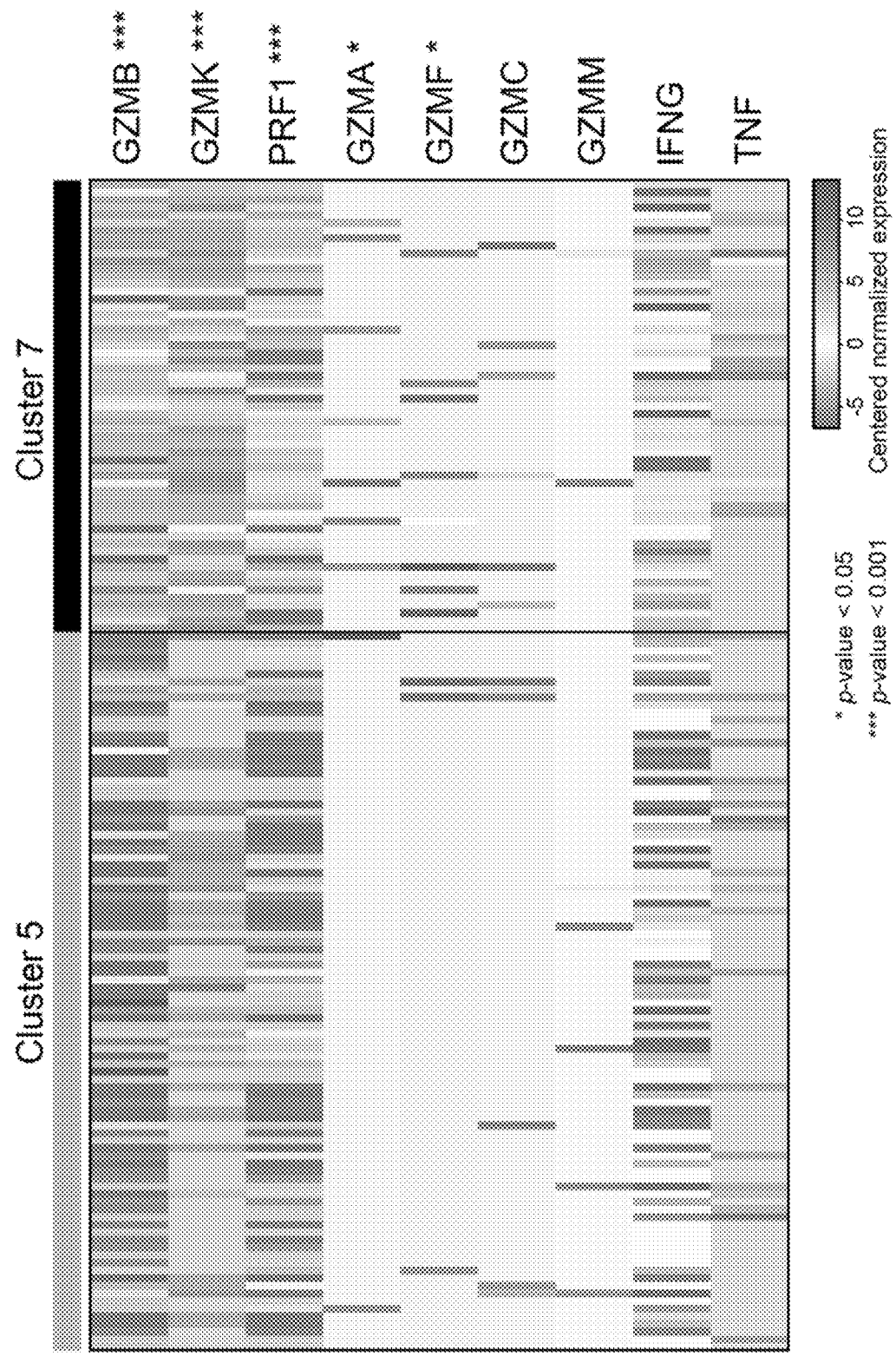
FIG. 12, related to FIG. 11. Cytokine and effector molecule expression in singlecell clusters 7 and 5. Centered and normalized RNA levels are shown for different cytokines or effector molecules (rows) for each of the cells (columns) in clusters 5 and 7 from the single-cell analysis of FIG. 5. To correct for differences in library complexity between cells and allow a comparison at the single-gene level, expression levels for all genes and cells analyzed (FIG. 5) were normalized by partitioning cells into 10 bins by their library complexity and conducting a median-normalization procedure for each gene, as previously described (Gaublomme et al., 2015). IL2, GZMD and GZME are not included in this analysis because they did not pass the required expression thresholds to be included in the overall single-cell analysis (Methods and Resources). *p-value <0.05, ***p-value <0.001. Overall p-value for cytokine/effector molecule signature was p<10-8, (Wilcoxon rank sum test).

Next, unsupervised clustering of the CD8+ TILs (using a k-nearest-neighbor graph followed by the Infomap clustering algorithm (Rosvall and Bergstrom, 2008, Proceedings of the National Academy of Sciences of the United States of America 105, 1118-1123) as previously described (Shekhar K. et al., Cell, in press); Methods and Resources) partitioned the cells into 7 clusters (visualized and colored in FIG. 11C). Cluster 7 was enriched for cells with high levels of the activation module signature, whereas Cluster 5 was enriched for cells with high expression of the dysfunction module signature (FIGS. 11D and F). Indeed, cells in cluster 7 had higher expression of perforin and several granzymes compared to those in cluster 5, suggesting better functional potential (FIG. 12; p<10-8, Wilcoxon rank sum test). Consistent with these transcriptional signatures, cluster 5 is significantly enriched with cells from WT, where Applicants observed T cell dysfunction (termed "dysfunction cluster"); whereas cluster 7 is enriched for MT$^{-/-}$ TILs, in which there is improved effector function (FIG. 11E-F). Thus, the dysfunction and activation transcriptional signatures are enriched in different cells and the presence of these modules in WT versus MT$^{-/-}$ CD8+ TILs is aligned with the observed differences in their functional phenotypes. Furthermore, cells expressing the activation versus dysfunction modules can indeed be distinguished and CD8+ T cells indeed exist in vivo that express the computationally-derived dysfunctional module (FIG. 5).

Genes useful in the present invention may include genes that were expressed in at least 4% of the analyzed cells (43 cells) and significantly up regulated in the single-cell dysfunction cluster (single-cell cluster 5) as compared to all cells not in that cluster that overlap with the population gene signature of dysfunction described herein. The overlap genes include, but are not limited to, CD74, CCR7, TBC1D4, SLC2A6, BCL6, JAK2, PARP3, ASAP1, RELB, H2-AB1, CD44, ABCA3, PFKFB3, SESN3, FAS, 4930523C07RIK, PCGF5, TNIP1, SPRY1, NCOA7, RPLP0, SMIM8, ANTXR2, NSMCE1, DEDD, B3GNT2, CABLES1, SLAMF6, UBL3, NR4A1, ATG7 and KDM5B. Not being bound by a theory, these overlap genes may provide targets for regulating dysfunction in T cells.

Example 11: Genome-Scale Screening of T-Cell Using CRISPR-Cas9 Based Perturbation Tools In certain embodiments, the gene signatures described herein are screened by perturbation of target genes within said signatures. Applicants have previously developed methods and tools for genome-scale screening of perturbations in single cells using CRISPR-Cas9. The perturbation methods and tools allow reconstructing of a cellular network or circuit. Such perturbation methods and tools are herein referred to as Perturb-seq. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by Drop-seq, as described herein. In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence and reduces the chance of false guide RNA assignment. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for Drop-seq methods. In certain embodiments a Unique Molecular Identifier (UMI) is added to each individual transcript. Not being bound by a theory, the UMI allows for determining the capture rate of measured signals, or preferably the number of transcripts captured. Not being bound by a theory, the data is more significant if the signal observed in RNA-seq is derived from more than one transcript. In preferred embodiments, Perturb-seq is performed using a guide RNA barcode expressed as a polyadenylated transcript, a cell barcode, and a UMI.

The approach combines the emerging technologies in the field of genome engineering, single-cell analysis, and immunology, in particular the CRISPR-Cas9 system and droplet single-cell RNA-seq analysis. In certain embodiments, a CRISPR system is used to create an INDEL at a target gene. In other embodiments, epigenetic screening is performed by applying CRISPRa/i technology. Numerous genetic variants associated with disease phenotypes are found to be in non-coding region of the genome, and frequently coincide with transcription factor (TF) binding sites and non-coding RNA genes. The immune system plays a critical role in many of these diseases. Not being bound by a theory, CRISPRa/i approaches may be used to achieve a more thorough and precise understanding of the implication of epigenetic regulation.

In certain embodiments, other CRISPR-based perturbations are readily compatible with Perturb-Seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

The cell(s) may comprise a cell in a model non-human organism, a model non-human mammal that expresses a Cas protein, a mouse that expresses a Cas protein, a mouse that expresses Cpf1, a cell in vivo or a cell ex vivo or a cell in vitro. The cell(s) may also comprise a human cell. Mouse cell lines may include, but are not limited to neuro-2a cells and EL4 cell lines (ATCC TIB-39). Primary mouse T cells may be isolated from C57/BL6 mice. Primary mouse T cells may be isolated from Cas9-expressing mice.

Applicants have developed and optimized methods and conditions for delivery of a CRISPR system to primary mouse T-cells. Applicants have achieved over 80% transduction efficiency with Lenti-CRISPR constructs in CD4 and CD8 T-cells. Despite success with lentiviral delivery, recent work by Hendel et al, (Nature Biotechnology 33, 985-989 (2015) doi:10.1038/nbt.3290) showed the efficiency of editing human T-cells with chemically modified RNA, and direct RNA delivery to T-cells via electroporation. In certain embodiments, perturbation in mouse primary T-cells may use these methods.

In certain embodiments, whole genome screens can be used for understanding the phenotypic readout of perturbing potential target genes. In preferred embodiments, perturbations target expressed genes as defined by RNA-seq using a focused sgRNA library. Libraries may be focused on expressed genes in specific networks or pathways. In other preferred embodiments, regulatory drivers are perturbed. In certain embodiments, Applicants perform systematic perturbation of key genes that regulate T-cell function in a high-throughput fashion. Applicants can use gene expression profiling data to define the target of interest and perform follow-up single-cell and population RNA-seq analysis. Not being bound by a theory, this approach will enhance the understanding of the biology of T-cells, and accelerate the development of therapeutics for human disorders, in particular autoimmune disease and cancer as described herein.

Not being bound by a theory, perturbation studies targeting the genes and gene signatures described herein could (1) generate new insights regarding regulation and interaction of molecules within the system that contribute to suppression of an immune response, such as in the case within the tumor microenvironment, and (2) establish potential therapeutic targets or pathways that could be translated into clinical application.

In certain embodiments, after determining Perturb-seq effects in primary T-cells, the cells are infused back to the tumor xenograft models (melanoma, such as B 16E10 and colon cancer, such as CT26) to observe the phenotypic effects of genome editing. Not being bound by a theory, detailed characterization can be performed based on (1) the phenotypes related to tumor progression, tumor growth, immune response, etc. (2) the TILs that have been genetically perturbed by CRISPR-Cas9 can be isolated from tumor samples, subject to cytokine profiling, qPCR/RNA-seq, and single-cell analysis to understand the biological effects of perturbing the key driver genes within the tumor-immune cell contexts. Not being bound by a theory, this will lead to validation of TILs biology as well as lead to therapeutic targets.

Experimental Procedures Used Throughout the Examples

Mice. 6-8 week old female Balb/c, C57BL/6, pmel transgenic, and OTI transgenic mice were purchased from the Jackson Laboratory. Mice deficient in metallothionein 1 and 2 ($MT^{-/-}$) were purchased from the Jackson Laboratory and backcrossed onto the C57BL/6 background for 5 generations and were confirmed to be >97% congenic with C57BL/6 by SNP analysis. All experiments involving laboratory animals were performed under protocols approved by the Harvard Medical Area Standing Committee on Animals (Boston, Mass.).

Tumor Experiments.

CT26 and B16F10 were purchased from ATCC. MC38-Ova was generously provided by Mark Smyth. CT26 and MC38-Ova ($1\times10^6$) or B16F10 ($5\times10^5$) were implanted subcutaneously into the right flank. Tumor size was measured in two dimensions by caliper and is expressed as the product of two perpendicular diameters. For adoptive transfer tumor experiments, tumor cells were implanted five days prior to intravenous injection of T cells. Naïve)($CD8^+$ $CD62L+CD44^{lo}$) T cells from PMEL (for crispr/cas9 targeting experiments) or OT-1 (for overexpression of MT) transgenic mice were isolated by cell sorting (BDFACS Aria) and activated by 2 µg/ml each of plate-bound anti-CD3 and anti-CD28 antibodies for 48 hours, rested for 3 days, and then reactivated with 1 ug/ml of anti-CD3 and antiCD28 antibodies for 2 days prior to transfer into recipient mice. Retroviral and lentiviral infections of primary T cells were optimized and experiments were performed as described in the respective figure legends. Briefly, retrovirus was used to spin-infect T cells one day after activation and lentivirus was used to infect T cells twice, at 16 hours prior to activation and at 4 hours post activation. Targeting efficiency of retrovirus was determined by measuring GFP expression in both control and MT overexpressing cultures; whereas effective CRISPR/cas9-mediated deletion of the target gene using lentivirus was determined by qPCR.

Isolation of Tumor Infiltrating Lymphocytes.

Tumor infiltrating lymphocytes were isolated by dissociating tumor tissue in the presence of collagenase D (2.5 mg/ml) for 20 min prior to centrifugation on a discontinuous Percoll gradient (GE Healthcare). Isolated cells were then used in various assays of T cell function. Cells were cultured in DMEM supplemented with 10% (vol/vol) FCS, 50 µM 2-mercaptoethanol, 1 mM sodium pyruvate, nonessential amino acids, L-glutamine and 100 U/ml penicillin and 100 µg/ml streptomycin.

Flow Cytometry. Single cell suspensions were stained with antibodies against surface molecules. CD4 (RM4-5), CD8 (53-6.7), and PD-1 (RMP1-30) antibodies are purchased from BioLegend. Tim-3 (5D12) antibody was generated in house. Fixable viability dye eF506 (eBioscience) was used to exclude dead cells. For intra-cytoplasmic cytokine staining, cells were stimulated with 12-myristate 13-acetate (PMA) (50 ng/ml, Sigma-Aldrich, MO), ionomycin (1 µg/ml, Sigma-Aldrich, MO) in the presence of Brefeldin A (Golgiplug, BD Bioscience) for four hours prior to staining with antibodies against surface proteins followed by fixation and permeabilization and staining with antibodies against IL-2 (JES6-5H4), TNF-α (MP6-XT22), IFN-γ (XMG-1.2) (eBioscience), and Granzyme B (GB11) (Biolegend). For measurement of intracellular zinc, cells were stained with 1 µM Zinpyr-1 (Sigma) in PBS for 20 min at 37 deg, washed with media, followed by regular surface staining. All data were collected on a BD LsrII (BD Biosciences) and analyzed with FlowJo software (Tree Star).

Proliferation Assays.

Tumor draining lymph nodes and tumor infiltrating lymphocytes were harvested and incubated with or without tumor specific antigen (gp100, 5 µM) for four consecutive days and cell proliferation was measured by $^3H$ incorporation assay.

Generation of Lentiviral Constructs Using CRISPR/CAS9 Targeting.

The initial guide sequences were selected based on the exon structure of target genes and ranked by the repertoire of potential off-target sites to select designs that minimize the possibility of off-target cleavage. The guides were then cloned into CRISPR-Cas9 vectors via golden-gate cloning as described previously (Cong et al., 2013, Science 339, 819-823). The vector used is a lenti-viral vector, pCKO_2, bearing mammalian-codon-optimized SaCas9 linked to puromycin selection cassette (Ran et al., 2015, Nature 520, 186-191; Shalem et al., 2014, Science 343, 84-87), and an sgRNA-expression cassette that has been modified to enhance RNA expression. The constructs were sequence verified and then tested to screen for the efficiency of each guide using a mouse T-lymphocyte cell line, EL4 (ATCC) before moving on to lentiviral production. To quantify the genomic modification induced by the CRISPR-Cas9 system, genomic DNA was extracted using QuickExtract Solution (Epicentre), as described previously (Cong et al., 2013, supra). Indel formation was measured by either SURVEYOR nuclease assay (IDT DNA) or targeted deep sequencing as described previously (Cong et al., 2013, supra). Briefly, the genomic region around the CRISPR-Cas9 targeting site was amplified, and then subject to either SURVEYOR nuclease digestion following re-annealing or re-amplified to add on Illumina P5/P7 adapters with barcodes for deep-sequencing analysis using the MiSeq sequencing system (Illumina).

After screening of guides in cell lines, the top-ranked guides based on their targeting efficiency were used for viral production. 293FT cells (Thermo Fisher) were maintained as recommended by the manufacturer in 150 mm plates. For each transfection, 10 µg of pVSVG envelope plasmid, 15 µg of pDelta packaging plasmids, and 20 µg of pCKO_2 vector carrying the construct of interest were used. The transfection was either carried out using lipofectamine 2000 (Thermo Fisher) following the manufacturer's recommendations, or with PEI, where 5:1 ratio of PEI solution was added to the DNA mixture, and incubated for 5 minutes before adding the final complex onto cells. After incubation for 16 hours, 20 mL of fresh warm media was applied to replace the old growth media. Virus was harvested between 48h and 72h post transfection by taking the supernatant and pelleting cell debris via centrifugation. The viral particles were then filtered through a 0.45 µm filtration system (Millipore), and then either directly used as purified supernatant, or concentrated further with 15-mL Amicon concentrator (Millipore). Lentiviral vectors were titered by real-time qPCR using a customized probe against the transgene.

For all primary T-cell experiments, the efficacy of the CRISPR-Cas9 lentiviral vectors was first tested by transducing in vitro primary mouse T-cell culture, followed by cleavage measurement and qPCR detection of target gene knock-down. The most efficient viral constructs were then used for downstream experiments.

Microarray Processing and Analysis.

Samples consisting of naive ($CD62L^{hi}CD44^{low}$) and effector/memory ($CD62L^{low}CD44^{hi}$) $CD8^+$ cells from non tumor-bearing Balb/c mice, $CD8^+Tim3^-PD1^-$ (DN) TILS, $CD8^+$ $Tim3^-PD1^+$ (SP), and $CD8^+$ $Tim3^+PD1^+$ (DP) TILs were loaded on Affymetrix GeneChip Mouse Genome 430 2.0 Arrays.

Individual .CEL files were RMA normalized and merged to an expression matrix using the ExpressionFileCreator of GenePattern with default parameters (Reich et al., 2006, supra). COMBAT (Johnson et al., 2007, supra) was used to correct for batch effects (samples were generated in three batches), and probe intensity values below 20 or above 20,000 were collapsed to 20 and 20,000, respectively. Gene-specific intensities were then computed by taking for each gene j and sample i the maximal probe value observed for that gene: $y_{ij}=\max(p_i|s.t.\ p_i$ in set_probes_gene_j), and samples were transferred to log-space by taking $\log_2$(intensity). Differentially expressed genes were annotated as genes with either (1) an FDR-corrected ANOVA p-value smaller or equal to 0.01 computed across the DN, SP and DP subpopulations and a fold-change of at least 1.3 between any of the three subpopulations, or (2) a fold-change of at least 2 between any of the three subpopulations. Fold-change between each two subpopulations was computed as the minimum between the fold-changes of the medians and the means of the subpopulation samples. A differential-expression rank was computed for each gene as the mean between the gene's ranking based on its ANOVA p-value and its ranking based on fold-change. Clusters of differentially expressed genes were generated by k-means clustering (Hartigan-Wong algorithm, run in R) to 10 clusters of the scaled median values of the five sample types clustered over: DN, SP, DP, EffMem and naïve CD8. Enrichment analysis for each cluster with MSigDB v5.0 (Subramanian et al., 2005, supra) gene sets was computed as the hypergeometric p-value for the overlap between the cluster and the gene set of interest, out of the differentially expressed gene list. P-values for enrichment were FDR-corrected.

Population RNA-Seq Processing and Normalization.

Applicants profiled RNA from DP, SP, and DN from four WT and five $MT^{-/-}$ male mice in two batches (batch #1: 2 WT, 2 $MT^{-/-}$, batch #2: 2 WT, 3 $MT^{-/-}$). Samples were processed with SMART-Seq2 (Picelli et al., 2013, Nat Methods 10, 1096-1098), reads were aligned to the mouse mm9 transcriptome using Bowtie (Langmead et al., 2009, Genome Biol 10, R25), and expression abundance TPM estimates were obtained using RSEM parameters (Li and Dewey, 2011). Three samples were excluded from further analysis due to poor sequencing quality, and three additional samples were excluded due to being strong outliers on the first three principle components of the initial PCA (generated as described in next section; a trend similar to PC2 of FIG. 4B, but not significant, was observed on PC4 prior to the latter sample exclusion). Each gene of each sample was assigned the value of log 2(TPM+1). COMBAT (Johnson et al., 2007, supra) was used to correct for batch effects, and was followed by Quantile Normalization to account for variability in library sizes.

To profile the RNA of in vitro activated $CD8^+$ T cells, Applicants isolated naïve $CD8^+$ cells from non tumor bearing C57BL/6 mice and activated them with anti-CD3 and anti-CD28 in vitro. Samples were processed with the SMART-Seq2 protocol (Picelli et al., 2013, supra), mapped to mm9 with Bowtie (Langmead et al., 2009, supra) and TPM values were computed by RSEM (Li and Dewey, 2011).

Principal Component Analysis.

PCA was run on the centered expression matrix (as obtained in the previous section) of the 4,155 genes with mean expression ≥3 and a fold-change of at least 1.5 between at least one pairs of samples. To investigate the association of the PCs with $CD8^+$ T cell activation, the profiles from naïve and in vitro stimulated $CD8^+$ T cells were quantile-normalized together with the samples by which the PCA was produced (above), and overlaid onto the PCA (following subtraction of the gene-specific values used for centering of the PCA-generating dataset).

To investigate the association of the PCs with CD8 activation, Applicants isolated naïve $CD8^+$ cells from non tumor bearing C57BL/6 mice and activated them in vitro. Samples were processed with the Smart-Seq2 protocol, mapped to mm9 with Bowtie and TPM values computed by RSEM. Sample-values were quantile-normalized with the samples by which the PCA was produced (see above), and overlaid onto the PCA (following subtraction of the gene-specific values used for centering of the PCA-generating dataset).

To extract a signature for differential expression across the different subpopulations of the WT and MT samples, Applicants selected differentially expressed genes from the samples used in the PCA analysis as follows: genes were binned by mean expression values and for each bin z-scores were assigned to genes based on their expression log 2-fold-change values. Genes with absolute z-scores larger than 1.5 were determined as differentially expressed. To exclude outliers with overall low expression, only genes for which at least 70% of the measured expression values were in the top 60% of expression (as measured from all values in the expression table) were included in the analysis. Applicants defined differentially expressed genes across the WT/$MT^{-/-}$ setting as genes that were differentially expressed between both of the following pairs: (1) $Tim3^-PD-1^-$ (WT) vs. $Tim3^+PD-1^+$ (WT), and (2) $Tim3^+PD-1^+$ (WT) vs. $Tim3^+PD-1^+$ ($MT^{-/-}$). Genes that were consistently upregulated or downregulated in both comparisons were labeled as "enhanced" genes (groups I and II, FIG. 4D). Genes that had an opposite expression trend across the two sets were labeled as "reversed" (groups III and IV, FIG. 4D). Applicants found that the majority of DE genes were of the "enhanced" type, as expected by the PCA trend of PC1 which explains the most variance.

Computing Rankings and Statistics for Association with Dysfunction/Activation/Dysfunction+Activation/Neither.

Each gene was assigned an "activation score" defined as the correlation of the gene's expression across the samples with the PC1 values, computed over the MTKO samples. Additionally, each gene was assigned a "dysfunction score" to be (−1) times the correlation of the gene's expression across the samples with the PC2 values, computed over the WT samples. These two scores placed the gene on the Activation/Dysfunction plot as shown in FIG. 5A. Applicants included in this analysis the 7,592 genes that had an assigned $\log_2(\text{TPM}+1)$ expression value $\geq 4$, in at least two of the samples. Following placement on the Activation/Dysfunction plot, each gene was assigned two rankings: on the Dysfunction↔Activation axis, and on the Activation\Dysfunction↔Neither axis, by projecting each point onto the x=(−y) and x=y axes, respectively. Applicants defined four rankings of the 7,592 genes, each ranking representing the association of these genes with one of the following: (1) dysfunction (and not activation): by the (−1)*x values of the x=(−y) projection (ranking from the Dysfunction corner to the Activation corner), (2) activation (and not dysfunction): by the x values of the x=(−y) projection (3) activation and dysfunction: by the x values of the x=y projection, and (4) neither: by the (−1)*x values of the x=y projection.

To check for statistically significant association of different expression signatures with these four rankings (dysfunction/activation/activation\dysfunction/neither) Applicants used the XL-mHG test (Eden et al., 2007; Wagner, 2015) to test for enrichment at the tops of the different ranked lists (one test for each module), requiring that the minimal number of genes in an enriched set to be 5 (X=5) and that the proportion of the ranked list to be considered in the enrichment portion be at most 30% of the list (L=30%). The reported significance results are robust to a variety of XL-mHG parameters, including the completely unconstrained ranked test (X=0; L=100%).

From each of the four rankings, Applicants annotated a gene signature of 100 genes, defining gene signatures for: (1) dysfunction (and not activation), (2) activation (and not dysfunction), (3) activation and dysfunction; and (4) neither. Each signature was defined to be the top-most ranked genes of the relevant ranking, which fulfilled the following constraints: all genes included in the Dysfunction signature had a dysfunction score of $\geq 0.3$, all genes included in the Activation signature had an activation score of $\geq 0.3$ and all genes included in the Activation/Dysfunction signature had activation and dysfunction scores $\geq 0.3$.

Single-Cell RNA-Seq.

For single-cell RNA-Seq experiments, TILs from B16 melanomas were collected in 96-well plates, incorporating a population-well and an empty well in each plate as controls, and were processed from the four WT mice (two plates per mouse; total of eight WT plates) and five $MT^{-/-}$ mice (one plate each from two of the mice ($MT^{-/-}$ 1,2) and two plates each from three of the mice ($MT^{-/-}$ 4, 5, 6)); total of eight $MT^{-/-}$ plates). Samples were produced in 2 biological batches (batch #1: WT1, 2, $MT^{-/-}$ 1, 2, 3, batch #2: WT3, 4, $MT^{-/-}$ 4, 5, 6), and processed in 4 sequencing batches, where each sequencing batch consisted of two WT plates and two $MT^{-/-}$ plates.

Cells were sorted into 96-well plates with 5 µl lysis buffer comprised of Buffer TCL (Qiagen 1031576) plus 1% 2-mercaptoethanol (Sigma 63689). Following sorting, plates were spun down for one minute at 3,000 rpm and immediately frozen at −80° C. For preparation of single-cell libraries Applicants thawed the cells and purified them with 2.2× RNAClean SPRI beads (Beckman Coulter Genomics) without final elution (Shalek et al., 2013, Nature 498, 236-240). The RNA captured beads were air-dried and processed immediately for cDNA synthesis. Applicants performed SMART-seq2 following the published protocol (Picelli et al., 2013) with minor modifications in the reverse transcription (RT) step (MSK and AR, in preparation). Applicants made a 25 µl reaction mix for each PCR and performed 21 cycles for cDNA amplification. Applicants used 0.25 ng cDNA of each cell and ¼ of the standard Illumina Nexter-aXT reaction volume in both the tagmentation and final PCR amplification steps. Applicants pooled plates to 384 single-cell libraries, and sequenced 50×25 paired-end reads using a single kit on the NextSeq500 5 instrument.

Single-cell RNA-Seq analysis. Paired reads were mapped to mouse annotation mm 10 using Bowtie (Langmead et al., 2009, supra) (allowing a maximum of one mismatch in seed alignment, and suppressing reads that had more than 10 valid alignments), TPMs were computed using RSEM (Li and Dewey, 2011), and $\log_2(\text{TPM}+1)$ values were used for subsequent analyses.

Applicants filtered out low quality cells and cell doublets, maintaining for subsequent analysis the 1,061 cells (516 WT and 545 $MT^{-/-}$) that had (1) 1,500-6,000 detected genes (defined by at least one mapped read), (2) at least 100,000 reads mapped to the transcriptome, and (3) at least 20% of the reads mapped to the transcriptome. Applicants restricted the genes considered in subsequent analyses to be the 9,863 genes expressed at $\log 2(\text{TPM}+1)\geq 2$ in at least twenty of the cells.

PCA of the Gene-by-Cell matrix revealed PC1 to be highly correlated with the cells' gene-counts (Gaublomme et al., 2015, Cell December 3; 163(6):1400-12), and it was therefore excluded from subsequent analyses to reduce technical bias. Applicants chose PCs 2-7 for subsequent analysis due to a drop in the proportion of variance explained following PC7. To visualize cell-to-cell variation Applicants used tSNE (van der Maaten and Hinton, 2008) to generate a two-dimensional non-linear embedding.

To obtain clusters of cells similar in their expression patterns, cells were clustered using the infomap algorithm (Rosvall and Bergstrom, 2008, supra) which was ran on the binary k-nearest-neighbor graph, where k=70 (Shekhar K. et al., Cell, in press).

P-values for enrichment of each cluster with a given gene signature were computed by ranking the cells by their cell-specific-gene-signature-scores (see below), and computing the XL-mHG test (X=5; L=30% of ranked cell list) to generate a p-value for the enrichment of cells from the given cluster at the top of the ranked list.

Single-Cell Gene Signature Scoring.

As an initial step, genes were binned into six bins based on their mean expression across cells, and into six (separate) bins based on their variance of expression across cells. Given a gene signature (list of genes), a cell-specific signature score was computed for each cell as follows: First, 1,000 random gene lists were generated, where each instance of a random gene-list was generated by sampling (with replacement) for each gene in the gene-list a gene that is equivalent to it with respect to the mean and variance bins it was placed in. Then, the sum of gene expression in the given cell was computed for all gene-lists (given the 1,000 random lists generated) and the z-score of the original gene-list for the generated 1,000 sample distribution is returned. For gene-signatures consisting of an upregulated and downregulated set of genes, two z-scores were obtained separately, and the down-regulated associated z-score was subtracted from the up-regulated generated z-score.

Generation of Gene Signatures.

For the $CD8^+$ in vivo activation signature, Applicants used the intersection of the sets of genes published in Sarkar et al (Sarkar et al., 2008, supra) as (1) DE between effector and naïve, (2) DE between effector and memory.

For the LCMV exhaustion (viral exhaustion) signature, Applicants identified differentially expressed genes between the acute and chronic conditions for each timepoint in (Doering et al., 2012, supra), as genes significantly different under an FDR-corrected t-test (P<0.05) and that had a fold-change in expression ≥2. The exhaustion set was taken as the union of the Day 15 DE genes and the Day 30 DE genes.

For the CD8$^+$ Ly49$^+$Treg signature, gene expression measurements for Ly49+ and Ly49− CD8$^+$ T cells (two replicates each) were downloaded from GEO (accession GSE73015) (Kim et al., 2015). Differentially expressed genes were determined as genes with (1) a mean fold-change ≥1.5 and (2) a fold-change ≥1.3 between the smallest sample from the upregulated condition and the largest sample of the downregulated condition.

For the in vitro activation signature, differentially expressed genes were determined as genes with (1) a mean fold-change ≥2 and (2) a fold-change ≥1.3 between the smallest sample from the upregulated condition and the largest sample of the downregulated condition.

For the naïve CD8$^+$ T cell signature, a signature was compiled from 26 MSigDB (v5.0, c7) (Subramanian et al., 2005, supra) gene signatures identified as up-regulated in naive CD8$^+$ T cells when compared to effector, memory, or exhausted CD8$^+$ T cells at various time points (Table 4). The 28 genes present in at least 10 of the analyzed sets were selected for this signature.

For the memory CD8$^+$ T cell signature, Applicants compiled 13 MSigDB (v5.0, c7) (Subramanian et al., 2005, Proceedings of the National Academy of Sciences of the United States of America 102, 15545-15550) gene signatures identified as upregulated in memory CD8$^+$ T cells when compared to naïve, effector or exhausted CD8$^+$ T cells at various time points (Table 4). The 23 genes present in at least 6 of the analyzed sets were selected for this signature.

T cell dysfunction, the data show that these two T cell states are separable transcriptionally and genetically. Single-cell RNA-Seq of TILs supports the observation that T cells with either state exist in vivo. Importantly, the dysfunction and activation gene modules are consistent with signatures in CD8$^+$ TILs in human melanoma (Tirosh et al. 2016, Science, vol. 352(6282), 189-96), supporting their clinical relevance.

Applicants generated a signature for dysfunctional CD8$^+$ tumor-infiltrating lymphocytes based on the transcriptomes of CD8$^+$ TILs populations that exhibit discrete effector phenotypes. From this signature Applicants identified metallothioneins, intracellular zinc chaperones, as candidate regulators of dysfunctional T cell phenotype.

Indeed, dysfunctional CD8$^+$ TILs show dysregulation of intracellular zinc, metallothioneins are highly enriched in the most dysfunctional CD8$^+$ TILs, and disruption of metallothioneins resulted in the loss of T cell dysfunction and recovery of anti-tumor immunity. Through analysis of metallothionein deficient CD8$^+$ TILs Applicants identified a dysfunction-specific transcriptional signature distinct from that of T cell activation and predicted key regulators that control this signature. Using inter alia CRISPR/CAS9 editing of primary T cells, Applicants identified a novel role for the zinc-finger transcription factor Gata3, as a key driver of the T cell dysfunction program. The identification of gene signatures for T cell dysfunction and T cell activation that are consistent across species is of critical value to the development of novel therapeutic approaches that specifically target these programs to modulate T cell function in disease. The ability to dampen the dysfunction program while not interfering with the activation program of a T cell is highly desirable in the chronic disease settings such as

| MSigDB Signatures used as basis for Memory Signature | MSigDB Signatures used as basis for Naive Signature |
| --- | --- |
| GSE10239_MEMORY_VS_DAY4.5_EFF_CD8_TCELL_UP | KAECH_NAIVE_VS_DAY8_EFF_CD8_TCELL_UP |
| GSE16522_MEMORY_VS_NAIVE_CD8_TCELL_UP | KAECH_NAIVE_VS_DAY15_EFF_CD8_TCELL_UP |
| GSE32423_MEMORY_VS_NAIVE_CD8_TCELL_UP | KAECH_NAIVE_VS_MEMORY_CD8_TCELL_UP |
| KAECH_NAIVE_VS_MEMORY_CD8_TCELL_DN | GOLDRATH_NAIVE_VS_EFF_CD8_TCELL_UP |
| KAECH_DAY8_EFF_VS_MEMORY_CD8_TCELL_DN | GOLDRATH_NAIVE_VS_MEMORY_CD8_TCELL_UP |
| KAECH_DAY15_EFF_VS_MEMORY_CD8_TCELL_DN | GSE10239_NAIVE_VS_MEMORY_CD8_TCELL_UP |
| GOLDRATH_NAIVE_VS_MEMORY_CD8_TCELL_DN | GSE10239_NAIVE_VS_DAY4.5_EFF_CD8_TCELL_UP |
| GOLDRATH_EFF_VS_MEMORY_CD8_TCELL_DN | GSE15324_NAIVE_VS_ACTIVATED_CD8_TCELL_UP |
| GSE10239_NAIVE_VS_MEMORY_CD8_TCELL_DN | GSE15930_NAIVE_VS_24H_IN_VITRO_STIM_CD8_TCELL_UP |
| GSE22886_NAIVE_CD8_TCELL_VS_MEMORY_-TCELL_DN | GSE15930_NAIVE_VS_24H_IN_VITRO_STIM_IL12_CD8_TCELL_UP |
| GSE9650_NAIVE_VS_MEMORY_CD8_TCELL_DN | GSE15930_NAIVE_VS_24H_IN_VITRO_STIM_INFAB_CD8_TCELL_UP |
| GSE9650_EFFECTOR_VS_MEMORY_CD8_TCELL_DN | GSE15930_NAIVE_VS_48H_IN_VITRO_STIM_CD8_TCELL_UP |
| GSE9650_EXHAUSTED_VS_MEMORY_CD8_TCELL_DN | GSE15930_NAIVE_VS_48H_IN_VITRO_STIM_IL12_CD8_TCELL_UP |
| | GSE15930_NAIVE_VS_48H_IN_VITRO_STIM_IFNAB_CD8_TCELL_UP |
| | GSE15930_NAIVE_VS_72H_IN_VITRO_STIM_CD8_TCELL_UP |
| | GSE15930_NAIVE_VS_72H_IN_VITRO_STIM_IL12_CD8_TCELL_UP |
| | GSE15930_NAIVE_VS_72H_IN_VITRO_STIM_IFNAB_CD8_TCELL_UP |
| | GSE15930_NAIVE_VS_72H_IN_VITRO_STIM_TRICHOSTATINA_-CD8_TCELL_UP |
| | GSE19825_NAIVE_VS_DAY3_EFF_CD8_TCELL_UP |
| | GSE26495_NAIVE_VS_PD1HIGH_CD8_TCELL_UP |
| | GSE26495_NAIVE_VS_PD1LOW_CD8_TCELL_UP |
| | GSE9650_NAIVE_VS_EFF_CD8_TCELL_UP |
| | GSE9650_NAIVE_VS_EXHAUSTED_CD8_TCELL_UP |
| | GSE9650_NAIVE_VS_MEMORY_CD8_TCELL_UP |
| | GSE16522_MEMORY_VS_NAIVE_CD8_TCELL_DN |
| | GSE32423_MEMORY_VS_NAIVE_CD8_TCELL_DN |

CONCLUSIONS

Here, Applicants combined computational, molecular, and functional systems immunology, to derive a distinct signature for T cell dysfunction that is uncoupled from T cell activation. Although chronic activation is a pre-requisite to cancer and chronic viral infection. In contrast, the ability to engage the dysfunction program while dampening the activation program is desirable in the setting of autoimmunity. In cancer, approaches that dampen up-regulated genes in the dysfunction signature can be exploited to achieve reversal of dysfunction program while allowing activation program to ensue. Conversely, approaches that maintain expression of genes that are down-regulated in the dysfunction signature can be exploited to make robust T cells for use in adoptive T cell therapy approaches.

Applicants find that the expression of co-inhibitory receptors can be uncoupled from dysfunctional phenotype. Indeed, many co-inhibitory receptors are not in the dysfunction module but rather are in the activation/dysfunction gene module. Thus, while co-inhibitory receptors may set the stage upstream for the development of T cell dysfunction, eventually chronic engagement of the TCR and co-inhibitory receptors must drive the cells to initiate a distinct gene program for T cell dysfunction.

The uncoupling of the dysfunction module from the activation module does not in itself determine any obvious relationship between the two modules or how they might be expressed in cells. The single-cell analysis of TILs revealed that not only are the two modules negatively correlated with each other, but they also can be exclusively enriched in distinct populations of $CD8^+$ T cells. These findings suggest that while dysfunctional T cells may have arisen from activated T cells, they acquire a distinct functional state with a transcriptional program that is no longer dependent on the activation module. Notably, some cells score highly for both the dysfunction and a naïve/memory-like module. Nevertheless, the fact that Applicants observe enrichment for the activation and dysfunction modules in different cells in the single-cell analysis does not mean that the newly defined modules cannot be expressed in the same cells. How these modules are expressed in individual cells will best be discerned by examining cells throughout a time course of tumor development. Such a study will shed light on potential transitional T cell states.

The data point to zinc regulation by metallothioneins and the function of zinc-dependent transcription factors as key features that lead to the development of dysfunctional T cell phenotype. Interestingly, MT1 and MT2 are among the differentially expressed genes found in a signature of dysfunctional T cells from chronic LCMV viral infection (Doering et al., 2012 supra), as are several zinc finger-containing transcription factors. These observations support a role for metallothioneins and zinc regulation in determining effector $CD8^+$ T cell phenotype and that zinc dysregulation may be at the core of dysfunctional phenotype across multiple chronic disease conditions. Indeed, zinc is an essential metal required for the structure and function of over 1,000 zinc-finger containing proteins that include several families of transcription factors (GATA, IKAROS, nuclear hormone receptors, Kruppel-like factors), RING-domain ubiquitin ligases, serine-threonine kinases, and matrix metallopeptidases. Thus, one can envision how disruption of intracellular zinc availability can impact the structure and activity of multiple proteins that regulate cellular functions.

Consistent with this observation, the studies identify a novel role for the zinc-finger transcription factor Gata-3, as driver of T cell dysfunction. Gata-3 has pleiotropic roles in immunity. While it is best known for promoting Type 2 immune responses, Gata-3 has also been implicated in playing a role in T cell lineage development, development of ILC2s, controlling $CD8^+$ T cell proliferation, and more recently in regulatory T cell function (Tindemans et al., 2014, Immunity 41, 191-206). In the latter context, the role of Gata-3 in $CD8^+$ T cell dysfunction may reflect aspects of its role in promoting regulatory functions in T cells. Identification of other factors that co-operate with Gata-3 to drive the dysfunction program in $CD8^+$ T cells will pave the way for identification of the complete ensemble of transcriptional regulators that induce T cell dysfunction distinct from other functional or differentiation states in T cells.

The newly identified dysfunction gene module shares some features with a recently identified signature for $Ly49^+$ $CD8^+$ T cells that have a regulatory phenotype (Kim et al., 2015) but not with the other annotated T cell signatures. Interestingly, the stability of this $Ly49^+$ $CD8^+$ Treg population is dependent on Helios (IKZF2), a zinc-finger of the IKAROS family, and the second-highest scoring TF (after Gata-3) in the dysfunction gene module. Together, these data suggest that dysfunctional T cells may have adopted a regulatory program to curb their activity in face of antigen persistence and chronic activation. Further annotation of genes in the dysfunction module identified through the single cell analysis shed light on the potential regulatory programs expressed by dysfunctional $CD8^+$ T cells.

The findings refine our current definition of the dysfunctional T cell state by providing precise molecular resolution of the distinct gene programs associated with T cell dysfunction versus activation. The presence of the newly defined gene modules in T cells isolated from human melanoma tissue indicate the robustness of the findings and opens the door for the identification of novel druggable targets for the treatment of cancer and other chronic diseases.

Figure 9:
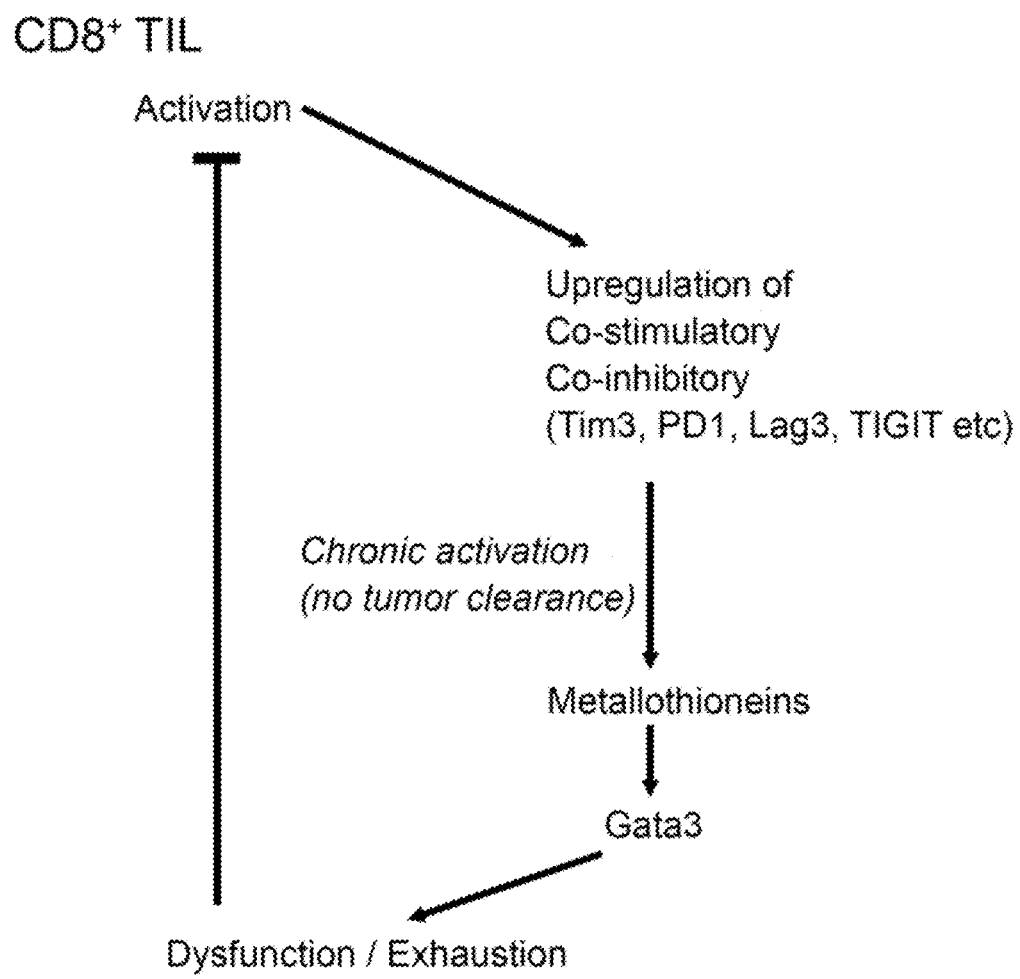
FIG. 9 illustrates a putative molecular model of T cell activation/dysfunction.

Without wishing to be bound to any theory, the Applicants put forward the putative molecular model shown in FIG. 9. In this model, the T cell activation program is upstream of the T cell dysfunction program, does not require MT and includes the expression of co-inhibitory receptors, while the T cell dysfunction program depends on MT to restrain T cell effector functions. Applicants have defined, for the first time, a novel dysfunction (exhaustion) signature. Applicants have also advanatageously decoupled for the first time a dysfunction signature which is not associated with activation, and an activation signature which is not associated with dysfunction.

The invention is further described by the following numbered paragraphs:

1. An isolated immune cell modified to comprise an altered expression or activity of GATA3 or FOXO1.

2. The isolated immune cell according to numbered paragraph 1, wherein the immune cell is a T cell, preferably a $CD8^+$ T cell.

3. The isolated immune cell according to any one of numbered paragraphs 1 or 2, wherein the immune cell displays tumor specificity.

4. The isolated immune cell according to numbered paragraph 3, wherein the immune cell has been isolated from a tumor of a subject, preferably wherein the immune cell is a tumor infiltrating lymphocyte.

5. The isolated immune cell according to numbered paragraph 3, wherein the immune cell comprises a tumor-specific chimeric antigen receptor (CAR).

6. The isolated immune cell according to any one of numbered paragraphs 1 to 5, modified to comprise downregulated or abolished expression or activity of GATA3 and/or FOXO1.

7. The isolated immune cell according to numbered paragraph 6, wherein the endogenous GATA3 and/or FOXO1 gene has been modified, whereby the cell comprises downregulated or abolished expression or activity of GATA3 and/or FOXO1.

8. The isolated immune cell according to numbered paragraph 7, wherein the endogenous GATA3 or FOXO1 gene has been modified using a nuclease.

9. The isolated immune cell according to numbered paragraph 8, wherein the nuclease comprises (i) a DNA-binding portion configured to specifically bind to the endogenous GATA3 or FOXO1 gene and (ii) a DNA cleavage portion.

10. The isolated immune cell according to numbered paragraph 9, wherein the DNA-binding portion comprises a zinc finger protein or DNA-binding domain thereof, a transcription activator-like effector (TALE) protein or DNA-binding domain thereof, or an RNA-guided protein or DNA-binding domain thereof.

11. The isolated immune cell according to numbered paragraph 9, wherein the DNA-binding portion comprises (i) a Cas protein modified to eliminate its nuclease activity, or (ii) DNA-binding domain of a Cas protein.

12. The isolated immune cell according to any one of numbered paragraphs 9 to 11, wherein the DNA cleavage portion comprises FokI or variant thereof or DNA cleavage domain of FokI or variant thereof.

13. The isolated immune cell according to numbered paragraph 8, wherein the nuclease is an RNA-guided nuclease, such as a Cas protein.

14. The isolated immune cell according to numbered paragraph 6, wherein the cell comprises a protein comprising a DNA-binding portion configured to specifically bind to the endogenous GATA3 or FOXO1 gene.

15. The isolated immune cell according to numbered paragraph 14, wherein the protein is a heterologous repressor protein capable of repressing the transcription of the endogenous GATA3 or FOXO1 gene.

16. The isolated immune cell according to numbered paragraph 15, wherein the heterologous repressor protein comprises at least a DNA-binding portion configured to specifically bind to the endogenous GATA3 or FOXO1 gene, preferably to the endogenous GATA3 or FOXO1 gene promoter.

17. The isolated immune cell according to any one of numbered paragraphs 15 or 16, wherein the heterologous repressor protein comprises (i) a DNA-binding portion configured to specifically bind to the endogenous GATA3 or FOXO1 gene, preferably to the endogenous GATA3 or FOXO1 gene promoter, and (ii) a transcription repression portion.

18. The isolated immune cell according to any one of numbered paragraphs 16 or 17, wherein the DNA-binding portion comprises a zinc finger protein or DNA-binding domain thereof, TALE protein or DNA-binding domain thereof, or RNA-guided nuclease protein or DNA-binding domain thereof.

19. The isolated immune cell according to any one of numbered paragraphs 16 or 17, wherein the DNA-binding portion comprises (i) a Cas protein modified to eliminate its nuclease activity, or (ii) DNA-binding domain of a Cas protein.

20. An isolated immune cell modified to comprise an agent capable of inducibly altering expression or activity of GATA3 or FOXO1.

21. The isolated immune cell according to numbered paragraph 20, wherein the agent comprises:
 (a) a nuclease capable of modifying the endogenous GATA3 or FOXO1 gene, such as to downregulate or abolish expression of GATA3 or FOXO1, such as the nuclease as defined in any one of numbered paragraphs 9 to 13; or
 (b) a heterologous repressor protein capable of repressing the transcription of the endogenous GATA3 or FOXO1 gene, such as the heterologous repressor protein as defined in any one of numbered paragraphs 15-18.

22. The isolated immune cell according to any one of numbered paragraphs 1 to 21, further modified to comprise:
 (a) an altered expression or activity of any one or more of GATA3, FOXO1, POU2AF1, BTLA, or NRP1;
 (b) an altered expression or activity of any one or more of PD1, CTLA4, TIGIT, TIM3, LAG3, or PD-L1;
 (c) an altered expression or activity of any one or more of GATA3, FOXO1, POU2AF1, BTLA, NRP1, PD1, CTLA4, TIGIT, TIM3, LAG3, or PD-L1;
 (d) an altered expression or activity of any one or more of GPR65, DEC1, PZLP, TCF4, TOSO, or CD5L;
 (e) an altered expression or activity of any one or more of MINA, PML, POU2AF1, PROCR, SMARCA4, ZEB1, EGR2, CCR6, or FAS;
 (f) an altered expression or activity of any one or more of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3;
 (g) an altered expression or activity of any one or more of SP4, IKZF4, or TSC22D3;
 (h) an altered expression or activity of any one or more of SP4, ETS2, IKZF4, TSC22D3, or IRF1;
 (i) an altered expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA;
 (j) an altered expression or activity of any one or more of C1QTNF6 or_PROS1;
 (k) an agent capable of inducibly altering expression or activity of any one or more of GPR65, DEC1, PZLP, TCF4, TOSO, or CD5L;
 (l) an agent capable of inducibly altering expression or activity of any one or more of GATA3, FOXO1, POU2AF1, BTLA, or NRP1;
 (m) an agent capable of inducibly altering expression or activity of PD1, CTLA4, TIGIT, TIM3, LAG3, or PD-L1;
 (n) an agent capable of inducibly altering expression or activity of GATA3, FOXO1, POU2AF1, BTLA, NRP1, PD1, CTLA4, TIGIT, TIM3, LAG3, or PD-L1;
 (o) an agent capable of inducibly altering expression or activity of any one or more of MINA, PML, POU2AF1, PROCR, SMARCA4, ZEB1, EGR2, CCR6, or FAS;
 (p) an agent capable of inducibly altering expression or activity of any one or more of MINA, MYC, NKFB1, NOTCH, PML, POU2AF1, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3;
 (q) an agent capable of inducibly altering expression or activity of any one or more of SP4, IKZF4, or TSC22D3;
 (r) an agent capable of inducibly altering expression or activity of any one or more of SP4, ETS2, IKZF4, TSC22D3, or IRF1;
 (s) an agent capable of inducibly altering expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA; or
 (t) an agent capable of inducibly altering expression or activity of any one or more of C1QTNF6 or PROS1.

23. A cell population of immune cells as defined in any one of numbered paragraphs 1-22.

24. A method for generating the modified immune cell as defined in any one of numbered paragraphs 1 to 19, the method comprising (i) providing an isolated immune cell, and (ii) modifying said isolated immune cell such as to comprise an altered expression or activity of GATA3 or FOXO1.

25. A method for generating the modified immune cell as defined in any one of numbered paragraphs 20 or 21, the method comprising (i) providing an isolated immune cell, and (ii) modifying said isolated immune cell such as to comprise an agent capable of inducibly altering expression or activity of GATA3 or FOXO1.

26. The method according to any one of numbered paragraphs 24 or 25, wherein the step of providing the isolated immune cell comprises providing the immune cell isolated from a subject, or isolating the immune cell from a subject.

27. The method according to numbered paragraph 26, wherein the immune cell isolated from the subject expresses GATA3 and/or FOXO1.

28. The method according to numbered paragraph 26, wherein the immune cell isolated from the subject is dysfunctional or is not dysfunctional.

29. The method according to numbered paragraph 26, wherein the immune cell isolated from the subject expresses a signature of dysfunction as defined in any one of numbered paragraphs 42 to 49.

30. The method of any one of numbered paragraphs 24 to 29, further comprising the step of expanding the isolated immune cell prior to and/or subsequent to the modification.

31. A pharmaceutical composition comprising the isolated immune cell according to any one of numbered paragraphs 1 to 22, or the cell population according to numbered paragraph 23.

32. The isolated immune cell according to any one of numbered paragraphs 1 to 22, or the cell population according to numbered paragraph 23, for use in therapy.

33. The isolated immune cell according to any one of numbered paragraphs 1 to 22, or the cell population according to numbered paragraph 23, for use in immunotherapy or adoptive immunotherapy, preferably immunotherapy or adoptive immunotherapy of a proliferative disease, such as a tumor or cancer, or a chronic infection, such as a chronic viral infection.

34. The isolated immune cell or cell population for use according to numbered paragraph 33 in a subject, wherein the subject has been determined to comprise immune cells which:
   express GATA3 and/or FOXO1;
   are dysfunctional, or are not dysfunctional; or
   express a signature of dysfunction as defined in any one of numbered paragraphs 42 to 49.

35. A method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising administering to said subject the isolated immune cell according to any one of numbered paragraphs 1 to 22, or the cell population according to numbered paragraph 23.

36. The method according to numbered paragraph 35, further comprising administering to said subject one or more other active pharmaceutical ingredient, preferably wherein said one or more other active pharmaceutical ingredient is useful in immunotherapy or adoptive immunotherapy, or wherein said one or more other active pharmaceutical ingredient is useful in the treatment of a proliferative disease, such as a tumor or cancer, or a chronic infection, such as a chronic viral infection.

37. The method according to numbered paragraph 36, wherein the one or more other active pharmaceutical ingredient is:
   (a) an agonist of a cell molecule, such as a cell surface molecule, which when activated is capable of upregulating immune response, such as one or more of an agonist of 4-1BB, an agonist of OX40, an agonist of GITR, an agonist of STING, an agonist of TLR, or an agonist of BTLA; and/or
   (b) an inhibitor of a cell molecule, such as a cell surface molecule, which when not inhibited is capable of downregulating immune response, such as a checkpoint inhibitor, or such as one or more of an antagonist of PD1, an antagonist of CTLA4, an antagonist of BTLA, an antagonist of TIGIT, an antagonist of TIM3, an antagonist of LAG3, an antagonist of VISTA, an antagonist of LILRB4, an antagonist of NRP1, an antagonist of CD160, an antagonist of CD274, or an antagonist of IDO.

38. The method according to any one of numbered paragraphs 35 to 37, wherein the subject has been determined to comprise immune cells which:
   express GATA3 and/or FOXO1;
   are dysfunctional or are not dysfunctional; or
   express a signature of dysfunction as defined in any one of numbered paragraphs 42 to 49.

39. A method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising:
   (a) providing an isolated immune cell from the subject, or isolating an immune cell from a subject;
   (b) modifying said isolated immune cell such as to comprise an altered expression or activity of GATA3 and/or FOXO1, or modifying said isolated immune cell such as to comprise an agent capable of inducibly altering expression or activity of GATA3 and/or FOXO1; and
   (c) reintroducing the modified isolated immune cell to the subject.

40. The method according to numbered paragraph 39, wherein the immune cell isolated from the subject:
   expresses GATA3 and/or FOXO1;
   is dysfunctional or is not dysfunctional; or
   expresses a signature of dysfunction as defined in any one of numbered paragraphs 42 to 49.

41. The method of any one of numbered paragraphs 39 or 40, further comprising the step of expanding the isolated immune cell prior to and/or subsequent to the modification, and before reintroduction to the subject.

42. A method of detecting dysfunctional immune cells comprising detection of a gene expression signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC88B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14.

43. The method according to numbered paragraph 42, wherein the signature comprises at least two markers, or at least three markers, or at least four markers, or at least five markers, or six or more markers, such as wherein the signature consists of two markers, three markers, four markers, or five markers.

44. The method according to any one of numbered paragraphs 42 or 43, wherein the signature comprises one or more markers selected from the group consisting of GATA3, FOXO1, POU2AF1, BTLA, NRP1, NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, and PTGER4.

45. The method according to any one of numbered paragraph 42 to 44, wherein the signature comprises two or more markers, and wherein:
 (a) one of said two or more markers is GATA3;
 (b) one of said two or more markers is FOXO1; or
 (c) two of said two or more markers are GATA3 and FOXO1.

46. The method according to any one of numbered paragraphs 42 to 45, wherein the signature comprises:
 (a) at least one transcription factor or intracellular marker;
 (b) at least one transcription factor or intracellular marker and at least one or at least two or at least three co-inhibitory receptors;
 (c) at least one transcription factor or intracellular marker and at least one or at least two or at least three co-stimulatory receptors;
 (d) at least one transcription factor or intracellular marker, at least one or at least two or at least three co-inhibitory receptors and at least one or at least two or at least three co-stimulatory receptors;
 (e) at least two transcription factors or intracellular markers and at least one or at least two or at least three co-inhibitory receptors;
 (f) at least two transcription factors or intracellular markers and at least one or at least two or at least three co-stimulatory receptors;
 (g) at least two transcription factors or intracellular markers, at least one or at least two or at least three co-inhibitory receptors and at least one or at least two or at least three co-stimulatory receptors;
 (h) at least three transcription factors or intracellular markers and at least one or at least two or at least three co-inhibitory receptors;
 (i) at least three transcription factors or intracellular markers and at least one or at least two or at least three co-stimulatory receptors;
 (j) at least three transcription factors or intracellular markers, at least one or at least two or at least three co-inhibitory receptors and at least one or at least two or at least three co-stimulatory receptors.

47. The method according to numbered paragraph 46, wherein the at least one, at least two or at least three transcription factors or intracellular markers are selected from the group consisting of NOTCH2, RELB, KLF3, POU2AF1, GATA3, PIAS2, FOXO1, RARA, CRTC3, BCL6, MYB, BCL3, KDM5B, KDM4B, KDM3A, PCGF5, SPRY1, NR4A1, PNRC1, IKZF2, ZFP62, MT1, MT2, WTAP, HDAC8, UBE2D3, and BRD4.

48. The method according to any one of numbered paragraphs 46 or 47, wherein the least one or at least two or at least three co-inhibitory receptors are selected from the group consisting of PD1, CTLA4, TIGIT, TIM3, LAG3, KLRC1, BTLA, NRP1, CD160, CD274, IDO, CD200, CD244, KLRD1, LAIR1, CEACAM1, KLRA7, FAS, GPR132, CD74, SLAMF6, CD5, GPR35, CD28, CD44, and PTGER4.

49. The method according to any one of numbered paragraphs 46 to 48, wherein the least one or at least two or at least three co-stimulatory receptors are selected from the group consisting of TNFRSF9, TNFRSF4, TNFSF4, TNFRSF18, TNFSF11, TNFRSF13C, CD27, CD28, CD86, ICOS, TNFSF14.

50. A kit of parts comprising means for detection of the signature of dysfunction as defined in any one of numbered paragraphs 42 to 49.

51. A method for determining whether or not an immune cell has a dysfunctional immune phenotype and/or whether or not an immune cell would benefit from upregulation of an immune response, said method comprising:
 (a) determining in said immune cell the expression of GATA3 and/or FOXO1, whereby expression of GATA3 and/or FOXO1 indicates that the immune cell has a dysfunctional immune phenotype and/or would benefit from upregulation of an immune response; or
 (b) determining in said immune cell the expression of the signature of dysfunction as defined in any one of numbered paragraphs 42 to 49, whereby expression of the signature indicates that the immune cell has a dysfunctional immune phenotype and/or would benefit from upregulation of an immune response.

52. The method according to any one of numbered paragraphs 42 to 49, wherein the immune cell is a T cell, preferably a CD8$^+$ T cell.

53. A method for determining whether or not a patient would benefit from a therapy aimed at reducing dysfunction of immune cells or a therapy aimed at upregulating of an immune response, the method comprising:

(a) determining, in immune cells from said patient the expression of GATA3 and/or FOXO1, whereby expression of GATA3 and/or FOXO1 indicates that the patient will benefit from the therapy; or (b) determining, in immune cells from said patient the expression of the signature of dysfunction as defined in any one of numbered paragraphs 42 to 49, whereby expression of the signature indicates the patient will benefit from the therapy.

54. The method according to numbered paragraph 53, wherein the therapy comprises treatment with the isolated immune cell according to any one of numbered paragraphs 1 to 22, or the cell population according to numbered paragraph 23.

55. The method according to numbered paragraph 54, wherein the therapy comprises treatment with one or more checkpoint inhibitors.

56. A method for determining the efficacy of a treatment of a patient with a therapy, particularly immune therapy, more particularly therapy or immune therapy aimed at reducing dysfunction of immune cells or a therapy aimed at upregulating of an immune response, said method comprising:

(a) determining in immune cells from said patient the expression of GATA3 and/or FOXO1 before and after said treatment and determining the efficacy of said therapy based thereon, whereby unchanged or increased expression of GATA3 and/or FOXO1 indicates that the treatment should be adjusted; or (b) determining in immune cells from said patient the expression of the signature of dysfunction as defined in any one of numbered paragraphs 42 to 49 before and after said treatment and determining the efficacy of said therapy based thereon, whereby unchanged or increased expression of the signature indicates that the treatment should be adjusted.

57. The method according to numbered paragraph 56, wherein the therapy comprises treatment with the isolated immune cell according to any one of numbered paragraphs 1 to 22, or the cell population according to numbered paragraph 23.

58. The method according to numbered paragraph 57, wherein the therapy comprises:

(a) activation of one or more cell molecules, such as cell surface molecules, which when activated are capable of upregulating immune response, such as activation of one or more of 4-1BB, OX40, GITR, STING or TLR; and/or (b) inhibition of one or more cell molecules, such as cell surface molecules, which when not inhibited are capable of downregulating immune response, such as treatment with one or more checkpoint inhibitors, or such as treatment with one or more of an antagonist of PD1, an antagonist of CTLA4, an antagonist of BTLA, an antagonist of TIGIT, an antagonist of TIM3, an antagonist of LAG3, an antagonist of VISTA, an antagonist of LILRB4, an antagonist of NRP1, an antagonist of CD160, an antagonist of CD274, or an antagonist of IDO.

59. A method for determining the suitability of a compound as a checkpoint inhibitor, said method comprising:

(a) contacting an immune cell expressing GATA3 and/or FOXO1 with said compound and determining whether or not said compound can affect the expression or activity of GATA3 and/or FOXO1 by said cell, whereby decreased expression or activity indicates that the compound is suitable as a checkpoint inhibitor; or (b) contacting an immune cell expressing the signature of dysfunction as defined in any one of numbered paragraphs 42 to 49 with said compound and determining whether or not said compound can affect the expression of the signature by said cell, whereby decreased expression indicates that the compound is suitable as a checkpoint inhibitor.

60. A method for determining the suitability of a compound for reducing an dysfunctional immune phenotype and/or upregulating of an immune response, said method comprising:

(a) contacting an immune cell expressing GATA3 and/or FOXO1 with said compound and determining whether or not said compound can affect the expression or activity of GATA3 and/or FOXO1 by said cell, whereby decreased expression or activity indicates that the compound is suitable for reducing dysfunctional immune phenotype and/or upregulating of an immune response; or (b) contacting an immune cell expressing the signature of dysfunction as defined in any one of numbered paragraphs 42 to 49 with said compound and determining whether or not said compound can affect the expression of the signature by said cell, whereby decreased expression indicates that the compound is suitable for reducing dysfunctional immune phenotype and/or upregulating of an immune response.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An immune cell isolated from a human subject and modified ex vivo to comprise an altered expression or activity of GATA3 and/or FOXO1 as compared to the immune cell in vivo,
   wherein the immune cell comprises an INDEL upstream of a protospacer adjacent motif (PAM) sequence in the GATA3 and/or FOXO1 gene, or
   wherein the immune cell comprises a protein comprising a DNA-binding portion configured to specifically bind to the endogenous GATA3 and/or FOXO1 gene, or
   wherein the immune cell comprises an agent capable of inducibly altering expression or activity of GATA3 and/or FOXO1.

2. The isolated immune cell according to claim 1, wherein the immune cell is a T cell.

3. The isolated immune cell according to claim 1, wherein the immune cell is modified to comprise downregulated or abolished expression or activity of GATA3 and/or FOXO1.

4. The isolated immune cell according to claim 3, wherein the endogenous GATA3 and/or FOXO1 gene has been modified using a nuclease.

5. The isolated immune cell according to claim 1, wherein the DNA-binding portion comprises a zinc finger protein or DNA-binding domain thereof, TALE protein or DNA-binding domain thereof, or RNA-guided nuclease protein or DNA-binding domain thereof; or
   wherein the DNA-binding portion comprises (i) a Cas protein modified to eliminate its nuclease activity, or (ii) DNA-binding domain of a Cas protein.

6. The isolated immune cell according to claim 1, wherein the immune cell is further modified to comprise:
   (a) an altered expression or activity of any one or more of GATA3, FOXO1, BTLA, or NRP1;
   (b) an altered expression or activity of any one or more of PD1, CTLA4, TIGIT, TIM3, LAG3, or PD-L1;
   (c) an altered expression or activity of any one or more of GATA3, FOXO1, BTLA, NRP1, PD1, CTLA4, TIGIT, TIM3, LAG3, or PD-L1;
   (d) an altered expression or activity of any one or more of GPR65, DEC1, PZLP, TCF4, TOSO, or CD5L;
   (e) an altered expression or activity of any one or more of MINA, PML, PROCR, SMARCA4, ZEB1, EGR2, CCR6, or FAS;
   (f) an altered expression or activity of any one or more of MINA, MYC, NKFB1, NOTCH, PML, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3;
   (g) an altered expression or activity of any one or more of SP4, IKZF4, or TSC22D3;
   (h) an altered expression or activity of any one or more of SP4, ETS2, IKZF4, TSC22D3, or IRF1;
   (i) an altered expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA;
   (j) an altered expression or activity of any one or more of C1QTNF6 or PROS1;
   (k) an agent capable of inducibly altering expression or activity of any one or more of GPR65, DEC1, PZLP, TCF4, TOSO, or CD5L;
   (l) an agent capable of inducibly altering expression or activity of any one or more of GATA3, FOXO1, BTLA, or NRP1;
   (m) an agent capable of inducibly altering expression or activity of PD1, CTLA4, TIGIT, TIM3, LAG3, or PD-L1;
   (n) an agent capable of inducibly altering expression or activity of GATA3, FOXO1, BTLA, NRP1, PD1, CTLA4, TIGIT, TIM3, LAG3, or PD-L1;
   (o) an agent capable of inducibly altering expression or activity of any one or more of MINA, PML, PROCR, SMARCA4, ZEB1, EGR2, CCR6, or FAS;

(p) an agent capable of inducibly altering expression or activity of any one or more of MINA, MYC, NKFB1, NOTCH, PML, PROCR, RBPJ, SMARCA4, ZEB1, BATF, CCR5, CCR6, EGR1, EGR2, ETV6, FAS, IL12RB1, IL17RA, IL21R, IRF4, IRF8, or ITGA3;

(q) an agent capable of inducibly altering expression or activity of any one or more of SP4, IKZF4, or TSC22D3;

(r) an agent capable of inducibly altering expression or activity of any one or more of SP4, ETS2, IKZF4, TSC22D3, or IRF1;

(s) an agent capable of inducibly altering expression or activity of any one or more of NOTCH2, FAS, GPR132, CD74, SLAMF6, RARA, WTAP, KDM5B, KDM4B, CD5, GPR35, TMEM55B, TMEM243, KDM3A, CD28, TNFRSF13C, CD44, HDAC8, UBE2D3, BRD4, CD160, CD274, PTGER4, BTLA, METTL3, or MINA; or (t) an agent capable of inducibly altering expression or activity of any one or more of C1QTNF6 or PROS1.

7. A cell population comprising immune cells as defined in claim 1.

8. A method for generating the modified immune cell as defined in claim 1, the method comprising:
(i) providing an immune cell isolated from a human subject, and (ii) modifying said isolated immune cell ex vivo such as to comprise an altered expression or activity of GATA3 and/or FOXO1; or
(i) providing an immune cell isolated from a human subject, and (ii) modifying said isolated immune cell ex vivo such as to comprise an agent capable of inducibly altering expression or activity of GATA3 and/or FOXO1.

9. The method according to claim 8, wherein the immune cell isolated from the subject expresses GATA3 and/or FOXO1; and/or
wherein the immune cell isolated from the subject is dysfunctional or is not dysfunctional; and/or
wherein the immune cell isolated from the subject expresses a signature of dysfunction, said signature comprising one or more markers of dysfunction selected from the group consisting of GATA3, FOXO1, POU2AF1, BTLA, NRP1, NPEPPS, NOTCH2, CABLES1, CERK, MTMR3, RELB, KLF3, CAMK2D, CCNG2, SLC25A33, PIM3, RNF149, SWAP70, PINK1, RAB2A, FAM168B, MAP2K7, MIR466I, ASAP1, GRASP, B3GNT2, FAS, PIAS2, SEC24B, TUBB2B, PARP3, PIGH, BRAP, ATP6V0D1, IFT80, FRRS1, GPR132, SFPI1, SH2B3, WFDC17, CD74, TBC1D22B, PHC2, TRAT1, SLAMF6, YPEL3, RARA, GM9159, MAN1A, CRTC3, MKRN1, BCL6, CLN6, MYB, NDUFV1, SLC28A2, FBXL20, SCIN, LGMN, WTAP, BCL3, SLC2A6, IL2RG, SNTB1, KDM5B, UTP15, LATS2, RASSF2, IFI30, KDM4B, IER5, CD5, MNDAL, PCGF5, GPR35, SPRY1, TNIP1, CSNK1D, NSMCE1, NR4A1, OSBPL11, PNRC1, ITGAE, SNX18, TMEM55B, IKZF2, ISCU, FAM196B, TMEM243, ZFP62, RASGEF1B, DTWD1, GNA13, JAK2, EIF3F, CCR7, SGPP1, SLAMF7, QRICH1, EML4, CACNB3, ATG7, SUV420H1, HBS1L, RAB2B, H2-AB1, DGKD, SESN3, ELK4, PIM1, JOSD1, SPIN1, LILRB3, CHIC2, H2-DMB2, TPRGL, IL4I1, ACAP2, SUDS3, ABCA3, TNRC6A, RPS5, MPLKIP, NEK7, SOD1, CRY1, MIDN, RBMS1, PRAMEF8, ATP2A3, RPS6KB2, MRS2, PLEKHG2, TCF12, MED8, LIMD1, SMIM8, KDM3A, BACH2, ILVBL, 4930523C07RIK, CD28, SLC52A2, ACBD6, ANKIB1, BANK1, KLHDC2, AHR, MLXIP, TRAF4, MFSD6, GM4070, PFKFB3, ANTXR2, GRWD1, MAP1LC3A, HP, RAP2B, TRPC4AP, SMG1, DEDD, UNC13D, RAB6A, CCDC188B, TNFRSF13C, TRP53INP1, SFPQ, CD44, HDAC8, UBE2D3, EIF3I, P2RY6, TBC1D4, 0610012G03RIK, RASSF5, AHCYL2, NDUFS4, PTP4A3, RNF111, SMAP1, IFITM3, PPAPDC1B, PRMT2, RPLP0, FOXN3, IFITM6, IFT20, CTAGE5, ZFP622, PPP2CA, WDR82, POLB, BRD4, UBL3, SLC12A9, NCOA7, TRAPPC3, MEF2D, LACTB, MALT1, LYZ2, CD160, CD274, PTGER4, MT1, MT2, PD1, CTLA4, TIGIT, TIM3, LAG3, KLRC1, CD160, CD274, IDO, CD200, CD244, KLRD1, LAIR1, CEACAM1, KLRA7, TNFRSF9, TNFRSF4, TNFSF4, TNFRSF18, TNFSF11, CD27, CD28, CD86, ICOS, and TNFSF14.

10. The isolated immune cell according to claim 1, wherein the immune cell is a $CD8^+$ T cell.

11. The isolated immune cell according to claim 1, wherein the immune cell displays tumor specificity.

12. The isolated immune cell according to claim 1, wherein the immune cell is a tumor infiltrating lymphocyte.

13. The isolated immune cell according to claim 1, wherein the immune cell further comprises an exogenous tumor-specific chimeric antigen receptor (CAR) or T cell receptor (TCR).

14. The isolated immune cell according to claim 4, wherein the nuclease is an RNA-guided nuclease, such as a Cas protein; and/or
wherein the nuclease comprises (i) a DNA-binding portion configured to specifically bind to the endogenous GATA3 and/or FOXO1 gene and (ii) a DNA cleavage portion.

15. The isolated immune cell according to claim 14, wherein the DNA-binding portion comprises a zinc finger protein or DNA-binding domain thereof, a transcription activator-like effector (TALE) protein or DNA-binding domain thereof, or an RNA-guided protein or DNA-binding domain thereof; and/or
wherein the DNA-binding portion comprises (i) a Cas protein modified to eliminate its nuclease activity, or (ii) DNA-binding domain of a Cas protein; and/or
wherein the DNA cleavage portion comprises FokI or variant thereof or DNA cleavage domain of FokI or variant thereof.

16. The isolated immune cell according to claim 1, wherein the protein is a heterologous repressor protein capable of repressing the transcription of the endogenous GATA3 and/or FOXO1 gene; and/or
wherein the protein is a heterologous repressor protein comprising at least a DNA-binding portion configured to specifically bind to the endogenous GATA3 and/or FOXO1 gene; and/or
wherein the protein is a heterologous repressor protein comprising at least a DNA-binding portion configured to specifically bind to the endogenous GATA3 and/or FOXO1 gene promoter; and/or
wherein the protein is a heterologous repressor protein comprising (i) a DNA-binding portion configured to specifically bind to the endogenous GATA3 and/or FOXO1 gene, such as to the endogenous GATA3 and/or FOXO1 gene promoter, and (ii) a transcription repression portion.

17. The isolated immune cell according to claim 1, wherein the agent comprises:

a nuclease capable of modifying the endogenous GATA3 and/or FOXO1 gene, such as to downregulate or abolish expression of GATA3 and/or FOXO1; or a heterologous repressor protein capable of repressing the transcription of the endogenous GATA3 and/or FOXO1 gene.

18. The isolated immune cell according to claim 17, wherein the nuclease comprises (i) a DNA-binding portion configured to specifically bind to the endogenous GATA3 and/or FOXO1 gene and (ii) a DNA cleavage portion; and/or wherein the DNA-binding portion comprises a zinc finger protein or DNA-binding domain thereof, a transcription activator-like effector (TALE) protein or DNA-binding domain thereof, or an RNA-guided protein or DNA-binding domain thereof; and/or wherein the DNA-binding portion comprises (i) a Cas protein modified to eliminate its nuclease activity, or (ii) DNA-binding domain of a Cas protein; and/or wherein the DNA cleavage portion comprises FokI or variant thereof or DNA cleavage domain of FokI or variant thereof; and/or wherein the nuclease is an RNA-guided nuclease, such as a Cas protein; or wherein the protein is a heterologous repressor protein capable of repressing the transcription of the endogenous GATA3 and/or FOXO1 gene; and/or wherein the protein is a heterologous repressor protein comprising at least a DNA-binding portion configured to specifically bind to the endogenous GATA3 and/or FOXO1 gene; and/or wherein the protein is a heterologous repressor protein comprising at least a DNA-binding portion configured to specifically bind to the endogenous GATA3 and/or FOXO1 gene promoter; and/or wherein the protein is a heterologous repressor protein comprising (i) a DNA-binding portion configured to specifically bind to the endogenous GATA3 and/or FOXO1 gene, such as to the endogenous GATA3 and/or FOXO1 gene promoter, and (ii) a transcription repression portion.

19. The cell population according to claim 7, wherein the cell population is a pharmaceutical composition.

20. The method according to claim 8, further comprising the step of expanding the isolated immune cell prior to and/or subsequent to the modification.

* * * * *

UNITED STATES PATENT AND TRADEMARK OFFICE
CERTIFICATE OF CORRECTION

PATENT NO. : 11,180,730 B2
APPLICATION NO. : 15/966290
DATED : November 23, 2021
INVENTOR(S) : Aviv Regev et al.

Page 1 of 2

It is certified that error appears in the above-identified patent and that said Letters Patent is hereby corrected as shown below:

In the Specification

In Column 15, Line 62, delete "5A-51I" and insert -- 5A-5H --.

In Column 22, Line 58, after "invention," insert -- T --.

In Column 25, Line 9, delete ""I"" and insert -- T --.

In Column 25, Line 29, delete "-WIC" and insert -- -MHC --.

In Column 25, Line 35, delete "-WIC" and insert -- -MHC --.

In Column 25, Line 37, delete "WIC" and insert -- MHC --.

In Column 25, Line 41, delete "WIC" and insert -- MHC --.

In Column 25, Line 43, delete "((32m)" and insert -- (β2m) --.

In Column 25, Line 43, delete "WIC" and insert -- MHC --.

In Column 25, Line 54, delete "Colo.)" and insert -- Colo.), --.

In Column 39, Line 48, delete "(IL)-1.alpha, IL-1.beta," and insert -- (IL)-I.alpha, IL-I.beta, --.

In Column 40, Line 5, delete "IL-1.a, IL-1.beta," and insert -- IL-I.a, IL-I.beta, --.

In Column 42, Line 54, delete "1a-CD18," and insert -- Ia-CD18, --.

In Column 46, Line 18, delete "PDLL" and insert -- PDL1 --.

Signed and Sealed this
Twenty-sixth Day of December, 2023

Katherine Kelly Vidal
*Director of the United States Patent and Trademark Office*

CERTIFICATE OF CORRECTION (continued)
U.S. Pat. No. 11,180,730 B2

In Column 95, Line 47, delete "$1\times10^{10}$" and insert -- $1\times10^7$ --.

In Column 101, Line 33, delete "µmon-" and insert -- µmol/L- --.

In Column 126, Line 36, delete "o.," and insert -- O., --.

In Column 152, Line 11, delete "8')," and insert -- (8'), --.

In Column 156, Line 45, delete "8*)," and insert -- (8*), --.

In Column 180, Line 12, delete "ZDHHCS," and insert -- ZDHHC5, --.

In Column 180, Line 13, delete "KCNQS," and insert -- KCNQ5, --.

In Column 180, Line 17, delete "WBPS," and insert -- WBP5, --.

In Column 180, Line 24, delete "CARSB," and insert -- CAR5B, --.

In Column 180, Line 28, delete "FZDS," and insert -- FZD5, --.

In Column 180, Line 32, delete "RABLS," and insert -- RABL5, --.

In Column 196, Line 66, delete "PCI" and insert -- PC1 --.

In Column 211, Line 3, delete "B 16E10" and insert -- B16E10 --.

In the Claims

In Column 239, Line 51, in Claim 9, delete "MANIA," and insert -- MAN1A, --.

In Column 240, Line 5, in Claim 9, delete "CCDCl88B," and insert -- CCDC88B, --.